(12) United States Patent
Pardridge et al.

(10) Patent No.: US 8,741,260 B2
(45) Date of Patent: *Jun. 3, 2014

(54) FUSION PROTEINS FOR DELIVERY OF GDNF TO THE CNS

(75) Inventors: William M. Pardridge, Pacific Palisades, CA (US); Ruben J. Boado, Agoura Hills, CA (US)

(73) Assignee: Armagen Technologies, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/323,232

(22) Filed: Nov. 25, 2008

(65) Prior Publication Data

US 2009/0156498 A1 Jun. 18, 2009

Related U.S. Application Data

(63) Continuation-in-part of application No. 11/245,546, filed on Oct. 7, 2005.

(60) Provisional application No. 60/990,290, filed on Nov. 26, 2007.

(51) Int. Cl.
| | | |
|---|---|---|
| A61K 39/395 | (2006.01) |
| A61K 38/18 | (2006.01) |
| C07K 14/48 | (2006.01) |
| C07K 14/485 | (2006.01) |
| C07K 14/49 | (2006.01) |
| C07K 14/495 | (2006.01) |

(52) U.S. Cl.
USPC ............... 424/1.41; 424/130.1; 424/152.1; 424/179.1; 424/143.1; 514/1.2; 514/5.8; 514/5.9; 514/7.6; 514/8.2; 514/8.4; 514/8.7; 514/8.9; 514/9.5; 514/9.6; 514/17.7; 514/17.9; 514/21.2

(58) Field of Classification Search
CPC combination set(s) only.
See application file for complete search history.

(56) References Cited

U.S. PATENT DOCUMENTS

| | | |
|---|---|---|
| 4,801,575 A | 1/1989 | Pardridge |
| 4,902,505 A | 2/1990 | Pardridge et al. |
| 4,946,778 A | 8/1990 | Ladner et al. |
| 5,154,924 A | 10/1992 | Friden |
| 5,180,820 A | 1/1993 | Barde et al. |
| 5,182,107 A | 1/1993 | Friden |
| 5,229,500 A | 7/1993 | Barde et al. |

(Continued)

FOREIGN PATENT DOCUMENTS

| | | |
|---|---|---|
| EP | 0613007 A2 | 8/1994 |
| EP | 0613007 A3 | 10/1995 |

(Continued)

OTHER PUBLICATIONS

Wu (1997. J Clin. Invest. 100:1804-1812).*

(Continued)

*Primary Examiner* — Jeffrey Stucker
*Assistant Examiner* — Aurora M Fontainhas
(74) *Attorney, Agent, or Firm* — Wilson, Sonsini, Goodrich & Rosati

(57) ABSTRACT

The invention provides compositions, methods, and kits for increasing transport of GDNF across the blood brain barrier while allowing its activity to remain substantially intact. The GDNF is transported across the blood brain barrier via one or more endogenous receptor-mediated transport systems.

23 Claims, 51 Drawing Sheets

(56) References Cited

U.S. PATENT DOCUMENTS

| | | | |
|---|---|---|---|
| 5,438,121 A | 8/1995 | Barde et al. | |
| 5,453,361 A | 9/1995 | Yancopoulos et al. | |
| 5,527,288 A | 6/1996 | Gross et al. | |
| 5,527,527 A | 6/1996 | Friden | |
| 5,562,903 A | 10/1996 | Co et al. | |
| 5,610,279 A | 3/1997 | Brockhaus et al. | |
| 5,618,920 A | 4/1997 | Robinson et al. | |
| 5,656,284 A | 8/1997 | Balkin | |
| 5,672,683 A * | 9/1997 | Friden et al. | 530/350 |
| 5,693,762 A | 12/1997 | Queen et al. | |
| 5,824,782 A | 10/1998 | Holzer et al. | |
| 5,837,231 A | 11/1998 | Low et al. | |
| 5,848,991 A | 12/1998 | Gross et al. | |
| 5,977,307 A | 11/1999 | Friden et al. | |
| 5,997,501 A | 12/1999 | Gross et al. | |
| 6,015,662 A | 1/2000 | Hackett | |
| 6,041,775 A | 3/2000 | Century | |
| 6,060,069 A | 5/2000 | Hill et al. | |
| 6,153,190 A | 11/2000 | Young et al. | |
| 6,165,783 A | 12/2000 | Weiss et al. | |
| 6,284,262 B1 | 9/2001 | Place | |
| 6,287,792 B1 | 9/2001 | Pardridge et al. | |
| 6,322,808 B1 | 11/2001 | Trautman et al. | |
| 6,329,508 B1 | 12/2001 | Friden | |
| 6,348,210 B1 | 2/2002 | Gale | |
| 6,361,760 B1 | 3/2002 | Murata et al. | |
| 6,372,250 B1 | 4/2002 | Pardridge | |
| 6,375,975 B1 | 4/2002 | Modi | |
| 6,531,309 B1 | 3/2003 | Hu et al. | |
| 6,582,945 B1 | 6/2003 | Raso | |
| 6,583,272 B1 | 6/2003 | Bailon | |
| 6,709,833 B2 | 3/2004 | Fukul et al. | |
| 6,743,427 B1 | 6/2004 | Schenk | |
| 6,858,206 B2 | 2/2005 | Kakkis | |
| 7,053,202 B2 | 5/2006 | O'Keefe et al. | |
| 7,078,376 B1 | 7/2006 | Thompson | |
| 7,214,658 B2 | 5/2007 | Tobinick | |
| 7,226,758 B1 | 6/2007 | Lin et al. | |
| 7,294,704 B2 | 11/2007 | Simon et al. | |
| 7,309,687 B1 | 12/2007 | Brines et al. | |
| 7,388,079 B2 | 6/2008 | Pardridge et al. | |
| 2002/0052311 A1 | 5/2002 | Solomon et al. | |
| 2002/0137684 A1 | 9/2002 | Tchistiakova et al. | |
| 2002/0169109 A1 | 11/2002 | Plata-Salaman et al. | |
| 2003/0129186 A1 | 7/2003 | Beliveau et al. | |
| 2003/0165853 A1 | 9/2003 | Pardridge et al. | |
| 2004/0072291 A1 | 4/2004 | Carr et al. | |
| 2004/0101904 A1 * | 5/2004 | Pardridge et al. | 435/7.1 |
| 2004/0102369 A1 | 5/2004 | Wu et al. | |
| 2004/0229250 A1 | 11/2004 | Figura et al. | |
| 2004/0248197 A1 | 12/2004 | Holtzman et al. | |
| 2005/0142141 A1 | 6/2005 | Pardridge | |
| 2007/0081992 A1 | 4/2007 | Pardridge et al. | |
| 2007/0082380 A1 | 4/2007 | Pardridge et al. | |
| 2007/0275882 A1 | 11/2007 | Meijer et al. | |
| 2007/0280940 A1 | 12/2007 | Winkles et al. | |
| 2008/0003211 A1 | 1/2008 | Fogh et al. | |
| 2008/0051564 A1 | 2/2008 | Pardridge et al. | |
| 2008/0152645 A1 | 6/2008 | Pardridge et al. | |
| 2008/0170994 A1 | 7/2008 | Pardridge et al. | |
| 2008/0171055 A1 | 7/2008 | Pardridge et al. | |
| 2008/0292639 A1 | 11/2008 | Shen et al. | |
| 2009/0053219 A1 | 2/2009 | Pardridge et al. | |
| 2009/0068206 A1 | 3/2009 | Pardridge et al. | |
| 2009/0156498 A1 | 6/2009 | Pardridge et al. | |
| 2009/0238789 A1 | 9/2009 | Guyon et al. | |
| 2010/0077498 A1 | 3/2010 | Pardridge et al. | |
| 2010/0098693 A1 | 4/2010 | Pardridge et al. | |
| 2010/0172919 A1 | 7/2010 | Grimm et al. | |
| 2010/0261647 A1 | 10/2010 | Pardridge et al. | |
| 2010/0290985 A1 | 11/2010 | Pardridge et al. | |
| 2011/0110935 A1 | 5/2011 | Pardridge et al. | |
| 2012/0269807 A1 | 10/2012 | Pardridge et al. | |
| 2013/0142794 A1 | 6/2013 | Pardridge et al. | |
| 2013/0287773 A1 | 10/2013 | Pardridge et al. | |

FOREIGN PATENT DOCUMENTS

| | | |
|---|---|---|
| JP | 6-228199 | 8/1994 |
| WO | WO 99/00150 A2 | 1/1999 |
| WO | WO 99/00951 A1 | 1/1999 |
| WO | WO 99/00150 A3 | 4/1999 |
| WO | WO 99/66951 A1 | 12/1999 |
| WO | WO 00/15759 A1 | 3/2000 |
| WO | WO 03/074081 A1 | 12/2003 |
| WO | WO 2004/050016 A2 | 6/2004 |
| WO | WO 2006/081171 A1 | 8/2006 |
| WO | WO 2007/022416 A2 | 2/2007 |
| WO | WO 2007/044323 A2 | 4/2007 |
| WO | WO 2007/022416 A3 | 5/2007 |
| WO | WO 2008/022349 A2 | 2/2008 |
| WO | WO 2009/018122 A2 | 2/2009 |
| WO | WO 2009/070597 A2 | 6/2009 |

OTHER PUBLICATIONS

Haisma et al. 1998 (Blood 92:184-190).*

Park et al. 1998 (Journal of Drug Targeting 6:53-64).*

McGrath 1997 (Journal of Neuroscience Research 47:123-133).*

Albeck et al., A non-invasive transport system for GDNF across the blood—brain barrier. Regeneration and Transplantation vol. 8 No. 9-10 Jul. 7, 1997, 2293-2298.*

Martell, et al. Efficacy of transferrin receptor-targeted immunotoxins in brain tumor cell lines and pediatric brain tumors. Cancer Res. Mar. 15, 1993;53(6):1348-53.

Office action dated Jun. 27, 2011 for U.S. Appl. No. 11/245,546.

Altschul et al. Gapped BLAST and PSI-BLAST: a new generation of protein database search programs. Nucleic Acids Res. 1977;25:3389-3402.

Altschul, et al. Optimal sequence alignment using affine gap costs. Bulletin of Mathematical Biology. 1986; 48(5-6):603-616.

Ausubel, et al. Current Protocols in Molecular Biology. John Wiley & Sons, New York, 1995 supplement.

Baloh, et al. Functional mapping of receptor specificity domains of glial cell line-derived neurotrophic factor (GDNF) family ligands and production of GFRalpha1 RET-specific agonists. J Biol Chem. Feb. 4, 2000;275(5):3412-20.

Batzer et al. Enhanced evolutionary PCR using oligonucleotides with inosine at the 3'-terminus. Nucleic Acid Res.1991;19:5081.

Boado et al. Fusion Antibody for Alzheimer's Disease with Bi-Directional Transport Across the Blood-Brain Barrier and Abeta Fibril Disaggregation. Bioconjug Chem. 2007;18(2):447-455.

Boado et al. Genetic engineering of a lysosomal enzyme fusion protein for targeted delivery across the human blood-brain barrier. Biotechnology and Bioengineering. 2008;99:475-484.

Carnicella, et al. GDNF is a fast-acting potent inhibitor of alcohol consumption and relapse. Proc Natl Acad Sci U S A. Jun. 10, 2008;105(23):8114-9.

Cassol, et al. Stability of dried blood spot specimens for detection of human immunodeficiency virus DNA by polymerase chain reaction. J Clin Microbiol. Dec. 1992;30(12):3039-42.

Eketjall, et al. Distinct structural elements in GDNF mediate binding to GFRalphal and activation of the GFRalphal-c-Ret receptor complex. Embo J. Nov. 1, 1999;18(21):5901-10.

Eslamboli et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005;25:769-777.

European search report dated Feb. 23, 2010 for Application No. 6825389.7.

Henikoff et al. Amino acid substitution matrices from protein blocks. Proceedings of the National Academy of Sciences. 1992;89:10915.

Karlin et al. Applications and statistics for multiple high—scoring segments in molecular sequences. Proc. Natl. Acad. Sci. USA. 1993;90:5873-5787.

Kastin et al. Glial cell line-derived neurotrophic factor does not enter normal mouse brain. Neuroscience Letters. 2003;340:239-241.

(56) References Cited

OTHER PUBLICATIONS

Kitagawa et al. Reduction of Ischemic Brain Injury by Topical Application of Glial Cell Line—Derived Neurotrophic Factor After Permanent Middle Cerebral Artery Occlusion in Rats. Stroke. 1998;29:1417-1422.
Kobayashi, et al. Intracerebral Infusion of Glial Cell Line-Derived Neurotrophic Factor Promotes Striatal Neurogenesis After Stroke in Adult Rats. Stroke. 2006;37:2361-2367.
Lang et al. Randomized controlled trial of intraputamenal glial cell line-derived neurotrophic factor infusion in Parkinson disease. Annals of Neurology. 2006;59:459-466.
Lapchak et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.
Lin et al. GDNF: a glial cell line-derived neurotrophic factor for midbrain dopaminergic neurons. Science. 1993;260:1130-1132.
Lu et al. Cationic Liposome-Mediated GDNF Gene Transfer after Spinal Cord Injury. Journal of Neurotrauma. 2002;19:1081-1090.
Needleman et al. A general method applicable to the search for similarities in the amino acid sequence of two proteins. J. Mol. Biol. 1970;48:443-453.
Ng, et al. Predicting the effects of amino acid substitutions on protein function. Annual Review of Genomics and Human Genetics. 2006;7:61-80.
Office Action dated Oct. 30, 2009 for U.S. Appl. No. 11/841,594.
Ohtsuka et al. An alternative approach to deoxyoligonucleotides as hybridization probes by insertion of Deoxyinosine at Ambiguous Codon Positions. J. Biol. Chem. 1985;260:2605-2608.
Pardridge, et al. Drug and gene targeting to the brain with molecular Trojan horses. Nat Rev Drug Discov. Feb. 2002;1(2):131-9.
Pardridge. Drug Targeting to the Brain. Pharmaceutical Research. 2007;24:1733-1744.
Pearson et al. Improved Tools for Biological Sequence Comparison. Proc. Nat'l Acad. Sci. USA. 1988;85:2444-2448.
Pearson. Rapid and sensitive sequence comparison with FASTP and FASTA. Meth. Enzymol. 1990;183:63-98.
Rossolini et al. Use of deoxyinosine-containing primers vs degenerate primers for polymerase chain reaction based on ambiguous sequence information. Mol. Cell. Probes. 1994;8(2):91-98.
Sellers. On the theory and computation of evolutionary distances. SIAM Journal on Applied Mathematics. 1974;26:787.
Smith, et al. Comparison of Biosequences. Adv. Appl. Math. 1981 1 482-489.
Wiesenhofer et al. Glial cell line-derived neurotrophic factor (GDNF) and its receptor (GFR-α1) are strongly expressed in human gliomas. Acta Neuropathol. (Berl). 2000;99:131-137.
Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.
Al Sawaf, et al. Neurological findings in Hunter disease: pathology and possible therapeutic effects reviewed. J Inherit Metab Dis. Aug. 2008:31(4):473-80.
Altschul, et al. Optimal sequence alignment using affine gap costs. Bulletin of Mathematical Biology. 1986; 48(5-6):603-16.
Arndt, et al. Generation of a highly stable, internalizing anti-CD22 single-chain Fv fragment for targeting non-Hodgkin's lymphoma. Int J Cancer. Dec. 10, 2003;107(5):822-829.
Boado, et al. AGT-181: expression in CHO cells and pharmacokinetics, safety, and plasma iduronidase enzyme activity in Rhesus monkeys. Oct. 2009;144(2):135-41.
Boado, et al. CHO cell expression, long-term stability, and primate pharmacokinetics and brain uptake of an IgG-paroxonase-1 fusion protein. Biotechnol Bioen. Jan. 2011;108(1):186-96.
Boado, et al. Drug delivery of antisense molecules to the brain for treatment of Alzheimer's disease and cerebral AIDS. J Pharm Sci. Nov. 1998;87(11):1308-15.

Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Boado, et al. Selective targeting of a TNFR decoy receptor pharmaceutical to the primate brain as a receptor-specific IgG fusion protein. J Biotechnol. Mar. 2010;146(1-2):84-91.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Casset, et al. A peptide mimetic of an anti-CD4 monoclonal antibody by rational design. Biochem Biophys Res Commun. Jul. 18, 2003;307(1):198-205.
Chothia, et al. Canonical structures for the hypervariable regions of immunoglobulins. J Mol Biol. Aug. 20, 1987;196(4):901-17.
Chung et al. Antibodies against West Nile Virus nonstructural protein NS1 prevent lethal infection through Fc gamma receptor-dependent and -independent mechanisms. J Virol. Feb. 2006;80(3):1340-51.
Colman, P.M. Effects of amino acid sequence changes on antibody-antigen interactions. Res Immunol. Jan. 1994:145(1):33-6.
Crow, et al. Biochemical and histopathological studies on patients with mucopolysaccharidoses, two of whom had been treated by fibroblast transplantation. J Clin Pathol. 1983:36(4):415-30.
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Deane, et al. IgG-assisted age-dependent clearance of Alzheimer's amyloid beta peptide by the blood-brain barrier neonatal Fc receptor. J Neurosci. 2005;25(50):11495-503.
Duffy, et al. 1988. Human blood-brain barrier insulin-like growth factor receptor. Metabolism. Feb;37(2):136-40.
Durrington, et al. Paraoxonase and atherosclerosis. Arterioscler Thromb Vasc Biol. Apr. 2001;21(4):473-80.
EP Appl. No. 08796594.3 Search Report and opinion dated Mar. 16, 2012.
Flowmen, et al. Determination of the organisation of coding sequences within the iduronate sulphate sulphatase (IDS)gene. Hum. Mol. Genet. 1993;2(1):5-10.
Frenkel, et al. Modulation of Alzheimer's beta-amyloid neurotoxicity by site-directed single-chain antibody. J Neuroimmunol. Jul. 1, 2000;106(1-2):23-31.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Golden, et al. Human blood-brain barrier leptin receptor. Binding and endocytosis in isolated human brain microvessels. J Clin Invest. Jan. 1, 1997;99(1):14-8.
Hansson et al. Prediction of Alzheimer's disease using the CSF Abeta42/Abeta40 ratio in patients with mild cognitive impairment. Dement Geriatr Cogn Disord. 2007;23(5):316-20.
He, et al. Identification and characterization of the molecular lesion causing mucopolysaccharidosis type I in cats. Mol Genet Metab. 1999; 67(2):106-12.
Henikoff et al. Predicting the effects of amino Acid substitutions on protein function. Annu Rev Genomics Hum Genet. 2006;7:61-80.
Holliger, et al. Engineered antibody fragments and the rise of single domains. Nat Biotechnol. Sep. 2005;23(9):1126-36.
Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.
Josse, et al. Identification of residues essential for human paraoxonase (PON1) arylesterase/organophosphatase activities. Biochemistry. Mar. 2, 1999;38(9):2816-25.
Josse, et al. Oligomeric states of the detergent-solubilized human serum paraoxonase (PON1). J Biol Chem. Sep. 6, 2002;277(36):33386-97.
Josse, et al. The active site of human paraoxonase (PON1). J Appl Toxicol. Dec. 2001;21 Suppl 1:S7-11.

(56) References Cited

OTHER PUBLICATIONS

Kabat, et al., Sequences of Proteins of Immunological Interest. 5th Ed. Public Health Service, National Institutes of Health, Bethesda, Md. 1991;pp. 647-9.

Kakkis, et al. Overexpression of the human lysosomal enzyme alpha-L-iduronidase in Chinese hamster ovary cells. Protein Expr Purif. 1994; 5(3):225-32.

Kashmiri, et al. SDR grafting—a new approach to antibody humanization. Methods. May 2005;36(1):25-34.

Kim, et al. Decreased paraoxonase-1 activity is a risk factor for ischemic stroke in Koreans. Biochem Biophys Res Commun. Dec. 7, 2007;364(1):157-62.

Lee, et al. Drug targeting to the brain using avidin-biotin technology in the mouse; {blood-brain barrier, monoclonal antibody, transferrin receptor, Alzheimer's disease). J Drug Target. 2000;8(6):413-24.

Lenz, et al. Stoichiometric and catalytic scavengers as protection against nerve agent toxicity: a mini review. Toxicology. Apr. 20, 2007;233(1-3):31-9.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Liu, et al. Anti beta-amyloid (Abeta) SCFV inhibits Abeta aggregation and neurotoxicity (P4-354). Neurobiology of Aging, Tarrytown, NY. 2004;25:S575-S576.

Liu, et al. Single chain variable fragments against beta-amyloid (Abeta) can inhibit Abeta aggregation and prevent abeta-induced neurotoxicity. Biochemistry. Jun. 8, 2004;43(22):6959-67.

MacCallum, et al. Antibody-antigen interactions: contact analysis and binding site topography. J Mol Biol. Oct. 11, 1996;262(5):732-45.

Manoutcharian, et al. Amyloid-beta peptide-specific single chain Fv antibodies isolated from an immune phage display library. J Neuroimmunol. 2003; 145(1-2):12-7.

Martin et al. Crystal structure at 2.8 A of an FcRn/heterodimeric Fc complex: mechanism of pH-dependent binding. Mol Cell. Apr. 2001;7(4):867-77.

Muenzer, et al. A phase II/III clinical study of enzyme replacement therapy with idursulfase in mucopolysaccharidosis II (Hunter syndrome). Genet Med Aug. 2006;8(8):465-73.

Muenzer, et al. Advances in the treatment of mucopolysaccharidosis type I. N Engl J Med. May 6, 2004;350(19):1932-4.

NCBI Reference Sequence: NM-000202.5 Homo sapiens iduronate 2-sulfatase (IDS), transcript variant 1, mRNA. 1992. http://www.ncbi.nlm.nih.gov/nuccore/NM000202.5.

Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.

Ober, et al. Differences in promiscuity for antibody-FcRn interactions across species: implications for therapeutic antibodies. Int Immunol. Dec. 2001;13(12):1551-9.

Osbourn, et al. Directed selection of MIP-1 alpha neutralizing CCR5 antibodies from a phage display human antibody library. Nat Biotechnol. Aug. 1998;16(8):778-81.

Padlan, et al. Structure of an antibody-antigen complex: crystal structure of the HyHEL-10 Fab-lysozyme complex. Proc Natl Acad Sci U S A. Aug. 1989;86(15):5938-42.

Paragh, et al. Ciprofibrate increases paraoxonase activity in patients with metabolic syndrome. Br J Clin Pharmacol. Jun. 2006;61(6):694-701.

Pardridge, 2005. Tyrosine Hydroxylase Replacement in Experimental Parkinson's Disease with Transvascular Gene Therapy. NueuoRx: Journal of the American Society for Experimental NeuroTherapeutics. 2(1):129-138.

Pardridge, et al. 1989. Transport of histone through the blood-brain barrier. J Pharmacol Exp Ther. Dec;251(3):821-6.

Park, et al. Production and characterization of fusion proteins containing transferrin and nerve growth factor. J Drug Target. 1998;6(1):53-64.

Paul, W. Fundamental Immunology. 3rd Edition. 1993;292-95.

PCT Application No. US10/52113 ISR dated Feb. 22, 2011.

Pluckthun, A. Antibodies from *Escherichia coli*. In the Pharmacology of Monoclonal Antibodies. vol. 113, Rosenburg and Moore eds. Springer-Verlag, New York. 1994;pp. 269-315.

Rempel, et al. A homology model for human α-L-Iduronidase: Insights into human disease. Mol. Genetics and Met. 2005; 85:28-37.

Rochu, et al. Human paraoxonase: a promising approach for pre-treatment and therapy of organophosphorus poisoning. Toxicology. Apr. 20, 2007;233(1-3):47-59.

Sampson et al. Unarmed, tumor-specific monoclonal antibody effectively treats brain tumors. Proc Natl Acad Sci U S A. Jun. 20, 2000;97(13):7503-8.

Schlachetzki, et al. Gene therapy of the brain: the trans-vascular approach. Neurology. Apr. 27, 2004;62(8):1275-81.

Scott, et al. Human alpha-L-iduronidase: cDNA isolation and expression. Proc Natl Acad Sci U S A. Nov. 1, 1991;88(21):9695-9.

Sifuentes, et al. A follow-up study of MPS I patients treated with laronidase enzyme replacement therapy for 6 years. Mol Genet Metab. Feb. 2007;90(2):171-80. Epub Sep. 29, 2006.

Soukharev, et al. A fluorogenic substrate for detection of organophosphatase activity. Anal Biochem. Apr. 1, 2004;327(1):140-8.

Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.

Tomatsu, et al. Murine model (Galns(tm(C76S)slu)) of MPS IVA with missense mutation at the active site cystein conserved among sulfatase proteins. Mol Genet Metab. Jul.2007;91(3):261-8.

Tougou, et al. Paraoxonase has a major role in the hydrolysis of prulifloxacin (NM441), a prodrug of a new antibacterial agent. Drug Metab Dispos. Apr. 1998;26(4):355-9.

Triguero, et al. Capillary depletion method for quantification of blood-brain barrier transport of circulating peptides and plasma proteins. J Neurochem. 1990; 54(6):1882-8.

Unger, et al. Recombinant α-iduronidase: characterization of the purified enzyme and correction of mucopolysaccharidosis type I fibroblasts. Biochem J. 1994; 384:43-49.

U.S. Appl. No. 11/245,546 Office Action dated Jun. 27, 2011.
U.S. Appl. No. 11/245,546 Office Action dated Jul. 1, 2010.
U.S. Appl. No. 11/245,710 Office Action dated Jun. 3, 2008.
U.S. Appl. No. 11/245,710 Office Action dated Jul. 2, 2009.
U.S. Appl. No. 11/841,594 Office Action dated Mar. 26, 2010.
U.S. Appl. No. 12/323,232 Office Action dated Aug. 20, 2009.
U.S. Appl. No. 12/574,571 Office Action dated Dec. 14, 2011.
U.S. Appl. No. 12/756,093 Office Action dated Jul. 20, 2012.
US Notice of Allowance—U.S. Appl. No. 11/245,546 dated Apr. 1, 2011.
US Notice of Allowance—U.S. Appl. No. 11/841,623 dated Jan. 28, 2010.

Voznyi, et al. A fluorimeteric enzyme assay for the diagnosis of MPS II (Hunter disease). J inherit Metab Dis. 2001;24:675-80.

Ward, E.S. Binding activities of a repertoire of single immunoglobulin variable domains secreted from *Escherichia coli*. Nature. Oct. 12, 1989;341(6242):484-5.

Warrington, et al. Human monoclonal antibodies reactive to oligodendrocytes promote remyelination in a model of multiple sclerosis. Proc Natl Acad Sci U S A. Jun. 6, 2000;97(12):6820-5.

Whittaker, et al. Characterization of the functional insulin binding epitopes of the full-length insulin receptor. J Biol Chem. 2005;280(22):20932-6.

Wraith, J. Enzyme replacement therapy in mucopolysaccharidosis type I: progress and emerging difficulties. J Inherit Metab Dis. Apr. 2001;24(2):245-50.

Wraith, et al. Mucopolysaccaridosis type II (Hunter syndrome): a clinical review and recommendations for treatment in the era of enzyme replacement therapy. Eur J Pediatr. Mar. 2008;167(3):267-77.

Wu, et al. Neuroprotection in Experimental Stroke with Targeted Neurotrophins. NeuroRX: The Journal of the American Society for Experimental NeuroTherapeutics. 2005:2(1):120-128.

Zhang, et al. Rapid transferrin efflux from brain to blood across the blood-brain barrier. J Neurochem. Mar. 2001;76(5):1597-600.

(56) References Cited

OTHER PUBLICATIONS

Zhou, et al. Brain penetrating IgG-erythropoietin fusion protein is neuroprotective following intravenous treatment in Parkinson's disease in the mouse, Brain Res. Mar. 25, 2011;1382:315-20. Epub Jan. 26, 2011.
Zito, et al. Sulphatase activities are regulated by the interaction of sulphatase-modifying factor 1 with SUMF2, EMBO Rep 2005;6(7):655-660.
Dreier, et al. Recombinant immunocytokines targeting the mouse transferrin receptor: construction and biological activities. Bioconjug Chem. Jul.-Aug. 1998;9(4):482-9.
International search report and written opinion dated Apr. 8, 2011 for PCT Application No. US11/21418.
Matis, et al. Erythropoietin in spinal cord injury. Eur Spine J. Mar. 2009;18(3):314-23.
Office action dated Feb. 16, 2011 for U.S. Appl. No. 11/893,281.
Office action dated Feb. 16, 2011 for U.S. Appl. No. 12/150,983.
Office action dated Apr. 6, 2011 for U.S. Appl. No. 11/245,710.
Office action dated May 12, 2010 for U.S. Appl. No. 11/893,281.
Office action dated May 13, 2011 for U.S. Appl. No. 12/688,842.
Office action dated Sep. 15, 2010 for U.S. Appl. No. 12/150,983.
Office action dated Oct. 13, 2009 for U.S. Appl. No. 11/893,281.
Sariola, et al. Novel functions and signalling pathways for GDNF. J Cell Sci. Oct. 1, 2003;116(Pt 19):3855-62.
Shanafelt, et al. Identification of critical amino acid residues in human and mouse granulocyte-macrophage colony-stimulating factor and their involvement in species specificity. J Biol Chem. Jul. 25, 1991;266(21):13804-10.
Wang, et al. Identification of the key amino acids of glial cell line-derived neurotrophic factor family receptor alpha1 involved in its biological function. J Biol Chem. Jan. 2, 2004;279(1):109-16.
Notice of Allowance dated Aug. 9, 2011 for U.S. Appl. No. 11/245,710.
Notice of Allowance dated Oct. 28, 2011 for U.S. Appl. No. 12/688,842.
Notice of Allowance dated Oct. 31, 2011 for U.S. Appl. No. 11/245,546.
Office action dated Oct. 18, 2011 for U.S. Appl. No. 11/245,546.
Brines, et al. Erythropoetin crosses the blood-brain barrier to protect against experimental brain injury, Proc Natl Acad Sci USA. 2000; 97:10526-10531.
Ehrenreich, et al. Erythropoetin therapy for acute stroke is both safe and beneficial. Mol Med. Aug. 2002;8(8):495-505.
Elliott, et al. Control of rHuEPO biological activity: the role of carbohydrate. Exp Hematol. Dec. 2004;32(12):1146-55.
European search report and search opinion dated Dec. 2, 2010 for Application No. 07841110.5.
Fu, et al. Neuroprotection in stroke in the mouse with intravenous erythropoietin-Trojan horse fusion protein. Brain Res. Jan. 19, 2011;1369:203-7. Epub Oct. 31, 2010.
Grasso, et al. Neuroprotection by erythropoietin administration after experimental traumatic brain injury. Brain Res. Nov. 28, 2007;1182:99-105.
Habgood, et al. Changes in blood-brain barrier permeability to large and small molecules following traumatic brain injury in mice. Eur J Neurosci. Jan. 2007;25(1):231-8.
International search report dated Sep. 7, 2010 for PCT Application No. US10-27882.
Iwasaki, et al. Protective effect of interleukin-3 and erythropoietin on motor neuron death after neonatal axotomy. Neurol Res. Oct. 2002;24(7):643-6.
Juul, et al. Erythropoietin concentrations in cerebrospinal fluid of nonhuman primates and fetal sheep following high-dose recombinant erythropoietin, Biol. Neonate. 2004;85:138-144.
Koehne, et al. Vascular endothelial growth factor and erythropoietin concentrations in cerebrospinal fluid of children with hydrocephalus. Childs Nerv Syst. Apr. 2002;18(3-4):137-41.
Ma, et al. Erythropoietin protects PC12 cells from beta-amyloid(25-35)-induced apoptosis via PI3K/Akt signaling pathway. Neuropharmacology. May-Jun. 2009;56(6-7):1027-3

Office action dated Feb. 10, 2006 for U.S. Appl. No. 10/307,165.
Office action dated Feb. 22, 2006 for U.S. Appl. No. 10/307,276.
Office action dated Mar. 1, 2007 for U.S. Appl. 10/307,165.
Office action dated Mar. 18, 2011 for U.S. Appl. No. 12/574,571.
Office action dated Apr. 9, 2007 for U.S. Appl. 10/307,276.
Office action dated May 9, 2008 for U.S. Appl. 11/061,956.
Office action dated May 23, 2006 for U.S. Appl. No. 11/061,956.
Office action dated Jul. 19, 2006 for U.S. Appl. No. 10/307,276.
Office action dated Aug. 17, 2007 for U.S. Appl. No. 10/307,165.
Office action dated Aug. 18, 2006 for U.S. Appl. 10/307,165.
Office action dated Nov. 13, 2007 for U.S. Appl. No. 11/061,956.
Office Action dated Oct. 12, 2010 for U.S. Appl. No. 11/245,710.
Office action dated Oct. 29, 2007 for U.S. Appl. No. 10/307,276.
Office action dated Dec. 21, 2006 for U.S. Appl. No. 11/061,956.
Office Action dated Mar. 7, 2011 for U.S. Appl. No. 12/558,348.
Patel et al. Intraputamenal infusion of glial cell line-derived neurotrophic factor in PD: A two-year outcome study. Annals of Neurology. 2005;57:298-302.
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Reiber, et al. Protein transfer at the blood cerebrospinal fluid barrier and the quantitation of the humoral immune response within the central nervous system. Clin Chim Acta. Mar. 30, 1987;163(3):319-28.
Sakanaka, et al. In vivo evidence that erythropoietin protects neurons from ischemic damage. Proc Natl Acad Sci U S A. Apr. 14, 1998;95(8):4635-40.
Siren, et al., Erythropoetin prevents neuronal apoptosis after cerebral ischemia and metabolic stress. Proc Natl Acad Sci U S A. Mar. 27, 2001;98(7):4044-9.
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Whetstone, et al. Blood-spinal cord barrier after spinal cord injury: relation to revascularization and wound healing. J Neurosci Res. Oct. 15, 2003;74(2):227-39.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Ai, et al., 2003. Intraputamenal Infusion of GDNF in Aged Rhesus Monkeys: Distribution and Dopaminergic Effects. The Journal of Comparative Neurology 461: 250-261.
Airavaara, et al. Effects of repeated morphine on locomotion, place preference and dopamine in heterozygous glial cell line-derived neurotrophic factor knockout mice. Genes Brain Behav. Apr. 2007; 6(3):287-98.
Albayrak, et al. 1997. Effect of transient *focal ischemia* on blood-brain barrier permeability in the rat: Correlation to Cell Injury. Acta Neuropathol 94: 158-163.
Alberts, et al. Molecular Biology of the Cell. 3rd Edition. Garland Publishing Inc. New York. 1994; pp. 1206-1207.
Bachis, et al. 2003. Brain-Derived Neurotropic Factor Inhibits Human Immunodeficiency Virus-1/gp 120- Mediated Cerebellar Granule Cell Death by Preventing gp 120 Internalization. The Journal of Neuroscience 23 (13): 5712-5722.
Barth et al. Boron neutron capture therapy of brain tumors: an emerging therapeutic modality. Neurosurgery. Mar. 1999; 44(3):433-50; discussion 450-1.
Boado et al, Genetic engineering, expression, and activity of a fusion protein of a human neurotrophin and a molecular Trojan horse for delivery across the human blood-brain barrier. Biotechnology and Bioengineering. 2007;97:1376-1386.
Boado et al. Humanization of anti-human insulin receptor antibody for drug targeting across the human blood-brain barrier. Biotechnology and Bioengineering. 2007;96:381-391.
Boado, et al. Engineering and expression of a chimeric transferrin receptor monoclonal antibody for blood-brain barrier delivery in the mouse. Bioteclmol Bioeng. Mar. 1, 2009;102(4):1251-8.

(56) References Cited

OTHER PUBLICATIONS

Boado, et al. GDNF fusion protein for targeted-drug delivery across the human blood-brain barrier. Biotechnol Bioeng. Jun. 1, 2008;100(2):387-96.
Brummell, et al. Probing the combining site of an anti-carbohydrate antibody by saturation-mutagenesis: role of the heavy-chain CDR3 residues. Biochemistry. 1993; 32(4):1180-7.
Buchli, et al. Inhibition of Nogo: a key strategy to increase regeneration, plasticity and functional recovery of the lesioned central nervous system. Ann Med. 2005;37(8):556-67.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Chen, et al. In vitro scanning saturation mutagenesis of all the specificity determining residues in an antibody binding site. Protein Engineering. 1999; vol. 12, No. 4, 349-356.
Cheng, et al. 1997. Marked Age-dependent Neuroprotection by Brain-derived Neurotropic Factor Against Neonatal Hypoxic-Ischemic Brain Injury. Annals of Neurology 41 (4): 521-529.
Cheng, et al. 2004. Neuroprotection for Ischemic Stroke: Two Decades of Success and Failure. The Journal of the American Society for Experimental Neuro Therapeutics 1: 36-45.
Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.
Coloma, et al. Design and production of novel tetravalent bispecific antibodies. Nat Biotechnol. Feb. 1997;15(2):159-63.
Coloma, et al. The hinge as a spacer contributes to covalent assembly and is required for function of IgG. J Immunol. Jan. 15, 1997;158(2):733-40.
Cowen, et al. 2004. Neuropeptides: implications for alcoholism. Journal of Neurochemistry 89: 273-285.
Dawson, et al. 2001. A comparative assessment of the efficacy and side-effect liability of the neuroprotective compounds in experimental stroke. Brain Research 892: 344-350.
Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.
Duchnowska, et al. Central nervous system metastases in breast cancer patients administered trastuzumab. Cancer Treat Rev. Jun. 2005;31(4):312-8.
Duffy, et al. 1987. Blood-brain barrier transcytosis of insulin in developing rabbits. Brain Research 420: 32-38.
Ferber, D. Bridging the blood-brain barrier: new methods improve the odds of getting drugs to the brain cells that need them. PLoS Biol. Jun. 2007;5(6):e169: 1191-1194.
Forough, et al. Differential transforming abilities of non-secreted and secreted forms of human fibroblast growth factor-1. J Biol Chem. Feb. 5, 1993;268(4):2960-8.
Gillies, et al. Bi-functional cytokine fusion proteins for gene therapy and antibody-targeted tratment of cancer. 2002, Cancer Immunology and Immunotherapy, vol. 51, pp. 449-460.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003;18(7):2093-8.
He, et al. Autoregulation of glial cell line-derived neurotrophic factor expression implications for the long-lasting actions of the anti-addiction drug, Ibogaine. FASEB J Nov. 2006;20(13):E1820-E1827; 2420-2422.
He, et al. Glial Cell Line-Derived Neurotrophic Factor Mediates the Desirablie Actions of the Anti-Addiction Drug Ibogaine against Alcohol Consumption. Journal of Neuroscience. 2005;25:619-628.
Hetman, et al. 1999. Neuroprotection by Brain-derived Neurotropic Factor Is Mediated by Extracellular Signal-regulated Kinase and Phoshatidylinositol 3-Kinase. The Journal of Biological Chemistry 274 (32): 22569-22580.
Hoshaw, et al. 2005. Central administration of IGF-I and BDNF leads to long-lasting antidepressant-like effects. Brain Research 1037: 204-208.
Ibanez, et al. An extended surface of binding to Trk tyrosine kinase receptors in NGF and BDNF allows the engineering of a multifunctional pan-neurotrophin. EMBO J. Jun. 1993;12(6):2281-93.
Ibanez, Structure-function relationships in the neurotrophin family. J Neurobiol. Nov. 1994;25(11):1349-61.
International search report dated Feb. 27, 2009 for PCT Application No. US08/71121.
International search report dated Jul. 1, 2008 for PCT Application No. US06/38587.
International Search Report dated Sep. 16, 2008 for PCT Application No. US2007/76316.
Jefferies, et al. Analysis of lymphopoietic stem cells with a monoclonal antibody to the rat transferrin receptor. Immunology. Feb. 1985;54(2):333-41.
Jiang, et al. 2005. BDNF Variation and Mood Disorders: A Novel Functional Promoter Polymorphism and Val66Met are Associated with Anxiety but Have Opposing Effects Neuropsychopharmacology 30: 1353-1361.
Kido, et al. 2000. Neuroprotective effects of brain-derived neurotropic factor in eyes with NMDA-induced neuronal death. Brain Research 884: 59-67.
Krewson, et al. 1995. Distribution of nerve growth factor following direct delivery to brain interstitium. Brain Research 680: 196-206.
Kurihara, et al. 1999. Imaging Brain Tumors by Targeting Peptide Radiopharmaceuticals through the Blood-Brain Barrier. Cancer Research 59: 6159-6163.
Lai, et al. Structural determinants of Trk receptor specificities using BDNF-based neurotrophin chimeras. J Neurosci Res. Dec. 1, 1996;46(5):618-29.
Lazar, et al. Transforming growth factor alpha: mutation of aspartic acid 47 and leucine 48 results in different biological activities. Mol Cell Biol. Mar. 1988;8(3):1247-52.
Lee, et al. 2002. Imaging Brain Amyloid of Alzheimer Disease In Vivo in Transgenic Mice With an Aβ Peptide Radiopharmaceutical. Journal of Cerebral Blood Flow and Metabolism 22: 223-231.
Lewin, B. Genes IV. Oxford University Press. 1990. Page 810.
Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.
Marvin, et al. Recombinant approaches to IgG-like bispecific antibodies. Acta Pharmacol Sin. Jun. 2005;26(6):649-58.
McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.
Menzies, et al. 1993. Contributions of ions and albumin to the formations and resolution of ischemic brain edema. Journal of Neurosurgery 78: 257-266.
Messer, et al. Role for GDNF in biochemical and behavioral adaptations to drugs of abuse. Neuron. Apr. 2000;26(1):247-57.
Mori, et al. 2004. Differential expression patterns of TrkB ligands in the macaque monkey brain. Developmental Neuroscience 15: 2507-2511.
Nutt, et al. 2003. Randomized, double-blind trial of glial cell line-derived neurotropic factor (GDNF) in PD. Neurology 60: 69-73.
Office Action dated Jan. 15, 2008 for U.S. Appl. No. 11/245,710.
Office Action dated Jan. 15, 2009 for U.S. Appl. No. 11/841,623.
Office Action dated Apr. 13, 2007 for U.S. Appl. No. 11/245,710.
Office Action dated Jun. 3, 2008 for U.S. Appl. No. 11/245,710.
Office Action dated Jun. 17, 2009 for U.S. Appl. No. 11/841,541.
Office Action dated Jul. 2, 2009 for U.S. Appl. No. 11/245,710.
Office Action dated Jul. 31, 2009 for U.S. Appl. No. 12/179,806.
Office Action dated Sep. 20, 2007 for U.S. Appl. No. 11/245,710.
Office Action dated Sep. 24, 2009 for U.S. Appl. No. 11/841,623.

(56) References Cited

OTHER PUBLICATIONS

Office Action dated Oct. 15, 2007 for U.S. Appl. No. 11/245,710.
Office Action dated Nov. 10, 2008 for U.S. Appl. No. 11/245,710.
Office Action dated Nov. 13, 2006 for U.S. Appl. No. 11/245,710.
Office Action dated Dec. 16, 2009 for U.S. Appl. No. 11/841,541.
Office Action dated Feb. 2, 2010 for U.S. Appl. No. 11/245,710.
Office Action dated Mar. 10, 2010 for U.S. Appl. No. 12/179,806.
Office Action dated Mar. 26, 2010 for U.S. Appl. No. 11/841,594.
Padlan, et al. Identification of specificity-determining residues in antibodies. FASEB J. 1995; 9(1):133-9.
Pardridge, 2001. Brain drug targeting: The future of brain drug development. Cambridge University Press.
Pardridge, 2002. Neurotrophins, neuroprotection and the blood-brain barrier Current Opinion in Investigational Drugs 3 (12): 1753-1757.
Pardridge, 2003. Blood-Brain Barrier Drug Targeting: The Future of Brain Drug Development. Molecular Interventions 3: 90-105.
Pardridge, 2005. The Blood-Brain Barrier and Neurotherapeutics. NeuroRx: The Journal of the American Society for Experimental NeuroTherapeutics 2 (1): 1-2.
Pencea, et al. 2001. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 21 (17): 6706-6717.
Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-4426.
Preston, et al. 1997. Evidence for pore-like opening of the blood-brain barrier following forebrain ischemia in rats. Brain Research 761: 4-10.
Raghavan, et al. Analysis of the pH dependence of the neonatal Fc receptor/immunoglobulin G interaction using antibody and receptor variants. Biochemistry. Nov. 14, 1995;34(45):14649-57.
Ratliff-Schaub, et al. 2005. Randomized controlled trial of transdermal secretion on behavior of children with autism. Autism 9 (3): 256-265.
Robinson, et al. 1999. The structures of the neurotrophin 4 homodimer and the brain-derived neurotrophic factor / neurotrophin 4 heterodimer reveal a common Trk-binding site. Protein Science 8: 2589-2597.
Rudikoff, et al. Single amino acid substitution altering antigen-binding specificity. Proc Natl Acad Sci U S A. Mar. 1982;79(6):1979-83.
Ruiz-Leon, et al. 2003. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120: 1019-1026.
Sakane, et al. 1997. Carboxyl-directed Pegylation of Brain-derived Neurotrophic Factor Markedly Reduces Systemic Clearance with Minimal Loss of Biologic Activity. Pharmaceutical Research 14 (8): 1085-1091.
Schabitz, et al. 1997. Intraventricular Brain-Derived Neurotrophic Factor Reduces Infarct Size After Focal Cerebral Ischemia in Rats. Journal of Cerebral Blood Flow and Metabolism 17: 500-506.
Schlachetzki, et al. Expression of the neonatal Fc receptor (FcRn) at the blood-brain barrier. J Neurochem. Apr. 2002;81(1):203-6.
Schwartz, et al. A superactive insulin: [B10-aspartic acid]insulin(human). Proc Natl Acad Sci U S A. Sep. 1987;84(18):6408-11.
Selmayr, et al. Induction of tumor immunity by autologous B lymphoma cells expressing a genetically engineered idiotype. Gene Ther. May 1999;6(5):778-84.
Shin, et al. Transferrin-antibody fusion proteins are effective in brain targeting, Proceedings of the Natinal Academy of Sciences, 1995. vol. 92, pp. 2820-2824.
Skolnick, et al. From genes to protein structure and function: novel applications of computational approaches in the genomic era. Trends Biotechriol. Jan. 2000;18(1):34-9. Review.
Spina, et al. 1992. Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry 59 (1): 99-106.

Strauss, et al. 2005. Brain-derived neurotrophic factor variants are associated with childhood-onset mood disorder: confirmation in a Hungarian sample. Molecular Psychiartry 10: 861-867.
Takahashi, et al. 1991. Inhibition of cell growth and tumorigenesis of human glioblastoma cells by a neutralizing antibody against human basic fibroblast growth factor. Federation of European Biochemical Societies 288 (1,2): 65-71.
The BDNF Study Group (Phase III). 1999. A controlled trial of recombinant methionyl human BDNF in ALS. Neurology 52: 1427-1433.
Thoenen, et al. 2002. Neurotrophins: from enthusiastic expectations through sobering experiences to rational therapeutic approaches. Nature Neuroscience Supplement 5: 1046-1050.
Triguero et al. Capillary depletion method for quantification of blood-brain barrier transport of circulating peptides and plasma proteins. J Neurochem. 1990; 54(6):1882-8.
Tsukahara, et al. 1994. The Role of Brain-derived Neurotrophic Factor in Transient Forebrain Ischemia in the Rat Brain. Neurosurgery 34 (2): 323-331.
Wu, et al. 1999. Neuroprotection with noninvasive neurotrophin delivery to the brain. Proceedings of the National Academy of Sciences of the USA: Neurobiology 96: 254-259.
Yan, et al. Enduring vulnerability to reinstatement of methamphetamine-seeking behavior in glial-cell-line-derived neurotrophic factor mutant mice. Faseb J. Jul. 2007;21(9):1994-2004.
Yip, et al. Three-dimensional structural interactions of insulin and its receptor. J Biol Chem. Jul. 25, 2003;278(30):27329-32.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-1384.
Zhang, et al. 2003. Global Non-Viral Gene Transfer to the Primate Brain Following Intravenous Administration. Molecular Therapy 7 (1): 11-18.
Zhang, et al. Mediated efflux of IgG molecules from brain to blood across the blood-brain barrier. J Neuroimmunol. Mar. 1, 2001;114(1-2):168-72.
Altschul et al. Basic Local Alignment Search Tool. J. Mol. Biol. 1990;215:403-410.
Altschul et al. Gapped BLAST and PSI-BLAST: a new generation of protein.
Amgen www.amgen.com Accessed Dec. 16, 2005.
Aronovich et al., "Molecular Genetic Defect Underlying α-L-Iduronidase pseudodeficiency," Am. Journ. Hum. Genet. 58: 75-85 (1996).
Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme.2009.10.002. Epub Oct. 13, 2009.
Beck, et al. 1994. Brain-Derived Neurotropic Factor Protects Against Ischemic Cell Damage in Rat Hippocampus. Journal of Cerebral Blood Flow and Metabolism 14: 689-92.
Begley et al., "Lysosomal storage diseases and the blood-brain barrier," Current Pharmaceutical Design, vol. 14, No. 16, pp. 1566-1580 (2008).
Bifare, et al. 2005. Brain-Derived Neurotropic Factor Protects against Multiple Forms of Brain Injury in Bacterial Meningitis. The Journal of Infectious Diseases 191: 40-45.
Biogen IDEC www.idecpharma.com/site/home.html Accessed Dec. 16, 2005.
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010.
Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).

(56) References Cited

OTHER PUBLICATIONS

Boado et al., "Pharmacokinetics and brain uptake of a genetically engineered bifunctional fusion antibody targeting the mouse transferrin receptor," Molecular Pharmaceutics, vol. 7, No. 1, pp. 237-244 (2010).
Boado et al., "Genetic Engineering of IgG-glucuronidase fusion proteins," J. Drug Targeting 18(3):205-11 (2010).
Board of Patent Appeals and Interferences (BPAI) Decision dated Jul. 22, 2010 from U.S. Appl. No. 11/061,956.
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
De Graaf, M. et al., "Expression of scFvs and scFv Fusion Proteins in Eukaryotic Cells." Methods Mol. Biol. 2002; 178:379-387.
European search report dated Mar. 1, 2013 for EP Application No. 10822810.7.
European search report dated Jul. 15, 2013 for EP Application No. 11733492.
European search report dated Dec. 20, 2012 for EP Application No. 10754139.
Fillebeen, et al. Receptor-mediated transcytosis of lactoferrin through the blood-brain barrier. J Biol Chem. Mar. 12, 1999;274(11):7011-17.
Franco, et al. A cluster of sulfatase genes on Xp22.3: mutations in chondrodysplasia punctata (CDPX) and implications for warfarin embryopathy. Cell. Apr. 7, 1995;81(1):15-25.
Friden, et al. Blood-brain barrier penetration and in vivo activity of an NGF conjugate. Science. Jan. 15, 1993;259(5093):373-77.
Gehrmann, et al. Biochemical properties of recombinant human beta-glucuronidase synthesized in baby hamster kidney cells. Biochem J. Aug. 1, 1994;301 (Pt 3):821-8.
Gennaro, 2000. Remington: The Science and Practice of Pharmacy. 20 ed.
Hui et al., "Tumor Necrosis Factor Receptor-IgG Fusion Protein for Targeted Drug Delivery across the Human Blood-Brain Barrier," Mol. Pharm. vol. 6, No. 5, pp. 1536-1543 (2009).
International search report and written opinion dated Feb. 22, 2013 for PCT/US2012/054520.
Jeffrey, et al. 26-10 Fab-digoxin complex. Affinity and specificity due to surface complementarity. Proc Natl. Acad. Sci USA. 1993; 90(21):10310-10314.
Jethwa, et al. 2004. Neuromedin U has a physiological role in the regulation of food intake and partially mediates the effects of leptin. American Journal of Physiology-Endocrinology and Metabolism 289: E301-E305.
Kim, et al., Continuous Brain-derived Neurotropic Factor (BDNF) Infusion After Methylprednisolone Treatment in Severe Spinal Cord Injury. Journal of Korean Medical Science 2004;19: 113-22.
Knaust, "Residues Critical for Formylglycine Formation and/or Catalytic Activity of Arylsulfatase a," Biochemistry, 37:13941-13946 (1998).
Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).
Lu et al., "Genetic Engineering of a Bifunctional IgG fusion protein with iduronate-2- sulfatase," Bioconjugate Chemistry, 21(1) pp. 151-156 (2010).
Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.
Nawashiro et al., "Neuroprotective effects of TNF binding protein in focal cerebral ischemia," Brain Research, vol. 778, No. 2, pp. 265-271 (1997).
NCBI GenBank Accession No. NM-000487 (Oct. 23, 2011).
Notice of allowance dated Sep. 23, 2013 for U.S. Appl. No. 12/756,093.
Notice of allowance dated Sep. 25, 2013 for U.S. Appl. No. 13/862,250.
Office action dated Jan. 9, 2013 for U.S. Appl. No. 12/901,481.
Office action dated Jan. 23, 2009 for U.S. Appl. No. 11/245,546.
Office action dated Apr. 24, 2013 for U.S. Appl. No. 12/179,806.
Office action dated Jul. 1, 2010 for U.S. Appl. No. 11/245,546.
Office action dated Jul. 2, 2008 for U.S. Appl. No. 11/245,546.
Office action dated Oct. 20, 2009 for U.S. Appl. No. 11/245,546.
Office action dated Oct. 22, 2013 for U.S. Appl. No. 12/901,481.
Office action dated Nov. 4, 2013 for U.S. Appl. No. 12/179,806.
Office action dated Nov. 8, 2007 for U.S. Appl. No. 11/245,546.
Office action dated Nov. 26, 2012 for U.S. Appl. No. 13/609,099.
Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Pardridge et al., "Biologic TNF[alpha]-inhibitors that cross the human blood-brain barrier," Bioengineered Bugs. vol. 1, No. 4, pp. 231-234 (2010).
Pardridge. "Blood-brain barrier delivery of protein and non-viral gene therapeutics with molecular Trojan horses," Journal of Controlled Release, vol. 122, No. 3, pp. 345-348 (2007).
Pardridge, The Blood-Brain Barrier: Bottleneck in Brain Drug Development. NeuroRx: The Journal of the American Society for Experimental NeuroTherapeutics 2: 3-14 (2005).
Pardridge, "Re-engineering biopharmaceuticals for delivery to brain with molecular Trojan horses," Bioconjugate Chemistry, vol. 19, No. 7, pp. 1327-1338 (2008).
Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).
Pardridge, et al. Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582 (1998).
Pardridge, et al. Human Blood-Brain Barrier Transferrin Receptor. Metabolism 36:892-95 (1987).
Pardridge, et al. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46 (1994).
Pardridge, Neuroprotection in stroke: is it time to consider large-molecule drugs? Drug Discovery Today 6: 751-53 (2001).
Polito et al., "IDS Crossing of the Blood-Brain Barrier Corrects CNS Defects in MPSII Mice," Amer. Journ. Human Genetics, vol. 85, No. 2, pp. 296-301 (2009).
Schoonjans, R. et al., "Fab Chains As an Efficient Heterodimerization Scaffold for the Production of Recombinant Bispecific and Trispecific Antibody Derivatives." The Journal of Immunology, 2000, 165 (12): 7050-7057.
Schuchman, et al. Human alpha-L-iduronidase: Purification and properties of the high uptake (higher molecular weight) and the low uptake (processed) forms. J. Biol. Chem. 1984; 259(5):3132-3140.
Shipley, et al. The role of glycosylation and phosphorylation in the expression of active human beta-glucuronidase. J Biol Chem. Jun. 5, 1993;268(16):12193-8.
Thompson, et al. Improved binding of a bivalent single-chain immunotoxin results in increased efficacy for in vivo T-cell depletion. Protein Eng. Dec. 2001;14(12):1035-41.
Tobinick et al., "Perispinal etanercept for neuroinflammatory disorders," Drug Discovery Today, vol. 14, No. 3-4, pp. 168-177 (2009).
Weich, et al. Interleukin-3/erythropoietin fusion proteins: in vitro effects on hematopoietic cells. Exp Hematol. May 1993;21(5):647-55.
Wu, et al. Simultaneous targeting of multiple disease mediators by a dual-variable-domain immunoglobulin. Nat Biotechnol. Nov. 2007;25(11):1290-7. Epub Oct. 14, 2007.
Yamashita, et al. Post-Occlusion Treatment with BDNF Reduces Infarct Size in a Model of Permanent Occlusion of the Middle Cerebral Artery in Rat. Metabolic Brain.Disease 12 (4);1997:271-80.

(56) References Cited

OTHER PUBLICATIONS

Yan, et al. 1994. Distribution of Intracerebral Ventricularly Administered Neurotrophins in Rat Brain and Its Correlation with Trk Receptor Expression Experimental Neurology 127: 23-36.

Zhang, et al. 2001. Conjugation of brain-derived neurotrophic factor to a blood-brain barrier drug targeting system enables neuroprotection in regional brain ischemia following intrvenous injection of the neurotrophin Brain Research 889: 49-56.

U.S. Appl. No. 14/144,460, filed Dec. 30, 2013, Pardridge et al.

Benito, et al. Beta-galactosidase enzymatic activity as a molecular probe to detect specific antibodies. J Biol Chem. Aug. 30, 1996;271(35):21251-6.

Corchero, et al. The position of the heterologous domain can influence the solubility and proteolysis of beta-galactosidase fusion proteins in E. coli. J Biotechnol. Jul. 31, 1996;48(3):191-200.

Notice of allowance dated Dec. 13, 2013 for U.S. Appl. No. 13/862,250.

Notice of allowance dated Dec. 16, 2013 for U.S. Appl. No. 12/756,093.

Notice of allowance dated Dec. 23, 2013 for U.S. Appl. No. 11/841,541.

\* cited by examiner

Engineering of intron-based expression vector for fusion protein heavy chain

FIG. 2
Engineering of vBDNF

A. 5'-end linker (Table 2)

BamHI
BpII
T4 ligase xhoI BsiWI BpI BamHI
hBDNF
pHTBS0

XhoI BsiWI BpI NruI-BamHI
vBDNF
Clone 412
(5'-engineered)

B. 3'-end linker (Table 2)

XhoI
BsiWI
T4 ligase

XhoI-NruI BsiWI BpII NruI-BamHI
vBDNF
Clone 413
(5'- & 3'-engineered)

Insertion of vBDNF at SspI in clone 405

NruI

Agarose gel electrophoresis

FIG. 4

Engineered cDNA and amino acid sequence corresponding to the end of CH3, CH3-vBDNF linker and vBDNF, of the fusion protein
(SEQ ID NO. 21 and 22)

```
CTG TCT CCG GGT AAA tcg agt atg cac tct gac cct gcc cgt cga ggt gag
ctg agc gtg
leu ser pro gly lys ser ser met his ser asp pro ala arg arg gly glu
leu ser val
    CH3 orf end         linker  BDNF orf
                                ────────▶ tgt gac agt att agt gag tgg gta acg gcg gca gac aaa aag act gca gtg
gac atg tcg
cys asp ser ile ser glu trp val thr ala ala asp lys lys thr ala val
asp met ser ggc ggg acg gtc aca gtc ctt gaa aag gtc cct gta tca aaa ggc caa ctg
aag caa tac
gly gly thr val thr val leu glu lys val pro val ser lys gly gln leu
lys gln tyr ttc tac gag acc aag tgc aat ccc atg ggt tac aca aaa gaa ggc tgc agg
ggc ata gac
phe tyr glu thr lys cys asn pro met gly tyr thr lys glu gly cys arg
gly ile asp aaa agg cat tgg aac tcc cag tgc cga act acc cag tcg tac gtg cgg gcc
ctt acc atg
lys arg his trp asn ser gln cys arg thr thr gln ser tyr val arg ala
leu thr met gat agc aaa aag aga att ggc tgg cga ttc ata agg ata gac act tct tgt
gta tgt aca
asp ser lys lys arg ile gly trp arg phe ile arg ile asp thr ser cys
val cys thr ttg acc att aaa agg tga
leu thr ile lys arg  *
```

FIG. 5A
Nucleotide Sequence of Fusion Protein Heavy Chain Gene Derived from Clone 416(2711nt)
(SEQ ID NO. 23)

TAGTCTTTCTCTTCAGTGACAAACACAGACATAGGATATTCCACC<u>A</u>TGGAATGCAGCTGGGTCATGC
TCTTCCTCCTGTCAGGAACTGCAGGTGTCCATTGCCAGGTTCAGCTGCAGCAGTCTGGACCTGAGCT
GGTGAAGCCTGGGGCTTTAGTGAAGATATCCTGCAAGGCTTCTGGTTACACCTTCACAAACTACGAT
ATACACTGGGTGAAGCAGAGGCCTGGACAGGGACTTGAGTGGATTGGATGGATTTATCCTGGAGATG
GTAGTACTAAGTACAATGAGAAATTCAAGGGCAAGGCCACACTGACTGCAGACAAATCCTCCAGCAC
AGCCTACATGCACCTCAGCAGCCTGACTTCTGAGAAATCTGCAGTCTATTTCTGTGCAAGAGAGTGG
GCTTACTGGGGCCAAGGGACTCTGGTCACTGTCTCTGCAGCTAGCACCAAGGGCCCATCGGTCTTCC
CCCTGGCACCCTCCTCCAAGAGCACCTCTGGGGGCACAGCGGCCCTGGGCTGCCTGGTCAAGGACTA
CTTCCCCGAACCGGTGACGGTGTCGTGGAACTCAGGCGCCCTGACCAGCGGCGTGCACACCTTCCCG
*GCTGTCCTACAGTCCTCAGGACTCTACTCCCTCAGCAGCGTGGTGACCGTGCCCTCCAGCAGCTTGG*
*GCACCCAGACCTACATCTGCAACGTGAATCACAAGCCCAGCAACACCAAGGTGGACAAGAAAGTTGG*
*TGAGAGGCCAGCACAGGGAGGGAGGGTGTCTGCTGGAAGCCAGGCTCAGCGCTCCTGCCTGGACGCA*
*TCCCGGCTATGCAGCCCCAGTCCAGGGCAGCAAGGCAGGCCCCGTCTGCCTCTTCACCCGGAGGCCT*
*CTGCCCGCCCCACTCATGCTCAGGGAGAGGGTCTTCTGGCTTTTTCCCCAGGCTCTGGGCAGGCACA*
*GGCTAGGTGCCCCTAACCCAGGCCCTGCACACAAAGGGGCAGGTGCTGGGCTCAGACCTGCCAAGAG*
*CCATATCCGGGAGGACCCTGCCCCTGACCTAAGCCCACCCCAAAGGCCAAACTCTCCACTCCCTCAG*
*CTCGGACACCTTCTCTCCTCCCAGATTCCAGTAACTCCCAATCTTCTCTCTGCAGAGCCCAAATCTT*
GTGACAAAACTCACACATGCCCACCGTGCCCAGGTAAGCCAGCCCAGGCCTCGCCCTCCAGCTCAAG
*GCGGGACAGGTGCCCTAGAGTAGCCTGCATCCAGGGACAGGCCCCAGCCGGGTGCTGACACGTCCAC*
*CTCCATCTCTTCCTCAG*CACCTGAACTCCTGGGGGGACCGTCAGTCTTCCTCTTCCCCCCAAAACCC
AAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCG
GGAGGAGCAGTACAACAGCACGTACCGTGTGGTCAGGGTCCTCACCGTCCTGCACCAGGACTGGCTG
AATGGCAAGGAGTACAAGTGCAAGGTCTCCAACAAAGCCCTCCCAGCCCCCATCGAGAAAACCATCT
CCAAAGCCAAAG*GTGGGACCCGTGGGGTGCGAGGGCCACATGGACAGAGGCCGGCTCGGCCCACCCT*
*CTGCCCTGAGAGTGACCGCTGTACCAACCTCTGTCCCTACAGGGCAGCCCCGAGAACCACAGGTGTA*
CACCCTGCCCCCATCCCGGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGACAAGAGCAG

FIG. 5B
Nucleotide Sequence of Fusion Protein Heavy Chain Gene Derived from Clone 416(2711nt)
(SEQ ID NO. 23 con't)

GTGGCAGCAGGGGAACGTCTTCTCATGCTCCGTGATGCATGAGGCTCTGCACAACCACTACACGCAG
AAGAGCCTCTCCCTGTCTCCGGGTAAATCGAGTATG<u>CACTCTGACCCTGCCCGTCGAGGTGAGCTGA
GCGTGTGTGACAGTATTAGTGAGTGGGTAACGGCGGCAGACAAAAAGACTGCAGTGGACATGTCGGG
CGGGACGGTCACAGTCCTTGAAAAGGTCCCTGTATCAAAAGGCCAACTGAAGCAATACTTCTACGAG
ACCAAGTGCAATCCCATGGGTTACACAAAAGAAGGCTGCAGGGGCATAGACAAAAGGCATTGGAACT
CCCAGTGCCGAACTACCCAGTCGTACGTGCGGGCCCTTACCATGGATAGCAAAAAGAGAATTGGCTG
GCGATTCATAAGGATAGACACTTCTTGTGTATGTACATTGACCATTAAAAGGTGATCGATTTTGCGA</u>
CGGCCGGCAAGCCCCCGCTCCCCGGGCTCTCGCGGTCGCACGAGGATGCTTGGCACGTACCCCCTGT
ACATACTTCCCGGGCGCCCAGCATGGAAATAAAGCACCCAGCGCTGCCCTGGGCCCCTGCGAGACTG
TGATGGTTCTTTCCACGGGTCAGGCCGAGTCTGAGGCCTGAGTGGCATGAGGGAGGCAGAGCGGGTC
CCACTGTCCCCACACTGGCCCAGGCTGTGCAGGTGTGCCTGGGCCGCCTAGGGTGGGGCTCAGCCAG
GGGCTGCCCTCGGCAGGGTGGGGATTTGCC

FIG. 6

Amino Acid Sequence of Heavy Chain of Fusion Protein (SEQ ID NO. 24)

NH2-

MECSWVMLFLLSGTAGVHCQVQLQQSGPELVKPGALVKISCKASGYTFTNYDIHWVKQ
RPGQGLEWIGWIYPGDGSTKYNEKFKGKATLTADKSSSTAYMHLSSLTSEKSAVYFCA
REWAYWGQGTLVTVSAASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKF
NWYVDGVEVHNAKTKPREEQYNSTYRVVRVLTVLHQDWLNGKEYKCKVSNKALPAPIE
KTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGKSS
MHSDPARRGELSVCDSISEWVTAADKKTAVDMSGGTVTVLEKVPVSKGQLKQYFYETK
CNPMGYTKEGCRGIDKRHWNSQCRTTQSYVRALTMDSKKRIGWRFIRIDTSCVCTLTI
KR-COOH

FIG. 7
Amino acid sequence of the fusion protein heavy chain
(SEQ. ID NO. 25)

Signal peptide:

MECSWVMLFLLSGTAGVHC

FR1:

QVQLQQSGPELVKPGALVKISCKAS

CDR1:

GYTFTNYDIH

FR2:

WVKQRPGQGLEWIG

CDR2:

WIYPGDGSTKYNEKFKG

FR3:

KATLTADKSSSTAYMHLSSLTSEKSAVYFCAR

CDR3:

EWAY

FR4:

WGQGTLVTVSA

CH1:

ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKV

Hinge:

EPKSCDKTHTCP

CH2:

PCPAPELLGGPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAK

CH3:

GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK linker:

SSM vBDNF:

HSDPARRGELSVCDSISEWVTAADKKTAVDMSGGTVTVLEKVPVSKGQLKQYFYETKCNPMGYTKEGCRGIDKR
HWNSQCRTTQSYVRALTMDSKKRIGWRFIRIDTSCVCTLTIKR

Engineering of intronless pCD-HC-120 expression vector

FIG. 9A

Nucleotide sequence of fusion protein heavy chain cDNA in clone 422a
(SEQ ID NO. 26)

ATTCCACCATGGAATGCAGCTGGGTCATGCTCTTCCTCCTGTCAGGAACTGCAGGTGTCCATTGCCAGGTTCAG
CTGCAGCAGTCTGGACCTGAGCTGGTGAAGCCTGGGGCTTTAGTGAAGATATCCTGCAAGGCTTCTGGTTACAC
CTTCACAAACTACGATATACACTGGGTGAAGCAGAGGCCTGGACAGGGACTTGAGTGGATTGGATGGATTTATC
CTGGAGATGGTAGTACTAAGTACAATGAGAAATTCAAGGGCAAGGCCACACTGACTGCAGACAAATCCTCCAGC
ACAGCCTACATGCACCTCAGCAGCCTGACTTCTGAGAAATCTGCAGTCTATTTCTGTGCAAGAGAGTGGGCTTA
CTGGGGCCAAGGGACTCTGGTCACTGTCTCTGCAGCTAGCACCAAGGGCCCATCGGTCTTCCCCCTGGCACCCT
CCTCCAAGAGCACCTCTGGGGGCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAAAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGACACCCTCATGATCTC
CCGGACCCCTGAGGTCACATGCGTGGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGG
CTCCTTCTTCCTCTACAGCAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGGGTAAATCGAGTATGCAC
TCTGACCCTGCCCGTCGAGGTGAGCTGAGCGTGTGTGACAGTATTAGTGAGTGGGTAACGGCGGCAGACAAAAA
GACTGCAGTGGACATGTCGGGCGGGACGGTCACAGTCCTTGAAAAGGTCCCTGTATCAAAAGGCCAACTGAAGC
AATACTTCTACGAGACCAAGTGCAATCCCATGGGTTACACAAAAGAAGGCTGCAGGGGCATAGACAAAAGGCAT
TGGAACTCCCAGTGCCGAACTACCCAGTCGTACGTGCGGGCCCTTACCATGGATAGCAAAAAGAGAATTGGCTG
GCGATTCATAAGGATAGACACTTCTTGTGTATGTACATTGACCATTAAAAGGTGA

ATT: ½ SspI
CCACC: Kozak

FIG. 9B

Deduced amino acid sequence of fusion protein heavy chain cDNA in clone 422a
(SEQ ID NO. 27)

```
Atggaatgcagctgggtcatgctcttcctcctgtcaggaactgca
 M  E  C  S  W  V  M  L  F  L  L  S  G  T  A
ggtgtccattgccaggttcagctgcagcagtctggacctgagctg
 G  V  H  C  Q  V  Q  L  Q  Q  S  G  P  E  L
gtgaagcctggggctttagtgaagatatcctgcaaggcttctggt
 V  K  P  G  A  L  V  K  I  S  C  K  A  S  G
tacaccttcacaaactacgatatacactgggtgaagcagaggcct
 Y  T  F  T  N  Y  D  I  H  W  V  K  Q  R  P
ggacagggacttgagtggattggatggatttatcctggagatggt
 G  Q  G  L  E  W  I  G  W  I  Y  P  G  D  G
agtactaagtacaatgagaaattcaagggcaaggccacactgact
 S  T  K  Y  N  E  K  F  K  G  K  A  T  L  T
gcagacaaatcctccagcacagcctacatgcacctcagcagcctg
 A  D  K  S  S  S  T  A  Y  M  H  L  S  S  L
acttctgagaaatctgcagtctatttctgtgcaagagagtgggct
 T  S  E  K  S  A  V  Y  F  C  A  R  E  W  A
tactggggccaagggactctggtcactgtctctgcagctagcacc
 Y  W  G  Q  G  T  L  V  T  V  S  A  A  S  T
aagggcccatcggtcttccccctggcaccctcctccaagagcacc
 K  G  P  S  V  F  P  L  A  P  S  S  K  S  T
tctgggggcacagcggccctgggctgcctggtcaaggactacttc
 S  G  G  T  A  A  L  G  C  L  V  K  D  Y  F
cccgaaccggtgacggtgtcgtggaactcaggcgccctgaccagc
 P  E  P  V  T  V  S  W  N  S  G  A  L  T  S
ggcgtgcacaccttcccggctgtcctacagtcctcaggactctac
 G  V  H  T  F  P  A  V  L  Q  S  S  G  L  Y
tccctcagcagcgtggtgaccgtgccctccagcagcttgggcacc
 S  L  S  S  V  V  T  V  P  S  S  S  L  G  T
cagacctacatctgcaacgtgaatcacaagcccagcaacaccaag
 Q  T  Y  I  C  N  V  N  H  K  P  S  N  T  K
gtggacaagaaagttgagcccaaatcttgtgacaaaactcacaca
 V  D  K  K  V  E  P  K  S  C  D  K  T  H  T
tgcccaccgtgcccagcacctgaactcctggggggaccgtcagtc
 C  P  P  C  P  A  P  E  L  L  G  G  P  S  V
ttcctcttccccccaaaacccaaggacaccctcatgatctcccgg
 F  L  F  P  P  K  P  K  D  T  L  M  I  S  R
acccctgaggtcacatgcgtggtggtggacgtgagccacgaagac
 T  P  E  V  T  C  V  V  V  D  V  S  H  E  D
cctgaggtcaagttcaactggtacgtggacggcgtggaggtgcat
```

FIG. 9C

Deduced amino acid sequence of fusion protein heavy chain cDNA in clone 422a
(SEQ ID NO. 28)

```
            P  E  V  K  F  N  W  Y  V  D  G  V  E  V  H
aatgccaagacaaagccgcgggaggagcagtacaacagcacgtac
            N  A  K  T  K  P  R  E  E  Q  Y  N  S  T  Y
cgtgtggtcagcgtcctcaccgtcctgcaccaggactggctgaat
            R  V  V  S  V  L  T  V  L  H  Q  D  W  L  N
ggcaaggagtacaagtgcaaggtctccaacaaagccctcccagcc
            G  K  E  Y  K  C  K  V  S  N  K  A  L  P  A
cccatcgagaaaaccatctccaaagccaaagggcagccccgagaa
            P  I  E  K  T  I  S  K  A  K  G  Q  P  R  E
ccacaggtgtacaccctgcccccatcccgggatgagctgaccaag
            P  Q  V  Y  T  L  P  P  S  R  D  E  L  T  K
aaccaggtcagcctgacctgcctggtcaaaggcttctatcccagc
            N  Q  V  S  L  T  C  L  V  K  G  F  Y  P  S
gacatcgccgtggagtgggagagcaatgggcagccggagaacaac
            D  I  A  V  E  W  E  S  N  G  Q  P  E  N  N
tacaagaccacgcctcccgtgctggactccgacggctccttcttc
            Y  K  T  T  P  P  V  L  D  S  D  G  S  F  F
ctctacagcaagctcaccgtggacaagagcaggtggcagcagggg
            L  Y  S  K  L  T  V  D  K  S  R  W  Q  Q  G
aacgtcttctcatgctccgtgatgcatgaggctctgcacaaccac
            N  V  F  S  C  S  V  M  H  E  A  L  H  N  H
tacacgcagaagagcctctccctgtctccgggtaaatcgagtatg
            Y  T  Q  K  S  L  S  L  S  P  G  K  S  S  M
cactctgaccctgcccgtcgaggtgagctgagcgtgtgtgacagt
            H  S  D  P  A  R  R  G  E  L  S  V  C  D  S
attagtgagtgggtaacggcggcagacaaaaagactgcagtggac
            I  S  E  W  V  T  A  A  D  K  K  T  A  V  D
atgtcgggcgggacggtcacagtccttgaaaaggtccctgtatca
            M  S  G  G  T  V  T  V  L  E  K  V  P  V  S
aaaggccaactgaagcaatacttctacgagaccaagtgcaatccc
            K  G  Q  L  K  Q  Y  F  Y  E  T  K  C  N  P
atgggttacacaaaagaaggctgcaggggcatagacaaaaggcat
            M  G  Y  T  K  E  G  C  R  G  I  D  K  R  H
tggaactcccagtgccgaactacccagtcgtacgtgcgggccctt
            W  N  S  Q  C  R  T  T  Q  S  Y  V  R  A  L
accatggatagcaaaaagagaattggctggcgattcataaggata
            T  M  D  S  K  K  R  I  G  W  R  F  I  R  I
gacacttcttgtgtatgtacattgaccattaaaaggtga    1757
            D  T  S  C  V  C  T  L  T  I  K  R  *
```

Engineering of intronless pCD-LC-1 expression vector

FIG. 11A

Nucleotide sequence of fusion protein light chain cDNA in clone 423a (SEQ ID NO. 29)

GATATCACC<u>ATG</u>GAGACAGACACACTCCTGCTATGGCTCTTGTTGCTCATGTTTCCAGGT
ACCAGATGTGACATCCAGATGACCCAGTCTCCATCCTCCTTATCTGCCTCTCTGGGAGAA
AGAGTCAGTCTCACTTGTCGGGCAAGTCAGGACATTGGTGGTAACTTATACTGGCTTCAG
CAGGGACCAGATGGAACTATTAAACGCCTGATCTACGCCACATCCAGTTTAGATTCTGG
TGTCCCCAAAAGGTTCAGTGGCAGTAGGTCTGGGTCAGATTATTCTCTCACCATCAGCAG
CCTTGAGTCTGAAGATTTTGTAGACTATTACTGTCTACAGTATTCTAGTTCTCCGTGGAC
GTTCGGTGGAGCGACAAAGATGGAAATAAAACGAACTGTGGCTGCACCATCTGTCTTCA
TCTTCCCGCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAGAGTGT<u>T</u>
<u>AG</u>

GATATC: EcoRV
CACC: Kozak

FIG. 11B

Deduced amino acid sequence of fusion protein light chain in clone 423a (SEQ ID NO. 30 and 31)

```
atggagacagacacactcctgctatggctcttgttgctcatgttt
 M   E   T   D   T   L   L   W   L   L   L   M   F
ccaggtaccagatgtgacatccagatgacccagtctccatcctcc
 P   G   T   R   C   D   I   Q   M   T   Q   S   P   S   S
ttatctgcctctctgggagaaagagtcagtctcacttgtcgggca
 L   S   A   S   L   G   E   R   V   S   L   T   C   R   A
agtcaggacattggtggtaacttatactggcttcagcagggacca
 S   Q   D   I   G   G   N   L   Y   W   L   Q   Q   G   P
gatggaactattaaacgcctgatctacgccacatccagtttagat
 D   G   T   I   K   R   L   I   Y   A   T   S   S   L   D
tctggtgtccccaaaaggttcagtggcagtaggtctgggtcagat
 S   G   V   P   K   R   F   S   G   S   R   S   G   S   D
tattctctcaccatcagcagccttgagtctgaagatttgtagac
 Y   S   L   T   I   S   S   L   E   S   E   D   F   V   D
tattactgtctacagtattctagttctccgtggacgttcggtgga
 Y   Y   C   L   Q   Y   S   S   P   W   T   F   G   G
gcgacaaagatggaaataaaacgaactgtggctgcaccatctgtc
 A   T   K   M   E   I   K   R   T   V   A   A   P   S   V
ttcatcttcccgccatctgatgagcagttgaaatctggaactgcc
 F   I   F   P   P   S   D   E   Q   L   K   S   G   T   A
tctgttgtgtgcctgctgaataacttctatcccagagaggccaaa
 S   V   V   C   L   L   N   N   F   Y   P   R   E   A   K
gtacagtggaaggtggataacgccctccaatcgggtaactcccag
 V   Q   W   K   V   D   N   A   L   Q   S   G   N   S   Q
gagagtgtcacagagcaggacagcaaggacagcacctacagcctc
 E   S   V   T   E   Q   D   S   K   D   S   T   Y   S   L
agcagcaccctgacgctgagcaaagcagactacgagaaacacaaa
 S   S   T   L   T   L   S   K   A   D   Y   E   K   H   K
gtctacgcctgcgaagtcacccatcagggcctgagctcgcccgtc
 V   Y   A   C   E   V   T   H   Q   G   L   S   S   P   V
acaaagagcttcaacaggggagagtgttag
 T   K   S   F   N   R   G   E   C   *
```

Engineering of fusion protein tandem expression vector

FIG. 13A

Nucleotide sequence of the fusion protein heavy chain (HC) and light chain (LC) genes, and the
DHFR gene in the tandem vector
(SEQ ID NO. 32)

HC gene (forward)

CGATGTACGGGCCAGATATACGCGTTGACATTGATTATTGACTAGTTATTAATAGTAATCAATTACGGGGTCATTAG
TTCATAGCCCATATATGGAGTTCCGCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCATTGACGTCAATGGGTGGA
GTATTTACGGTAAACTGCCCACTTGGCAGTACATCAAGTGTATCATATGCCAAGTACGCCCCCTATTGACGTCAATG
ACGGTAAATGGCCCGCCTGGCATTATGCCCAGTACATGACCTTATGGGACTTTCCTACTTGGCAGTACATCTACGTA
TTAGTCATCGCTATTACCATGGTGATGCGGTTTTGGCAGTACATCAATGGGCGTGGATAGCGGTTTGACTCACGGGG
ATTTCCAAGTCTCCACCCCATTGACGTCAATGGGAGTTTGTTTTGGCACCAAAATCAACGGGACTTTCCAAAATGTC
GTAACAACTCCGCCCCATTGACGCAAATGGGCGGTAGGCGTGTACGGTGGGAGGTCTATATAAGCAGAGCTCTCTGG
CTAACTAGAGAACCCACTGCTTACTGGCTTATCGAAATTAATACGACTCACTATAGGGAGACCCTTGCTAGCGATAT
CCACCATGGAATGCAGCTGGGTCATGCTCTTCCTCCTGTCAGGAACTGCAGGTGTCCATTGCCAGGTTCAGCTGCA
GCAGTCTGGACCTGAGCTGGTGAAGCCTGGGGCTTTAGTGAAGATATCCTGCAAGGCTTCTGGTTACACCTTCACAA
ACTACGATATACACTGGGTGAAGCAGAGGCCTGGACAGGGACTTGAGTGGATTGGATGGATTTATCCTGGAGATGGT
AGTACTAAGTACAATGAGAAATTCAAGGGCAAGGCCACACTGACTGCAGACAAATCCTCCAGCACAGCCTACATGCA
CCTCAGCAGCCTGACTTCTGAGAAATCTGCAGTCTATTTCTGTGCAAGAGAGTGGGCTTACTGGGGCCAAGGGACTC
TGGTCACTGTCTCTGCAGCTAGCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACCAAGGTGGACAAGAAA
GTTGAGCCCAAATCTTGTGACAAAACTCACACATGCCCACCGTGCCCAGCACCTGAACTCCTGGGGGGACCGTCAGT
CTTCCTCTTCCCCCCAAAACCCAAGGACACCCTCATGATCTCCCGGACCCCTGAGGTCACATGCGTGGTGGTGGACG
TGAGCCACGAAGACCCTGAGGTCAAGTTCAACTGGTACGTGGACGGCGTGGAGGTGCATAATGCCAAGACAAAGCCG
CGGGAGGAGCAGTACAACAGCACGTACCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGAGCAGGTGGCAGCAGG
GGAACGTCTTCTCATGCTCCGTGATGCATGAGGCTCTGCACAACCACTACACGCAGAAGAGCCTCTCCCTGTCTCCG
GGTAAATCGAGTATGCACTCTGACCCTGCCCGTCGAGGTGAGCTGAGCGTGTGTGACAGTATTAGTG

FIG. 13B

AGTGGGTAACGGCGGCAGACAAAAAGACTGCAGTGGACATGTCGGGCGGGACGGTCACAGTCCTTGAAAAGGTCCCT
GTATCAAAAGGCCAACTGAAGCAATACTTCTACGAGACCAAGTGCAATCCCATGGGTTACACAAAAGAAGGCTGCAG
GGGCATAGACAAAAGGCATTGGAACTCCCAGTGCCGAACTACCCAGTCGTACGTGCGGGCCCTTACCATGGATAGCA
AAAAGAGAATTGGCTGGCGATTCATAAGGATAGACACTTCTTGTGTATGTACATTGACCATTAAAAGGTGAGGATCC
CTCGAGCATGCATCTAGAGGGCCCTATTCTATAGTGTCACCTAAATGCTAGAGCTCGCTGATCAGCCTCGACTGTGC
CTTCTAGTTGCCAGCCATCTGTTGTTTGCCCCTCCCCGTGCCTTCCTTGACCCTGGAAGGTGCCACTCCCACTGTC
CTTTCCTAATAAAATGAGGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGCTGGGGATGCGGTGGGCTCTATGGCTTCTGAGGCGG
AAAGAACCAGTGGCGGTAATACGGTTATCCACAGAATCAGGGGATAACGCAGGAAAGAACATGTGAGCAAAAGGCCA
GCAAAAGGCCAGGAACC

LC gene (forward)

GAATTCGATATTCCATACACATACTTCTGTGTTCCTTTGAAAGCTGGACTTTTGCAGGCTCCACCAGACCTCTCTAG
ATCAATTCCTTTGCCTAATTTCGCTTACAATTTACGCGCGCGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGC
TGACCGCCCAACGACCCCCGCCCATTGACGTCAATAATGACGTATGTTCCCATAGTAACGCCAATAGGGACTTTCCA
TTGACGTCAATGGGTGGAGTATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGACCTTATGGGACTTTCCTACT
TGGCAGTACATCTACGTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTTGGCACCAAAATCAAC
GGGACTTTCCAAAATGTCGTAACAACTCCGCCCCATTGACGCAAATGGGCGGTAGGCGTGTACGGTGGGAGGTCTAT
ATAAGCAGAGCTCTCTGGCTAACTAGAGAACCCACTGCTTACTGGCTTATCGAAATTAATACGACTCACTATAGGGA
GACCCAAGCTGGCTAGCGATATCACCATGGAGACAGACACACTCCTGCTATGGCTCTTGTTGCTCATGTTTCCAGGT
ACCAGATGTGACATCCAGATGACCCAGTCTCCATCCTCCTTATCTGCCTCTCTGGGAGAAAGAGTCAGTCTCACTTG
TCGGGCAAGTCAGGACATTGGTGGTAACTTATACTGGCTTCAGCAGGGACCAGATGGAACTATTAAACGCCTGATCT
ACGCCACATCCAGTTTAGATTCTGGTGTCCCCAAAAGGTTCAGTGGCAGTAGGTCTGGGTCAGATTATTCTCTCACC
ATCAGCAGCCTTGAGTCTGAAGATTTTGTAGACTATTACTGTCTACAGTATTCTAGTTCTCCGTGGACGTTCGGTGG
AGCGACAAAGATGGAAATAAAACGAACTGTGGCTGCACCATCTGTCTTCATCTTCCCGCCATCTGATGAGCAGTTGA
AATCTGGAACTGCCTCTGTTGTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGACAGCACCTACAGCCTCAGCAG
CACCCTGACGCTGAGCAAAGCAGACTACGAGAAACACAAAGTCTACGCCTGCGAAGTCACCCATCAGGGCCTGAGCT
CGCCCGTCACAAAGAGC

FIG. 13C

TTCAACAGGGGAGAGTGTTAGCTCGAGTCTAGAGGGCCCGTTTAAACCCGCTGATCAGCCTCGACTGTGCCTTCTAG

TTGCCAGCCATCTGTTGTTTGCCCCTCCCCCGTGCCTTCCTTGACCCTGGAAG

GTGCCACTCCCACTGTCCTTTCCTAATAAAATGAGGAAATTGCATCGCATTGTCTGAGTAGGTGTCATTCTATTCTG

GGGGGTGGGGTGGGGCAGGACAGCAAGGGGGAGGATTGGGAAGACAATAGCAGGCATGCTGGGGATGCGGTGGGCTC

TATGGCTTCTGAGGCGGAAAGAACCAGTGGCGGTAATACGGTTATCCACAGAATCAGGGGATAACGAAATGAGGACT

TAACCTGTGGAAATATCAAGCTT

LC gene-DHFR gene linker

GCGGCCGCGTA

DHFR gene (reverse)

TCGACGCTCTCCCTTATGCGACTCCTGCATTAGGAAGCAGCCCAGTAGTAGGTTGAGGCCGTTGAGCACCGCCGCCG

CAAGGAATGGTGCATGCAAGGAGATGGCGCCCAACAGTCCCCCGGCCACGGGGCCTGCCACCATACCCACGCCGAAA

CAAGCGCTCATGAGCCCGAAGTGGCGAGCCCGATCTTCCCCATCGGTGATGTCGGCGATATAGGCGCCAGCAACCGC

ACCTGTGGCGCCGGTGATGCCGGCCACGATGCGTCCGGCGTAGAGGATCTCTGACGGAAGGAAAGAAGTCAGAAGGC

AAAAACGAGAGTAACTCCACAGTAGCTCCAAATTCTTTATAAGGGTCAATGTCCATGCCCCAAAGCCACCCAAGGCA

CAGCTTGGAGGCTTGAACAGTGGGACATGTACAAGAGATGATTAGGCAGAGGTGAAAAAGTTGCATGGTGCTGGTGC

GCAGACCAATTTATGCCTACAGCCTCCTAATACAAAGACCTTTAACCTAATCTCCTCCCCAGCTCCTCCCAGTCCT

TAAACACACAGTCTTTGAAGTAGGCCTCAAGGTCGGTCGTTGACATTGCTGGGAGTCCAAGAGTCCTCTTATGTAAG

ACCTTGGGCAGGATCTGATGGGCGTTCACGGTGGTCTCCATGCAACGTGCAGAGGTGAAGCGAAGTGCACACGGACC

GGCAGATGAGAAGGCACAGACGGGGAGACCGCGTAAAGAGAGGTGCGCCCCGTGGTCGGCTGGAACGGCAGACGGAG

AAGGGGACGAGAGAGTCCCAAGCGGCCCCGCGAGGGGTCGTCCGCGGGATTCAGCGCCGACGGGACGTAAACAAAGG

ACGTCCCGCGAAGGATCTAAAGCCAGCAAAAGTCCCATGGTCTTATAAAAATGCATAGCTTTAGGAGGGGAGCAGAG

AACTTGAAAGCATCTTCCTGTTAGTCTTTCTTCTCGTAGACTTCAAACTTATACTTGATGCCTTTTTCCTCCTGGAC

CTCAGAGAGGACGCCTGGGTATTCTGGGAGAAGTTTATATTTCCCCAAATCAATTTCTGGGAAAAACGTGTCACTTT

CAAATTCCTGCATGATCCTTGTCACAAAGAGTCTGAGGTGGCCTGGTTGATTCATGGCTTCCTGGTAAACAGAACTG

CCTCCGACTATCCAAACCATGTCTACTTT

FIG. 13D

```
ACTTGCCAATTCCGGTTGTTCAATAAGTCTTAAGGCATCATCCAAACTTTTGGCAAGAAAATGAGCTCCTCGT
GGTGGTTCTTTGAGTTCTCTACTGAGAACTATATTAATTCTGTCCTTTAAAGGTCGATTCTTCTCAGGAATGG
AGAACCAGGTTTTCCTACCCATAATCACCAGATTCTGTTTACCTTCCACTGAAGAGGTTGTGGTCATTCTTTG
GAAGTACTTGAACTCGTTCCTGAGCGGAGGCCAGGGTCGGTCTCCGTTCTTGCCAATCCCCATATTTTGGGAC
ACGGCGACGATGCAGTTCAATGGTCGAACCATGATGGCAAATTCTAGAATCGATAAGCTTTTTGCAAAAGCCT
AGGCCTCCAAAAAAGCCTCCTCACTACTTCTGGAATAGCTCAGAGGCCGAGGCGGCCTCGGCCTCTGCATAAA
TAAAAAAAATTAGTCAGCCATGGGGCGGAGAATGGGCGGAACTGGGCGGAGTTAGGGGCGGGATGGGCGGAGT
TAGGGGCGGGACTATGGTTGCTGACTAATTGAGATGCAGATCTCGAGCTAGCACGCGTAAGAGCTCGGTACCT
CCCTAC
```

FIG. 14A
Nucleotide and deduced amino acid sequence of heavy chain of fusion
protein cDNA and protein encoded by tandem vector
(SEQ ID NO. 33)

```
atggaatgcagctgggtcatgctcttcctcctgtcaggaactgca
 M  E  C  S  W  V  M  L  F  L  L  S  G  T  A
ggtgtccattgccaggttcagctgcagcagtctggacctgagctg
 G  V  H  C  Q  V  Q  L  Q  Q  S  G  P  E  L
gtgaagcctggggctttagtgaagatatcctgcaaggcttctggt
 V  K  P  G  A  L  V  K  I  S  C  K  A  S  G
tacaccttcacaaactacgatatacactgggtgaagcagaggcct
 Y  T  F  T  N  Y  D  I  H  W  V  K  Q  R  P
ggacagggacttgagtggattggatggatttatcctggagatggt
 G  Q  G  L  E  W  I  G  W  I  Y  P  G  D  G
agtactaagtacaatgagaaattcaagggcaaggccacactgact
 S  T  K  Y  N  E  K  F  K  G  K  A  T  L  T
gcagacaaatcctccagcacagcctacatgcacctcagcagcctg
 A  D  K  S  S  S  T  A  Y  M  H  L  S  S  L
acttctgagaaatctgcagtctatttctgtgcaagagagtgggct
 T  S  E  K  S  A  V  Y  F  C  A  R  E  W  A
tactggggccaagggactctggtcactgtctctgcagctagcacc
 Y  W  G  Q  G  T  L  V  T  V  S  A  A  S  T
aagggcccatcggtcttccccctggcaccctcctccaagagcacc
 K  G  P  S  V  F  P  L  A  P  S  S  K  S  T
tctgggggcacagcggccctgggctgcctggtcaaggactacttc
 S  G  G  T  A  A  L  G  C  L  V  K  D  Y  F
cccgaaccggtgacggtgtcgtggaactcaggcgccctgaccagc
 P  E  P  V  T  V  S  W  N  S  G  A  L  T  S
ggcgtgcacaccttcccggctgtcctacagtcctcaggactctac
 G  V  H  T  F  P  A  V  L  Q  S  S  G  L  Y
tccctcagcagcgtggtgaccgtgccctccagcagcttgggcacc
 S  L  S  S  V  V  T  V  P  S  S  S  L  G  T
cagacctacatctgcaacgtgaatcacaagcccagcaacaccaag
 Q  T  Y  I  C  N  V  N  H  K  P  S  N  T  K
gtggacaagaaagttgagcccaaatcttgtgacaaaactcacaca
 V  D  K  K  V  E  P  K  S  C  D  K  T  H  T
tgcccaccgtgcccagcacctgaactcctggggggaccgtcagtc
 C  P  P  C  P  A  P  E  L  L  G  G  P  S  V
ttcctcttccccccaaaacccaaggacaccctcatgatctcccgg
 F  L  F  P  P  K  P  K  D  T  L  M  I  S  R
acccctgaggtcacatgcgtggtggtggacgtgagccacgaagac
 T  P  E  V  T  C  V  V  V  D  V  S  H  E  D
cctgaggtcaagttcaactggtacgtggacggcgtggaggtgcat
```

FIG. 14B

Nucleotide and deduced amino acid sequence of heavy chain of fusion protein cDNA and protein encoded by tandem vector
(SEQ ID NO. 34)

```
                P  E  V  K  F  N  W  Y  V  D  G  V  E  V  H
aatgccaagacaaagccgcgggaggagcagtacaacagcacgtac
 N  A  K  T  K  P  R  E  E  Q  Y  N  S  T  Y
cgtgtggtcagcgtcctcaccgtcctgcaccaggactggctgaat
 R  V  V  S  V  L  T  V  L  H  Q  D  W  L  N
ggcaaggagtacaagtgcaaggtctccaacaaagccctcccagcc
 G  K  E  Y  K  C  K  V  S  N  K  A  L  P  A
cccatcgagaaaaccatctccaaagccaaagggcagccccgagaa
 P  I  E  K  T  I  S  K  A  K  G  Q  P  R  E
ccacaggtgtacaccctgcccccatcccgggatgagctgaccaag
 P  Q  V  Y  T  L  P  P  S  R  D  E  L  T  K
aaccaggtcagcctgacctgcctggtcaaaggcttctatcccagc
 N  Q  V  S  L  T  C  L  V  K  G  F  Y  P  S
gacatcgccgtggagtgggagagcaatgggcagccggagaacaac
 D  I  A  V  E  W  E  S  N  G  Q  P  E  N  N
tacaagaccacgcctcccgtgctggactccgacggctccttcttc
 Y  K  T  T  P  P  V  L  D  S  D  G  S  F  F
ctctacagcaagctcaccgtggacaagagcaggtggcagcagggg
 L  Y  S  K  L  T  V  D  K  S  R  W  Q  Q  G
aacgtcttctcatgctccgtgatgcatgaggctctgcacaaccac
 N  V  F  S  C  S  V  M  H  E  A  L  H  N  H
tacacgcagaagagcctctccctgtctccgggtaaatcgagtatg
 Y  T  Q  K  S  L  S  L  S  P  G  K  S  S  M
cactctgaccctgcccgtcgaggtgagctgagcgtgtgtgacagt
 H  S  D  P  A  R  R  G  E  L  S  V  C  D  S
attagtgagtgggtaacggcggcagacaaaaagactgcagtggac
 I  S  E  W  V  T  A  A  D  K  K  T  A  V  D
atgtcgggcgggacggtcacagtccttgaaaaggtccctgtatca
 M  S  G  G  T  V  T  V  L  E  K  V  P  V  S
aaaggccaactgaagcaatacttctacgagaccaagtgcaatccc
 K  G  Q  L  K  Q  Y  F  Y  E  T  K  C  N  P
atgggttacacaaaagaaggctgcaggggcatagacaaaaggcat
 M  G  Y  T  K  E  G  C  R  G  I  D  K  R  H
tggaactcccagtgccgaactacccagtcgtacgtgcgggccctt
 W  N  S  Q  C  R  T  T  Q  S  Y  V  R  A  L
accatggatagcaaaaagagaattggctggcgattcataaggata
 T  M  D  S  K  K  R  I  G  W  R  F  I  R  I
gacacttcttgtgtatgtacattgaccattaaaaggtga   2448
 D  T  S  C  V  C  T  L  T  I  K  R  *
```

FIG. 15

Nucleotide and deduced amino acid sequence of light chain encoded by tandem vector
(SEQ ID NO. 35 and 36)

```
atggagacagacacactcctgctatggctcttgttgctcatgttt
 M  E  T  D  T  L  L  L  W  L  L  L  M  F
ccaggtaccagatgtgacatccagatgacccagtctccatcctcc
 P  G  T  R  C  D  I  Q  M  T  Q  S  P  S  S
ttatctgcctctctgggagaaagagtcagtctcacttgtcgggca
 L  S  A  S  L  G  E  R  V  S  L  T  C  R  A
agtcaggacattggtggtaacttatactggcttcagcagggacca
 S  Q  D  I  G  G  N  L  Y  W  L  Q  Q  G  P
gatggaactattaaacgcctgatctacgccacatccagtttagat
 D  G  T  I  K  R  L  I  Y  A  T  S  S  L  D
tctggtgtccccaaaaggttcagtggcagtaggtctgggtcagat
 S  G  V  P  K  R  F  S  G  S  R  S  G  S  D
tattctctcaccatcagcagccttgagtctgaagatttgtagac
 Y  S  L  T  I  S  S  L  E  S  E  D  F  V  D
tattactgtctacagtattctagttctccgtggacgttcggtgga
 Y  Y  C  L  Q  Y  S  S  P  W  T  F  G  G
gcgacaaagatggaaataaaacgaactgtggctgcaccatctgtc
 A  T  K  M  E  I  K  R  T  V  A  A  P  S  V
ttcatcttcccgccatctgatgagcagttgaaatctggaactgcc
 F  I  F  P  P  S  D  E  Q  L  K  S  G  T  A
tctgttgtgtgcctgctgaataacttctatcccagagaggccaaa
 S  V  V  C  L  L  N  N  F  Y  P  R  E  A  K
gtacagtggaaggtggataacgccctccaatcgggtaactcccag
 V  Q  W  K  V  D  N  A  L  Q  S  G  N  S  Q
gagagtgtcacagagcaggacagcaaggacagcacctacagcctc
 E  S  V  T  Q  D  S  K  D  S  T  Y  S  L
agcagcaccctgacgctgagcaaagcagactacgagaaacacaaa
 S  S  T  L  T  L  S  K  A  D  Y  E  K  H  K
gtctacgcctgcgaagtcacccatcagggcctgagctcgcccgtc
 V  Y  A  C  E  V  T  H  Q  G  L  S  S  P  V
acaaagagcttcaacaggggagagtgttag
 T  K  S  F  N  R  G  E  C  *
```

FIG. 16

Nucleotide and deduced amino acid sequence of DHFR encoded by tandem vector (SEQ ID NO. 37 and 38)

```
atggttcgaccattgaactgcatcgtcgccgtgtcccaaaatatg
 M   V   R   P   L   N   C   I   V   A   V   S   Q   N   M
gggattggcaagaacggagaccgaccctggcctccgctcaggaac
 G   I   G   K   N   G   D   R   P   W   P   P   L   R   N
gagttcaagtacttccaaagaatgaccacaacctcttcagtggaa
 E   F   K   Y   F   Q   R   M   T   T   T   S   S   V   E
ggtaaacagaatctggtgattatgggtaggaaaacctggttctcc
 G   K   Q   N   L   V   I   M   G   R   K   T   W   F   S
attcctgagaagaatcgacctttaaaggacagaattaatatagtt
 I   P   E   K   N   R   P   L   K   D   R   I   N   I   V
ctcagtagagaactcaaagaaccaccacgaggagctcattttctt
 L   S   R   E   L   K   E   P   P   R   G   A   H   F   L
gccaaaagtttggatgatgccttaagacttattgaacaaccggaa
 A   K   S   L   D   D   A   L   R   L   I   E   Q   P   E
ttggcaagtaaagtagacatggtttggatagtcggaggcagttct
 L   A   S   K   V   D   M   V   W   I   V   G   G   S   S
gtttaccaggaagccatgaatcaaccaggccacctcagactcttt
 V   Y   Q   E   A   M   N   Q   P   G   H   L   R   L   F
gtgacaaggatcatgcaggaatttgaaagtgacacgttttccca
 V   T   R   I   M   Q   E   F   E   S   D   T   F   F   P
gaaattgatttggggaaatataaacttctcccagaatacccaggc
 E   I   D   L   G   K   Y   K   L   L   P   E   Y   P   G
gtcctctctgaggtccaggaggaaaaaggcatcaagtataagttt
 V   L   S   E   V   Q   E   E   K   G   I   K   Y   K   F
gaagtctacgagaagaaagactaa
 E   V   Y   E   K   K   D   *
```

FIG. 24
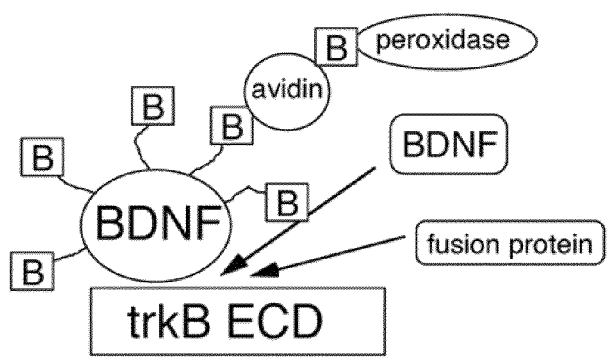
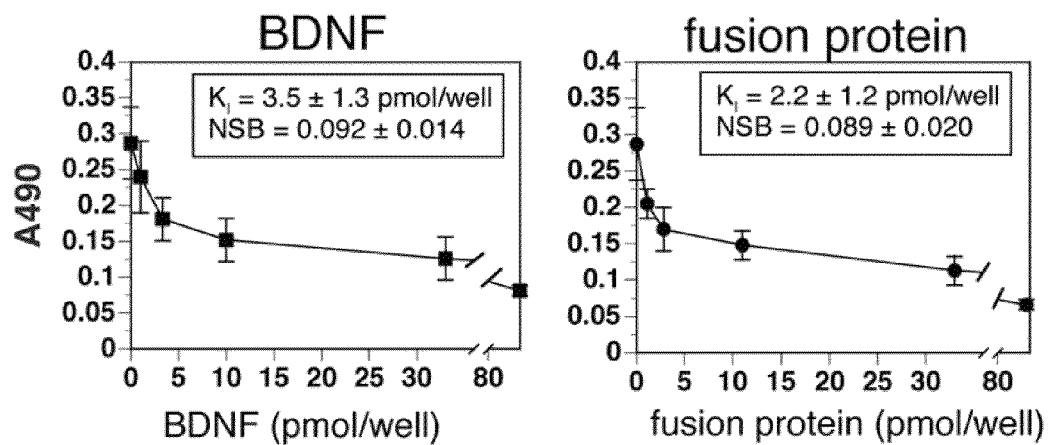

FIG. 29
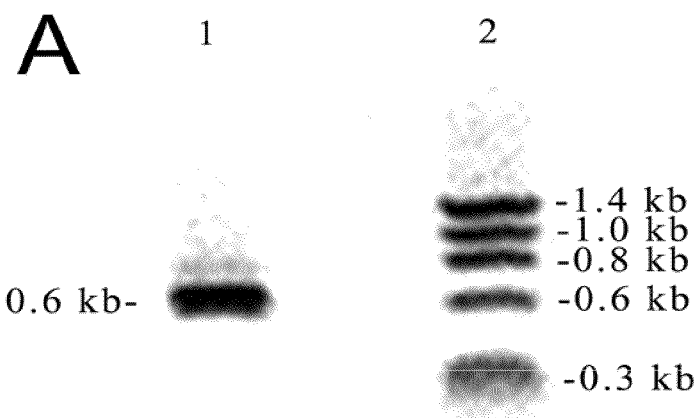
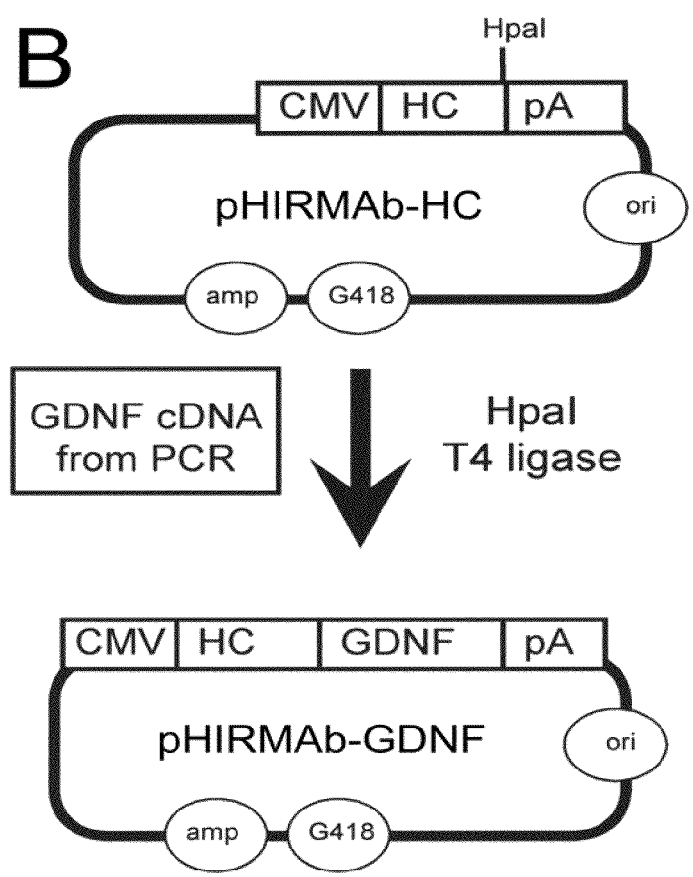

FIG. 34
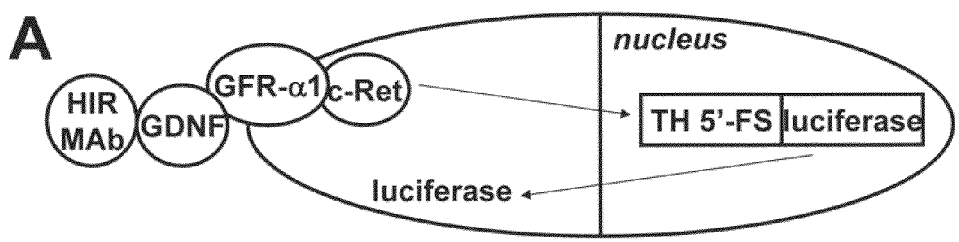
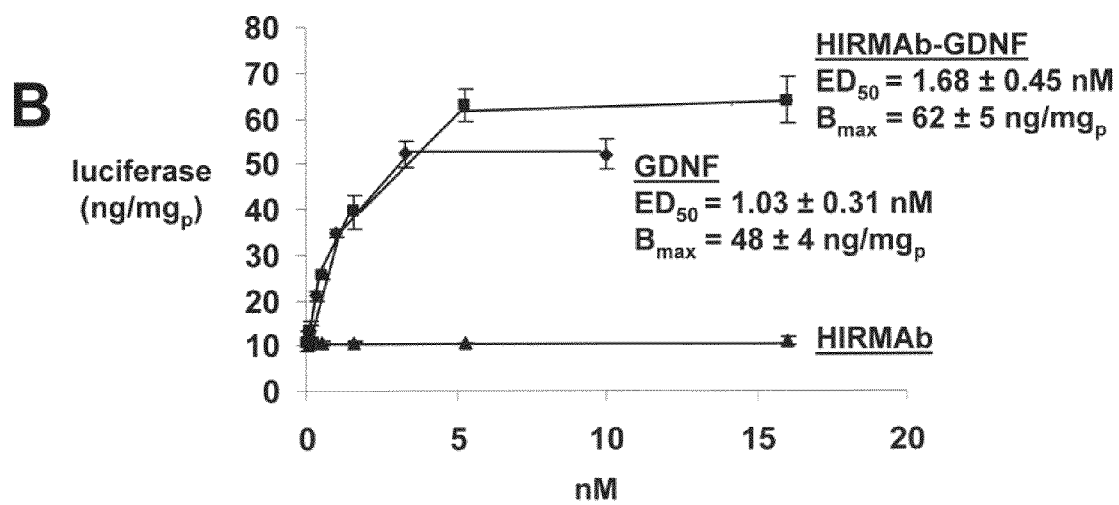

FIG. 35
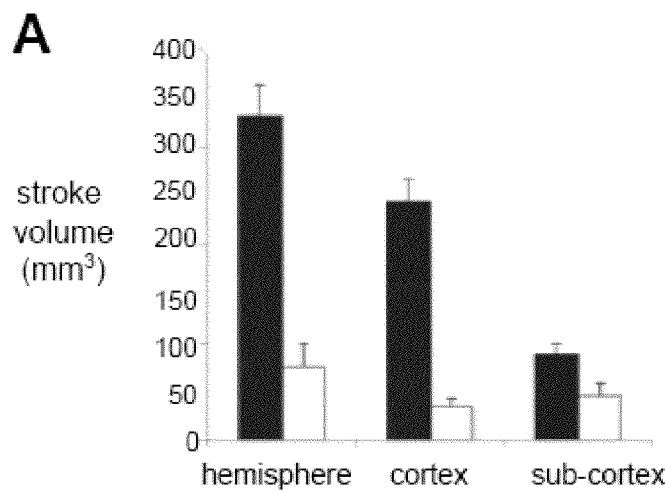
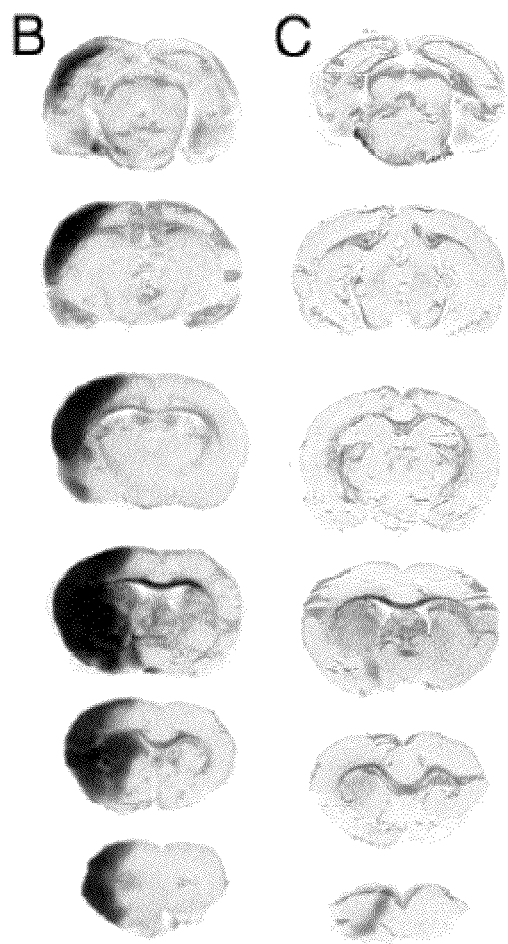

SEQUENCE LISTING

<160> NUMBER OF SEQ ID NOS: 52

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctgtctccg ggtaaatatt tgcgacggcc ggcaag                             36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttgccggcc gtcgcaaata tttacccgga gacagg                             36

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgctcgagg aattcccatg gatgatggct agcaagctta tg                      42

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cataagcttg ctagccatca tccatgggaa ttcctcgagc at                      42

<210> SEQ ID NO 5
<211> LENGTH: 56

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccggatcct cgcgagtatg cactctgacc ctgcccgtcg aggtgagctg agcgtg         56

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cacgctcagc tcacctcgac gggcagggtc agagtgcata ctcgcgagga tccgga         56

<210> SEQ ID NO 7
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agtcgtacgt gcgggccctt accatggata gcaaaaagag aattggctgg cgattcataa     60
ggatagacac ttcttgtgta tgtacattga ccattaaaag gtgatcgcga ctcgagatg    119

<210> SEQ ID NO 8
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
catctcgagt cgcgatcacc ttttaatggt caatgtacat acacaagaag tgtctatcct     60
tatgaatcgc cagccaattc tcttttttgct atccatggta agggcccgca cgtacgact   119

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atctcgcgag tatgcactct gaccctgcc                                       29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atctcgcgat cacctttaa tggtcaa                                          27
```

```
<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atggctagcg atatcggtac cgtatacgga tccctcgaga tg                         42

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catctcgagg gatccgtata cggtaccgat atcgctagcc at                         42

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgacaaaca cagacatagg atatc                                            25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgctcgagc taacactctc ccct                                             24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgaatattc caccatggaa tgcagc                                           26

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataggatcct cacctttta tggtcaa                                           27

<210> SEQ ID NO 17
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaggccag gaaccgaatt cagatctcgt tgctggcgtt tt                          42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaacgccag caacgagatc tgaattcggt tcctggcctt tt                          42

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atcgaattca agcttgcggc cgcgtataca gatctatc                               38

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatagatctg tatacgcggc cgcaagcttg aattcgat                               38

<210> SEQ ID NO 21
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(375)

<400> SEQUENCE: 21 ctg tct ccg ggt aaa tcg agt atg cac tct gac cct gcc cgt cga ggt        48
Leu Ser Pro Gly Lys Ser Ser Met His Ser Asp Pro Ala Arg Arg Gly
1               5                   10                  15 gag ctg agc gtg tgt gac agt att agt gag tgg gta acg gcg gca gac        96
Glu Leu Ser Val Cys Asp Ser Ile Ser Glu Trp Val Thr Ala Ala Asp
            20                  25                  30 aaa aag act gca gtg gac atg tcg ggc ggg acg gtc aca gtc ctt gaa       144
Lys Lys Thr Ala Val Asp Met Ser Gly Gly Thr Val Thr Val Leu Glu
        35                  40                  45 aag gtc cct gta tca aaa ggc caa ctg aag caa tac ttc tac gag acc       192
Lys Val Pro Val Ser Lys Gly Gln Leu Lys Gln Tyr Phe Tyr Glu Thr
    50                  55                  60 aag tgc aat ccc atg ggt tac aca aaa gaa ggc tgc agg ggc ata gac       240
```

```
Lys Cys Asn Pro Met Gly Tyr Thr Lys Glu Gly Cys Arg Gly Ile Asp
 65                  70                  75                  80 aaa agg cat tgg aac tcc cag tgc cga act acc cag tcg tac gtg cgg    288
Lys Arg His Trp Asn Ser Gln Cys Arg Thr Thr Gln Ser Tyr Val Arg
                 85                  90                  95 gcc ctt acc atg gat agc aaa aag aga att ggc tgg cga ttc ata agg    336
Ala Leu Thr Met Asp Ser Lys Lys Arg Ile Gly Trp Arg Phe Ile Arg
            100                 105                 110 ata gac act tct tgt gta tgt aca ttg acc att aaa agg tga            378
Ile Asp Thr Ser Cys Val Cys Thr Leu Thr Ile Lys Arg
        115                 120                 125

<210> SEQ ID NO 22
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Ser Pro Gly Lys Ser Ser Met His Ser Asp Pro Ala Arg Arg Gly
1               5                   10                  15

Glu Leu Ser Val Cys Asp Ser Ile Ser Glu Trp Val Thr Ala Ala Asp
            20                  25                  30

Lys Lys Thr Ala Val Asp Met Ser Gly Gly Thr Val Thr Val Leu Glu
        35                  40                  45

Lys Val Pro Val Ser Lys Gly Gln Leu Lys Gln Tyr Phe Tyr Glu Thr
    50                  55                  60

Lys Cys Asn Pro Met Gly Tyr Thr Lys Glu Gly Cys Arg Gly Ile Asp
65                  70                  75                  80

Lys Arg His Trp Asn Ser Gln Cys Arg Thr Thr Gln Ser Tyr Val Arg
                85                  90                  95

Ala Leu Thr Met Asp Ser Lys Lys Arg Ile Gly Trp Arg Phe Ile Arg
            100                 105                 110

Ile Asp Thr Ser Cys Val Cys Thr Leu Thr Ile Lys Arg
        115                 120                 125

<210> SEQ ID NO 23
<211> LENGTH: 2711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tagtctttct cttcagtgac aaacacagac ataggatatt ccaccatgga atgcagctgg     60
gtcatgctct tcctcctgtc aggaactgca ggtgtccatt gccaggttca gctgcagcag    120
tctggacctg agctggtgaa gcctggggct ttagtgaaga tatcctgcaa ggcttctggt    180
tacaccttca caaactacga tatacactgg gtgaagcaga ggcctggaca gggacttgag    240
tggattggat ggatttatcc tggagatggt agtactaagt acaatgagaa attcaagggc    300
aaggccacac tgactgcaga caaatcctcc agcacagcct acatgcacct cagcagcctg    360
acttctgaga atctgcagt ctatttctgt gcaagagagt gggcttactg gggccaaggg    420
actctggtca ctgtctctgc agctagcacc aagggcccat cggtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
```

```
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtggacaaga aagttggtga gaggccagca caggagggga gggtgtctgc tggaagccag    780
gctcagcgct cctgcctgga cgcatcccgg ctatgcagcc ccagtccagg gcagcaaggc    840
aggccccgtc tgcctcttca cccggaggcc tctgcccgcc ccactcatgc tcagggagag    900
ggtcttctgg cttttccccc aggctctggg caggcacagg ctaggtgccc ctaacccagg    960
ccctgcacac aaaggggcag gtgctgggct cagacctgcc aagagccata tccgggagga   1020
ccctgcccct gacctaagcc cacccaaag gccaaactct ccactccctc agctcggaca    1080
ccttctctcc tcccagattc cagtaactcc caatcttctc tctgcagagc ccaaatcttg    1140
tgacaaaact cacacatgcc caccgtgccc aggtaagcca gcccaggcct cgccctccag    1200
ctcaaggcgg gacaggtgcc ctagagtagc ctgcatccag ggacaggccc cagccgggtg    1260
ctgacacgtc cacctccatc tcttcctcag cacctgaact cctgggggga ccgtcagtct    1320
tcctcttccc cccaaaaccc aaggacaccc tcatgatctc ccggacccct gaggtcacat    1380
gcgtggtggt ggacgtgagc cacgaagacc ctgaggtcaa gttcaactgg tacgtggacg    1440
gcgtggaggt gcataatgcc aagacaaagc cgcgggagga gcagtacaac agcacgtacc    1500
gtgtggtcag ggtcctcacc gtcctgcacc aggactggct gaatggcaag gagtacaagt    1560
gcaaggtctc caacaaagcc ctcccagccc catcgagaa accatctcc aaagccaaag    1620
gtgggacccg tggggtgcga gggccacatg gacagaggcc ggctcggccc accctctgcc    1680
ctgagagtga ccgctgtacc aacctctgtc cctacagggc agccccgaga accacaggtg    1740
tacaccctgc ccccatcccg ggatgagctg accaagaacc aggtcagcct gacctgcctg    1800
gtcaaaggct tctatcccag cgacatcgcc gtggagtggg agagcaatgg gcagccggag    1860
aacaactaca agaccacgcc tcccgtgctg gactccgacg gctccttctt cctctacagc    1920
aagctcaccg tggacaagag caggtggcag caggggaacg tcttctcatg ctccgtgatg    1980
catgaggctc tgcacaacca ctacacgcag aagagcctct ccctgtctcc gggtaaatcg    2040
agtatgcact ctgaccctgc ccgtcgaggt gagctgagcg tgtgtgacag tattagtgag    2100
tgggtaacgg cggcagacaa aaagactgca gtggacatgt cgggcgggac ggtcacagtc    2160
cttgaaaagg tccctgtatc aaaaggccaa ctgaagcaat acttctacga gaccaagtgc    2220
aatcccatgg gttacacaaa agaaggctgc aggggcatag acaaaaggca ttggaactcc    2280
cagtgccgaa ctacccagtc gtacgtgcgg gcccttacca tggatagcaa aaagagaatt    2340
ggctggcgat tcataaggat agacacttct tgtgtatgta cattgaccat taaaaggtga    2400
tcgattttgc gacggccggc aagcccccgc tccccgggct ctcgcggtcg cacgaggatg    2460
cttggcacgt accccctgta catacttccc gggcgcccag catggaaata aagcacccag    2520
cgctgccctg ggcccctgcg agactgtgat ggttctttcc acgggtcagg ccgagtctga    2580
ggcctgagtg gcatgaggga ggcagagcgg gtcccactgt ccccacactg gcccaggctg    2640
tgcaggtgtg cctgggccgc ctagggtggg gctcagccag gggctgccct cggcagggtg    2700
ggggatttgc c                                                         2711
```

<210> SEQ ID NO 24
<211> LENGTH: 582
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 24

```
Met Glu Cys Ser Trp Val Met Leu Phe Leu Leu Ser Gly Thr Ala Gly
1               5                  10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Arg Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
```

```
                    405                 410                 415
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
            500                 505                 510

Gln Leu Lys Gln Tyr Phe Tyr Glu Thr Lys Cys Asn Pro Met Gly Tyr
        515                 520                 525

Thr Lys Glu Gly Cys Arg Gly Ile Asp Lys Arg His Trp Asn Ser Gln
    530                 535                 540

Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
                565                 570                 575

Thr Leu Thr Ile Lys Arg
            580

<210> SEQ ID NO 25
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
```

```
                    180                 185                 190
Gly Leu Tyr Ser Leu Ser Ser Val Val Thr Val Pro Ser Ser Ser Leu
            195                 200                 205
Gly Thr Gln Thr Tyr Ile Cys Asn Val Asn His Lys Pro Ser Asn Thr
        210                 215                 220
Lys Val Asp Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys Ser Ser
    450                 455                 460
Met His Ser Asp Pro Ala Arg Arg Gly Glu Leu Ser Val Cys Asp Ser
465                 470                 475                 480
Ile Ser Glu Trp Val Thr Ala Ala Asp Lys Lys Thr Ala Val Asp Met
                485                 490                 495
Ser Gly Gly Thr Val Thr Val Leu Glu Lys Val Pro Val Ser Lys Gly
            500                 505                 510
Gln Leu Lys Gln Tyr Phe Tyr Glu Thr Lys Cys Asn Pro Met Gly Tyr
        515                 520                 525
Thr Lys Glu Gly Cys Arg Gly Ile Asp Lys Arg His Trp Asn Ser Gln
    530                 535                 540
Cys Arg Thr Thr Gln Ser Tyr Val Arg Ala Leu Thr Met Asp Ser Lys
545                 550                 555                 560
Lys Arg Ile Gly Trp Arg Phe Ile Arg Ile Asp Thr Ser Cys Val Cys
                565                 570                 575
Thr Leu Thr Ile Lys Arg
            580

<210> SEQ ID NO 26
<211> LENGTH: 1757
```

-continued

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

| attccaccat | ggaatgcagc | tgggtcatgc | tcttcctcct | gtcaggaact | gcaggtgtcc | 60 |
| attgccaggt | tcagctgcag | cagtctggac | ctgagctggt | gaagcctggg | gctttagtga | 120 |
| agatatcctg | caaggcttct | ggttacacct | tcacaaacta | cgatatacac | tgggtgaagc | 180 |
| agaggcctgg | acagggactt | gagtggattg | gatggattta | tcctggagat | ggtagtacta | 240 |
| agtacaatga | gaaattcaag | ggcaaggcca | cactgactgc | agacaaatcc | tccagcacag | 300 |
| cctacatgca | cctcagcagc | ctgacttctg | agaaatctgc | agtctatttc | tgtgcaagag | 360 |
| agtgggctta | ctggggccaa | gggactctgg | tcactgtctc | tgcagctagc | accaagggcc | 420 |
| catcggtctt | cccccctggca | ccctcctcca | gagcacctc | tgggggcaca | gcggccctgg | 480 |
| gctgcctggt | caaggactac | ttccccgaac | cggtgacggt | gtcgtggaac | tcaggcgccc | 540 |
| tgaccagcgg | cgtgcacacc | ttcccggctg | tcctacagtc | ctcaggactc | tactccctca | 600 |
| gcagcgtggt | gaccgtgccc | tccagcagct | tgggcaccca | gacctacatc | tgcaacgtga | 660 |
| atcacaagcc | cagcaacacc | aaggtggaca | agaaagttga | gcccaaatct | tgtgacaaaa | 720 |
| ctcacacatg | cccaccgtgc | ccagcacctg | aactcctggg | gggaccgtca | gtcttcctct | 780 |
| tccccccaaa | acccaaggac | accctcatga | tctcccggac | ccctgaggtc | acatgcgtgg | 840 |
| tggtggacgt | gagccacgaa | gaccctgagg | tcaagttcaa | ctggtacgtg | gacggcgtgg | 900 |
| aggtgcataa | tgccaagaca | aagccgcggg | aggagcagta | caacagcacg | taccgtgtgg | 960 |
| tcagcgtcct | caccgtcctg | caccaggact | ggctgaatgg | caaggagtac | aagtgcaagg | 1020 |
| tctccaacaa | agcccctccca | gcccccatcg | agaaaaccat | ctccaaagcc | aaagggcagc | 1080 |
| cccgagaacc | acaggtgtac | accctgcccc | catcccggga | tgagctgacc | aagaaccagg | 1140 |
| tcagcctgac | ctgcctggtc | aaaggcttct | atcccagcga | catcgccgtg | gagtgggaga | 1200 |
| gcaatgggca | gccggagaac | aactacaaga | ccacgcctcc | cgtgctggac | tccgacggct | 1260 |
| ccttcttcct | ctacagcaag | ctcaccgtgg | acaagagcag | gtggcagcag | gggaacgtct | 1320 |
| tctcatgctc | cgtgatgcat | gaggctctgc | acaaccacta | cacgcagaag | agcctctccc | 1380 |
| tgtctccggg | taaatcgagt | atgcactctg | accctgcccg | tcgaggtgag | ctgagcgtgt | 1440 |
| gtgacagtat | tagtgagtgg | gtaacggcgg | cagacaaaaa | gactgcagtg | gacatgtcgg | 1500 |
| gcgggacggt | cacagtcctt | gaaaaggtcc | ctgtatcaaa | aggccaactg | aagcaatact | 1560 |
| tctacgagac | caagtgcaat | cccatgggtt | acacaaaaga | aggctgcagg | ggcatagaca | 1620 |
| aaaggcattg | gaactcccag | tgccgaacta | cccagtcgta | cgtgcgggcc | cttaccatgg | 1680 |
| atagcaaaaa | gagaattggc | tggcgattca | taaggataga | cacttcttgt | gtatgtacat | 1740 |
| tgaccattaa | aaggtga | | | | | 1757 |

<210> SEQ ID NO 27
<211> LENGTH: 1749
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1746)

<400> SEQUENCE: 27

```
atg gaa tgc agc tgg gtc atg ctc ttc ctc ctg tca gga act gca ggt      48
Met Glu Cys Ser Trp Val Met Leu Phe Leu Leu Ser Gly Thr Ala Gly
1               5                   10                  15 gtc cat tgc cag gtt cag ctg cag cag tct gga cct gag ctg gtg aag      96
Val His Cys Gln Val Gln Leu Gln Gln Ser Gly Pro Glu Leu Val Lys
            20                  25                  30 cct ggg gct tta gtg aag ata tcc tgc aag gct tct ggt tac acc ttc     144
Pro Gly Ala Leu Val Lys Ile Ser Cys Lys Ala Ser Gly Tyr Thr Phe
        35                  40                  45 aca aac tac gat ata cac tgg gtg aag cag agg cct gga cag gga ctt     192
Thr Asn Tyr Asp Ile His Trp Val Lys Gln Arg Pro Gly Gln Gly Leu
    50                  55                  60 gag tgg att gga tgg att tat cct gga gat ggt agt act aag tac aat     240
Glu Trp Ile Gly Trp Ile Tyr Pro Gly Asp Gly Ser Thr Lys Tyr Asn
65                  70                  75                  80 gag aaa ttc aag ggc aag gcc aca ctg act gca gac aaa tcc tcc agc     288
Glu Lys Phe Lys Gly Lys Ala Thr Leu Thr Ala Asp Lys Ser Ser Ser
                85                  90                  95 aca gcc tac atg cac ctc agc agc ctg act tct gag aaa tct gca gtc     336
Thr Ala Tyr Met His Leu Ser Ser Leu Thr Ser Glu Lys Ser Ala Val
            100                 105                 110 tat ttc tgt gca aga gag tgg gct tac tgg ggc caa ggg act ctg gtc     384
Tyr Phe Cys Ala Arg Glu Trp Ala Tyr Trp Gly Gln Gly Thr Leu Val
        115                 120                 125 act gtc tct gca gct agc acc aag ggc cca tcg gtc ttc ccc ctg gca     432
Thr Val Ser Ala Ala Ser Thr Lys Gly Pro Ser Val Phe Pro Leu Ala
    130                 135                 140 ccc tcc tcc aag agc acc tct ggg ggc aca gcg gcc ctg ggc tgc ctg     480
Pro Ser Ser Lys Ser Thr Ser Gly Gly Thr Ala Ala Leu Gly Cys Leu
145                 150                 155                 160 gtc aag gac tac ttc ccc gaa ccg gtg acg gtg tcg tgg aac tca ggc     528
Val Lys Asp Tyr Phe Pro Glu Pro Val Thr Val Ser Trp Asn Ser Gly
                165                 170                 175 gcc ctg acc agc ggc gtg cac acc ttc ccg gct gtc cta cag tcc tca     576
Ala Leu Thr Ser Gly Val His Thr Phe Pro Ala Val Leu Gln Ser Ser
            180                 185                 190 gga ctc tac tcc ctc agc agc gtg gtg acc gtg ccc tcc agc agc ttg     624
Gly Leu Tyr Ser Leu Ser Ser Val Val Thr Val Pro Ser Ser Ser Leu
        195                 200                 205 ggc acc cag acc tac atc tgc aac gtg aat cac aag ccc agc aac acc     672
Gly Thr Gln Thr Tyr Ile Cys Asn Val Asn His Lys Pro Ser Asn Thr
    210                 215                 220 aag gtg gac aag aaa gtt gag ccc aaa tct tgt gac aaa act cac aca     720
Lys Val Asp Lys Lys Val Glu Pro Lys Ser Cys Asp Lys Thr His Thr
225                 230                 235                 240 tgc cca ccg tgc cca gca cct gaa ctc ctg ggg gga ccg tca gtc ttc     768
Cys Pro Pro Cys Pro Ala Pro Glu Leu Leu Gly Gly Pro Ser Val Phe
                245                 250                 255 ctc ttc ccc cca aaa ccc aag gac acc ctc atg atc tcc cgg acc cct     816
Leu Phe Pro Pro Lys Pro Lys Asp Thr Leu Met Ile Ser Arg Thr Pro
            260                 265                 270 gag gtc aca tgc gtg gtg gtg gac gtg agc cac gaa gac cct gag gtc     864
Glu Val Thr Cys Val Val Val Asp Val Ser His Glu Asp Pro Glu Val
        275                 280                 285 aag ttc aac tgg tac gtg gac ggc gtg gag gtg cat aat gcc aag aca     912
Lys Phe Asn Trp Tyr Val Asp Gly Val Glu Val His Asn Ala Lys Thr
    290                 295                 300 aag ccg cgg gag gag cag tac aac agc acg tac cgt gtg gtc agc gtc     960
Lys Pro Arg Glu Glu Gln Tyr Asn Ser Thr Tyr Arg Val Val Ser Val
```

```
ctc acc gtc ctg cac cag gac tgg ctg aat ggc aag gag tac aag tgc      1008
Leu Thr Val Leu His Gln Asp Trp Leu Asn Gly Lys Glu Tyr Lys Cys
                325                 330                 335 aag gtc tcc aac aaa gcc ctc cca gcc ccc atc gag aaa acc atc tcc      1056
Lys Val Ser Asn Lys Ala Leu Pro Ala Pro Ile Glu Lys Thr Ile Ser
            340                 345                 350 aaa gcc aaa ggg cag ccc cga gaa cca cag gtg tac acc ctg ccc cca      1104
Lys Ala Lys Gly Gln Pro Arg Glu Pro Gln Val Tyr Thr Leu Pro Pro
        355                 360                 365 tcc cgg gat gag ctg acc aag aac cag gtc agc ctg acc tgc ctg gtc      1152
Ser Arg Asp Glu Leu Thr Lys Asn Gln Val Ser Leu Thr Cys Leu Val
    370                 375                 380 aaa ggc ttc tat ccc agc gac atc gcc gtg gag tgg gag agc aat ggg      1200
Lys Gly Phe Tyr Pro Ser Asp Ile Ala Val Glu Trp Glu Ser Asn Gly
385                 390                 395                 400 cag ccg gag aac aac tac aag acc acg cct ccc gtg ctg gac tcc gac      1248
Gln Pro Glu Asn Asn Tyr Lys Thr Thr Pro Pro Val Leu Asp Ser Asp
                405                 410                 415 ggc tcc ttc ttc ctc tac agc aag ctc acc gtg gac aag agc agg tgg      1296
Gly Ser Phe Phe Leu Tyr Ser Lys Leu Thr Val Asp Lys Ser Arg Trp
            420                 425                 430 cag cag ggg aac gtc ttc tca tgc tcc gtg atg cat gag gct ctg cac      1344
Gln Gln Gly Asn Val Phe Ser Cys Ser Val Met His Glu Ala Leu His
        435                 440                 445 aac cac tac acg cag aag agc ctc tcc ctg tct ccg ggt aaa tcg agt      1392
Asn His Tyr Thr Gln Lys Ser Leu Ser Leu Ser Pro Gly Lys Ser Ser
    450                 455                 460 atg cac tct gac cct gcc cgt cga ggt gag ctg agc gtg tgt gac agt      1440
Met His Ser Asp Pro Ala Arg Arg Gly Glu Leu Ser Val Cys Asp Ser
465                 470                 475                 480 att agt gag tgg gta acg gcg gca gac aaa aag act gca gtg gac atg      1488
Ile Ser Glu Trp Val Thr Ala Ala Asp Lys Lys Thr Ala Val Asp Met
                485                 490                 495 tcg ggc ggg acg gtc aca gtc ctt gaa aag gtc cct gta tca aaa ggc      1536
Ser Gly Gly Thr Val Thr Val Leu Glu Lys Val Pro Val Ser Lys Gly
            500                 505                 510 caa ctg aag caa tac ttc tac gag acc aag tgc aat ccc atg ggt tac      1584
Gln Leu Lys Gln Tyr Phe Tyr Glu Thr Lys Cys Asn Pro Met Gly Tyr
        515                 520                 525 aca aaa gaa ggc tgc agg ggc ata gac aaa agg cat tgg aac tcc cag      1632
Thr Lys Glu Gly Cys Arg Gly Ile Asp Lys Arg His Trp Asn Ser Gln
    530                 535                 540 tgc cga act acc cag tcg tac gtg cgg gcc ctt acc atg gat agc aaa      1680
Cys Arg Thr Thr Gln Ser Tyr Val Arg Ala Leu Thr Met Asp Ser Lys
545                 550                 555                 560 aag aga att ggc tgg cga ttc ata agg ata gac act tct tgt gta tgt      1728
Lys Arg Ile Gly Trp Arg Phe Ile Arg Ile Asp Thr Ser Cys Val Cys
                565                 570                 575 aca ttg acc att aaa agg tga                                          1749
Thr Leu Thr Ile Lys Arg
            580

<210> SEQ ID NO 28
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

-continued

```
Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
```

```
              420             425              430
Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
            500                 505                 510

Gln Leu Lys Gln Tyr Phe Tyr Glu Thr Lys Cys Asn Pro Met Gly Tyr
        515                 520                 525

Thr Lys Glu Gly Cys Arg Gly Ile Asp Lys Arg His Trp Asn Ser Gln
    530                 535                 540

Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
                565                 570                 575

Thr Leu Thr Ile Lys Arg
            580
```

```
<210> SEQ ID NO 29
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gatatcacca tggagacaga cacactcctg ctatggctct tgttgctcat gtttccaggt    60
accagatgtg acatccagat gacccagtct ccatcctcct tatctgcctc tctgggagaa   120
agagtcagtc tcacttgtcg ggcaagtcag gacattggtg gtaacttata ctggcttcag   180
cagggaccag atggaactat taaacgcctg atctacgcca catccagttt agattctggt   240
gtccccaaaa ggttcagtgg cagtaggtct gggtcagatt attctctcac catcagcagc   300
cttgagtctg aagattttgt agactattac tgtctacagt attctagttc ccgtggacg    360 ttcggtggag cgacaaagat ggaaataaaa cgaactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttag          714

<210> SEQ ID NO 30
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)

<400> SEQUENCE: 30
```

| | | |
|---|---|---|
| atg gag aca gac aca ctc ctg cta tgg ctc ttg ttg ctc atg ttt cca<br>Met Glu Thr Asp Thr Leu Leu Leu Trp Leu Leu Leu Leu Met Phe Pro<br>1               5                   10                  15 | | 48 |
| ggt acc aga tgt gac atc cag atg acc cag tct cca tcc tcc tta tct<br>Gly Thr Arg Cys Asp Ile Gln Met Thr Gln Ser Pro Ser Ser Leu Ser<br>            20                  25                  30 | | 96 |
| gcc tct ctg gga gaa aga gtc agt ctc act tgt cgg gca agt cag gac<br>Ala Ser Leu Gly Glu Arg Val Ser Leu Thr Cys Arg Ala Ser Gln Asp<br>        35                  40                  45 | | 144 |
| att ggt ggt aac tta tac tgg ctt cag cag gga cca gat gga act att<br>Ile Gly Gly Asn Leu Tyr Trp Leu Gln Gln Gly Pro Asp Gly Thr Ile<br>    50                  55                  60 | | 192 |
| aaa cgc ctg atc tac gcc aca tcc agt tta gat tct ggt gtc ccc aaa<br>Lys Arg Leu Ile Tyr Ala Thr Ser Ser Leu Asp Ser Gly Val Pro Lys<br>65                  70                  75                  80 | | 240 |
| agg ttc agt ggc agt agg tct ggg tca gat tat tct ctc acc atc agc<br>Arg Phe Ser Gly Ser Arg Ser Gly Ser Asp Tyr Ser Leu Thr Ile Ser<br>                85                  90                  95 | | 288 |
| agc ctt gag tct gaa gat ttt gta gac tat tac tgt cta cag tat tct<br>Ser Leu Glu Ser Glu Asp Phe Val Asp Tyr Tyr Cys Leu Gln Tyr Ser<br>            100                 105                 110 | | 336 |
| agt tct ccg tgg acg ttc ggt gga gcg aca aag atg gaa ata aaa cga<br>Ser Ser Pro Trp Thr Phe Gly Gly Ala Thr Lys Met Glu Ile Lys Arg<br>        115                 120                 125 | | 384 |
| act gtg gct gca cca tct gtc ttc atc ttc ccg cca tct gat gag cag<br>Thr Val Ala Ala Pro Ser Val Phe Ile Phe Pro Pro Ser Asp Glu Gln<br>    130                 135                 140 | | 432 |
| ttg aaa tct gga act gcc tct gtt gtg tgc ctg ctg aat aac ttc tat<br>Leu Lys Ser Gly Thr Ala Ser Val Val Cys Leu Leu Asn Asn Phe Tyr<br>145                 150                 155                 160 | | 480 |
| ccc aga gag gcc aaa gta cag tgg aag gtg gat aac gcc ctc caa tcg<br>Pro Arg Glu Ala Lys Val Gln Trp Lys Val Asp Asn Ala Leu Gln Ser<br>                165                 170                 175 | | 528 |
| ggt aac tcc cag gag agt gtc aca gag cag gac agc aag gac agc acc<br>Gly Asn Ser Gln Glu Ser Val Thr Glu Gln Asp Ser Lys Asp Ser Thr<br>            180                 185                 190 | | 576 |
| tac agc ctc agc agc acc ctg acg ctg agc aaa gca gac tac gag aaa<br>Tyr Ser Leu Ser Ser Thr Leu Thr Leu Ser Lys Ala Asp Tyr Glu Lys<br>        195                 200                 205 | | 624 |
| cac aaa gtc tac gcc tgc gaa gtc acc cat cag ggc ctg agc tcg ccc<br>His Lys Val Tyr Ala Cys Glu Val Thr His Gln Gly Leu Ser Ser Pro<br>    210                 215                 220 | | 672 |
| gtc aca aag agc ttc aac agg gga gag tgt tag<br>Val Thr Lys Ser Phe Asn Arg Gly Glu Cys<br>225                 230 | | 705 |

<210> SEQ ID NO 31
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Glu Thr Asp Thr Leu Leu Leu Trp Leu Leu Leu Leu Met Phe Pro
1               5                   10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
 50                  55                  60

Lys Arg Leu Ile Tyr Ala Thr Ser Ser Leu Asp Ser Gly Val Pro Lys
 65                  70                  75                  80

Arg Phe Ser Gly Ser Arg Ser Gly Ser Asp Tyr Ser Leu Thr Ile Ser
                 85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Ala Thr Lys Met Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 32
<211> LENGTH: 6505
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cgatgtacgg gccagatata cgcgttgaca ttgattattg actagttatt aatagtaatc      60
aattacgggg tcattagttc atagcccata tatggagttc cgcgttacat aacttacggt     120
aaatggcccg cctggctgac cgcccaacga ccccgcccca ttgacgtcaa taatgacgta     180
tgttcccata gtaacgccaa tagggacttt ccattgacgt caatgggtgg agtatttacg     240
gtaaactgcc cacttggcag tacatcaagt gtatcatatg ccaagtacgc cccctattga     300
cgtcaatgac ggtaaatggc ccgcctggca ttatgcccag tacatgacct tatgggactt     360
tcctacttgg cagtacatct acgtattagt catcgctatt accatggtga tgcggttttg     420
gcagtacatc aatgggcgtg gatagcggtt tgactcacgg ggatttccaa gtctccaccc     480
cattgacgtc aatgggagtt gttttggca ccaaaatcaa cgggactttc caaaatgtcg      540
taacaactcc gccccattga cgcaaatggg cggtaggcgt gtacggtggg aggtctatat     600
aagcagagct ctctggctaa ctagagaacc cactgcttac tggcttatcg aaattaatac     660
gactcactat agggagaccc ttgctagcga tattccacca tggaatgcag ctgggtcatg     720
ctcttcctcc tgtcaggaac tgcaggtgtc cattgccagg ttcagctgca gcagtctgga     780
cctgagctgg tgaagcctgg ggctttagtg aagatatcct gcaaggcttc tggttacacc     840
ttcacaaact acgatataca ctgggtgaag cagaggcctg acagggact tgagtggatt      900 ggatggattt atcctggaga tggtagtact aagtacaatg agaaattcaa gggcaaggcc     960

-continued

```
acactgactg cagacaaatc ctccagcaca gcctacatgc acctcagcag cctgacttct      1020
gagaaatctg cagtctattt ctgtgcaaga gagtgggctt actggggcca agggactctg      1080
gtcactgtct ctgcagctag caccaagggc ccatcggtct tccccctggc accctcctcc      1140
aagagcacct ctgggggcac agcggccctg ggctgcctgg tcaaggacta cttccccgaa      1200
ccggtgacgg tgtcgtggaa ctcaggcgcc ctgaccagcg gcgtgcacac cttcccggct      1260
gtcctacagt cctcaggact ctactccctc agcagcgtgg tgaccgtgcc ctccagcagc      1320
ttgggcaccc agacctacat ctgcaacgtg aatcacaagc ccagcaacac caaggtggac      1380
aagaaagttg agcccaaatc ttgtgacaaa actcacacat gcccaccgtg cccagcacct      1440
gaactcctgg ggggaccgtc agtcttcctc ttccccccaa acccaagga caccctcatg       1500 atctcccgga cccctgaggt cacatgcgtg gtggtggacg tgagccacga agaccctgag      1560
gtcaagttca actggtacgt ggacggcgtg gaggtgcata atgccaagac aaagccgcgg      1620
gaggagcagt acaacagcac gtaccgtgtg gtcagcgtcc tcaccgtcct gcaccaggac      1680
tggctgaatg gcaaggagta caagtgcaag gtctccaaca aagccctccc agcccccatc      1740
gagaaaacca tctccaaagc caaagggcag ccccgagaac cacaggtgta caccctgccc      1800
ccatcccggg atgagctgac caagaaccag gtcagcctga cctgcctggt caaaggcttc      1860
tatcccagcg acatcgccgt ggagtgggag agcaatgggc agccggagaa caactacaag      1920
accacgcctc ccgtgctgga ctccgacggc tccttcttcc tctacagcaa gctcaccgtg      1980
gacaagagca ggtggcagca ggggaacgtc ttctcatgct ccgtgatgca tgaggctctg      2040
cacaaccact acacgcagaa gagcctctcc ctgtctccgg gtaaatcgag tatgcactct      2100
gaccctgccc gtcgaggtga gctgagcgtg tgtgacagta ttagtgagtg ggtaacggcg      2160
gcagacaaaa agactgcagt ggacatgtcg ggcgggacgg tcacagtcct tgaaaaggtc      2220
cctgtatcaa aaggccaact gaagcaatac ttctacagaga ccaagtgcaa tcccatgggt      2280
tacacaaaag aaggctgcag gggcatagac aaaaggcatt ggaactccca gtgccgaact      2340
acccagtcgt acgtgcgggc ccttaccatg gatagcaaaa agagaattgg ctggcgattc      2400
ataaggatag acacttcttg tgtatgtaca ttgaccatta aaaggtgagg atccctcgag      2460
catgcatcta gagggcccta ttctatagtg tcacctaaat gctagagctc gctgatcagc      2520
ctcgactgtg ccttctagtt gccagccatc tgttgtttgc ccctcccccg tgccttcctt      2580
gaccctggaa ggtgccactc ccactgtcct ttcctaataa aatgaggaaa ttgcatcgca      2640
ttgtctgagt aggtgtcatt ctattctggg ggtggggtg gggcaggaca gcaaggggga       2700
ggattgggaa gacaatagca ggcatgctgg ggatgcggtg gctctatgg cttctgaggc       2760 ggaaagaacc agtggcggta atacggttat ccacagaatc aggggataac gcaggaaaga     2820
acatgtgagc aaaaggccag caaaaggcca ggaaccgaat tcgatattcc atacacatac      2880
ttctgtgttc ctttgaaagc tggacttttg caggctccac cagacctctc tagatcaatt      2940
cctttgccta atttcgctta caatttacgc gcgcgttgac attgattatt gactagttat      3000
taatagtaat caattacggg gtcattagtt catagcccat atatggagtt ccgcgttaca      3060
taacttacgg taaatggccc gcctggctga ccgcccaacg acccccgccc attgacgtca      3120
ataatgacgt atgttcccat agtaacgcca tagggacttt ccattgacg tcaatgggtg       3180 gagtatttac ggtaaactgc ccacttggca gtacatcaag tgtatcatat gccaagtacg      3240 cccccctattg acgtcaatga cggtaaatgg cccgcctggc attatgccca gtacatgacc      3300
ttatgggact ttcctacttg gcagtacatc tacgtattag tcatcgctat taccatggtg      3360
```

```
atgcggtttt ggcagtacat caatgggcgt ggatagcggt ttgactcacg gggatttcca    3420
agtctccacc ccattgacgt caatgggagt ttgttttggc accaaaatca acgggacttt    3480
ccaaaatgtc gtaacaactc cgccccattg acgcaaatgg gcggtaggcg tgtacggtgg    3540
gaggtctata taagcagagc tctctggcta actagagaac ccactgctta ctggcttatc    3600
gaaattaata cgactcacta tagggagacc caagctggct agcgatatca ccatggagac    3660
agacacactc ctgctatggc tcttgttgct catgtttcca ggtaccagat gtgacatcca    3720
gatgacccag tctccatcct ccttatctgc ctctctggga aaagagtca gtctcacttg    3780
tcgggcaagt caggacattg gtggtaactt atactggctt cagcagggac cagatggaac    3840
tattaaacgc ctgatctacg ccacatccag tttagattct ggtgtcccca aaaggttcag    3900
tggcagtagg tctgggtcag attattctct caccatcagc agccttgagt ctgaagattt    3960
tgtagactat tactgtctac agtattctag ttctccgtgg acgttcggtg gagcgacaaa    4020
gatgaaaata aaacgaactg tggctgcacc atctgtcttc atcttcccgc catctgatga    4080
gcagttgaaa tctggaactg cctctgttgt gtgcctgctg aataacttct atcccagaga    4140
ggccaaagta cagtggaagg tggataacgc cctccaatcg ggtaactccc aggagagtgt    4200
cacagagcag gacagcaagg acagcaccta cagcctcagc agcaccctga cgctgagcaa    4260
agcagactac gagaaacaca agtctacgc ctgcgaagtc acccatcagg gcctgagctc    4320
gcccgtcaca aagagcttca cagggagaa gtgttagctc gagtctagag ggcccgttta    4380
aacccgctga tcagcctcga ctgtgccttc tagttgccag ccatctgttg tttgcccctc    4440
ccccgtgcct tccttgaccc tggaaggtgc cactcccact gtcctttcct aataaaatga    4500
ggaaattgca tcgcattgtc tgagtaggtg tcattctatt ctgggggtg gggtggggca    4560
ggacagcaag ggggaggatt gggaagacaa tagcaggcat gctggggatg cggtgggctc    4620
tatggcttct gaggcggaaa gaaccagtgg cggtaatacg gttatccaca gaatcagggg    4680
ataacgaaat gaggacttaa cctgtggaaa tatcaagctt gcggccgcgt atcgacgctc    4740
tcccttatgc gactcctgca ttaggaagca gcccagtagt aggttgaggc cgttgagcac    4800
cgccgccgca aggaatggtg catgcaagga gatggcgccc aacagtcccc cggccacggg    4860
gcctgccacc atacccacgc cgaaacaagc gctcatgagc ccgaagtggc gagcccgatc    4920
ttccccatcg gtgatgtcgg cgatataggc gccagcaacc gcacctgtgg cgccggtgat    4980
gccggccacg atgcgtccgg cgtagaggat ctctgacgga aggaaagaag tcagaaggca    5040
aaaacgagag taactccaca gtagctccaa attctttata agggtcaatg tccatgcccc    5100
aaagccaccc aaggcacagc ttggaggctt gaacagtggg acatgtacaa gagatgatta    5160
ggcagaggtg aaaagttgc atggtgctgg tgcgcagacc aatttatgcc tacagcctcc    5220
taatacaaag accttaacc taatctcctc ccccagctcc tcccagtcct aaacacaca    5280
gtctttgaag taggcctcaa ggtcggtcgt tgacattgct gggagtccaa gagtcctctt    5340
atgtaagacc ttgggcagga tctgatgggc gttcacggtg gtctccatgc aacgtgcaga    5400
ggtgaagcga agtgcacacg gaccggcaga tgagaaggca cagacgggga gaccgcgtaa    5460
agagaggtgc gccccgtggt cggctggaac ggcagacgga aagggacg agagagtccc    5520
aagcggcccc gcgaggggtc gtccgcggga ttcagcgccg acgggacgta aacaaaggac    5580
gtcccgcgaa ggatctaaag ccagcaaaag tcccatggtc ttataaaaat gcatagcttt    5640
aggaggggag cagagaactt gaaagcatct tcctgttagt cttcttctc gtagacttca    5700
aacttatact tgatgccttt ttcctcctgg acctcagaga ggacgcctgg gtattctggg    5760
```

-continued

```
agaagtttat atttccccaa atcaatttct gggaaaaacg tgtcactttc aaattcctgc    5820
atgatccttg tcacaaagag tctgaggtgg cctggttgat tcatggcttc ctggtaaaca    5880
gaactgcctc cgactatcca aaccatgtct actttacttg ccaattccgg ttgttcaata    5940
agtcttaagg catcatccaa acttttggca agaaaatgag ctcctcgtgg tggttctttg    6000
agttctctac tgagaactat attaattctg tcctttaaag gtcgattctt ctcaggaatg    6060
gagaaccagg ttttcctacc cataatcacc agattctgtt taccttccac tgaagaggtt    6120
gtggtcattc tttggaagta cttgaactcg ttcctgagcg gaggccaggg tcggtctccg    6180
ttcttgccaa tccccatatt ttgggacacg gcgacgatgc agttcaatgg tcgaaccatg    6240
atggcaaatt ctagaatcga taagcttttt gcaaaagcct aggcctccaa aaaagcctcc    6300
tcactacttc tggaatagct cagaggccga ggcggcctcg gcctctgcat aaataaaaaa    6360
aattagtcag ccatggggcg gagaatgggc ggaactgggc ggagttaggg gcgggatggg    6420
cggagttagg ggcgggacta tggttgctga ctaattgaga tgcagatctc gagctagcac    6480
gcgtaagagc tcggtacctc cctac                                          6505
```

<210> SEQ ID NO 33
<211> LENGTH: 1749
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(1746)

<400> SEQUENCE: 33

```
atg gaa tgc agc tgg gtc atg ctc ttc ctc ctg tca gga act gca ggt     48
Met Glu Cys Ser Trp Val Met Leu Phe Leu Leu Ser Gly Thr Ala Gly
1               5                   10                  15 gtc cat tgc cag gtt cag ctg cag cag tct gga cct gag ctg gtg aag     96
Val His Cys Gln Val Gln Leu Gln Gln Ser Gly Pro Glu Leu Val Lys
            20                  25                  30 cct ggg gct tta gtg aag ata tcc tgc aag gct tct ggt tac acc ttc    144
Pro Gly Ala Leu Val Lys Ile Ser Cys Lys Ala Ser Gly Tyr Thr Phe
        35                  40                  45 aca aac tac gat ata cac tgg gtg aag cag agg cct gga cag gga ctt    192
Thr Asn Tyr Asp Ile His Trp Val Lys Gln Arg Pro Gly Gln Gly Leu
    50                  55                  60 gag tgg att gga tgg att tat cct gga gat ggt agt act aag tac aat    240
Glu Trp Ile Gly Trp Ile Tyr Pro Gly Asp Gly Ser Thr Lys Tyr Asn
65                  70                  75                  80 gag aaa ttc aag ggc aag gcc aca ctg act gca gac aaa tcc tcc agc    288
Glu Lys Phe Lys Gly Lys Ala Thr Leu Thr Ala Asp Lys Ser Ser Ser
                85                  90                  95 aca gcc tac atg cac ctc agc agc ctg act tct gag aaa tct gca gtc    336
Thr Ala Tyr Met His Leu Ser Ser Leu Thr Ser Glu Lys Ser Ala Val
            100                 105                 110 tat ttc tgt gca aga gag tgg gct tac tgg ggc caa ggg act ctg gtc    384
Tyr Phe Cys Ala Arg Glu Trp Ala Tyr Trp Gly Gln Gly Thr Leu Val
        115                 120                 125 act gtc tct gca gct agc acc aag ggc cca tcg gtc ttc ccc ctg gca    432
Thr Val Ser Ala Ala Ser Thr Lys Gly Pro Ser Val Phe Pro Leu Ala
    130                 135                 140 ccc tcc tcc aag agc acc tct ggg ggc aca gcg gcc ctg ggc tgc ctg    480
Pro Ser Ser Lys Ser Thr Ser Gly Gly Thr Ala Ala Leu Gly Cys Leu
145                 150                 155                 160
```

```
gtc aag gac tac ttc ccc gaa ccg gtg acg gtg tcg tgg aac tca ggc         528
Val Lys Asp Tyr Phe Pro Glu Pro Val Thr Val Ser Trp Asn Ser Gly
            165                 170                 175 gcc ctg acc agc ggc gtg cac acc ttc ccg gct gtc cta cag tcc tca         576
Ala Leu Thr Ser Gly Val His Thr Phe Pro Ala Val Leu Gln Ser Ser
        180                 185                 190 gga ctc tac tcc ctc agc agc gtg gtg acc gtg ccc tcc agc agc ttg         624
Gly Leu Tyr Ser Leu Ser Ser Val Val Thr Val Pro Ser Ser Ser Leu
    195                 200                 205 ggc acc cag acc tac atc tgc aac gtg aat cac aag ccc agc aac acc         672
Gly Thr Gln Thr Tyr Ile Cys Asn Val Asn His Lys Pro Ser Asn Thr
210                 215                 220 aag gtg gac aag aaa gtt gag ccc aaa tct tgt gac aaa act cac aca         720
Lys Val Asp Lys Lys Val Glu Pro Lys Ser Cys Asp Lys Thr His Thr
225                 230                 235                 240 tgc cca ccg tgc cca gca cct gaa ctc ctg ggg gga ccg tca gtc ttc         768
Cys Pro Pro Cys Pro Ala Pro Glu Leu Leu Gly Gly Pro Ser Val Phe
            245                 250                 255 ctc ttc ccc cca aaa ccc aag gac acc ctc atg atc tcc cgg acc cct         816
Leu Phe Pro Pro Lys Pro Lys Asp Thr Leu Met Ile Ser Arg Thr Pro
        260                 265                 270 gag gtc aca tgc gtg gtg gtg gac gtg agc cac gaa gac cct gag gtc         864
Glu Val Thr Cys Val Val Val Asp Val Ser His Glu Asp Pro Glu Val
    275                 280                 285 aag ttc aac tgg tac gtg gac ggc gtg gag gtg cat aat gcc aag aca         912
Lys Phe Asn Trp Tyr Val Asp Gly Val Glu Val His Asn Ala Lys Thr
290                 295                 300 aag ccg cgg gag gag cag tac aac agc acg tac cgt gtg gtc agc gtc         960
Lys Pro Arg Glu Glu Gln Tyr Asn Ser Thr Tyr Arg Val Val Ser Val
305                 310                 315                 320 ctc acc gtc ctg cac cag gac tgg ctg aat ggc aag gag tac aag tgc        1008
Leu Thr Val Leu His Gln Asp Trp Leu Asn Gly Lys Glu Tyr Lys Cys
            325                 330                 335 aag gtc tcc aac aaa gcc ctc cca gcc ccc atc gag aaa acc atc tcc        1056
Lys Val Ser Asn Lys Ala Leu Pro Ala Pro Ile Glu Lys Thr Ile Ser
        340                 345                 350 aaa gcc aaa ggg cag ccc cga gaa cca cag gtg tac acc ctg ccc cca        1104
Lys Ala Lys Gly Gln Pro Arg Glu Pro Gln Val Tyr Thr Leu Pro Pro
    355                 360                 365 tcc cgg gat gag ctg acc aag aac cag gtc agc ctg acc tgc ctg gtc        1152
Ser Arg Asp Glu Leu Thr Lys Asn Gln Val Ser Leu Thr Cys Leu Val
370                 375                 380 aaa ggc ttc tat ccc agc gac atc gcc gtg gag tgg gag agc aat ggg        1200
Lys Gly Phe Tyr Pro Ser Asp Ile Ala Val Glu Trp Glu Ser Asn Gly
385                 390                 395                 400 cag ccg gag aac aac tac aag acc acg cct ccc gtg ctg gac tcc gac        1248
Gln Pro Glu Asn Asn Tyr Lys Thr Thr Pro Pro Val Leu Asp Ser Asp
            405                 410                 415 ggc tcc ttc ttc ctc tac agc aag ctc acc gtg gac aag agc agg tgg        1296
Gly Ser Phe Phe Leu Tyr Ser Lys Leu Thr Val Asp Lys Ser Arg Trp
        420                 425                 430 cag cag ggg aac gtc ttc tca tgc tcc gtg atg cat gag gct ctg cac        1344
Gln Gln Gly Asn Val Phe Ser Cys Ser Val Met His Glu Ala Leu His
    435                 440                 445 aac cac tac acg cag aag agc ctc tcc ctg tct ccg ggt aaa tcg agt        1392
Asn His Tyr Thr Gln Lys Ser Leu Ser Leu Ser Pro Gly Lys Ser Ser
450                 455                 460 atg cac tct gac cct gcc cgt cga ggt gag ctg agc gtg tgt gac agt        1440
Met His Ser Asp Pro Ala Arg Arg Gly Glu Leu Ser Val Cys Asp Ser
465                 470                 475                 480
```

```
att agt gag tgg gta acg gcg gca gac aaa aag act gca gtg gac atg    1488
Ile Ser Glu Trp Val Thr Ala Ala Asp Lys Lys Thr Ala Val Asp Met
            485                 490                 495 tcg ggc ggg acg gtc aca gtc ctt gaa aag gtc cct gta tca aaa ggc    1536
Ser Gly Gly Thr Val Thr Val Leu Glu Lys Val Pro Val Ser Lys Gly
        500                 505                 510 caa ctg aag caa tac ttc tac gag acc aag tgc aat ccc atg ggt tac    1584
Gln Leu Lys Gln Tyr Phe Tyr Glu Thr Lys Cys Asn Pro Met Gly Tyr
    515                 520                 525 aca aaa gaa ggc tgc agg ggc ata gac aaa agg cat tgg aac tcc cag    1632
Thr Lys Glu Gly Cys Arg Gly Ile Asp Lys Arg His Trp Asn Ser Gln
530                 535                 540 tgc cga act acc cag tcg tac gtg cgg gcc ctt acc atg gat agc aaa    1680
Cys Arg Thr Thr Gln Ser Tyr Val Arg Ala Leu Thr Met Asp Ser Lys
545                 550                 555                 560 aag aga att ggc tgg cga ttc ata agg ata gac act tct tgt gta tgt    1728
Lys Arg Ile Gly Trp Arg Phe Ile Arg Ile Asp Thr Ser Cys Val Cys
                565                 570                 575 aca ttg acc att aaa agg tga                                        1749
Thr Leu Thr Ile Lys Arg
            580

<210> SEQ ID NO 34
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220
```

```
Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
            500                 505                 510

Gln Leu Lys Gln Tyr Phe Tyr Glu Thr Lys Cys Asn Pro Met Gly Tyr
        515                 520                 525

Thr Lys Glu Gly Cys Arg Gly Ile Asp Lys Arg His Trp Asn Ser Gln
    530                 535                 540

Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
                565                 570                 575

Thr Leu Thr Ile Lys Arg
            580

<210> SEQ ID NO 35
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (1)..(702)

<400> SEQUENCE: 35

```
atg gag aca gac aca ctc ctg cta tgg ctc ttg ttg ctc atg ttt cca        48
Met Glu Thr Asp Thr Leu Leu Leu Trp Leu Leu Leu Leu Met Phe Pro
1               5                   10                  15 ggt acc aga tgt gac atc cag atg acc cag tct cca tcc tcc tta tct        96
Gly Thr Arg Cys Asp Ile Gln Met Thr Gln Ser Pro Ser Ser Leu Ser
            20                  25                  30 gcc tct ctg gga gaa aga gtc agt ctc act tgt cgg gca agt cag gac       144
Ala Ser Leu Gly Glu Arg Val Ser Leu Thr Cys Arg Ala Ser Gln Asp
        35                  40                  45 att ggt ggt aac tta tac tgg ctt cag cag gga cca gat gga act att       192
Ile Gly Gly Asn Leu Tyr Trp Leu Gln Gln Gly Pro Asp Gly Thr Ile
    50                  55                  60 aaa cgc ctg atc tac gcc aca tcc agt tta gat tct ggt gtc ccc aaa       240
Lys Arg Leu Ile Tyr Ala Thr Ser Ser Leu Asp Ser Gly Val Pro Lys
65                  70                  75                  80 agg ttc agt ggc agt agg tct ggg tca gat tat tct ctc acc atc agc       288
Arg Phe Ser Gly Ser Arg Ser Gly Ser Asp Tyr Ser Leu Thr Ile Ser
                85                  90                  95 agc ctt gag tct gaa gat ttt gta gac tat tac tgt cta cag tat tct       336
Ser Leu Glu Ser Glu Asp Phe Val Asp Tyr Tyr Cys Leu Gln Tyr Ser
            100                 105                 110 agt tct ccg tgg acg ttc ggt gga gcg aca aag atg gaa ata aaa cga       384
Ser Ser Pro Trp Thr Phe Gly Gly Ala Thr Lys Met Glu Ile Lys Arg
        115                 120                 125 act gtg gct gca cca tct gtc ttc atc ttc ccg cca tct gat gag cag       432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat       480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg       528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc       576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa       624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc       672
His Lys Val Tyr Ala Cys Glu Val Thr His Gln Gly Leu Ser Ser Pro
    210                 215                 220 gtc aca aag agc ttc aac agg gga gag tgt tag                           705
Val Thr Lys Ser Phe Asn Arg Gly Glu Cys
225                 230
```

<210> SEQ ID NO 36
<211> LENGTH: 234
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 36

```
Met Glu Thr Asp Thr Leu Leu Leu Trp Leu Leu Leu Leu Met Phe Pro
1               5                   10                  15

Gly Thr Arg Cys Asp Ile Gln Met Thr Gln Ser Pro Ser Ser Leu Ser
            20                  25                  30
```

```
Ala Ser Leu Gly Glu Arg Val Ser Leu Thr Cys Arg Ala Ser Gln Asp
            35                  40                  45

Ile Gly Gly Asn Leu Tyr Trp Leu Gln Gln Gly Pro Asp Gly Thr Ile
 50                  55                  60

Lys Arg Leu Ile Tyr Ala Thr Ser Ser Leu Asp Ser Gly Val Pro Lys
 65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
                100                 105                 110

Ser Ser Pro Trp Thr Phe Gly Ala Thr Lys Met Glu Ile Lys Arg
            115                 120                 125

Thr Val Ala Ala Pro Ser Val Phe Ile Phe Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 37
<211> LENGTH: 564
<212> TYPE: DNA
<213> ORGANISM: Mus musculus
<220> FEATURE:
<221> NAME/KEY: CDS
<222> LOCATION: (1)..(561)

<400> SEQUENCE: 37 atg gtt cga cca ttg aac tgc atc gtc gcc gtg tcc caa aat atg ggg   48
Met Val Arg Pro Leu Asn Cys Ile Val Ala Val Ser Gln Asn Met Gly
 1               5                  10                  15 att ggc aag aac gga gac cga ccc tgg cct ccg ctc agg aac gag ttc   96
Ile Gly Lys Asn Gly Asp Arg Pro Trp Pro Pro Leu Arg Asn Glu Phe
                20                  25                  30 aag tac ttc caa aga atg acc aca acc tct tca gtg gaa ggt aaa cag  144
Lys Tyr Phe Gln Arg Met Thr Thr Thr Ser Ser Val Glu Gly Lys Gln
            35                  40                  45 aat ctg gtg att atg ggt agg aaa acc tgg ttc tcc att cct gag aag  192
Asn Leu Val Ile Met Gly Arg Lys Thr Trp Phe Ser Ile Pro Glu Lys
 50                  55                  60 aat cga cct tta aag gac aga att aat ata gtt ctc agt aga gaa ctc  240
Asn Arg Pro Leu Lys Asp Arg Ile Asn Ile Val Leu Ser Arg Glu Leu
 65                  70                  75                  80 aaa gaa cca cca cga gga gct cat ttt ctt gcc aaa agt ttg gat gat  288
Lys Glu Pro Pro Arg Gly Ala His Phe Leu Ala Lys Ser Leu Asp Asp
                85                  90                  95 gcc tta aga ctt att gaa caa ccg gaa ttg gca agt aaa gta gac atg  336
Ala Leu Arg Leu Ile Glu Gln Pro Glu Leu Ala Ser Lys Val Asp Met
                100                 105                 110 gtt tgg ata gtc gga ggc agt tct gtt tac cag gaa gcc atg aat caa  384
Val Trp Ile Val Gly Gly Ser Ser Val Tyr Gln Glu Ala Met Asn Gln
```

```
Val Trp Ile Val Gly Gly Ser Ser Val Tyr Gln Glu Ala Met Asn Gln
        115                 120                 125 cca ggc cac ctc aga ctc ttt gtg aca agg atc atg cag gaa ttt gaa        432
Pro Gly His Leu Arg Leu Phe Val Thr Arg Ile Met Gln Glu Phe Glu
        130                 135                 140 agt gac acg ttt ttc cca gaa att gat ttg ggg aaa tat aaa ctt ctc        480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc        528
Pro Glu Tyr Pro Gly Val Leu Ser Glu Val Gln Glu Glu Lys Gly Ile
                165                 170                 175 aag tat aag ttt gaa gtc tac gag aag aaa gac taa                        564
Lys Tyr Lys Phe Glu Val Tyr Glu Lys Lys Asp
                180                 185

<210> SEQ ID NO 38
<211> LENGTH: 187
<212> TYPE: PRT
<213> ORGANISM: Mus musculus

<400> SEQUENCE: 38

Met Val Arg Pro Leu Asn Cys Ile Val Ala Val Ser Gln Asn Met Gly
1               5                   10                  15

Ile Gly Lys Asn Gly Asp Arg Pro Trp Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Val Tyr Gln Glu Ala Met Asn Gln
        115                 120                 125

Pro Gly His Leu Arg Leu Phe Val Thr Arg Ile Met Gln Glu Phe Glu
        130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
                180                 185

<210> SEQ ID NO 39
<211> LENGTH: 119
<212> TYPE: PRT
<213> ORGANISM: Homo sapiens

<400> SEQUENCE: 39

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45
```

```
Leu Lys Gln Tyr Phe Tyr Glu Thr Lys Cys Asn Pro Met Gly Tyr Thr
         50                  55                  60

Lys Glu Gly Cys Arg Gly Ile Asp Lys Arg His Trp Asn Ser Gln Cys
 65                  70                  75                  80

Arg Thr Thr Gln Ser Tyr Val Arg Ala Leu Thr Met Asp Ser Lys Lys
                 85                  90                  95

Arg Ile Gly Trp Arg Phe Ile Arg Ile Asp Thr Ser Cys Val Cys Thr
            100                 105                 110

Leu Thr Ile Lys Arg Gly Arg
            115

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atgaagttat gggatgtcgt ggctg                                    25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcagatacat ccacaccttt tagcg                                    25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catcaccaga taaacaaatg gcagtg                                   26

<210> SEQ ID NO 43
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgaagttat gggatgtcgt ggctgtctgc ctggtgctgc tccacaccgc gtccgccttc     60
ccgctgcccg ccggtaagag gcctcccgag gcgcccgccg aagaccgctc cctcggccgc    120
cgccgcgcgc ccttcgcgct gagcagtgac tcaaatatgc cagaggatta tcctgatcag    180
ttcgatgatg tcatggattt tattcaagcc accattaaaa gactgaaaag gtcaccagat    240
aaacaaatgg cagtgcttcc tagaagagag cggaatcgga ggctgcagc tgccaaccca    300 gagaattcca gaggaaaagg tcggagaggc cagaggggca aaaaccgggg ttgtgtctta    360
actgcaatac atttaaatgt cactgacttg ggtctgggct atgaaaccaa ggaggaactg    420
atttttaggt actgcagcgg ctcttgcgat gcagctgaga caacgtacga caaaatattg    480
```

```
aaaaacttat ccagaaatag aaggctggtg agtgacaaag tagggcaggc atgttgcaga    540
cccatcgcct ttgatgatga cctgtcgttt ttagatgata acctggttta ccatattcta    600
agaaagcatt ccgctaaaag gtgtggatgt atctga                              636
```

```
<210> SEQ ID NO 44
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Ala Pro Phe Ala Leu Ser
        35                  40                  45

Ser Asp Ser Asn Met Pro Glu Asp Tyr Pro Asp Gln Phe Asp Val
50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210

```
<210> SEQ ID NO 45
<211> LENGTH: 1797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggactgga cctggagggt gttctgcctg cttgcagtgg cccccggagc ccacagccag    60
gttcagctgc agcagtctgg acctgagctg gtgaagcctg ggctttagt gaagatatcc    120 tgcaaggctt ctggttacac cttcacaaac tacgatatac actgggtgaa gcagaggcct    180
ggacagggac ttgagtggat tgatggatt tatcctggag atggtagtac taagtacaat    240
gagaaattca aggcaaggc cacactgact gcagacaaat cctccagcac agcctacatg    300
```

```
cacctcagca gcctgacttc tgagaaatct gcagtctatt tctgtgcaag agagtgggct    360
tactggggcc aagggactct ggtcactgtc tctgcagcta gcaccaaggg cccatcggtc    420
ttccccctgg cacctcctc caagagcacc tctgggggca gcggccct gggctgcctg      480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcctg ggggaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc    1260
ctctacagca agctcaccgt ggacaagagc aggtggcagc aggggaacgt cttctcatgc   1320
tccgtgatgc atgaggctct gcacaaccac tacacgcaga gagcctctc cctgtctccg    1380
ggtaaaagtt catcaccaga taaacaaatg gcagtgcttc ctagaagaga gcggaatcgg   1440
caggctgcag ctgccaaccc agagaattcc agaggaaaag gtcggagagg ccagagggc    1500
aaaaaccggg gttgtgtctt aactgcaata catttaaatg tcactgactt gggtctgggc   1560
tatgaaacca aggaggaact gattttagg tactgcagcg gctcttgcga tgcagctgag    1620
acaacgtacg acaaaatatt gaaaaactta tccagaaata gaaggctggt gagtgacaaa   1680
gtagggcagg catgttgcag acccatcgcc tttgatgatg acctgtcgtt tttagatgat   1740
aacctggttt accatattct aagaaagcat tccgctaaaa ggtgtggatg tatctga    1797
```

<210> SEQ ID NO 46
<211> LENGTH: 598
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

-continued

```
Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Ser Pro Asp Lys Gln Met Ala Val Leu Pro Arg Arg Glu Arg Asn Arg
465                 470                 475                 480

Gln Ala Ala Ala Ala Asn Pro Glu Asn Ser Arg Gly Lys Gly Arg Arg
                485                 490                 495

Gly Gln Arg Gly Lys Asn Arg Gly Cys Val Leu Thr Ala Ile His Leu
            500                 505                 510

Asn Val Thr Asp Leu Gly Leu Gly Tyr Glu Thr Lys Glu Glu Leu Ile
        515                 520                 525
```

Phe Arg Tyr Cys Ser Gly Ser Cys Asp Ala Ala Glu Thr Thr Tyr Asp
                530                 535                 540

Lys Ile Leu Lys Asn Leu Ser Arg Asn Arg Arg Leu Val Ser Asp Lys
545                 550                 555                 560

Val Gly Gln Ala Cys Cys Arg Pro Ile Ala Phe Asp Asp Leu Ser
                565                 570                 575

Phe Leu Asp Asp Asn Leu Val Tyr His Ile Leu Arg Lys His Ser Ala
                580                 585                 590

Lys Arg Cys Gly Cys Ile
        595

<210> SEQ ID NO 47
<211> LENGTH: 6342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

| | | | | | |
|---|---|---|---|---|---|
| gttgacattg | attattgact | agttattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtacgcccc | ctattgacgt | caatgacggt | aaatggcccg | 300 |
| cctggcatta | tgcccagtac | atgaccttat | gggactttcc | tacttggcag | tacatctacg | 360 |
| tattagtcat | cgctattacc | atggtgatgc | ggttttggca | gtacatcaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | caactccgcc | ccattgacgc | 540 |
| aaatgggcgg | taggcgtgta | cggtgggagg | tctatataag | cagagctctc | tggctaacta | 600 |
| gagaacccac | tgcttactgg | cttatcgaaa | ttaatacgac | tcactatagg | gagacccaag | 660 |
| ctggctagcg | tttaaactta | agcttggtac | cgagctcgga | tccactagtc | cagtgtggtg | 720 |
| gaattctgca | gccgccacc | atggagaccc | ccgcccagct | gctgttcctg | ttgctgcttt | 780 |
| ggcttccaga | tactaccggc | gacatccaga | tgacccagtc | tccatcctcc | ttatctgcct | 840 |
| ctctgggaga | aagagtcagt | ctcacttgtc | gggcaagtca | ggacattggt | ggtaacttat | 900 |
| actggcttca | gcagggacca | gatggaacta | ttaaacgcct | gatctacgcc | acatccagtt | 960 |
| tagattctgg | tgtccccaaa | aggttcagtg | gcagtaggtc | tgggtcagat | tattctctca | 1020 |
| ccatcagcag | ccttgagtct | gaagattttg | tagactatta | ctgtctacag | tattctagtt | 1080 |
| ctccgtggac | gttcggtgga | ggcacaaaga | tggaaataaa | acgaactgtg | gctgcaccat | 1140 |
| ctgtcttcat | cttcccgcca | tctgatgagc | agttgaaatc | tggaactgcc | tctgttgtgt | 1200 |
| gcctgctgaa | taacttctat | cccagagagg | ccaaagtaca | gtggaaggtg | gataacgccc | 1260 |
| tccaatcggg | taactcccag | gagagtgtca | cagagcagga | cagcaaggac | agcacctaca | 1320 |
| gcctcagcag | caccctgacg | ctgagcaaag | cagactacga | gaaacacaaa | gtctacgcct | 1380 |
| gcgaagtcac | ccatcagggc | ctgagctcgc | ccgtcacaaa | gagcttcaac | aggggagagt | 1440 |
| gttagctcga | gtctagaggg | cccgtttaaa | cccgctgatc | agcctcgact | gtgccttcta | 1500 |
| gttgccagcc | atctgttgtt | tgcccctccc | ccgtgccttc | cttgaccctg | gaaggtgcca | 1560 |
| ctcccactgt | cctttcctaa | taaaatgagg | aaattgcatc | gcattgtctg | agtaggtgtc | 1620 |

```
attctattct gggggtggg gtggggcagg acagcaaggg ggaggattgg gaagacaata    1680
gcaggcatgc tggggatgcg gtgggctcta tggcttctga ggcggaaaga accagccgat    1740
gtacgggcca gatatacgcg ttgacattga ttattgacta gttattaata gtaatcaatt    1800 acgggtcat tagttcatag cccatatatg gagttccgcg ttacataact tacggtaaat    1860
ggcccgcctg gctgaccgcc caacgacccc cgcccattga cgtcaataat gacgtatgtt    1920
cccatagtaa cgccaatagg gactttccat tgacgtcaat gggtggagta tttacggtaa    1980
actgcccact tggcagtaca tcaagtgtat catatgccaa gtacgccccc tattgacgtc    2040
aatgacggta aatggcccgc ctggcattat gcccagtaca tgaccttatg gactttcct    2100 acttggcagt acatctacgt attagtcatc gctattacca tggtgatgcg gttttggcag    2160
tacatcaatg ggcgtggata gcggtttgac tcacgggat ttccaagtct ccaccccatt    2220
gacgtcaatg ggagtttgtt ttggcaccaa aatcaacggg actttccaaa atgtcgtaac    2280
aactccgccc cattgacgca aatgggcggt aggcgtgtac ggtgggaggt ctatataagc    2340
agagctctct ggctaactag agaacccact gcttactggc ttatcgaaat taatacgact    2400
cactataggg agacccaagc tggctagcgt ttaaacgggc cctctagact cgagcggccg    2460
ccactgtgct ggagccgcca ccatggactg gacctggagg gtgttctgcc tgcttgcagt    2520
ggcccccgga gcccacagcc aggttcagct gcagcagtct ggacctgagc tggtgaagcc    2580
tggggcttta gtgaagatat cctgcaaggc ttctggttac accttcacaa actacgatat    2640
acactgggtg aagcagaggc ctggacaggg acttgagtgg attggatgga tttatcctgg    2700
agatggtagt actaagtaca atgagaaatt caagggcaag gccacactga ctgcagacaa    2760
atcctccagc acagcctaca tgcacctcag cagcctgact tctgagaaat ctgcagtcta    2820
tttctgtgca agagagtggg cttactgggg ccaagggact ctggtcactg tctctgcagc    2880
tagcaccaag ggcccatcgg tcttcccct ggcaccctcc tccaagagca cctctggggg    2940
cacagcggcc ctgggctgcc tggtcaagga ctacttcccc gaaccggtga cggtgtcgtg    3000
gaactcaggc gccctgacca gcggcgtgca caccttcccg gctgtcctac agtcctcagg    3060
actctactcc ctcagcagcg tggtgaccgt gccctccagc agcttgggca cccagaccta    3120
catctgcaac gtgaatcaca agcccagcaa caccaaggtg gacaagaaag ttgagcccaa    3180
atcttgtgac aaaactcaca catgcccacc gtgcccagca cctgaactcc tggggggacc    3240
gtcagtcttc ctcttccccc caaaacccaa ggacaccctc atgatctccc ggacccctga    3300
ggtcacatgc gtggtggtgg acgtgagcca cgaagaccct gaggtcaagt tcaactggta    3360
cgtggacggc gtggaggtgc ataatgccaa gacaaagccg cgggaggagc agtacaacag    3420
cacgtaccgt gtggtcagcg tcctcaccgt cctgcaccag gactggctga atggcaagga    3480
gtacaagtgc aaggtctcca acaaagccct cccagccccc atcgagaaaa ccatctccaa    3540
agccaaaggg cagccccgag aaccacaggt gtacaccctg cccccatccc gggatgagct    3600
gaccaagaac caggtcagcc tgacctgcct ggtcaaaggc ttctatccca gcgacatcgc    3660
cgtggagtgg gagagcaatg ggcagccgga gaacaactac aagaccacgc ctcccgtgct    3720
ggactccgac ggctccttct tcctctacag caagctcacc gtggacaaga gcaggtggca    3780
gcaggggaac gtcttctcat gctccgtgat gcatgaggct ctgcacaacc actacacgca    3840
gaagagcctc tccctgtctc cgggtaaaag ttcatcacca gataaacaaa tggcagtgct    3900
tcctagaaga gagcggaatc ggcaggctgc agctgccaac ccagagaatt ccagaggaaa    3960
aggtcggaga ggccagaggg gcaaaaaccg gggttgtgtc ttaactgcaa tacatttaaa    4020
```

```
tgtcactgac ttgggtctgg gctatgaaac caaggaggaa ctgatttta ggtactgcag    4080 cggctcttgc gatgcagctg agacaacgta cgacaaaata ttgaaaaact tatccagaaa    4140
tagaaggctg gtgagtgaca aagtagggca ggcatgttgc agaccatcg cctttgatga    4200 tgacctgtcg tttttagatg ataacctggt ttaccatatt ctaagaaagc attccgctaa    4260
aaggtgtgga tgtatctgaa acccgagctc ggtaccaagc ttaagtttaa accgctgatc    4320
agcctcgact gtgccttcta gttgccagcc atctgttgtt tgcccctccc ccgtgccttc    4380
cttgaccctg gaaggtgcca ctcccactgt cctttcctaa taaaatgagg aaattgcatc    4440
gcattgtctg agtaggtgtc attctattct ggggggtggg gtggggcagg acagcaaggg    4500
ggaggattgg gaagacaata gcaggcatgc tggggatgcg gtgggctcta tggcttctga    4560
ggcggaaaga accaggggag gtaccgagct cttacgcgtg ctagctcgag atctgcatct    4620
caattagtca gcaaccatag tcccgcccct aactccgccc atcccgcccc taactccgcc    4680
cagttccgcc cattctccgc cccatggctg actaattttt tttatttatg cagaggccga    4740
ggccgcctcg gcctctgagc tattccagaa gtagtgagga ggcttttttg gaggcctagg    4800
cttttgcaaa aagcttatcg attctagaag ccgccaccat ggttcgacca ttgaactgca    4860
tcgtcgccgt gtcccaaaat atggggattg gcaagaacgg agacctaccc tggcctccgc    4920
tcaggaacga gttcaagtac ttccaaagaa tgaccacaac ctcttcagtg gaaggtaaac    4980
agaatctggt gattatgggt aggaaaacct ggttctccat tcctgagaag aatcgacctt    5040
taaaggacag aattaatata gttctcagta gagaactcaa agaaccacca cgaggagctc    5100
attttcttgc caaaagtttg gatgatgcct taagacttat tgaacaaccg gaattggcaa    5160
gtaaagtaga catggtttgg atagtcgagg cagttctgt ttaccaggaa gccatgaatc    5220
aaccaggcca cctcagactc tttgtgacaa ggatcatgca ggaatttgaa agtgacacgt    5280 tttcccaga aattgatttg gggaaatata aacttctccc agaataccca ggcgtcctct    5340
ctgaggtcca ggaggaaaaa ggcatcaagt ataagtttga agtctacgag aagaaagact    5400
aacaggaaga tgcttccaag ttctctgctc ccctcctaaa gctatgcatt tttataagac    5460
catgggactt ttgctggctt tagatccttc gcgggacgtc ctttgtttac gtcccgtcgg    5520
cgctgaatcc cgcggacgac ccctcgcggg gccgcttggg actctctcgt ccccttctcc    5580
gtctgccgtt ccagccgacc acggggcgca cctctctttta cgcggtctcc ccgtctgtgc    5640
cttctcatct gccggtccgt gtgcacttcg cttcacctct gcacgttgca tggagaccac    5700
cgtgaacgcc catcagatcc tgcccaaggt cttacataag aggactcttg gactcccagc    5760
aatgtcaacg accgaccttg aggcctactt caaagactgt gtgtttaagg actgggagga    5820
gctgggggag gagattaggt taaaggtctt tgtattagga ggctgtaggc ataaattggt    5880
ctgcgcacca gcaccatgca actttttcac ctctgcctaa tcatctcttg tacatgtccc    5940
actgttcaag cctccaagct gtgccttggg tggctttggg gcatggacat tgacccttat    6000
aaagaatttg gagctactgt ggagttactc tcgttttttgc cttctgactt ctttccttcc    6060
gtcagagatc tcctacgccg gacgcatcgt ggccggcatc accggcgcca caggtgcggt    6120
tgctggcgcc tatatcgccg acatcaccga tgggggaagat cgggctcgcc acttcgggct    6180
catgagcgct tgtttcggcg tgggtatggt ggcaggcccc gtggccgggg gactgttggg    6240
cgccatctcc ttgcatgcac cattccttgc ggcggcggtg ctcaacggcc tcaacctact    6300
actgggctgc ttcctaatgc aggagtcgca taagggagag cg                      6342
```

<210> SEQ ID NO 48
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Met Glu Thr Pro Ala Gln Leu Leu Phe Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 49
<211> LENGTH: 598
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

```
Glu Lys Phe Lys Gly Lys Ala Thr Leu Thr Ala Asp Lys Ser Ser
                85                  90                  95
Thr Ala Tyr Met His Leu Ser Ser Leu Thr Ser Glu Lys Ser Ala Val
            100                 105                 110
Tyr Phe Cys Ala Arg Glu Trp Ala Tyr Trp Gly Gln Gly Thr Leu Val
        115                 120                 125
Thr Val Ser Ala Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys Ser Ser
    450                 455                 460
Ser Pro Asp Lys Gln Met Ala Val Leu Pro Arg Arg Glu Arg Asn Arg
465                 470                 475                 480
Gln Ala Ala Ala Ala Asn Pro Glu Asn Ser Arg Gly Lys Gly Arg Arg
                485                 490                 495
Gly Gln Arg Gly Lys Asn Arg Gly Cys Val Leu Thr Ala Ile His Leu
```

```
                      500                 505                 510
Asn Val Thr Asp Leu Gly Leu Gly Tyr Glu Thr Lys Glu Glu Leu Ile
        515                 520                 525

Phe Arg Tyr Cys Ser Gly Ser Cys Asp Ala Ala Glu Thr Thr Tyr Asp
    530                 535                 540

Lys Ile Leu Lys Asn Leu Ser Arg Asn Arg Arg Leu Val Ser Asp Lys
545                 550                 555                 560

Val Gly Gln Ala Cys Cys Arg Pro Ile Ala Phe Asp Asp Asp Leu Ser
                565                 570                 575

Phe Leu Asp Asp Asn Leu Val Tyr His Ile Leu Arg Lys His Ser Ala
            580                 585                 590

Lys Arg Cys Gly Cys Ile
        595

<210> SEQ ID NO 50
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 51
<211> LENGTH: 405
<212> TYPE: DNA
<213> ORGANISM: Homo sapiens

<400> SEQUENCE: 51
tcaccagata aacaaatggc agtgcttcct agaagagagc ggaatcggca ggctgcagct      60
gccaacccag agaattccag aggaaaaggt cggagaggcc agaggggcaa aaaccggggt     120
tgtgtcttaa ctgcaataca tttaaatgtc actgacttgg gtctgggcta tgaaaccaag     180
```

```
gaggaactga tttttaggta ctgcagcggc tcttgcgatg cagctgagac aacgtacgac      240
aaaatattga aaaacttatc cagaaataga aggctggtga gtgacaaagt agggcaggca      300
tgttgcagac ccatcgcctt tgatgatgac ctgtcgtttt tagatgataa cctggtttac      360
catattctaa gaaagcattc cgctaaaagg tgtggatgta tctga                     405
```

```
<210> SEQ ID NO 52
<211> LENGTH: 134
<212> TYPE: PRT
<213> ORGANISM: Homo sapiens

<400> SEQUENCE: 52

Ser Pro Asp Lys Gln Met Ala Val Leu Pro Arg Arg Glu Arg Asn Arg
1               5                   10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
    130
```

FUSION PROTEINS FOR DELIVERY OF GDNF TO THE CNS

CROSS-REFERENCE TO RELATED APPLICATIONS

This application in a continuation-in-part of U.S. patent application Ser. No. 11/245,546 filed Oct. 7, 2005. This application also claims priority to U.S. Provisional Patent Application Ser. No. 60/990,290 filed Nov. 26, 2007, the contents of which are incorporated herein by reference in their entirety.

BACKGROUND OF THE INVENTION

Neurological disorders represent a major cause of mortality and disability worldwide. Despite extensive progress, current treatment options remain limited in some aspects. One major reason for this limitation is that the brain is unique in allowing only select access to molecules. While this is a useful protective mechanism, it also means that many potentially beneficial molecular entities do not have access to the central nervous system (CNS), and thus are unable to exert a therapeutic effect in many neurological disorders or other conditions of the CNS. The present invention represents an advance in providing accessibility of the CNS for molecular entities whose ability to cross the blood brain barrier is limited.

SUMMARY OF THE INVENTION

In one aspect, the invention provides a composition comprising a neurotherapeutic peptide comprising an amino acid sequence which is at least 80% (e.g., 95%) identical to the amino acid sequence of mature human GDNF (SEQ ID NO:52) covalently linked to a structure that is capable of crossing the blood brain barrier (BBB) (e.g., an antibody). In some embodiments, the structure that is capable of crossing the BBB crosses the BBB on an endogenous BBB receptor. In some embodiments, the endogenous BBB receptor is the insulin receptor, transferrin receptor, leptin receptor, lipoprotein receptor, and the IGF receptor. In some embodiments, the structure that is capable of crossing the BBB is a monoclonal antibody. In some embodiments, the monoclonal antibody is a chimeric monoclonal antibody. In one embodiment, the chimeric antibody contains sufficient human sequences to avoid significant immunogenic reaction when administered to a human. In some embodiments, the above-mentioned neurotherapeutic peptide is covalently linked at its amino terminus to the carboxy terminus of the heavy chain of the MAb. In one embodiment, the neurotherapeutic peptide of the above-mentioned composition comprises the amino acid sequence of mature human GDNF.

In a further aspect provided herein is a composition for treating a neurological disorder comprising a neurotherapeutic peptide comprising an amino acid sequence which is at least 80% identical to the amino acid sequence of mature human GDNF covalently linked to an immunoglobulin that is capable of crossing the blood brain barrier, wherein the composition is capable of crossing the BBB in an amount that is effective in treating the neurological disorder. In some embodiments provided herein is a mammalian cell comprising the just-mentioned composition.

In another aspect provided herein is a method of transport of a neurotherapeutic peptide comprising an amino acid sequence which is at least 80% identical to the amino acid sequence of mature human GDNF (SEQ ID NO:52) from the peripheral circulation across the BBB in an effective amount, comprising peripherally administering to an individual the GDNF covalently attached to a structure that crosses the BBB, under conditions where the agent covalently attached to a structure that crosses the BBB is transported across the BBB in an effective amount.

In yet another aspect provided herein is a method for treating a CNS disorder in an individual comprising peripherally administering to the individual an effective amount of a composition comprising a neurotherapeutic peptide comprising an amino acid sequence which is at least 80% (e.g., 95%) identical to the amino acid sequence of human GDNF covalently attached to a structure capable of crossing the BBB. In one embodiment, the neurotherapeutic peptide comprises the amino acid sequence of human GDNF. In some embodiments, the administering is oral, intravenous, intramuscular, subcutaneous, intraperitoneal, rectal, transbuccal, intranasal, transdermal, or inhalation administration. In some embodiments, the CNS disorder is an acute CNS disorder (e.g., spinal cord injury, brain injury focal brain ischemia and global brain ischemia). In other embodiments, the CNS disorder is a chronic CNS disorder (e.g., a chronic neurodegenerative disease, drug addiction, or alcohol addiction). In some embodiments, the chronic neurodegenerative disease is Parkinson's disease or a motor neuron disease (e.g., amyotrophic lateral sclerosis). In some embodiments, the individual to be treated is administered about 1 to about 100 mg of the composition used in above-mentioned method.

In yet another aspect provided herein is a composition comprising a neurotherapeutic peptide comprising an amino acid sequence which is at least 80% identical to the amino acid sequence of human GDNF covalently linked to an immunoglobulin, wherein the neurotherapeutic peptide has a serum half-life that is an average of at least about 5-fold greater than the serum half-life of the neurotherapeutic peptide alone. In some embodiments, the immunoglobulin is an antibody to an endogenous BBB receptor (e.g., the insulin receptor, transferrin receptor, leptin receptor, lipoprotein receptor, or the IGF receptor). In one embodiment, the neurotherapeutic peptide comprises the amino acid sequence of human GDNF.

In a further aspect provided herein is a method for treating substance abuse in an individual, comprising administering to the individual an effective amount of a composition comprising a neurotherapeutic peptide comprising an amino acid sequence which is at least 80% identical to the amino acid sequence of mature human GDNF (SEQ ID NO:52) covalently attached to a structure capable of crossing the BBB.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2. Diagram showing genetic engineering of a bacterial expression plasmid encoding vBDNF cDNA with modified 5'-linker (FIG. 2A) and modified 3'-linkers (FIG. 2B).

FIG. 4. Nucleotide (SEQ ID NO: 21) and amino acid (SEQ ID NO: 22) sequence of fusion site between carboxyl terminus of the fusion protein HC and the amino terminus of the vBDNF. The 3-amino acid linker between the HIRMAb HC and the vBDNF is shown, as well as the new stop codon at the carboxyl terminus of vBDNF.

FIG. 5. Nucleotide sequence (SEQ ID NO: 23) of fusion protein HC gene cloned into plasmid 416. Italics: human IgG1 constant region introns; bold font: human IgG1 exon sequence; underline font: vBDNF.

FIG. 6. Amino acid sequence (SEQ ID NO: 24) of the fusion protein HC. The 19 amino acid signal peptide is underlined, as is the 3-amino acid linker between the CH3 region and the vBDNF. The N-linked glycosylation consensus sequence within CH2 is underlined.

FIG. 7. The amino acid sequence (SEQ ID NO: 25) of the different domains of the fusion protein HC are shown. FIG. 7 discloses the "Signal Peptide" sequence as residues 1-19 of SEQ ID NO: 25, the "FR1" sequence as residues 20-44 of SEQ ID NO: 25, the "CDR1" sequence as residues 45-54 of SEQ ID NO: 25, the "FR2" sequence as residues 55-68 of SEQ ID NO: 25, the "CDR2" sequence as residues 69-85 of SEQ ID NO: 25, the "FR3" sequence as residues 86-117 of SEQ ID NO: 25, the "CDR3" sequence as residues 118-121 of SEQ ID NO: 25, the "FR4" sequence as residues 122-132 of SEQ ID NO: 25, the "CH1" sequence as residues 133-230 of SEQ ID NO: 25, the "Hinge" sequence as residues 231-242 of SEQ ID NO: 25, the "CH2" sequence as residues 243-355 of SEQ ID NO: 25, the "CH3" sequence as residues 356-462 of SEQ ID NO: 25, the "linker" sequence as residues 463-465 of SEQ ID NO: 25 and the "vBDNF" sequence as residues 466-582 of SEQ ID NO: 25.

FIG. 8, part A, indicates the step of obtaining mRNA from cells transfected with the fusion protein HC gene; FIG. 8, part B, indicates the step of obtaining the cDNA for the fusion protein HC gene by RT-PCR.

FIG. 9. (A) Nucleotide sequence (SEQ ID NO: 26) of the fusion protein HC cDNA inserted in clone 422a. (B) and (C) Amino acid sequence (SEQ ID NO: 28) of the fusion protein HC that is deduced from the nucleotide sequence (SEQ ID NO: 27) shown in panel A. The sequence of the signal peptide is underlined.

FIG. 10, part A, indicates the step of obtaining mRNA from cells transfected with the fusion protein LC gene; FIG. 10, part B, indicates the step of obtaining the cDNA for the fusion protein LC gene by RT-PCR.

FIG. 11. (A) Nucleotide sequence (SEQ ID NO: 29) of the fusion protein LC cDNA inserted in clone 423a. (B) (SEQ ID NOS 30 & 31) Amino acid sequence of the fusion protein LC that is deduced from the nucleotide sequence shown in panel A. The sequence of the signal peptide is underlined.

FIGS. 13A-D. Nucleotide sequence (SEQ ID NO: 32) of the fusion protein HC gene expression cassette (Nucleotides 1-2,856 of SEQ ID NO: 32) and LC gene expression cassette (Nucleotides 2,857-4,720 of SEQ ID NO: 32), and the DHFR gene expression cassette (Nucleotides 4,732-6,505 of SEQ ID NO: 32) incorporated in the tandem vector.

FIG. 14. Deduced amino acid sequence (SEQ ID NO: 34) of the fusion protein HC based on tandem vector nucleotide sequence (SEQ ID NO: 33) analysis. The signal peptide sequence is underlined.

FIG. 15. Deduced amino acid sequence of the fusion protein LC based on tandem vector nucleotide sequence analysis (SEQ ID NO 35 & 36). The signal peptide sequence is underlined.

FIG. 16. Deduced amino acid sequence of the DHFR based on tandem vector nucleotide sequence analysis (SEQ ID NO 37 & 38).

FIG. 24. (A) Design of trkB competitive ligand binding assay (CLBA). The advantage of the PEG linker is that this modification eliminates the high non-specific binding (NSB) of the cationic BDNF to the ELISA wells, which gives an assay with a high signal/noise ratio. The binding of the BDNF-PEG$^{2000}$-biotin to the trkB ECD was detected with a peroxidase system using avidin and biotinylated peroxidase. (B) The binding of the BDNF-PEG$^{2000}$-biotin to the trkB ECD is competitively displaced by recombinant BDNF. This binding data was analyzed by non-linear regression analysis to yield the $K_I$ of BDNF binding, 3.5±1.3 pmol/well and the NSB parameter. (C) The binding of the BDNF-PEG$^{2000}$-biotin to the trkB ECD is competitively displaced by the fusion protein. This binding data was analyzed by non-linear regression analysis to yield the $K_I$ of fusion protein binding, 2.2±1.2 pmol/well, which is not significantly different than the $K_I$ for native BDNF. These data show that the affinity of the fusion protein for the trkB receptor is equal to that of native BDNF.

FIG. 29. (A) Ethidium bromide stain of agarose gel of human GDNF cDNA (lane 1), which was produced by PCR from cDNA produced by reverse transcription of RNA from human U87 glial cells, and GDNF-specific ODN primers (Table 6). Lane 2: DNA sizing standards. (B) Genetic engineering of pHIRMAb-GDNF, the eukaryotic expression plasmid encoding the fusion protein of GDNF and the heavy chain (HC) of the chimeric HIRMAb. The fusion gene is 5'-flanked by the cytomegalovirus (CMV) promoter and 3'-flanked by the bovine growth hormone polyA (pA) sequence.

FIG. 34. (A) Binding by either GDNF or the HIRMAb-GDNF fusion protein to the GFRα1 on the cell membrane of c-ret kinase transfected human neural SK-N-MC cells activates the tyrosine hydroxylase (TH) 5'-flanking sequence (FS), which drives luciferase gene expression. (B) Both GDNF and the COS cell-derived HIRMAb-GDNF fusion protein activate luciferase gene expression in a saturable manner, with ED50 values comparable to GFRα1 binding (FIG. 33B). There is no activation of luciferase gene expression by the chimeric HIRMAb.

FIG. 35. (A) Effect of intra-cerebral injection of the HIRMAb-GDNF versus saline on stroke volume in rats. Serial coronal sections of rat brain at 24 hours after permanent MCAO and intra-cerebral saline (B) or HIRMAb-GDNF fusion protein (C) are stained with 2% 2,3,5-triphenyltetrazolium chloride (TTC). A representative stain is shown for 1 rat from each treatment group. In these inverted grayscale images, the infarcted brain is black, and the healthy brain is white. Most rostral section is top and most caudal section is bottom.

FIG. 36 discloses the "signal peptide" sequence as residues 1-19 of SEQ ID NO: 46, the "FR1" sequence as residues 20-44 of SEQ ID NO: 46, the "CDR1" sequence as residues 45-54 of SEQ ID NO: 46, the "FR2" sequence as residues 55-68 of SEQ ID NO: 46, the "CDR2" sequence as residues 69-85 of SEQ ID NO: 46, the "FR3" sequence as residues 86-117 of SEQ ID NO: 46, the "CDR3" sequence as residues 118-121 of SEQ ID NO: 46, the "FR4" sequence as residues 122-132 of SEQ ID NO: 46, the "CH1" sequence as residues 133-230 of SEQ ID NO: 46, the "hinge" sequence as residues 231-242 of SEQ ID NO: 46, the "CH2" sequence as residues 243-355 of SEQ ID NO: 46, the "CH3" sequence as residues 356-462 of SEQ ID NO: 46 and the "GDNF" sequence as residues 463-598 of SEQ ID NO: 46.

FIG. 38 discloses the "signal peptide" sequence as residues 1-20 of SEQ ID NO: 48, the "FR1" sequence as residues 21-43 of SEQ ID NO: 48, the "CDR1" sequence as residues 44-54 of SEQ ID NO: 48, the "FR2" sequence as residues 55-69 of SEQ ID NO: 48, the "CDR2" sequence as residues 70-76 of SEQ ID NO: 48, the "FR3" sequence as residues 77-108 of SEQ ID NO: 48, the "CDR3" sequence as residues 109-117 of SEQ ID NO: 48, the "FR4" sequence as residues 118-128 of SEQ ID NO: 48 and the "kappa" sequence as residues 129-234 of SEQ ID NO: 48.

DETAILED DESCRIPTION OF THE INVENTION

Figure 1:
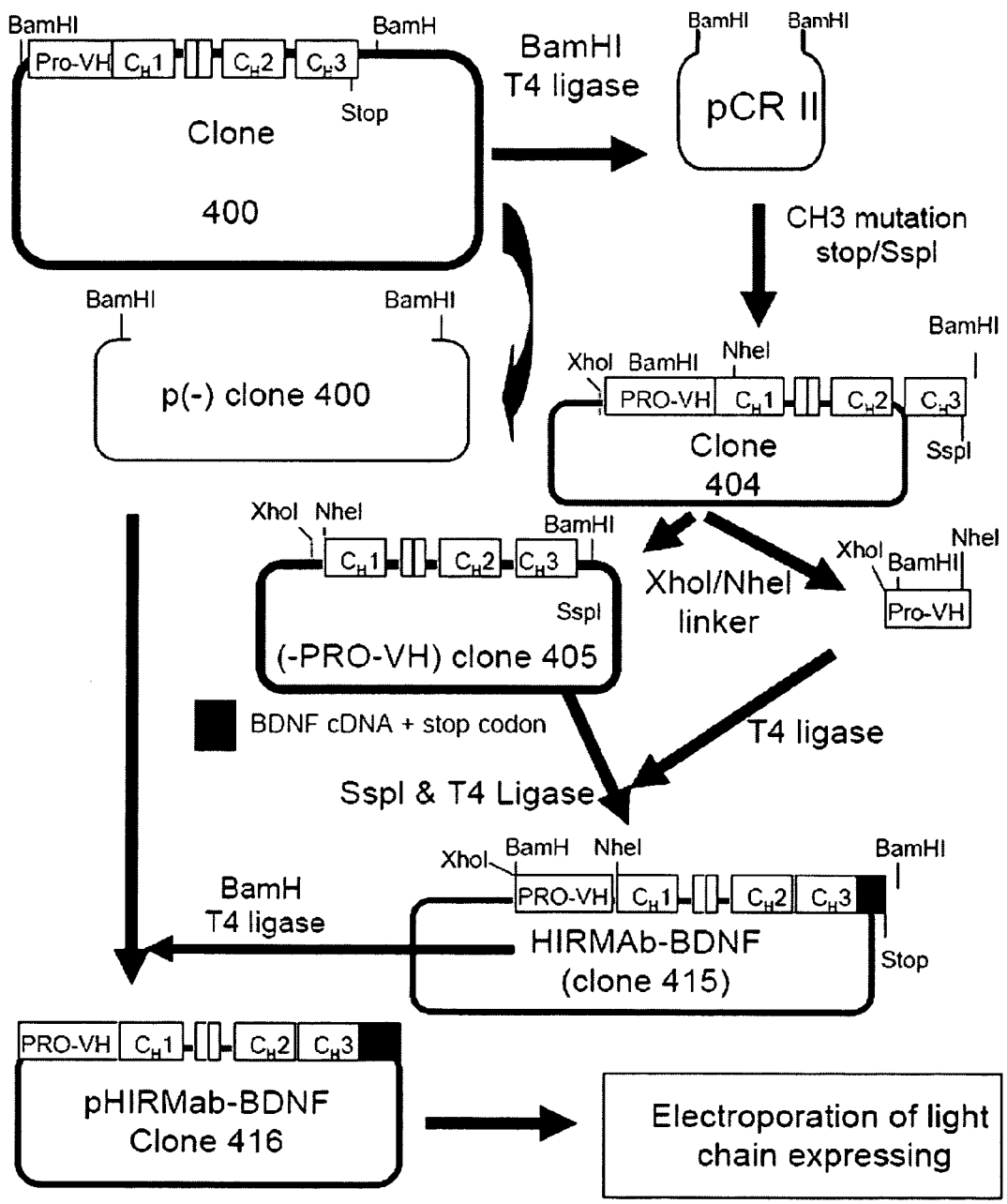
FIG. 1. Diagram showing genetic engineering of a eukaryotic expression vector encoding a fusion gene comprised of the variable region of the heavy chain (VH) of the chimeric HIRMAb, a genomic fragment encoding the constant region of human IgG1, which is comprised of 4 regions (CH1, hinge, CH2, and CH3), and the cDNA for the BDNF variant (vBDNF). Transcription of the gene is driven by the human IgG1 promoter (PRO). This vector produces the heavy chain (HC) of the fusion protein.

I. Introduction
II. Definitions
III. The blood brain barrier
   A. Transport systems
   B. Structures that bind to a blood brain barrier receptor-mediated transport system
IV. Agents for transport across the blood brain barrier
   A. Neurotrophins
   B. Brain-derived neurotrophic factor
   C. Glial-derived neutrotrophic factor
V. Compositions
VI. Nucleic acids, vectors, cells, and manufacture
   A. Nucleic acids
   B. Vectors
   C. Cells
   D. Manufacture
VII. Methods
VIII. Kits

| Abbreviations | |
|---|---|
| AA | amino acid |
| ALS | amyotrophic lateral sclerosis |
| AP | alkaline phosphatase |
| BBB | blood-brain barrier |
| BCA | bicinchoninic acid |
| BDNF | brain derived neurotrophic factor |
| BGH | bovine growth hormone |
| Bmax | dose causing maximal effect |
| BSA | bovine serum albumin |
| C | cysteine |
| CDR | compementarity determining region |
| CED | convection enhanced diffusion |
| CHO | Chinese hamster ovary |
| CMV | cytomegalovirus |
| CNTF | ciliary neurotrophic factor |
| DC | dilutional cloning |
| DHFR | dihydrofolate reductase |
| ECD | extracellular domain |
| ED50 | effective dose causing 50% saturation |
| FR | framework region |
| FS | flanking sequence |
| FWD | forward |
| GDNF | glial derived neurotrophic factor |
| GFR | GDNF receptor |
| HC | heavy chain |
| HIR | human insulin receptor |
| HIRMAb | MAb to HIR |
| HIRMAb-GDNF | fusion protein of HIRMAb and GDNF |
| HPLC | high pressure liquid chromatography |
| HT | hypoxanthine-thymidine |
| ICV | intra-cerebroventricular |
| ID | injected dose |
| IgG | immunoglobulin G |
| LC | light chain |
| MAb | monoclonal antibody |
| MAH | mouse anti-human IgG |
| MCAO | middle cerebral artery occlusion |
| MTX | methotrexate |
| MW | molecular weight |
| N | asparagine |
| nt | nucleotide |
| ODN | oligodeoxynucleotide |
| pA | poly-adenylation |
| PAGE | polyacrylamide gel electrophoresis |
| PBS | phosphate buffered saline |
| PBST | PBS plus Tween-20 |
| PCR | polymerase chain reaction |
| PD | Parkinson's disease |
| pI | isoelectric point |
| RAG | rabbit anti-goat IgG |
| REV | reverse |
| RNase A | ribonuclease A |

-continued

| Abbreviations | |
|---|---|
| RT | reverse transcriptase |
| RT | room temperature |
| SDM | site-directed mutagenesis |
| SDS | sodium dodecyl sulfate |
| SEC | size exclusion chromatography |
| Ser | serine |
| SFM | serum free medium |
| SMA | spinal muscular atrophy |
| TH | tyrosine hydroxylase |
| TTC | triphenyltetrazolium chloride |
| TV | tandem vector |
| UTV | universal TV |
| VH | variable region of heavy chain |
| VL | variable region of light chain |

I. Introduction

The blood brain barrier is a limiting factor in the delivery of many peripherally-administered agents to the central nervous system. The present invention addresses three factors that are important in delivering an agent across the BBB to the CNS: 1) a pharmacokinetic profile for the agent that allows sufficient time in the peripheral circulation for the agent to have enough contact with the BBB to traverse it; 2) modification of the agent to allow it to cross the BBB; and 3) retention of activity of the agent once across the BBB. Various aspects of the invention address these factors, by providing fusion structures (e.g., fusion proteins) of an agent (e.g., a therapeutic agent) covalently linked to a structure that causes the agent to have increased serum half life, to be transported across the BBB, and/or to retain some or all of its activity in the brain while still attached to the structure.

Accordingly, in one aspect, the invention provides compositions and methods that utilize an agent covalently linked to a structure capable of crossing the blood brain barrier (BBB). The compositions and methods are useful in transporting agents, e.g. therapeutic agents such as neurotherapeutic agents, from the peripheral blood and across the BBB into the CNS. Neurotherapeutic agents useful in the invention include neurotrophins, e.g. brain-derived neurotrophic factor (BDNF) and glial-derived neurotrophic factor (GDNF). In some embodiments, the structure that is capable of crossing the BBB is capable of binding to an endogenous BBB receptor mediated transport system and crossing the BBB. In some embodiments, the structure that is capable of crossing the BBB is an antibody, e.g., a monoclonal antibody (MAb) such as a chimeric MAb.

In some embodiments, the invention provides a fusion protein that includes a structure capable of crossing the BBB covalently linked to a peptide that is active in the central nervous system (CNS), where the structure capable of crossing the blood brain barrier and the peptide that is active in the central nervous system each retain a proportion (e.g., 10-100%) of their activities or their binding affinities for their respective receptors, compared to their activities or their binding affinities for their respective receptors as separate entities.

In another aspect, the invention provides a composition containing a cationic therapeutic peptide covalently linked to an immunoglobulin, where the cationic therapeutic peptide in the composition has a serum and/or circulating half-life that is an average of at least about five fold greater than the serum and/or circulating half-life of the cationic therapeutic peptide alone.

The invention also provides nucleic acids coding for peptides and proteins. In some embodiments, the invention provides a single nucleic acid sequence that contains a gene coding for a light chain of an immunoglobulin and a gene coding for a fusion protein made up of a heavy chain of the immunoglobulin covalently linked to a peptide. In some embodiments the peptide of the fusion protein is a therapeutic peptide, e.g., a neurotherapeutic peptide such as a neurotrophin. The invention also provides vectors containing the nucleic acids of the invention, and cells containing the vectors. Further provided are methods of manufacturing an immunoglobulin fusion protein, where the fusion protein contains an immunoglobulin heavy chain fused to a therapeutic agent, where the methods include integrating into a eukaryotic cell a single tandem expression vector in which both the immunoglobulin light chain gene and the gene for the immunoglobulin heavy chain fused to the therapeutic agent are incorporated into a single piece of DNA.

The invention further provides therapeutic compositions, such as pharmaceutical compositions that contain an agent covalently linked to a structure capable of crossing the blood brain barrier (BBB) and a pharmaceutically acceptable excipient. In some embodiments, the invention provides a composition for treating a neurological disorder that includes a BDNF or a GDNF (e.g., human GDNF) covalently linked to an immunoglobulin that is capable of crossing the blood brain barrier, wherein the composition is capable of crossing the BBB in an amount that is effective in treating the neurological disorder.

The invention also provides methods for treating a neurological disorder in an individual that include peripherally administering to the individual an effective amount of one or more of the compositions of the invention, optionally in combination with other therapy for the disorder.

II. Definitions

As used herein, an "agent" includes any substance that is useful in producing an effect, including a physiological or biochemical effect in an organism. A "therapeutic agent" is a substance that produces or is intended to produce a therapeutic effect, i.e., an effect that leads to amelioration, prevention, and/or complete or partial cure of a disorder. A "therapeutic effect," as that term is used herein, also includes the production of a condition that is better than the average or normal condition in an individual that is not suffering from a disorder, i.e., a supranormal effect such as improved cognition, memory, mood, or other characteristic attributable at least in part to the functioning of the CNS, compared to the normal or average state. A "neurotherapeutic agent" is an agent that produces a therapeutic effect in the CNS. A "therapeutic peptide" includes therapeutic agents that consists of a peptide. A "cationic therapeutic peptide" encompasses therapeutic peptides whose isoelectric point is above about 7.4, in some embodiments, above about 8, 8.5, 9, 9.5, 10, 10.5, 11, 11.5, 12, or above about 12.5. A subcategory of cationic therapeutic peptides is cationic neurotherapeutic peptides.

As used herein, a "peptide that is active in the central nervous system (CNS)" includes peptides that have an effect when administered to the CNS. The effect may be a therapeutic effect or a non-therapeutic effect, e.g., a diagnostic effect or an effect useful in research. If the effect is a therapeutic effect, then the peptide is also a therapeutic peptide. A therapeutic peptide that is also a peptide that is active in the CNS is encompassed by the term "neurotherapeutic peptide," as used herein.

"Treatment" or "treating" as used herein includes achieving a therapeutic benefit and/or a prophylactic benefit. By therapeutic benefit is meant eradication or amelioration of the underlying disorder or condition being treated. For example, in an individual with a neurological disorder, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a neurological disorder), or decreasing the likelihood of occurrence of a condition. As used herein, "treating" or "treatment" includes prophylaxis.

As used herein, the term "effective amount" can be an amount sufficient to effect beneficial or desired results, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions of the CNS include dementia, neurodegenerative diseases as described herein, suboptimal memory or cognition, mood disorders, general CNS aging, or other undesirable conditions. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the specific activity of the therapeutic agent being used, the type of disorder (e.g., acute vs. chronic neurological disorder), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from a neurological disorder.

In some embodiments, an agent is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, subcutaneous, intramuscular, intraperitoneal, transdermal, inhalation, transbuccal, intranasal, rectal, and oral administration.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins P A, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof, including, but not limited to, degenerate codon substitutions, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and peptides are well known in the art.

III. The Blood Brain Barrier

In one aspect, the invention provides compositions and methods that utilize an agent covalently linked to a structure capable of crossing the blood brain barrier (BBB). The compositions and methods are useful in transporting agents, e.g. therapeutic agents such as neurotherapeutic agents, from the peripheral blood and across the BBB into the CNS. As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB is a limiting step in the development of new neurotherapeutics, diagnostics, and research tools for the brain and CNS. In general, large molecule therapeutics such as recombinant proteins, antisense drugs, gene medicines, monoclonal antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers BDNF only to the ependymal surface of the brain, not into brain parenchyma, which is typical for drugs given by the ICV route. The IC administration of a neurotrophin, such as nerve growth factor (NGF), only delivers drug to the local injection site, owing to the low efficiency of drug diffusion within the brain. The CED of neurotrophin results in preferential fluid flow through the white matter tracts of brain, which causes demyelination, and astrogliosis.

The present invention offers an alternative to these highly invasive and generally unsatisfactory methods for bypassing the BBB, allowing agents, e.g., neuroprotective factors to cross the BBB from the peripheral blood. It is based on the use of endogenous transport systems present in the BBB to provide a mechanism to transport a desired substance from the peripheral blood to the CNS.

A. Transport Systems

In some embodiments, the invention provides compositions that include a structure that binds to a BBB receptor mediated transport system, coupled to an agent for which transport across the BBB is desired, e.g., a neurotherapeutic agent. The compositions and methods of the invention may utilize any suitable structure that is capable of transport by the selected endogenous BBB receptor-mediated transport system, and that is also capable of attachment to the desired agent. In some embodiments, the structure is an antibody. In some embodiment the antibody is a monoclonal antibody (MAb), e.g., a chimeric MAb.

Endogenous BBB receptor-mediated transport systems

The BBB has been shown to have specific receptors that allow the transport from the blood to the brain of several macromolecules; these transporters are suitable as transporters for compositions of the invention. Endogenous BBB receptor-mediated transport systems useful in the invention include those that transport insulin, transferrin, insulin-like growth factors 1 and 2 (IGF1 and IGF2), leptin, and lipoproteins. In some embodiments, the invention utilizes a structure that is capable of crossing the BBB via the endogenous insulin BBB receptor-mediated transport system, e.g., the human endogenous insulin BBB receptor-mediated transport system.

B. Structures that Bind to a BBB Receptor Mediated Transport System

One noninvasive approach for the delivery of drugs to the CNS is to attach the agent of interest to a structure, e.g., molecule that binds with receptors on the BBB. The structure then serves as a vector for transport of the agent across the BBB. Such structures are referred to herein as "molecular Trojan horses (MTH)." Typically, though not necessarily, a MTH is an exogenous peptide or peptidomimetic moiety (e.g., a MAb) capable of binding to an endogenous BBB receptor mediated transport system that traverses the BBB on the endogenous BBB receptor-mediated transport system. In certain embodiments, the MTH can be an antibody to a receptor of the transport system, e.g., the insulin receptor. In some embodiments, the antibody is a monoclonal antibody (MAb). In some embodiments, the MAb is a chimeric MAb. Thus, despite the fact that Abs normally are excluded from the brain, they can be an effective vehicle for the delivery of molecules into the brain parenchyma if they have specificity for receptors on the BBB.

Accordingly, antibodies are particularly useful in embodiments of the invention, especially MAbs. Certain receptor-specific MAbs may mimic the endogenous ligand and function as a MTH and traverse a plasma membrane barrier via transport on the specific receptor system. In certain embodiments, the MTH is a MAb to the human insulin receptor (HIR) on the human BBB. The HIR MAb binds an exofacial epitope on the human BBB HIR and this binding enables the MAb to traverse the BBB via a transport reaction that is mediated by the human BBB insulin receptor.

An "antibody," as that term is used herein, includes reference to any molecule, whether naturally-occurring, artificially induced, or recombinant, which has specific immunoreactive activity. Generally, though not necessarily, an antibody is a protein that includes two molecules, each molecule having two different polypeptides, the shorter of which functions as the light chains of the antibody and the longer of which polypeptides function as the heavy chains of the antibody. Normally, as used herein, an antibody will include at least one variable region from a heavy or light chain. Additionally, the antibody may comprise combinations of variable regions. The combination may include more than one variable region of a light chain or of a heavy chain. The antibody may also include variable regions from one or more light chains in combination with variable regions of one or more heavy chains. An antibody can be an immunoglobulin molecule obtained by in vitro or in vivo generation of the humoral response, and includes both polyclonal and monoclonal antibodies. Furthermore, the present invention includes antigen binding fragments of the antibodies described herein, such as Fab, Fab', F(ab)$_2$, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Synthetic methods of generating such fragments are also contemplated. Heavy and light chain monomers may similarly be produced by treating an intact antibody with a reducing agent, such as dithiothreitol or beta-mercaptoethanol, or by using host cells transformed with DNA encoding either the desired heavy chain or light chain or both. An antibody immunologically reactive with a particular antigen can be generated in vivo or by recombinant methods such as selection of libraries of recombinant antibodies in phage or similar vectors.

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a chimeric MAb is preferred that contains enough human sequence that it is not significantly immunogenic when administered to humans, e.g., at least about 80% human and about 20% mouse, or about 85% human and about 15% mouse, or about 90% human and about 10% mouse, or about 95% human and 5% mouse, or greater than about 95% human and less than about 5% mouse. Chimeric antibodies to the human BBB insulin receptor with sufficient human sequences for use in the invention are described in, e.g., Coloma et al. (2000) *Pharm. Res.* 17: 266-274, which is incorporated by reference herein in its entirety. A more highly humanized form of the HIR MAb can also be engineered, and the humanized HIRMAb has activity comparable to the murine HIRMAb and can be used in embodiments of the invention. See, e.g., U.S. Patent Application Publication No. 20040101904, filed Nov. 27, 2002, incorporated by reference herein in its entirety.

Antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

Accordingly, in some embodiments, a genetically engineered HIR MAb, with the desired level of human sequences, is fused to an agent for which transport across the BBB is desired, e.g., a neurotherapeutic agent such as a neurotrophin such as human BDNF, to produce a recombinant fusion protein that is a bi-functional molecule. The recombinant therapeutic neuroprotective factor/HIRMAb is able to both (i) cross the human BBB, via transport on the BBB HIR, and (ii) activate the factor's target, e.g., neuronal BDNF receptor, trkB, to cause neurotherapeutic effects once inside the brain, following peripheral administration.

IV. Agents for Transport Across the BBB

The agent for which transport across the BBB is desired may be any suitable substance for introduction into the CNS. Generally, the agent is a substance for which transport across the BBB is desired, which does not, in its native form, cross the BBB in significant amounts. The agent may be, e.g., a therapeutic agent, a diagnostic agent, or a research agent. Diagnostic agents include peptide radiopharmaceuticals, such as radiolabeled epidermal growth factor (EGF) for imaging brain cancer (Kurihara and Pardridge (1999) *Canc. Res.* 54: 6159-6163), and amyloid peptides for imaging brain amyloid such as in Alzheimers disease (Lee et al (2002) *J. Cereb. Blood Flow Metabol.* 22: 223-231). In some embodiments, the agent is a therapeutic agent, such as a neurotherapeutic agent. Apart from neurotrophins, potentially useful therapeutic protein agents include recombinant enzymes for lysosomal storage disorders (see, e.g., U.S. Patent Application Publication No. 20050142141, filed Feb. 17, 2005, incorporated by reference herein in its entirety), monoclonal antibodies that either mimic an endogenous peptide or block the action of an endogenous peptide, polypeptides for brain disorders, such as secretin for autism (Ratliff-Schaub et al (2005) Autism 9: 256-265), opioid peptides for drug or alcohol addiction (Cowen et al, (2004) J. Neurochem. 89: 273-285), or neuropeptides for appetite control (Jethwa et al (2005) Am. J. Physiol. 289: E301-305). In some embodiments, the agent is a neurotrophic factor, also referred to herein as a "neurotrophin." Thus, in some embodiments, the invention provides compositions and methods that utilize a neurotrophin. In some embodiments, a single neurotrophin may be used. In others, combinations of neurotrophins are used. In some embodiments, the invention utilizes a brain-derived neurotrophic factor (BDNF). In other embodiments, the invention utilizes a glial-derived neurotrophic factor.

A. Neurotrophins

Many neurotrophic factors are neuroprotective in brain, but do not cross the blood-brain barrier. These factors are suitable for use in the compositions and methods of the invention and include brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF). Particularly useful in some embodiments of the invention utilizing neurotrophins that are used as precursors for fusion proteins that cross the BBB are those that naturally form dimeric structures, similar to BDNF. Certain neurotrophins such as BDNF or NT-3 may form hetero-dimeric structures, and in some embodiments the invention provides a fusion protein constructed of one neurotrophin monomer fused to one chain (e.g., a light or heavy chain) of an antibody, e.g., of the HIRMAb, and another neurotrophin monomer fused to the second chain (e.g., a light or heavy chain) of the antibody. Typically, the molecular weight range of recombinant proteins that may be fused to the molecular Trojan horse ranges from 1000 Daltons to 500,000 Daltons.

B. Brain-Derived Neurotrophic Factor

One particularly useful neurotrophin in embodiments of the invention is brain-derived neurotrophic factor (BDNF). In experimental models of chronic neurodegenerative disease such as prion diseases, Alzheimer's disease (AD), Parkinson's disease (PD), Huntington's disease (HD), or amyotrophic lateral sclerosis (ALS), the direct intracerebral injection of BDNF is neuroprotective.

In studies demonstrating the pharmacologic efficacy of BDNF in experimental brain disease, it is necessary to administer the neurotrophin directly into the brain following a transcranial drug delivery procedure. The transcranial drug delivery is required because BDNF does not cross the brain capillary wall, which forms the blood-brain barrier (BBB) in vivo. Owing to the lack of transport of BDNF across the BBB, it is not possible for the neurotrophin to enter the CNS, including the brain or spinal cord, following a peripheral administration unless the BBB is experimentally disrupted. Clinical trials showed that subcutaneous administration of BDNF was not effective in the treatment of chronic neurodegenerative conditions, which derives from the lack of transport of BDNF across the BBB. The lack of utility of BDNF as a CNS therapeutic following peripheral administration is expected and follows from the limiting role that is played by the BBB in the development of neurotherapeutics, especially large molecule drugs such as BDNF. BDNF does not cross the BBB, and the lack of transport of the neurotrophin across the BBB prevents the molecule from being pharmacologically active in the brain following peripheral administration. The lack of BDNF transport across the BBB means that the neurotrophin must be directly injected into the brain across the skull bone to be pharmacologically active in the CNS. However, when the BDNF is fused to a Trojan horse such as the HIR MAb, this neurotrophin is now able to enter brain from blood following a non-invasive peripheral route of administration such as intravenous intramuscular, subcutaneous, intraperitoneal, or even oral administration. Owing to the BBB transport properties of this new class of molecule, it is not necessary to administer the BDNF directly into the CNS with an invasive delivery procedure requiring penetration of the skull or spinal canal. The reformulated fusion protein of the BDNF variant and the HIR MAb now enables entry of BDNF into the brain from the blood, and the development of BDNF as a neurotherapeutic for human diseases.

The forms of BDNF used in various embodiments of the invention may include pharmaceutically acceptable salts and prodrugs, and prodrugs of the salts, polymorphs, hydrates, solvates, biologically-active fragments, biologically active variants and stereoisomers of the naturally-occurring BDNF, as well as agonist, mimetic, and antagonist variants of the naturally-occurring BDNF and polypeptide fusions thereof. Variants that include one or more deletions, substitutions, or insertions in the natural sequence of the BDNF, in particular truncated versions of the native BDNF comprising deletion of one or more amino acids at the amino terminus, carboxyl terminus, or both, may also be used in certain embodiments.

In some embodiments, the invention utilizes a carboxy-truncated variant of the native BDNF, e.g., a variant in which 1, 2, 3, 4, 5, 6, 7, 8, 9, 10, or more than 10 amino acids are absent from the carboxy-terminus of the BDNF. BDNF variants include the complete 119 amino acid BDNF, the 117 or 118 amino acid variant with a truncated carboxyl terminus, variants with a truncated amino terminus, or variants with up to about a 20, 30, or 40% change in amino acid composition, as long as the fusion protein variant still binds to the brain neuroprotection receptor with high affinity. When an Ab, e.g., a MAb such as HIRMAb is used, additional fusion protein variants can be produced with the substitution of amino acids within either the framework region (FR) or the complementarity determining region (CDR) of either the light chain or the heavy chain of the Ab, e.g., HIRMAb, as long as the fusion protein binds with high affinity to the endogenous receptor, e.g., HIR to promote transport across the human BBB. Additional fusion protein variants can be produced by changing the composition or length of the linker peptide separating the fusion protein from the HIRMAb.

In some embodiments, the full-length 119 a.a. sequence of BDNF is utilized (SEQ ID NO: 39). In some embodiments, a one amino-acid carboxy-truncated variant of BDNF is utilized (amino acids 1-118 of SEQ ID NO: 39). In some embodiments, a two amino-acid carboxy-truncated variant of BDNF is utilized (amino acids 1-117 of SEQ ID NO: 39). In some embodiments, a three amino-acid carboxy-truncated variant of BDNF is utilized (amino acids 1-116 of SEQ ID NO: 39). In some embodiments, a four amino-acid carboxy-truncated variant of BDNF is utilized (amino acids 1-115 of SEQ ID NO: 39). In some embodiments, a five amino-acid carboxy-truncated variant of BDNF is utilized (amino acids 1-114 of SEQ ID NO: 39).

The sequence of human BDNF is given in SEQ ID NO: 39. In some embodiments, the invention utilizes a BDNF that is about 60, 70, 80, 90, 95, 99, or 100% identical with the sequence of SEQ ID NO: 39, or a truncated version thereof, e.g., the 117 or 118 amino acid variant with a one- or two-amino acid truncated carboxyl terminus, or variants with a truncated amino terminus. In some embodiments, the invention utilizes a two amino-acid carboxy-truncated 117 amino acid variant human BDNF with a sequence that is at least about 60, 70, 80, 90, 95, 99 or 100% identical to the sequence of amino acids 466-582 of SEQ ID NO: 24. In some embodiments, the invention utilizes a two amino-acid carboxy-truncated human 117 amino acid BDNF with a sequence that includes amino acids 466-582 of SEQ ID NO: 24.

Accordingly, BDNFs useful in the invention include peptides having at least about 60%, at least about 70%, at least about 80%, at least about 90%, at least about 95%, at least about 99%, or greater than 95% or greater than 99% sequence identity, e.g., 100% sequence identity, to the amino acid sequences disclosed herein.

C. Glial-Derived Neurotrophic Factor.

Another particularly useful neurotrophin in embodiments of the invention is glial-derived neurotrophic factor (GDNF). GDNF is a neurotrophic factor that can be used in the treatment of many acute and chronic brain diseases. However, the lack of transport of GDNF across the BBB has prevented the development of this molecule as a neurotherapeutic for the brain and spinal cord.

Acute brain conditions that can be treated by the GDNF-containing compositions described herein include, but are not limited to, spinal cord injury, brain injury (e.g., traumatic brain injury), focal brain ischemia, and global brain ischemia.

Chronic brain conditions that can be treated by the GDNF-containing compositions described herein include, but are not limited to neurodegenerative disease such as Parkinson's disease, motor neuron disease (e.g., spinal cord motor neuron disease such as amyotrophic lateral sclerosis); and substance abuse, e.g., addiction, including drug addiction and alcohol addiction.

The forms of GDNF used in various embodiments of the invention may include acceptable salts and prodrugs, and prodrugs of the salts, polymorphs, hydrates, solvates, biologically-active fragments, biologically active variants and stereoisomers of the naturally-occurring GDNF (e.g., human GDNF and mature human GDNF), as well as agonist, mimetic, and antagonist variants of the naturally-occurring GDNF and polypeptide fusions thereof. Variants that include one or more deletions, substitutions, or insertions in the natural sequence of the GDNF may also be used in certain embodiments. Insofar as the variants retain binding and/or activation of GFRα1. The structure-function relationship of GDNF and its ability to bind and activate GFRα1 has been studied extensively. See, e.g., Eketjäl et al (1999), *EMBO J.* 18(21):5901-5910; and Baloh et al (2000), *J Biol Chem,* 275(5):3412-3420. For example mutations known to be particularly sensitive to mutation include, e.g., the following residues in rat GDNF: D52, E61, E62, D116, I64, L114, L118, Y120, I122, and C101. Functional assays for GDNF are known in the art. See, e.g., Eketjäl et al, or Baloh et al supra. Functional assays for GDNF are also described in Example 15 herein.

When an Ab, e.g., a MAb such as HIRMAb is used, additional fusion protein variants can be produced with the substitution of amino acids within either the framework region (FR) or the complementarity determining region (CDR) of either the light chain or the heavy chain of the Ab, e.g., HIRMAb, as long as the fusion protein binds with high affinity to the endogenous receptor, e.g., HIR to promote transport across the human BBB. Additional fusion protein variants can be produced by changing the composition or length of the linker peptide separating the fusion protein from the HIRMAb.

In some embodiments, the full-length 211 a.a. sequence of human prepro GDNF is utilized (GenBank P39905). The sequence of human preproGDNF is given in SEQ ID NO: 44. In other embodiments, the mature form of human GDNF comprising amino acids Ser-78 to Ile 211 (SEQ ID NO: 52) is utilized:

```
                                                      (SEQ ID NO: 52)
SPDKQMAVLPRRERNRQAAAANPENSRGKGRRGQRGKNRGCVLTAIHLNV

TDLGLGYETKEELIFRYCSGSCDAAETTYDKILKNLSRNRRLVSDKVGQA

CCRPIAFDDDLSFLDDNLVYHILRKHSAKRCGCI.
```

In some embodiments, the invention utilizes a GDNF that is about 60, 70, 80, 90, 95, 99, or 100% identical with the sequence of SEQ ID NO:52.

Accordingly, GDNFs useful in the invention include peptides having at least about 60%, at least about 70%, at least about 80%, at least about 90%, at least about 95%, at least about 99%, or greater than 95% or greater than 99% sequence identity, e.g., 100% sequence identity, to the amino acid sequences disclosed herein Percent sequence identity is determined by conventional methods. See, for example, Altschul et al., *Bull. Math. Bio.* 48:603 (1986), and Henikoff and Henikoff, *Proc. Natl. Acad. Sci.* USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci.* USA 85:2444 (1988), and by Pearson, *Meth. Enzymol.* 183:63 (1990). Briefly, FASTA first characterizes sequence similarity by identifying regions shared by the query sequence (e.g., SEQ ID NO:44 or SEQ ID NO:52) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM *J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present invention also includes peptides having a conservative amino acid change, compared with an amino acid sequence disclosed herein. Many such changes have been described specifically. More generally, for example, variants can be obtained that contain one or more amino acid substitutions of SEQ ID NO:52. In some embodiments sequence variants include conservative amino acid substitutions, e.g., an alkyl amino acid is substituted for an alkyl amino acid in a GDNF peptide amino acid sequence, an aromatic amino acid is substituted for an aromatic amino acid in a GDNF peptide amino acid sequence, a sulfur-containing amino acid is substituted for a sulfur-containing amino acid in a GDNF peptide amino acid sequence, a hydroxy-containing amino acid is substituted for a hydroxy-containing amino acid in a GDNF peptide amino acid sequence, an acidic amino acid is substituted for an acidic amino acid in a GDNF peptide amino acid sequence, a basic amino acid is substituted for a basic amino acid in GDNF peptide amino acid sequence, or a dibasic monocarboxylic amino acid is substituted for a dibasic monocarboxylic amino acid in a GDNF peptide amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci.* USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

In some embodiments, where GDNF sequence variants (e.g., variants of SEQ ID NO:52) are to be utilized, mutation tolerance prediction programs can be used to greatly reduce the number of non-functional sequence variants that would be generated by strictly random mutagenesis. Various programs for predicting the effects of amino acid substitutions in a protein sequence on protein function (e.g., SIFT, PolyPhen, PANTHER PSEC, PMUT, and TopoSNP) are described in, e.g., Henikoff et al., (2006), *Annu. Rev. Genomics Hum. Genet.,* 7:61-80.

V. Compositions

Compositions of the invention are useful in one or more of: increasing serum half-life of a cationic compound, transporting an agent across the BBB, and/or retaining activity of the agent once transported across the BBB. Accordingly, in some embodiments, the invention provides compositions containing a neurotherapeutic agent covalently linked to a structure that is capable of crossing the blood brain barrier (BBB), where the composition is capable of producing an average elevation of concentration in the brain of the neurotherapeutic agent of at least about 1, 2, 3, 4, 5, 10, 20, 30, 40, or 50 ng/gram brain following peripheral administration. The invention also provides compositions containing an agent that is covalently linked to a chimeric MAb to the human BBB insulin receptor. The invention further provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 10, 20, 30, 40, 50, 60, 70, 80, 90, 95, 99, or 100% of their activities, compared to their activities as separate entities. In certain embodiments, the invention further provides compositions that increase the serum half-life of cationic substances. The invention also provides pharmaceutical compositions that contain one or more compositions of the invention and a pharmaceutically acceptable excipient.

In some embodiments, the invention provides compositions containing a neurotherapeutic agent covalently linked to a structure that is capable of crossing the blood brain barrier (BBB), where the composition is capable of producing an average elevation of concentration in the brain of the neurotherapeutic agent of at least about 1, 2, 3, 4, 5, 10, 20, 30, 40, or 50 ng/gram brain following peripheral administration.

"Elevation" of the agent is an increase in the brain concentration of the agent compared to the concentration of the agent administered alone (i.e., not covalently linked to a structure that is capable of crossing the BBB). In the case of agents for which only a small amount of the agent alone normally crosses the BBB, "elevation" may be an increase in the agent compared to resting brain levels. "Average" refers to the mean of at least three, four, five, or more than five measurements, preferably in different individuals. The individual in which the elevation is measured is a mammal, such as a rat, or, preferably, a primate, e.g., a monkey. An example of measurements of elevation of the level of a neurotherapeutic agent (BDNF) is given in Example 7.

In some embodiments, the structure that is capable of crossing the BBB utilizes an endogenous BBB receptor mediated transport system, such as a system that utilizes the insulin receptor, transferrin receptor, leptin receptor, LDL receptor, or IGF receptor. In some embodiments, the endogenous BBB receptor mediated transport system is the insulin BBB receptor mediated transport system. In some embodiments, the structure that is capable of crossing the BBB is an antibody, e.g., a monoclonal antibody (MAb) such as a chimeric MAb. The antibody can be a chimeric antibody with sufficient human sequence that it is suitable for administration to a human. The antibody can be glycosylated or nonglycosylated; in some embodiments, the antibody is glycosylated, e.g., in a glycosylation pattern produced by its synthesis in a CHO cell. In embodiments in which the structure is an antibody, the covalent linkage between the antibody and the neurotherapeutic agent may be a linkage between any suitable portion of the antibody and the neurotherapeutic agent, as long as it allows the antibody-agent fusion to cross the blood brain barrier and the neurotherapeutic agent to retain a therapeutically useful portion of its activity within the CNS. In certain embodiments, the covalent link is between one or more light chains of the antibody and the neurotherapeutic agent. In the case of a peptide neurotherapeutic agent (e.g., a neurotrophin such as GDNF), the peptide can be covalently linked by its carboxy or amino terminus to the carboxy or amino terminus of the light chain (LC) or heavy chain (HC) of the antibody. Any suitable linkage may be used, e.g., carboxy terminus of light chain to amino terminus of peptide, carboxy terminus of heavy chain to amino terminus of peptide, amino terminus of light chain to amino terminus of peptide, amino terminus of heavy chain to amino terminus of peptide, carboxy terminus of light chain to carboxy terminus of peptide, carboxy terminus of heavy chain to carboxy terminus of peptide, amino terminus of light chain to carboxy terminus of peptide, or amino terminus of heavy chain to carboxy terminus of peptide. In some embodiments, the linkage is from the carboxy terminus of the HC to the amino terminus of the peptide. It will be appreciated that a linkage between terminal amino acids is not required, and any linkage which meets the requirements of the invention may be used; such linkages between non-terminal amino acids of peptides are readily accomplished by those of skill in the art.

In some embodiments, the invention utilizes BDNF, either the native form or truncated variants. Strikingly, it has been found that fusion proteins of these forms of BDNF retain full transport and activity. This is surprising because the neurotrophin is translated in vivo in cells as a prepro form and the prepro-BDNF is then converted into mature BDNF following cleavage of the prepro peptide from the amino terminus of the BDNF. In order to preserve the prepro form of the BDNF, and the subsequent cleavability of the prepro peptide, it would seem to be necessary to fuse the prepro BDNF to the amino terminus of either the HC or the LC of the targeting MAb. This could, however, inhibit the binding of the MAb for the target antigen, since the complementarity determining regions (CDR) of the heavy chain or light chain of the MAb molecule, which comprise the antigen binding site of the MAb, are situated near the amino terminus of the heavy chain or light chains of the antibody. Therefore, fusion of the prepro-neurotrophin to the amino terminus of the antibody chains is expected to result in not only impairment of antibody activity, but also an impairment of antibody folding following translation. The present invention shows the unexpected finding that it is possible to fuse the mature form of a neurotrophin, such as a BDNF variant (vBDNF), to the carboxyl terminus of the heavy chain of the HIR MAb. The production of this new genetically engineered fusion protein creates a bi-functional molecule that binds with high affinity to both the HIR and the trkB receptors.

In other embodiments, the invention utilizes GDNF (e.g., mature human GDNF) or a sequence variant of GDNF as described herein.

Figure 18:
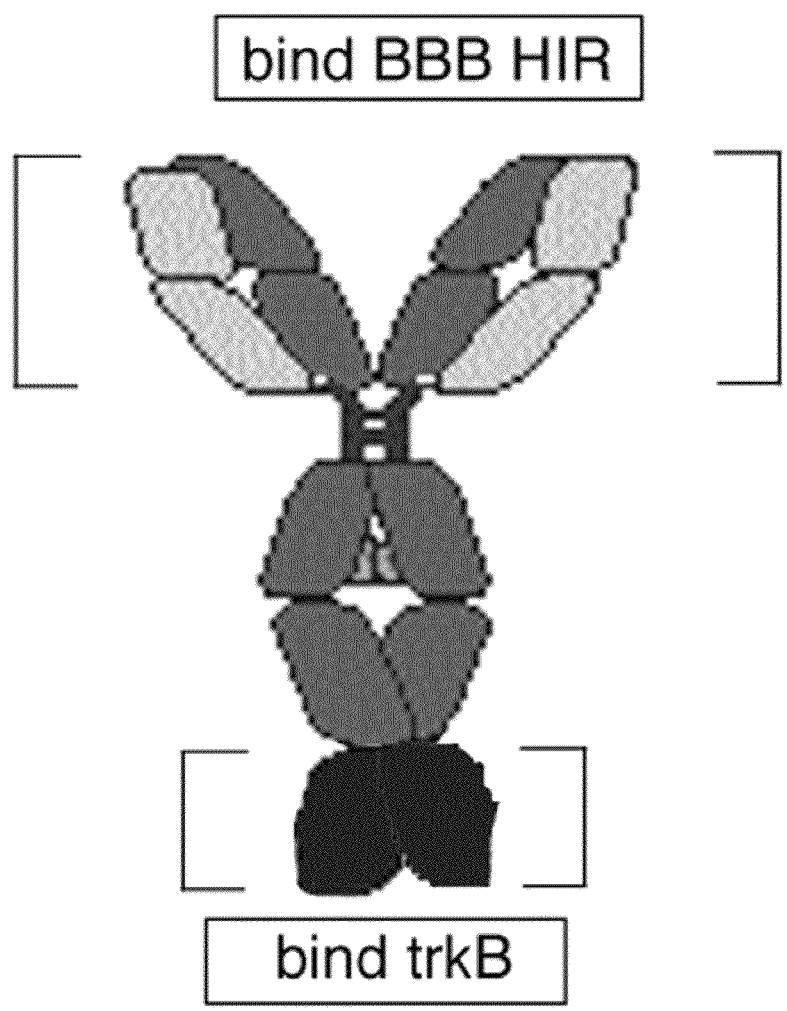
FIG. 18. Structure of fusion protein, a bi-functional molecule that both (a) binds to the human BBB human insulin receptor (HIR) to enable transport across the BBB from blood, and (b) binds to the trkB on neurons to induce neuroprotection.

In some embodiments, more than one molecule of the same neurotherapeutic agent is attached to the structure that crosses the BBB. For example, in compositions of the invention where a single neurotrophin is attached to an antibody, one molecule of the neurotrophin is attached to each heavy chain, naturally producing a structure that is ideal for homodimer formation. This is the case for compositions containing BDNF or GDNF. Neurotrophins such as BDNF or GDNF require an obligatory formation of a homo-dimeric structure to be biologically active, and to bind with high affinity to the cognate receptor, e.g. TrkB or GFRα1. A naturally occurring homo-dimeric structure between two BDNF molecules is formed when the neurotrophin is fused to a carboxyl terminus of the CH3 region of an IgG molecule, as illustrated in FIG. 18. Without being bound by theory, it is thought that this may account for the unexpected finding of essentially 100% of activity for the BDNF when bound to the IgG (see, e.g., FIG. 24).

In some embodiments, more than one type of neurotherapeutic agent can be attached to the structure that is capable of crossing the blood brain barrier. In some embodiments, 2, 3, 4, 5, 6, 7, 8, 9, 10, or more than 10 different neurotherapeutic agents may be attached to the structure that is capable of crossing the blood brain barrier. In certain embodiments, 2 different neurotrophins are attached to an antibody to an endogenous BBB receptor-mediated transport system. Any combination of neurotrophins may be used. Particularly useful in some embodiments of the invention are neurotrophins used as precursors for fusion proteins that cross the BBB are those that naturally form dimeric structures, similar to BDNF or GDNF. Certain neurotrophins such as BDNF or NT-3 may form hetero-dimeric structures, and in some embodiments the invention provides a fusion protein constructed of one neurotrophin monomer fused to one chain (e.g., heavy chain) of an antibody, e.g., of the HIRMAb, and another neurotrophin monomer fused to the second chain of the antibody. Typically, the molecular weight range of recombinant proteins that may be fused to the molecular Trojan horse ranges from 1000 Daltons to 500,000 Daltons.

In some embodiments, more than one type of structure capable of crossing the BBB, e.g., molecular Trojan horse, may be used. The different structures may be covalently attached to a single neurotherapeutic agent, e.g., a single neurotrophin such as GDNF, or multiple neurotherapeutics, e.g., multiple neurotrophins, or any combination thereof. Thus, for example, in some embodiments either with the same neurotrophin attached to each MTH or a different neurotrophin attached, or combinations of neurotrophins attached. Thus the neuroprotective recombinant protein can be fused to multiple molecular Trojan horses that undergo receptor-mediated transport across the blood-brain barrier, including monoclonal antibodies to the insulin receptor, transferrin receptor, insulin-like growth factor (IGF) receptor, or the low density lipoprotein (LDL) receptor or the endogenous ligand, including insulin, transferrin, the IGFs, or LDL. Ligands that traverse the blood-brain barrier via absorptive-mediated transport may also be used as molecular Trojan horses including cationic proteins, or carbohydrate bearing proteins that bind to membrane lectins. The molecular weight range of molecular Trojan horses is 1000 Daltons to 500,000 Daltons.

The covalent linkage between the structure capable of crossing the BBB and the neurotherapeutic agent may be direct, e.g., a peptide bond between the terminal amino acid of one peptide and the terminal amino acid of the other peptide to which it is linked, or indirect, via a linker. If a linker is used, it may be any suitable linker, e.g., a peptide linker. If a peptide linker is used, it may be 1, 2, 3, 4, 5, 6, 7, 8, 9, 10, or more than 10 amino acids in length. In some embodiments, a three amino acid linker is used. In some embodiments, the linker has the sequence ser-ser-met. The covalent linkage may be cleavable, however this is not a requirement for activity of the system in some embodiments; indeed, an advantage of these embodiments of the present invention is that the fusion protein, without cleavage, is partially or fully active both for transport and for activity once across the BBB.

In some embodiments, a noncovalent attachment may be used. An example of noncovalent attachment of the MTH, e.g., MAb, to the large molecule therapeutic neuroprotective factor is avidin/streptavidin-biotin attachment. Such an approach is further described in U.S. patent application Ser. No. 10/858,729, entitled "Anti-growth factor receptor avidin fusion proteins as universal vectors for drug delivery," filed Apr. 21, 2005, which is hereby incorporated by reference in its entirety.

The neurotherapeutic agent may be any suitable neurotherapeutic agent, such as a neurotrophin. In some embodiments, the neurotherapeutic agent is a neurotrophin such as brain derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, or stem cell factor (SCF). In some embodiments, the neurotrophin is BDNF. The BDNF may be native BDNF or a variant BDNF. Some embodiments utilize a two amino acid carboxyl-truncated variant. The BDNF can be a human BDNF. In some embodiments, the BDNF contains a sequence that is about 60, 70, 80, 90, 95, 99, or 100% identical to the sequence of amino acids 466-582 of SEQ ID NO: 24.

In some embodiments, the invention provides compositions containing a neurotherapeutic agent covalently linked to a structure that is capable of crossing the BBB where the composition is capable of producing an average elevation of concentration in the brain of the neurotherapeutic agent of at least about 1, 2, 3, 4, 5, 10, 20, 30, 40, or 50 ng/gram brain following peripheral administration, where the neurotherapeutic agent is a neurotrophin and the structure that is capable of crossing the BBB is a MAb to an endogenous BBB receptor mediated transport system. The antibody can be glycosylated or nonglycosylated; in some embodiments, the antibody is glycosylated, e.g., in a glycosylation pattern produced by its synthesis in a CHO cell. In certain embodiments, the neurotrophin is GDNF, e.g., a mature human GDNF (SEQ ID NO:52) or a sequence variant thereof. The MAb can be an antibody to the insulin BBB receptor mediated transport system, e.g., a chimeric MAb. The antibody can be a chimeric antibody with sufficient human sequence that it is suitable for administration to a human, e.g., at least about 80% human sequence, e.g., 85%, 90%, 95%, or another percent human amino acid sequence from about 80% to about 100% human sequence. In some embodiments, the insulin receptor is a human insulin receptor and the GDNF is a human GDNF. In some embodiments, the GDNF contains a sequence that is about 60, 70, 80, 90, 95, 99, or 100% identical to the sequence of SEQ ID NO: 44. The GDNF can be covalently linked at its amino terminus to the carboxy terminus of the heavy chain of the MAb, optionally with a linker between the termini, such as the three amino-acid linker ser-ser-met, or the two amino acid linker ser-ser. In some embodiments, the heavy chain of the MAb contains a sequence that is about 60, 70, 80, 90, 95, 99, or 100% identical to amino acids 20-462 of SEQ ID NO: 24. In some embodiments, the light chain of the MAb contains a sequence that is about 60, 70, 80, 90, 95, 99, or 100% identical to amino acids 21-234 of SEQ ID NO: 36.

The invention also provides compositions containing an agent that is covalently linked to a chimeric MAb to the human BBB insulin receptor. In some embodiments, the heavy chain of the MAb is covalently linked to the agent to form a fusion protein. The agent can be any agent described herein, i.e., any agent for which transport across the BBB is desired. In some embodiments, the agent is a therapeutic agent, such as a neurotherapeutic agent as described herein, e.g., a neurotrophin such as GDNF Strikingly, it has been found that multifunctional fusion proteins of the invention, e.g., difunctional fusion proteins, retain a high proportion of the activity of the separate portions, e.g., the portion that is capable of crossing the BBB and the portion that is active in the CNS. Accordingly, the invention further provides a fusion protein containing a structure capable of crossing the BBB, covalently linked to a peptide that is active in the central nervous system (CNS), where the structure capable of crossing the BBB and the peptide that is active in the central nervous system each retain an average of at least about 10, 20, 30, 40, 50, 60, 70, 80, 90, 95, 99, or 100% of their activities, compared to their activities as separate entities. In some embodiments, the structure capable of crossing the BBB, and the peptide that is active in the central nervous system each retain about 20% to about 80% of their activities (e.g., about 30% to about 70, or about 40% to about 60%) compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 50% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 60% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 70% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 80% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 90% of their activities, compared to their activities as separate entities. In some embodiments, the structure capable of crossing the blood brain barrier retains at least about 10, 20, 30, 40, 50, 60, 70, 80, 90, 95, 99, or 100% of its activity, compared to its activity as a separate entity, and the peptide that is active in the central nervous system retains at least about 10, 20, 30, 40, 50, 60, 70, 80, 90, 95, 99, or 100% of its activity, compared to its activity as a separate entity.

As used herein, "activity" includes physiological activity, e.g., ability to cross the BBB and/or therapeutic activity and also binding affinity of the structures for their respective receptors.

Transport of the structure capable of crossing the BBB across the BBB may be compared for the structure alone and for the structure as part of a fusion structure of the invention by standard methods. For example, pharmacokinetics and brain uptake of the fusion structure, e.g., fusion protein, by a model animal, e.g., a mammal such as a primate, may be used. Such techniques are illustrated in Example 7, which demonstrates pharmacokinetics and brain uptake of a fusion protein of the invention by the adult Rhesus monkey. Similarly, standard models for the function of an agent, e.g. the therapeutic or protective function of a therapeutic agent, may also be used to compare the function of the agent alone and the function of the agent as part of a fusion structure of the invention. See, e.g., Example 5, which demonstrates the activity of a neurotrophin alone and the same neurotrophin bound to a fusion protein in a model system (hypoxia-reoxygenation in human neural cells). In both Example 5 and Example 7, the fusion protein of the invention retained about 100% of the transport ability and the therapeutic function of its individual components, i.e., a structure capable of crossing the BBB (a MAb to the human insulin receptor) and a therapeutic agent (BDNF).

Alternatively, binding affinity for receptors may be used as a marker of activity. Binding affinity for the receptor is compared for the structure alone and for the structure when part of the fusion protein. A suitable type of binding affinity assay is the competitive ligand binding assay (CLBA). For example, for fusion proteins containing MAbs to endogenous BBB receptor-mediated transport systems fused to a neurotrophin, a CLBA may be used both to assay the affinity of the MAb for its receptor and the neurotrophin for its receptor, either as part of the fusion protein or as separate entities, and percentage affinity calculated. If, as in some embodiments, the peptide that is active in the CNS is highly ionic, e.g., cationic, causing a high degree of non-specific binding, suitable measures should be taken to eliminate the nonspecific binding. See, e.g., Example 4. "Average" measurements are the average of at least three separate measurements.

In embodiments of the above fusion proteins, the structure capable of crossing the blood brain barrier crosses the BBB on an endogenous BBB receptor-mediated transporter, such as a transporter selected from the group consisting of the insulin transporter, the transferrin transporter, the leptin transporter, the LDL transporter, and the IGF receptor. In some embodiments, the endogenous BBB receptor-mediated transporter is selected from the group consisting of the insulin transporter and the transferrin transporter. In some embodiments, the endogenous BBB receptor-mediated transporter is the insulin transporter, e.g., the human insulin transporter. The structure capable of crossing the BBB can be an antibody, e.g., a MAb such as a chimeric MAb. The antibody can be an antibody to an endogenous BBB receptor-mediated transporter, as described herein. The peptide that is active in the CNS can be a neurotherapeutic agent, e.g., a neurotrophin. In some embodiments, the neurotrophin is selected from the group consisting of brain-derived neurotrophic factor, nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, or stem cell factor (SCF). In some embodiments, the neurotrophin is BDNF such as a truncated BDNF, e.g., a carboxyl-truncated BDNF. The carboxyl-truncated BDNF is lacking the two carboxyl terminal amino acids in some embodiments. The structure capable of crossing the BBB and the neurotherapeutic agent are covalently linked by a peptide linker in some embodiments.

In certain embodiments, the invention provides compositions that increase the serum half-life of cationic substances. One limitation for many current therapeutics, especially cationic therapeutic peptides (e.g., BDNF) is their rapid clearance from the circulation. The positive charge on the cationic substance, such as cationic peptides, rapidly interacts with negative charges on cell membranes, which triggers an absorptive-mediated endocytosis into the cell, particularly liver and spleen. This is true not only for neurotherapeutics (where rapid clearance means only limited contact with the BBB and thus limited ability to cross the BBB) but for other agents as well, such as cationic import peptides such as the tat peptide, or cationic proteins (e.g. protamine, polylysine, polyarginine) that bind nucleic acids, or cationic proteins such as avidin that bind biotinylated drugs. Surprisingly, fusion compositions of the invention that include a cationic therapeutic peptide covalently linked to an immunoglobulin show greatly enhanced serum half-life compared to the same peptide when it was not covalently part of a fusion immunoglobulin. This is an important finding, because it shows that the fusion of a highly cationic protein, e.g., BDNF, to an immunoglobulin, e.g. HIRMAb, has two important and unexpected effects: 1) it greatly enhances the serum half-life of the cationic protein, and 2) it does not accelerate the blood clearance of the immunoglobulin to which it is attached, e.g., the HIRMAb. Prior work shows that the noncovalent attachment of a cationic therapeutic peptide, e.g., the cationic BDNF to a monoclonal antibody greatly accelerated the blood clearance of the antibody, owing to the cationic nature of the BDNF, which greatly enhances hepatic uptake. The work in FIG. 27A and Example 7 shows that when the cationic therapeutic peptide, e.g., BDNF is re-engineered as an IgG fusion protein, the plasma pharmacokinetics is dominated by the IgG moiety, and that the blood level of the BDNF remains high for a prolonged period; indeed, the serum half-life of the BDNF in the fusion protein is at least about 100 times that of the BDNF alone.

Accordingly, in some embodiments, the invention provides composition comprising a cationic therapeutic peptide covalently linked to an immunoglobulin, wherein the cationic therapeutic peptide in the composition has a serum half-life that is an average of at least about 1.5, 2, 3, 4, 5, 6, 7, 8, 9, 10, 15, 20, 30, 40, 50, 60, 70, 80, 90, 100, or more than about 100-fold greater than the serum half-life of the cationic therapeutic peptide alone. In some embodiments, the invention provides a composition comprising a cationic therapeutic peptide covalently linked to an immunoglobulin, wherein the cationic therapeutic peptide in the composition has a mean residence time (MRT) in the serum that is an average of at least about 1.5, 2, 3, 4, 5, 6, 7, 8, 9, 10, 15, 20, 30, 40, 50, 60, 70, 80, 90, 100, or more than about 100-fold greater than the serum half-life of the cationic therapeutic peptide alone. In some embodiments, the invention provides composition comprising a cationic therapeutic peptide covalently linked to an immunoglobulin, wherein the cationic therapeutic peptide in the composition has a systemic clearance rate that is an average of at least about 1.5, 2, 3, 4, 5, 6, 7, 8, 9, 10, 15, 20, 30, 40, 50, 60, 70, 80, 90, 100, or more than about 100-fold slower than the systemic clearance rate of the cationic therapeutic peptide alone. In some embodiments, the invention provides composition comprising a cationic therapeutic peptide covalently linked to an immunoglobulin, wherein the cationic therapeutic peptide in the composition has average blood level after peripheral administration that is an average of at least about 1.5, 2, 3, 4, 5, 6, 7, 8, 9, 10, 15, 20, 30, 40, 50, 60, 70, 80, 90, 100, or more than about 100-fold greater than the average blood level after peripheral administration of the cationic therapeutic peptide alone.

In some embodiments, the cationic therapeutic peptide comprises a neurotherapeutic agent. Examples of neurotherapeutic agents that are cationic peptides interferons, interleukins, cytokines, or growth factors with an isoelectric point (pI) above 8. In some embodiments, the neurotherapeutic agent is a neurotrophin. Cationic peptide neurotrophins include BDNF, GDNF, NT-3, NT-4/5, NGF, and FGF-2. In some embodiments, the neurotrophin is BDNF or GDNF.

In some embodiments, the immunoglobulin is an antibody to an endogenous BBB receptor-mediated transport system. In some embodiments, the endogenous BBB receptor-mediated transport system is selected from the group consisting of the insulin BBB transport system, the BBB transferrin receptor, the BBB leptin receptor, the BBB IGF receptor, or the BBB lipoprotein receptor. In some embodiments, the antibody is an antibody to the endogenous insulin BBB receptor-mediated transport system. Antibodies can be any suitable antibody as described herein.

Pharmaceutical Compositions

The invention also provides pharmaceutical compositions that contain one or more compositions of the invention and a pharmaceutically acceptable excipient. A thorough discussion of pharmaceutically acceptable carriers/excipients can be found in *Remington's Pharmaceutical Sciences*, Gennaro, A R, ed., 20th edition, 2000: Williams and Wilkins PA, USA. Pharmaceutical compostions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compostions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.0001 to 1.0 milligrams, or about 0.001 to 0.1 milligrams, or about 1.0 to 100 milligrams or even about 0.01 to 1.0 grams per dose or so. Multiple doses can also be administered. In some embodiments, a dosage of about 2.5 to about 25 mg of a fusion protein of the invention is used as a unit dose for administration to a human, e.g., about 2.5 to about 25 mg of a fusion protein of GDNF and a HIR MAb.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284,262), transdermal administration (See U.S. Pat. Nos. 6,348,210; and 6,322,808) and transmucosal administration (See U.S. Pat. No. 5,656,284). All such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

VI. Nucleic Acids, Vectors, Cells, and Manufacture

The invention also provides nucleic acids, vectors, cells, and methods of production.

A. Nucleic Acids

In some embodiments, the invention provides nucleic acids that code for proteins or peptides of the invention. In certain embodiments, the invention provides a single nucleic acid sequence containing a first sequence coding for a light chain of an immunoglobulin and second sequence coding a heavy chain of the immunoglobulin, where either the first sequence also codes for a peptide that is expressed as a fusion protein of the peptide covalently linked to the light chain, or the second sequence also codes for a peptide that is expressed as a fusion protein of the peptide covalently linked to the heavy chain. In some embodiments, the invention provides nucleic acid sequences, and in some embodiments the invention provides nucleic acid sequences that are at least about 60, 70, 80, 90, 95, 99, or 100% identical to a particular nucleotide sequence. For example, in some embodiments, the invention provides a nucleic acid containing a first sequence that is at least about 60, 70, 80, 90, 95, 99, or 100% identical to SEQ ID NO:45 and a second sequence that is at least about 60, 70, 80, 90, 95, 99, or 100% identical to nucleotides 1396-1746 of SEQ ID NO: 33.

In other embodiments, the invention provides a nucleic acid containing a sequence that is at least about 60, 70, 80, 90, 95, 99, or 100% identical to SEQ ID NO:45.

For sequence comparison, of two nucleic acids, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. The BLAST algorithm is typically performed with the "low complexity" filter turned off. The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The invention provides nucleic acids that code for any of the peptides of the invention. In some embodiments, the invention provides a single nucleic acid sequence containing a gene coding for a light chain of an immunoglobulin and a gene coding for a fusion protein, where the fusion protein includes a heavy chain of the immunoglobulin covalently linked to a peptide. In some embodiments, the peptide is a therapeutic peptide. In some embodiments the peptide is a neurotherapeutic peptide, e.g., a neurotrophin such as BDNF or GDNF (e.g., mature human GDNF). In some embodiments, the BDNF is a two amino acid carboxy-truncated BDNF. In some embodiments, the immunoglobulin is an IgG. In some embodiments, the IgG is a MAb, such as a chimeric MAb. The antibody can be an antibody to a transport system, e.g., an endogenous BBB receptor-mediated transport system such as the endogenous BBB receptor-mediated insulin transport system. In some embodiments, the endogenous BBB receptor-mediated insulin transport system is a human endogenous BBB receptor-mediated insulin transport system and wherein the peptide to which the immunoglobulin heavy chain is covalently linked is human BDNF or human GDNF. Any suitable peptide, neurotherapeutic peptide, neurotrophin, BDNF, GDNF (e.g., mature human GDNF), antibody, monoclonal antibody, or chimeric antibody, as described herein, may be coded for by the nucleic acid, combined as a fusion protein and coded for in a single nucleic acid sequence. As is well-known in the art, owing to the degeneracy of the genetic code, any combination of suitable codons may be used to code for the desired fusion protein. In addition, other elements useful in recombinant technology, such as promoters, termination signals, and the like, may also be included in the nucleic acid sequence. Such elements are well-known in the art. In addition, all nucleic acid sequences described and claimed herein include the complement of the sequence.

In some embodiments the nucleic acid codes for a BDNF, e.g., a variant BDNF, or GDNF (e.g., mature human GDNF) as a component of the fusion protein, which also comprises an immunoglobulin sequence. In some embodiments, the BDNF contains a sequence that is about 60, 70, 80, 90, 95, 99, or 100% identical to the sequence of amino acids 466-582 of SEQ ID NO: 24. In some embodiments, the GDNF contains a sequence that is at least about 60, 70, 80, 90, 95, 99, or 100% identical to the sequence of SEQ ID NO:52. In some embodiments, the amino acid sequence of the encoded GDNF consists essentially of SEQ ID NO:52. In some embodiments, the nucleic acid codes for a fusion protein comprising an amino acid sequence that is at least about 60, 70, 80, 90, 95, 99, or 100% identical to the sequence of SEQ ID NO:46. In some embodiments, the encoded nucleic acid comprises the amino acid sequence of SEQ ID NO:46. In some embodiments, the BDNF or GDNF is linked at its amino terminus to carboxy terminus of the heavy chain of the immunoglobulin, e.g., MAb. The heavy chain of the MAb can comprise a sequence that is about 60, 70, 80, 90, 95, 99 or 100% identical to amino acids 20-462 of SEQ ID NO: 24. In some embodiments, the light chain of the immunoglobulin, e.g., MAb, comprises a sequence that is about 60, 70, 80, 90, 95, 99 or 100% identical to amino acids 21-234 of SEQ ID NO: 36. The nucleic acid can further contain a nucleic acid sequence that codes for a peptide linker between the heavy chain of the MAb and the BDNF or GDNF. In some embodiments, the linker is S-S-M. The nucleic acid may further contain a nucleic acid sequence coding for a signal peptide, wherein the signal peptide is linked to the heavy chain. Any suitable signal peptide, as known in the art or subsequently developed, may be used. In some embodiments, the signal peptide attached to the heavy chain comprises a sequence that is about 60, 70, 80, 90, 95, 99, or 100% identical to amino acids 1-19 of SEQ ID NO: 24. In some embodiments, the nucleic acid contains a nucleic acid sequence coding for another signal peptide, wherein the other signal peptide is linked to the light chain. The signal peptide linked to the light chain can comprise a sequence that is about 60, 70, 80, 90, 95, 99, or 100% identical to amino acids 1-20 of SEQ ID NO: 36. The nucleic acid can contain a nucleic acid sequence coding for a selectable marker. In some embodiments the selectable marker is DHFR. The sequence of the DHFR can be about 60, 70, 80, 90, 95, 99, or 100% identical to amino acids 1-187 of SEQ ID NO: 38.

In certain embodiments, the invention provides a nucleic acid comprising a first sequence that codes for a neurotherapeutic peptide, e.g., a neurotrophin such as BDNF, in the same open reading frame as a second sequence that codes for an immunoglobulin component. The immunoglobulin component can be, e.g., a light chain or a heavy chain, e.g., that is at least about 60, 70, 80, 90, 95, 99, or 100% identical to nucleotides 58-1386- of SEQ ID NO: 33 and a second sequence that is at least about 60, 70, 80, 90, 95, 99, or 100% identical to nucleotides 1396-1746 of SEQ ID NO: 33. In some embodiments, the nucleic acid also contains a third sequence that is at least about 60, 70, 80, 90, 95, 99, or 100% identical to nucleotides 61-702 of SEQ ID NO: 35. In some embodiments, the nucleic acid further contains a fourth sequence that codes for a first signal peptide and a fifth sequence that codes for a second signal peptide. In some embodiments, the fourth sequence is at least about 60, 70, 80, 90, 95, 99, or 100% identical to nucleotides 1-57 of SEQ ID NO: 33 and the fifth sequence is at least about 60, 70, 80, 90, 95, 99, or 100% identical to nucleotides 1-60 of SEQ ID NO: 35. In some embodiments, the nucleic acid further contains a sequence that codes for a selectable marker, such as dihydrofolate reductase (DHFR). In some embodiments, the sequence that codes for the DHFR is at least about 60, 70, 80, 90, 95, 99, or 100% identical to nucleotides 1-561 of SEQ ID NO: 37.

B. Vectors

The invention also provides vectors. The vector can contain any of the nucleic acid sequences described herein. In some embodiments, the invention provides a single tandem expression vector containing nucleic acid coding for an antibody heavy chain fused to a peptide, e.g., a therapeutic peptide such as a neurotrophin, and nucleic acid coding for a light chain of the antibody, all incorporated into a single piece of nucleic acid, e.g., a single piece of DNA. The single tandem vector can also include one or more selection and/or amplification genes. A method of making an exemplary vector of the invention is provided in the Examples. However, any suitable techniques, as known in the art, may be used to construct the vector.

The use of a single tandem vector has several advantages over previous techniques. The transfection of a eukaryotic cell line with immunoglobulin G (IgG) genes generally involves the co-transfection of the cell line with separate plasmids encoding the heavy chain (HC) and the light chain (LC) comprising the IgG. In the case of a IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The approach to manufacturing the fusion protein utilized in certain embodiments of the invention is the production of a cell line that is stably transfected with a single plasmid DNA that contains all the required genes on a single strand of DNA, including the HC-fusion protein gene, the LC gene, the selection gene, e.g. neo, and the amplification gene, e.g. the dihydrofolate reductase gene. As shown in the diagram of the fusion protein tandem vector in FIG. 12, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

C. Cells

The invention further provides cells that incorporate one or more of the vectors of the invention. The cell may be a prokaryotic cell or a eukaryotic cell. In some embodiments, the cell is a eukaryotic cell. In some embodiments, the cell is a mouse myeloma hybridoma cell. In some embodiments, the cell is a Chinese hamster ovary (CHO) cell. Exemplary methods for incorporation of the vector(s) into the cell are given in the Examples. However, any suitable techniques, as known in the art, may be used to incorporate the vector(s) into the cell. In some embodiments, the invention provides a cell capable of expressing an immunoglobulin fusion protein, where the cell is a cell into which has been introduced a single tandem expression vector, where both the immunoglobulin light chain gene and the gene for the immunoglobulin heavy chain fused to the therapeutic agent, are incorporated into a single piece of nucleic acid, e.g., DNA. In some embodiments, the invention provides a cell capable of expressing an immunoglobulin fusion protein, where the cell is a cell into which has been stably transfected a single tandem expression vector, where both the immunoglobulin heavy chain gene and the gene for the immunoglobulin light chain fused to the therapeutic agent, are incorporated into a single piece of nucleic acid, e.g., DNA. The introduction of the tandem vector may be by, e.g., permanent integration into the chromosomal nucleic acid, or by, e.g., introduction of an episomal genetic element.

D. Methods of Manufacture

In addition, the invention provides methods of manufacture. In some embodiments, the invention provides a method of manufacturing an immunoglobulin fusion protein, where the fusion protein contains an immunoglobulin heavy chain fused to a therapeutic agent, by introducing into a eukaryotic cell a single tandem expression vector, where both the immunoglobulin light chain gene and the gene for the immunoglobulin heavy chain fused to the therapeutic agent, are incorporated into a single piece of nucleic acid, e.g., DNA. In some embodiments, the invention provides a method of manufacturing an immunoglobulin fusion protein, where the fusion protein contains an immunoglobulin light chain fused to a therapeutic agent, by ly introducing into a eukaryotic cell a single tandem expression vector, where both the immunoglobulin heavy chain gene and the gene for the immunoglobulin light chain fused to the therapeutic agent, are incorporated into a single piece of nucleic acid, e.g., DNA. In some embodiments, the introduction of the vector is accomplished by integration into the host cell genome. In some embodiments, the introduction of the vector is accomplished by introduction of an episomal genetic element containing the vector into the host cell. Episomal genetic elements are well-known in the art In some embodiments, the therapeutic agent is a neurotherapeutic agent. In some embodiments, the single piece of nucleic acid further includes one or more genes for selectable markers. In some embodiments, the single piece of nucleic acid further includes one or more amplification genes. In some embodiments, the immunoglobulin is an IgG, e.g., a MAb such as a chimeric MAb. The methods may further include expressing the immunoglobulin fusion protein, and/or purifying the immunoglobulin fusion protein. Exemplary methods for manufacture, including expression and purification, are given in the Examples.

However, any suitable techniques, as known in the art, may be used to manufacture, optionally express, and purify the proteins. These include non-recombinant techniques of protein synthesis, such as solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al. in *Solid Phase Peptide Synthesis* (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexylcarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

VII. Methods

The invention also provides methods. In some embodiments, the invention provides methods for transport of an agent active in the CNS across the BBB in an effective amount. In some embodiments, the invention provides therapeutic, diagnostic, or research methods. Diagnostic methods include the development of peptide radiopharmaceuticals capable of transport across the BBB, such as the fusion of a peptide ligand, or peptidomimetic MAb for an endogenous receptor in the brain, followed by the radiolabelling of the fusion protein, followed by systemic administration, and external imaging of the localization within the brain of the peptide radiopharmaceutical.

Prior to the present invention, neurotrophins such as BDNF or GDNF were injected directly into the brain to achieve a therapeutic effect, because the neurotrophin does not cross the BBB. Therefore, it is not expected that neurotrophic factors will have beneficial effects on brain disorders following the peripheral (intravenous, subcutaneous) administration of these molecules.

However, neurotherapeutics can be developed as drugs for peripheral routes of administration, providing the neurotherapeutic is enabled to cross the BBB. Attachment of the neurotherapeutic, e.g. a neurotrophin such as BDNF or GDNF to a MTH, e.g., the chimeric HIRMAb, offers a new approach to the non-invasive delivery of neurotherapeutics to the CNS in animals, e.g., mammals such as humans for the treatment of acute brain and spinal cord conditions, such as focal brain ischemia, global brain ischemia, and spinal cord injury, and chronic treatment of neurodegenerative disease, including prion diseases, Alzheimer's disease (AD), Parkinson's disease (PD), Huntington's disease (HD), ALS, multiple sclerosis, transverse myelitis, motor neuron disease, Pick's disease, addiction (e.g., drug addiction), tuberous sclerosis, lysosomal storage disorders, Canavan's disease, Rett's syndrome, spinocerebellar ataxias, Friedreich's ataxia, optic atrophy, and retinal degeneration.

Accordingly, in some embodiments the invention provides methods of transport of an agent active in the CNS from the peripheral circulation across the BBB in an effective amount, where the agent is covalently attached to a structure that crosses the BBB, and where the agent alone is not transported across the BBB in an effective amount. In some embodiments the invention provides methods of transport of neurotherapeutic agent from the peripheral circulation across the BBB in a therapeutically effective amount, where the neurotherapeutic agent is covalently attached to a structure that crosses the BBB, and where the neurotherapeutic agent alone is not transported across the BBB in a therapeutically effective amount.

The invention also provides, in some embodiments, methods of treatment of disorders of the CNS by peripheral administration of an effective amount of a therapeutic agent, e.g., a neurotherapeutic agent covalently linked to a structure that is capable of crossing the BBB, where the agent alone is not capable of crossing the BBB in an effective amount when administered peripherally. In some embodiments, the CNS disorder is an acute disorder, and, in some cases, may require only a single administration of the agent. In some embodiments, the CNS disorder is a chronic disorder and may require more than one administration of the agent.

In some embodiments, the effective amount, e.g., therapeutically effective amount is such that a concentration in the brain is reached of at least about 0.001, 0.01, 0.1, 0.5, 1, 2, 3, 4, 5, 6, 7, 8, 9, 10, 15, 20, 25, 30, 35, 40, 45, 50, 100, or more than 100 ng/gram brain. In some embodiments, a therapeutically effective amount, e.g., of a neurotrophin such as BDNF or GDNF, is such that a brain level is achieved of about 0.1 to 1000, or about 1-100, or about 5-50 ng/g brain. In some embodiments, the neurotherapeutic agent is a neurotrophin. In some embodiments, the neurotrophin is selected from the group consisting of BDNF, nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, or stem cell factor (SCF). In some embodiments, the neurotrophin is BDNF, e.g. a truncated BDNF, such as the carboxyl-truncated BDNFs described herein.

In some embodiments, the invention provides methods of treating a disorder of the CNS by peripherally administering to an individual in need of such treatment an effective amount of a neurotrophin, where the neurotrophin is capable of crossing the BBB to produce an average elevation of neurotrophin concentration in the brain of at least about 0.1, 1, 2, 3, 4, 5, 6, 7, 8, 9, 10, 15, 20, 25, 30, 35, 40, 45, 50, 100, or more than 100 ng/gram brain following said peripheral administration, and where the neurotrophin remains at the elevated level for about 1, 2, 3, 4, 5, 6, 7, 8, 9, 10, or more than 10 days after a single administration. In some embodiments, the neurotrophin remains at a level of greater than about 1 ng/g brain, or about 2 ng/g brain, or about 5 ng/g brain for about 2, 3, 4, 5, 6, 7, 8, 9, 10, or more than 10 days after a single administration. In some embodiments, the neurotrophin is BDNF, including truncated versions thereof.

In some embodiments, the invention provides methods of treating a disorder of the CNS by peripherally administering to an individual in need of such treatment an effective amount of a composition of the invention. The term "peripheral administration," as used herein, includes any method of administration that is not direct administration into the CNS, i.e., that does not involve physical penetration or disruption of the BBB. "Peripheral administration" includes, but is not limited to, intravenous intramuscular, subcutaneous, intraperitoneal, intranasal, transbuccal, transdermal, rectal, transalveolar (inhalation), or oral administration. Any suitable composition of the invention, as described herein, may be used. In some embodiments, the composition is a neurotrophin covalently linked to a chimeric HIR-MAb. In some embodiments, the neurotrophin is a BDNF. In some embodiments, the BDNF is a variant as described herein, such as a carboxyl-terminal truncated variant. In other embodiments, the neurotrophin is a GDNF (e.g., mature human GDNF).

A "disorder of the CNS" or "CNS disorder," as those terms are used herein, encompasses any condition that affects the brain and/or spinal cord and that leads to suboptimal function. In some embodiments, the disorder is an acute disorder. Acute disorders of the CNS include focal brain ischemia, global brain ischemia, brain trauma, spinal cord injury, acute infections, status epilepticus, migraine headache, acute psychosis, suicidal depression, and acute anxiety/phobia. In some embodiments, the disorder is a chronic disorder. Chronic disorders of the CNS include chronic neurodegeneration, retinal degeneration, depression, chronic affective disorders, lysosomal storage disorders, chronic infections of the brain, brain cancer, stroke rehabilitation, inborn errors of metabolism, autism, mental retardation. Chronic neurodegeneration includes neurodegenerative diseases such as prion diseases, Alzheimer's disease (AD), Parkinson's disease (PD), Huntington's disease (HD), multiple sclerosis (MS), amyotrophic lateral sclerosis (ALS), transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration, and aging of the CNS.

In some embodiments, the invention provides methods of treatment of the retina, or for treatment or prevention of blindness. The retina, like the brain, is protected from the blood by the blood-retinal barrier (BRB). The insulin receptor is expressed on both the BBB and the BRB, and the HIRMAb has been shown to deliver therapeutics to the retina via RMT across the BRB. BDNF is neuroprotective in retinal degeneration, but it was necessary to inject the neurotrophin directly into the eyeball, because BDNF does not cross the BRB. In some embodiments, fusion proteins of the invention are used to treat retinal degeneration and blindness with a route of administration no more invasive than an intravenous or subcutaneous injection, because the HIRMAb delivers the BDNF across the BRB, so that the neurotrophin is exposed to retinal neural cells from the blood compartment.

In some embodiments, the invention provides a method of treatment for depression. A subset of patients with depression may have a brain deficiency of BDNF, and the correlation of single nucleotide polymorphisms (SNPs) with affective disorders has been reported. The direct injection of BDNF into the brain has durable anti-depressant effects in rodent model. The BDNF must be injected directly into the brain, because the neurotrophin does not cross the BBB. In some embodiments, the invention provides a method for treating depression by chronic administration of a fusion protein of the invention, thus elevating the brain levels of BDNF and being therapeutic in those patients with depression and a reduced production of brain BDNF.

Formulations and administration. Any suitable formulation, route of administration, and dose of the compositions of the invention may be used. Formulations, doses, and routes of administration are determined by those of ordinary skill in the art with no more than routine experimentation. Compositions of the invention, e.g., GDNF fusion proteins are typically administered in a single dose, e.g., an intravenous dose, of about 0.01-1000 mg, or about 0.05-500 mg, or about 0.1-100 mg, or about 1-100 mg, or about 0.5-50 mg, or about 5-50 mg, or about 1, 2, 3, 4, 5, 6, 7, 8, 9, 10, 11, 12, 15, 20, 25, 30, 25, 40, 45, 50, 60, 70, 80, 90, or 100 mg. Typically, for the treatment of acute brain disease, such as stroke, cardiac arrest, spinal cord injury, or brain trauma, higher doses may be used, whereas for the treatment of chronic conditions such as Alzheimer's disease, Parkinson's disease, Huntington's disease, MS, ALS, transverse myelitis, motor neuron disease, Pick's disease, tuberous sclerosis, addiction (e.g., drug addiction), lysosomal storage disorders, Canavan's disease, Rett's syndrome, spinocerebellar ataxias, Friedreich's ataxia, optic atrophy, and retinal degeneration, and aging, lower, chronic dosing may be used. Oral administration can require a higher dosage than intravenous or subcutaneous dosing, depending on the efficiency of absorption and possible metabolism of the protein, as is known in the art, and may be adjusted from the foregoing based on routine experimentation.

For intravenous or subcutaneous administration, formulations of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

Figure 27:
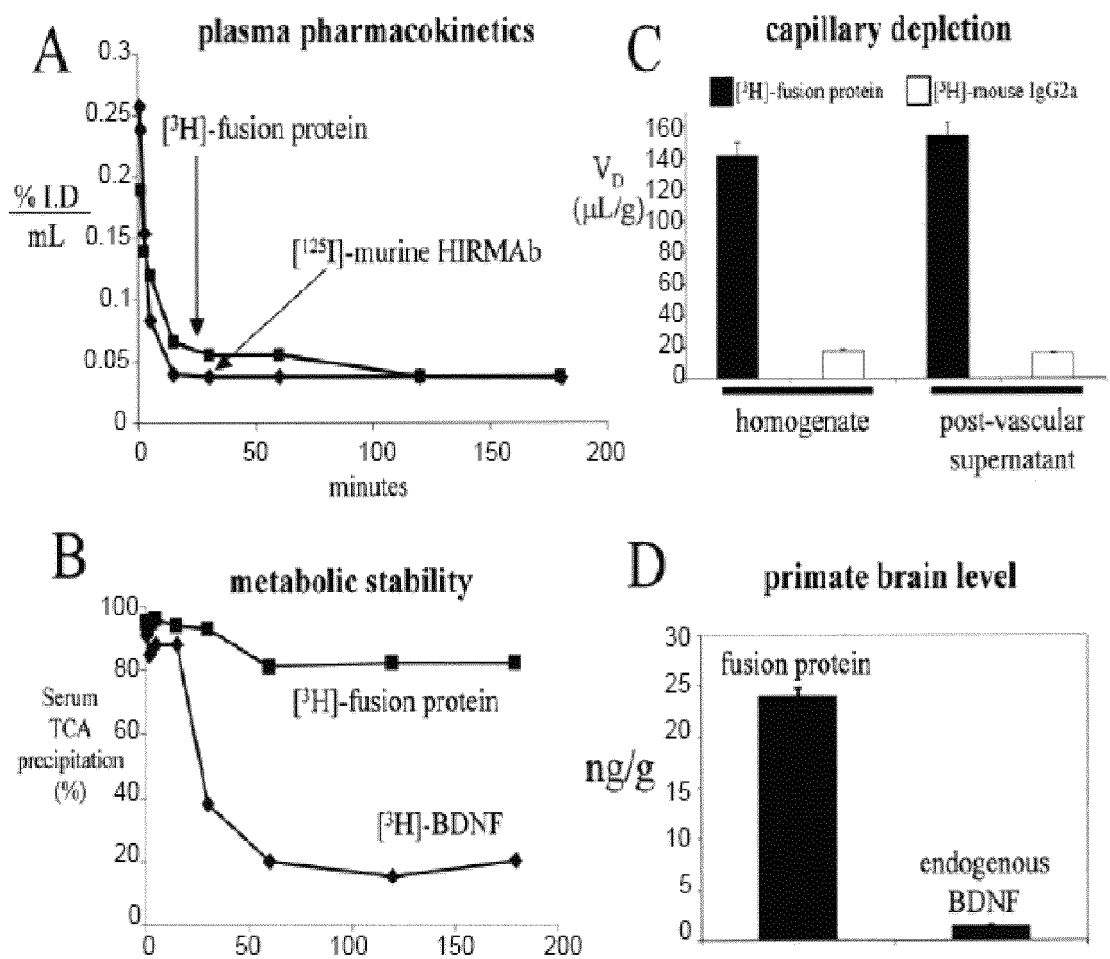
FIG. 27. Pharmacokinetics and brain uptake of fusion protein in the adult Rhesus monkey. (A) The serum concentration of [$^3$H]-fusion protein, or [$^{125}$I]-murine HIRMAb, is plotted vs. time after a single intravenous injection of either protein in anesthetized adult Rhesus monkeys. (B) The serum radioactivity that is precipitable by trichloroacetic acid (TCA) is plotted vs time after a single intravenous injection of either [$^3$H]-fusion protein in the anesthetized adult Rhesus monkey, or [$^3$H]-BDNF in the anesthetized adult rat. (C) Capillary depletion analysis of brain distribution at 180 minutes after a single intravenous injection of either [$^3$H]-fusion protein, or [$^3$H]-mouse IgG2a, in the anesthetized adult Rhesus monkey. (D) Primate brain concentrations of fusion protein at 180 minutes after an intravenous injection of 373 μg fusion protein, as compared to the endogenous primate brain concentration of BDNF.

Dosages for humans can be calculated from appropriate animal data. For example, human dosing of a BDNF-MAB conjugate is based on pre-clinical pharmacokinetic studies, and these measurements have been performed in 2 species, rats, and Rhesus monkeys. Prior work in 3 models of cerebral ischemia in rats demonstrated the range of effective doses of the BDNF-MAb conjugate is 5-50 µg/rat or 20-200 µg/kg of BDNF in the form of the BDNF-MAb conjugate. Since the BDNF component of the fusion protein molecule is 16%, and the HIRMAb component is 84%, the dose of fusion protein is 6-fold greater than the equivalent BDNF dose. Pharmacokinetic studies in rats show these doses produce a concentration of the BDNF in the form of conjugate in plasma of 50-500 ng/mL, and in brain of 5-50 ng/g. Pharmacokinetic studies in adult Rhesus monkeys with the HIRMAb show that the average plasma concentration in the first hour is 0.1% injected dose (ID)/mL, and that the brain concentration is 0.02% ID/g. The brain concentration of the fusion protein is about 0.01% ID/g (FIG. 27). Owing to the scaling effect between species, and to the 10-fold larger body size and brain size of humans relative to Rhesus monkeys, the projected plasma and brain concentrations in humans are 0.01% ID/mL and 0.001% ID/g respectively. Since the human brain is 1200 grams, then >1% of the injected dose is delivered to the human brain, which is a level of brain uptake comparable to small molecules. Given an injected dose of fusion protein of 2.5-25 mg in humans, the expected 60 min plasma concentration is 250-2500 ng/ml of fusion protein, and the expected 60 min brain concentration is 25-250 ng/g of fusion protein, which is equivalent to 4-40 ng/gram brain of BDNF. The 5 mg and 25 mg fusion protein doses in humans will produce a brain concentration of the BDNF that is neuroprotective in either global or regional brain ischemia. Since the BDNF comprises 16% of the fusion protein, the effective doses of BDNF administered to humans is 0.4 or 4.0 mg, respectively, for the 2.5 or 25 mg dose of fusion protein.

The fusion protein may also be formulated for chronic use for the treatment of a chronic CNS disorder, e.g., neurodegenerative disease, stroke or brain/spinal cord injury rehabilitation, or depression. Chronic treatment may involve daily, weekly, bi-weekly administration of the composition of the invention, e.g., fusion protein either intravenously, intra-muscularly, or subcutaneous in formulations similar to that used for acute treatment. Alternatively, the composition, e.g., fusion protein may be formulated as part of a bio-degradable polymer, and administered on a monthly schedule.

Combination Therapies.

The composition of the invention, e.g., fusion protein may be administered as part of a combination therapy. The combination therapy involves the administration of a composition of the invention in combination with another therapy for the CNS disorder being treated. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

Other CNS disorder treatment agents that may be used in methods of the invention include, without limitation, thrombolytic therapy for stroke, amyloid-directed therapy for Alzheimers disease, dopamine restoration therapy for Parkinsons disease, RNA interference therapy for genetic disorders, cancer, or infections, and anti-convulsant therapy for epilepsy. Dosages, routes of administration, administration regimes, and the like for these agents are well-known in the art.

In some embodiments, the composition, e.g., fusion protein is co-administered to the patient with another medication, either within the same formulation or as a separate composition. For example, the fusion protein could be formulated with another fusion protein that is also designed to deliver across the human blood-brain barrier a recombinant protein other than BDNF (e.g., GDNF). The fusion protein may be formulated in combination with other large or small molecules.

VIII. Kits

Compositions of the invention, e.g., fusion proteins, may be provided as a kit that includes the formulation, e.g., fusion protein in a container and in suitable packaging. The composition can be provided in a dry powder form, in solid form (i.e., lyophilized), in solution, or in suspension. If the composition is a protein, to the proteins may have been added emulsifiers, salts, preservatives, other proteins, nucleic acids, protease inhibitors, antibiotics, perfumes, polysaccharides, adhesive agents, polymers, microfibrils, oils, etc. The composition is packaged for transport, storage and/or use by a consumer. Such packaging of therapeutic compositions for transport, storage, and use is well-known in the art. Packaged compositions may include further components for the dispensing and storage of the composition, and may also include separately packaged diluent comprised of, e.g., sterile water or a suitable buffer, for solubilizing the formulation, e.g., fusion protein prior to administration to the patient. Kits of the invention may also include written materials, including instructions for use, results of clinical studies, desired outcome and expected course of treatment, information about precautions and side effects, and the like. The kits may optionally further contain other components, such as gloves, scissors, tape, implements for disposal of used vials and other waste, masks, antiseptic, antibiotics, and the like.

EXAMPLES

Example 1

Figure 3:
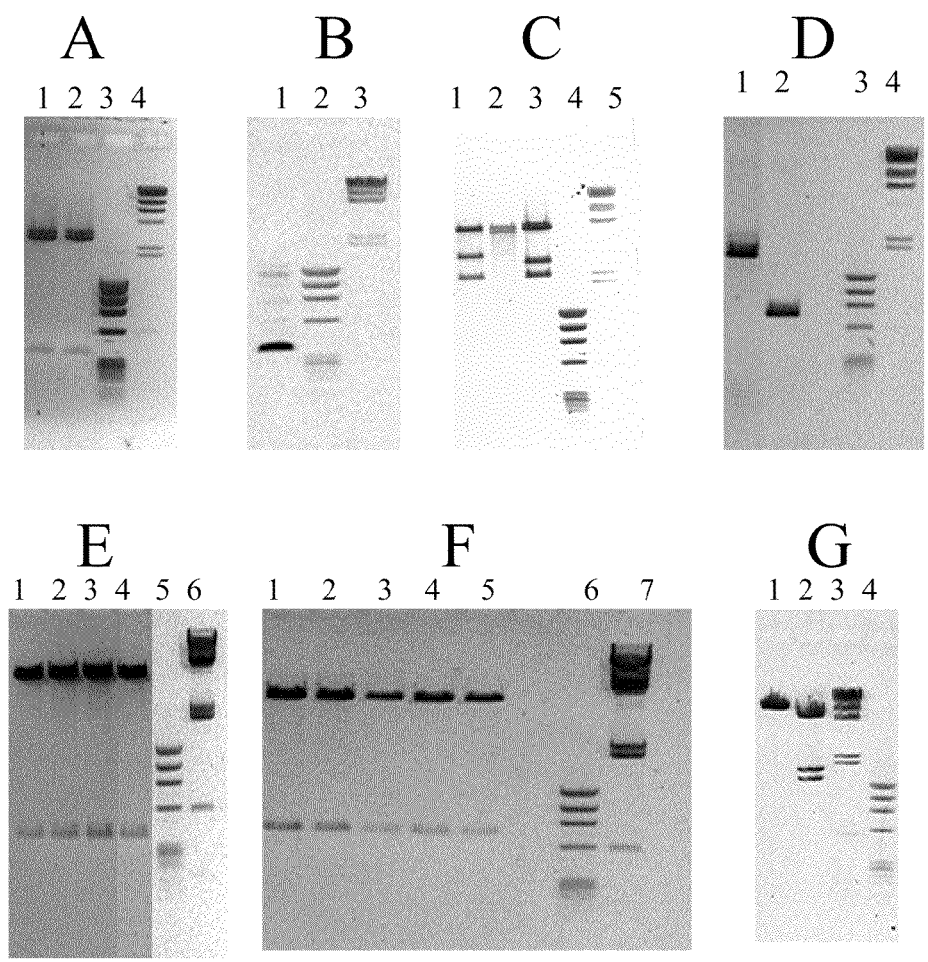
FIG. 3. Ethidium bromide stained agarose gels showing size of various constructs that are intermediates in construction of a tandem vector that produces the fusion protein. (A) Lanes 1-2: plasmid from FIG. 2 digested with NruI showing 0.4 kb vBDNF and 3.5 kb vector backbone. Lane 3: MW size standards ranging from 1.4-0.1 kb. Lane 4: MW size standards ranging from 23-0.6 kb. (B) Lane 1: the 0.4 kb vBDNF cDNA is produced by the polymerase chain reaction (PCR) using cDNA reverse transcribed from polyA+ RNA isolated from human U87 glioma cells; the PCR primer sequences are given in Table 2. Lanes 2 and 3: same MW size standards as shown in panel A. (C) lane 1: clone 416 following digestion with NheI and BamHI; lane 2: negative clone; lane 3: clone 400 following digestion with NheI and BamHI: lanes 4 and 5: same MW size standards as shown in panel A. (D) PCR fragments of DNA encoding fusion protein HC (lane 1) and LC (lane 2); lanes 3-4: same MW size standards as shown in panel A. (E) lanes 1-4: 4 different but identical copies of clone 422a following digestion with NheI, showing release of 0.4 kb fusion protein HC variable region (VH) cDNA; lanes 5-6: same MW size standards as shown in panel A. (F) lanes 1-4: 5 different but identical copies of clone 423a following digestion with EcoRV and BamHI, showing release of 0.7 kb entire LC cDNA; lanes 5-6: same MW size standards as shown in panel A. (G) Restriction endonuclease mapping of tandem vector (FIG. 12) with PvuI (lane 1), and EcoRI-HindIII (lane 2). PvuI (single cut) produced the expected linear DNA band of ~11 kb. Digestion with EcoRI and HindIII releases both the fusion protein light chain (i.e. 1.8 kb) and DHFR (i.e. 1.5 kb) expression cassettes. The 8 kb band represents the backbone vector with the fusion protein heavy chain expression cassette; lanes 3-4: same MW size standards as shown in panel A, albeit in reverse order.

Construction of the Single Tandem Vector Containing Complete Genes for IgG-Neurotherapeutic Fusion Genetic engineering of a eukaryotic expression vector encoding the heavy chain (HC) of the fusion protein is outlined in FIG. 1. The final fusion protein HC expression vector was designated pHIRMAb-BDNF, or clone 416. This vector was designed to produce a fusion protein, comprised of a BDNF variant fused to the HC of the HIRMAb. Either BDNF or a variant of BDNF (vBDNF) can be fused to the HIRMAb. The vBDNF differs from native human BDNF by substitution of certain amino acids, such as a vBDNF where the 2 amino acids at the carboxyl terminus of BDNF are absent in vBDNF. The clone 416 plasmid was derived from clone 400, which produces the HC of the chimeric form of the HIRMAb, and a cDNA encoding mature human vBDNF, which was produced as described in FIG. 2. Clone 400 encodes a chimeric human IgG1 that is derived from a chromosomal fragment encoding the human IgG1 constant region, and is comprised of both intron and exon sequences. The HC gene of the chimeric HIRMAb in clone 400 was subcloned at the BamHI site of the pCR II plasmid to facilitate engineering of the stop codon located at the 3'-end of the CH3 region by site directed mutagenesis (SDM). The engineering of the stop codon located at the end of the CH3 region was performed by site-directed mutagenesis to produce a SspI site. The SspI site allows for insertion of the vBDNF cDNA (FIG. 3) by blunt-end ligation into clone 400 to form clone 415. SDM was performed using the QuickChange SDM kit (Stratagene, Calif.). Sense and complementary mutagenic primers were designed in a way that the CH3 stop codon (aaTGAg) is mutated to SspI site (aaTATt). In addition, primers contained 15 nucleotides of the stop codon 5'- and 3'-surrounding region; the sequence of these primers, designated SDM-SspI forward (FWD) and reverse (REV) are given in Table 1.

TABLE 1

| Nucleotide sequence of oligodeoxynucleotides used for engineering plasmid clone 416 |
|---|
| SDM-SspI-FWD (SEQ ID NO. 1)<br>CCTGTCTCCGGGTAAATATTTGCGACGGCCGGCAAG |
| SDM-SspI-REV (SEQ ID NO. 2)<br>CTTGCCGGCCGTCGCAAATATTTACCCGGAGACAGG |
| XhoI-NheI linker FWD (SEQ ID NO. 3)<br>ATGCTCGAGGAATTCCCATGGATGATGGCTAGCAAGCTTATG |
| XhoI-NheI linker REV (SEQ ID NO. 4)<br>CATAAGCTTGCTAGCCATCATCCATGGGAATTCCTCGAGCAT |

XhoI-NheI (underlined) is a Universal linker that contains the following RE sites: XhoI-EcoRI-NcoI-NheI-HindIII. SDM = site-directed mutagenesis; FWD = forward; REV = reverse DNA sequence analysis of the IgG promoter region revealed the presence of additional SspI sites in this region. Therefore, it was first necessary to release the HC promoter region (PRO-VH) by digestion of clone 404 with XhoI and NheI, and the clone 404 was re-closed with a XhoI-NheI linker which produced clone 405 (-Pro-VH). The sequence of the forward and reverse ODNs used to produce the XhoI-NheI linker are given in Table 1. Plasmid clone 405 (-Pro-VH) now carries the single SspI site introduced by SDM. The human vBDNF cDNA was subcloned at SspI to form an intermediate plasmid named clone 414 (not shown). The complete fusion protein HC expression cassette was then reconstructed by subcloning of the PRO-VH fragment previously deleted to form clone 415. The fusion protein HC gene was then subcloned in the eukaryotic expression vector, clone 400, at the BamHI site to form clone 416.

The vBDNF cDNA was produced by PCR via either of 2 equivalent approaches. In one approach, a prokaryotic expression plasmid, pHTBS01, isolated as an expressed sequence tag (EST), and encoding human BDNF, was digested with BamHI and BpII, and gel purified, and religated with T4 ligase and the 5'-end linker to produce clone 412 (FIG. 2). The sequence of the forward and reverse ODNs used to produce the 5'-end linker are given in Table 2.

TABLE 2

| Engineering of 5'- and 3'-end linkers of vBDNF cDNA |
|---|
| 1) 5'-end linker of vBDNF FWD-ODN (SEQ ID NO. 5)<br>TCCGGATCCTCGCGAGTATGCACTCTGACCCTGCCCGTCGAGGTGAGCTGAGCGTG |
| 2) 5'-end linker of vBDNF REV-ODN (SEQ ID NO. 6)<br>CACGCTCAGCTCACCTCGACGGGCAGGGTCAGAGTGCATACTCGCGAGGATCCGGA |
| 3) 3'-end linker of vBDNF FWD-ODN (SEQ ID NO. 7)<br>AGTCGTACGTGCGGGCCCTTACCATGGATAGCAAAAAGAGAATTGGCTGGCGATTCATAAGGATAGACACTTCTTGTGTATGTACATTGACCATTAAAAGGTGATCGCGACTCGAGATG |
| 4) 3'-end linker of vBDNF REV-ODN (SEQ ID NO. 8)<br>CATCTCGAGTCGCGATCACCTTTTAATGGTCAATGTACATACACAAGAAGTGTCTATCCTTATGAATCGCCAGCCAATTCTCTTTTTGCTATCCATGGTAAGGGCCCGCACGTACGACT |
| 5) vBDNF-PCR-U87 FWD-ODN (SEQ ID NO. 9)<br>ATCTCGCGAGTATGCACTCTGACCCTGCC |
| 6) vBDNF-PCR-U87 REV-ODN (SEQ ID NO. 10)<br>ATCTCGCGATCACCTTTTAATGGTCAA |

SEQ ID NO 5 and 6: Artificial forward (FWD) and reverse (REV) oligodeoxynucleotide (ODN) duplex linkers were designed to engineer a mature vBDNF cDNA that allows for insertion into the CH3 open reading frame (orf) of clone 400 heavy chain (HC) to form clone 416 (FIG. 1). The 5'-end linker is flanked by BamHI and EspI, respectively, and it reconstructs the amino terminus of the mature vBDNF. BamHI and EspI allow for directional subcloning into the vBDNF intermediate plasmid clone 413 (FIG. 2). A NruI site follows BamHI and it enables insertion of the vBDNF into the HC vector (clone 405, FIG. 1) at the SspI site. In addition, the linker also has "GI" immediately after NruI to maintain the orf of the CH3 (FIG. 1). This modification introduces a Ser-Ser-Met linker between CH3 and the vBDNF amino terminus.
SEQ ID NO 7 and 8: The 3'-end linker contains SplI and XhoI to reconstruct the COOH terminus of the mature vBDNF and introduces a stop codon "TGA". This linker has SplI, XhoI and NruI sites for directional subcloning and insertion into clone 405 (FIGS. 1 and 2).
SEQ ID NO 9 and 10: FWD ODN reconstructs the amino terminus of the mature vBDNF and introduces a Ser-Ser-Met linker. NruI site for insertion into the expression vector is underlined. REV ODN introduces the TGA stop codon. NruI site for insertion into the expression vector is underlined.

Clone 412 was then digested with XhoI and BsiWI, and gel purified, and religated with T4 ligase and the 3' end linker to produce clone 413 (FIG. 2). The sequence of the forward and reverse ODNs used to produce the 3'-end linker are given in Table 2. The vBDNF cDNA, encoding the vBDNF with a reconstructed stop codon, was released from clone 413 by NruI, and gel purified; the ethidium bromide stain of the agarose gel is shown in FIG. 3A. This gel shows the expected size of the vBDNF cDNA, 0.4 kb, and the vector backbone, 3.5 kb. Alternatively, the BDNF cDNA was produced by PCR from cDNA derived by reverse transcription of polyA+RNA isolated from human U87 glioma cells, which produce neurotrophins. The primers used to produce the vBDNF by PCR from the U87-derived cDNA are given in Table 2. This PCR produced the expected 0.4 kb vBDNF cDNA (FIG. 3B). The 0.4 kb vBDNF fragment was then digested with NruI, and subcloned into clone 415, as described in FIG. 1, to produce the full fusion protein HC expression cassette, which was released by BamHI and subcloned into the original eukaryotic expression plasmid to produce clone 416 (FIG. 1), the final expression plasmid for the fusion protein HC. Clone 416 was analyzed by double digestion with NheI and BamHI and compared with that of the original clone 400, which lacks the vBDNF. The agarose gel-separated products are shown in FIG. 3C, where lanes 1 and 3 show the fragments generated from clone 416 and clone 400, respectively. Both plasmids produce a 6 kb vector backbone (upper of 3 bands in lanes 1 and 3), and a 2.5 kb promoter region (lower of 3 bands in lanes 1 and 3). However, the size of the middle band is 0.4 kb larger for clone 416, as compared to clone 400 (middle band, lanes 1 and 3). A negative clone is shown in lane 2 of FIG. 3C.

The nucleotide and amino acid sequence of the reconstructed carboxyl terminus at the CH3 region of the HIRMAb HC, a 3-amino acid linker (Ser-Ser-Met), the vBDNF sequence, followed by a stop codon is shown in FIG. 4. The entire 2711 nucleotides (nt) comprising the fusion protein HC gene of clone 416 is shown in FIG. 5. The ATG initiation codon and the TGA stop codon are underlined. The human IgG1 constant region intron and exon sequences are shown in italics and bold font, respectively, in FIG. 5. The vBDNF nt sequence in the clone 416 vector is underlined in FIG. 5. These data show that intronic sequence is found between CH1 and the hinge region, between the hinge region and CH2, and between CH2 and CH3 regions of the human IgG1 constant region. The open reading frame (orf) of the fusion protein HC gene encodes for a 563 amino acid protein, following cleavage of a 19 amino acid signal peptide, and the amino acid sequence of the fusion protein HC is shown in FIG. 6. The signal peptide is underlined; the cysteine (C) residues within the constant region that form inter- or intra-chain disulfide bridges are shown in bold font; the serine-serine-methionine (SSM) linker between the CH3 region of the IgG and the vBDNF is underlined; the single N-linked glycosylation site, at the asparagine residue within CH2 in shown by bold underlined font (FIG. 6). The amino acid sequences of the individual domains of the fusion protein HC protein are given in FIG. 7. The vBDNF domain of the fusion protein is comprised of 117 amino acids.

Clone 416 plasmid DNA was electroporated into mouse myeloma cells that had previously been transfected with an expression plasmid encoding the light chain (LC) of the chimeric HIRMAb. Since the vBDNF is fused only to the HC, there is no modification of the LC of the chimeric HIRMAb. Following selection of transfected cell lines, media from 96-well plates were screened with an ELISA comprised of 2 anti-human IgG antibodies; one antibody is directed against the heavy chain of human IgG1, and the other antibody is directed against human kappa light chains. Myeloma clones encoding for intact fusion protein were isolated, and propagated in a 10 L bioreactor. However, the production levels of the fusion protein were low. This low production was attributed to several factors, including (i) transfection of the myeloma line by 3 separate expression plasmids encoding the heavy chain gene, the light chain gene, and the antibiotic resistance gene; and (ii) the use of genomic fragment of the heavy and light chain genes with large intronic sequences. Therefore, the fusion protein expression plasmid was re-engineered with the following features:

(1) the polymerase chain reaction (PCR) was used to convert genomic fragments of the fusion protein HC and LC genes into 'intron-less' cDNA forms of the 2 genes
(2) the cDNA forms the fusion protein HC and LC genes were placed on a single 'tandem vector' in which the 2 genes were placed in separate and tandem expression cassettes with separate promoters
(3) the promoter driving the expression of the fusion protein HC and LC genes was changed from the human IgG promoters to the cytomegalovirus (CMV) promoter, to enable transfection of non-myeloma cells, such as Chinese hamster ovary (CHO) cells
(4) the tandem vector encoding fusion protein contains a gene encoding for the dihydrofolate reductase (DHFR) gene, under a separate SV40 promoter, to allow for methotrexate (MTX) selection of CHO lines which contain amplification of the genome in the region of the insertion of the expression vector.

Figure 8:
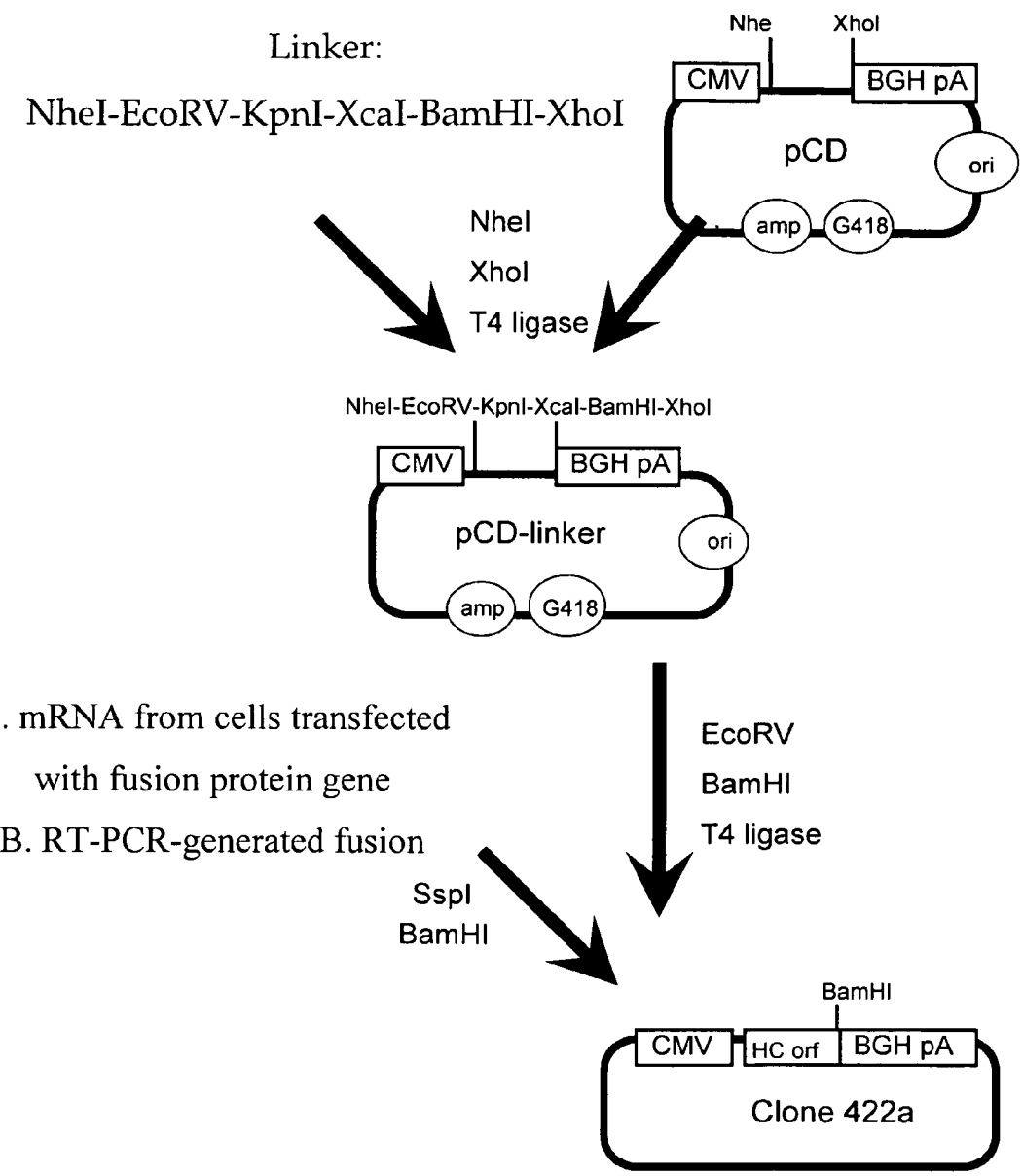
FIG. 8. Diagram showing production of the intronless eukaryotic expression vector, clone 422a, which encodes the fusion protein HC. The fusion protein HC cDNA was produced by PCR from cDNA generated by reverse transcription of RNA isolated from myeloma cells transfected with clone 416.

In order to produce the fusion protein tandem vector, it was first necessary to produce intermediate plasmids, which separately encode cDNA forms of the fusion protein HC and LC genes. Eukaryotic expression plasmids carrying the CMV promoter and the bovine growth hormone (BGH) poly-A (pA) transcription termination sequences, and designated pCD, were digested with NheI and XhoI and religated with T4 ligase and an NheI-EcoRV-KpnI-ScaI-BamHI-XhoI linker, as shown in FIG. 8. The sequence of the forward and reverse ODNs used to produce this linker are given in Table 3.

TABLE 3

Nucleotide sequence of ODNs used for
engineering of intronless expression vectors 1) Linker NheI-EcoRV-KpnI-XcaI-BamHI-XhoI FWD ODN
(SEQ ID NO. 11)
ATGGCTAGCGATATCGGTACCGTATACGGATCCCTCGAGATG 2) Linker NheI-EcoRV-KpnI-XcaI-BamHI-XhoI REV ODN
(SEQ ID NO. 12)
CATCTCGAGGGATCCGTATACGGTACCGATATCGCTAGCCAT 3) PCR cloning of LC FWD ODN primer
(SEQ ID NO. 13)
GTGACAAACACAGACATAG<u>GATATC</u>

4) PCR cloning of LC REV ODN primer
(SEQ ID NO. 14)
ATG<u>CTCGAG</u>CTAACACTCTCCCCT 5) PCR cloning of fusion protein HC FWD ODN primer
(SEQ ID NO. 15)
ATG<u>AATATT</u>CCACCATGGAATGCAGC 6) PCR cloning of fusion protein HC REV ODN primer
(SEQ ID NO. 16)
ATA<u>GGATCC</u>TCACCTTTTAATGGTCAA RE cloning sites are underlined: <u>GATATC</u>: EcoRV, <u>CTCGAG</u>: XhoI, <u>AATATT</u>: SspI, <u>GGATCC</u>: BamHI.

The resulting plasmid, designated pCD-linker (FIG. 8) was digested with EcoRV and BamHI and reclosed with T4 ligase and the fusion protein HC cDNA generated by PCR. For the PCR reaction, the above mentioned myeloma line that had been dual transfected with genomic constructs of the fusion protein HC (clone 416) and LC genes were digested and myeloma derived polyA+ RNA was produced (part A in FIG. 8). Oligodeoxythymidine (ODT) primers were used to produced myeloma cDNA with reverse transcriptase from 0.5 ug of myeloma polyA+RNA, followed by a final RNase digestion. From this cDNA, PCR was used to produce the cDNA form of the fusion protein HC gene, using the forward and reverse primers shown in Table 3, and high fidelity Pfu DNA polymerase. Similarly, the fusion protein LC cDNA was produced by PCR from the myeloma derived cDNA, and the sequences of the forward and reverse PCR primers used to amplify the fusion protein LC cDNA are given in Table 3. Following PCR, the cDNA was applied to an 0.8% agarose gel, and all amplifications yielded a single product, a 1.8 kb fusion protein HC cDNA (lane 1, FIG. 3D), and a 0.7 kb fusion protein LC cDNA (lane 2, FIG. 3D). The fusion protein HC PCR product was digested with SspI and BamHI and subcloned into CD-linker to produce the clone 422a (FIG. 8), which is an intronless eukaryotic expression plasmid encoding the fusion protein HC cDNA. Clone 422a was analyzed by restriction endonuclease using NheI; digestion with this enzyme, which has a site in the new multiple cloning region of the pCD vector, produced the expected 0.4 kb fragment corresponding to the fusion protein heavy chain variable region (VH) cDNA (lanes 1-4, FIG. 3E). The nucleotide sequence of the fusion protein HC cDNA encoded by clone 422a is shown in FIG. 9A, which shows the intron sequences present in clone 416 (FIG. 5) have been deleted by the PCR of processed myeloma RNA. The amino acid sequence encoded by the fusion protein HC cDNA is given in FIG. 9B, and this amino acid sequence is identical to that produced by the genomic fragment in clone 416 (FIG. 6).

Figure 10:
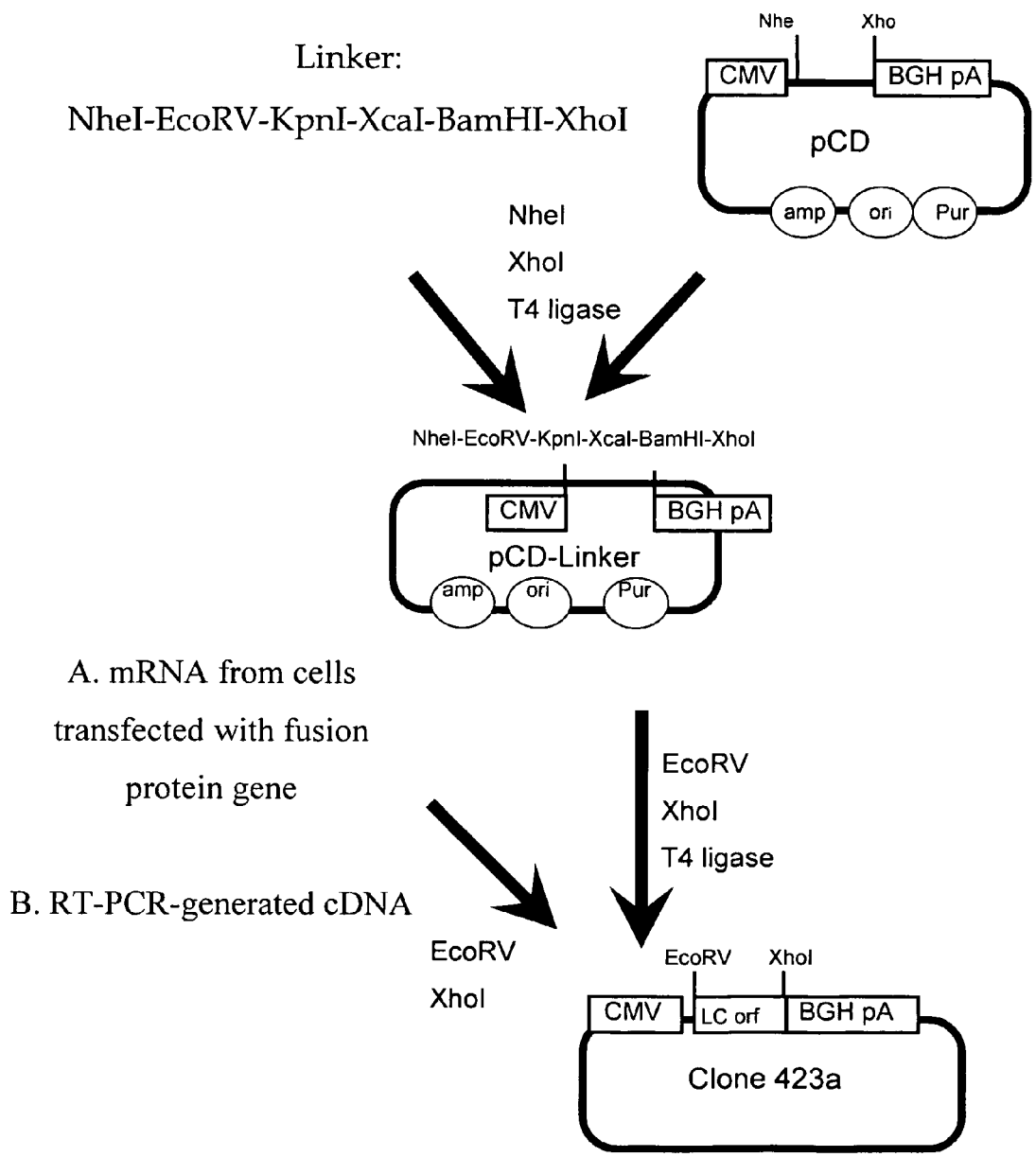
FIG. 10. Diagram showing production of the intronless eukaryotic expression vector, clone 423a, which encodes the fusion protein LC. The fusion protein LC cDNA was produced by PCR from cDNA generated by reverse transcriptase of RNA isolated from myeloma cells transfected with an expression vector producing the LC gene that was derived from chromosomal fragment encoding intron/exon sequence of the human kappa LC gene with the VL of the chimeric HIRMAb LC.

The fusion protein LC PCR product was digested with EcoRV and XhoI and subcloned into CD-linker to produce the clone 423a (FIG. 10), which is an intronless eukaryotic expression plasmid encoding the fusion protein LC cDNA. Clone 423a was analyzed by restriction endonuclease using EcoRV and BamHI; digestion with these enzymes, which have a site in the new multiple cloning region of the pCD vector, produced the expected 0.7 kb fragment corresponding to the fusion protein LC cDNA (lanes 1-5, FIG. 3F). The nucleotide sequence of the fusion protein LC cDNA encoded by clone 423a is shown in FIG. 11A, which shows the intron sequences have been deleted by the PCR of processed myeloma RNA. The amino acid sequence encoded by the fusion protein LC cDNA is shown in FIG. 11B.

Figure 12:
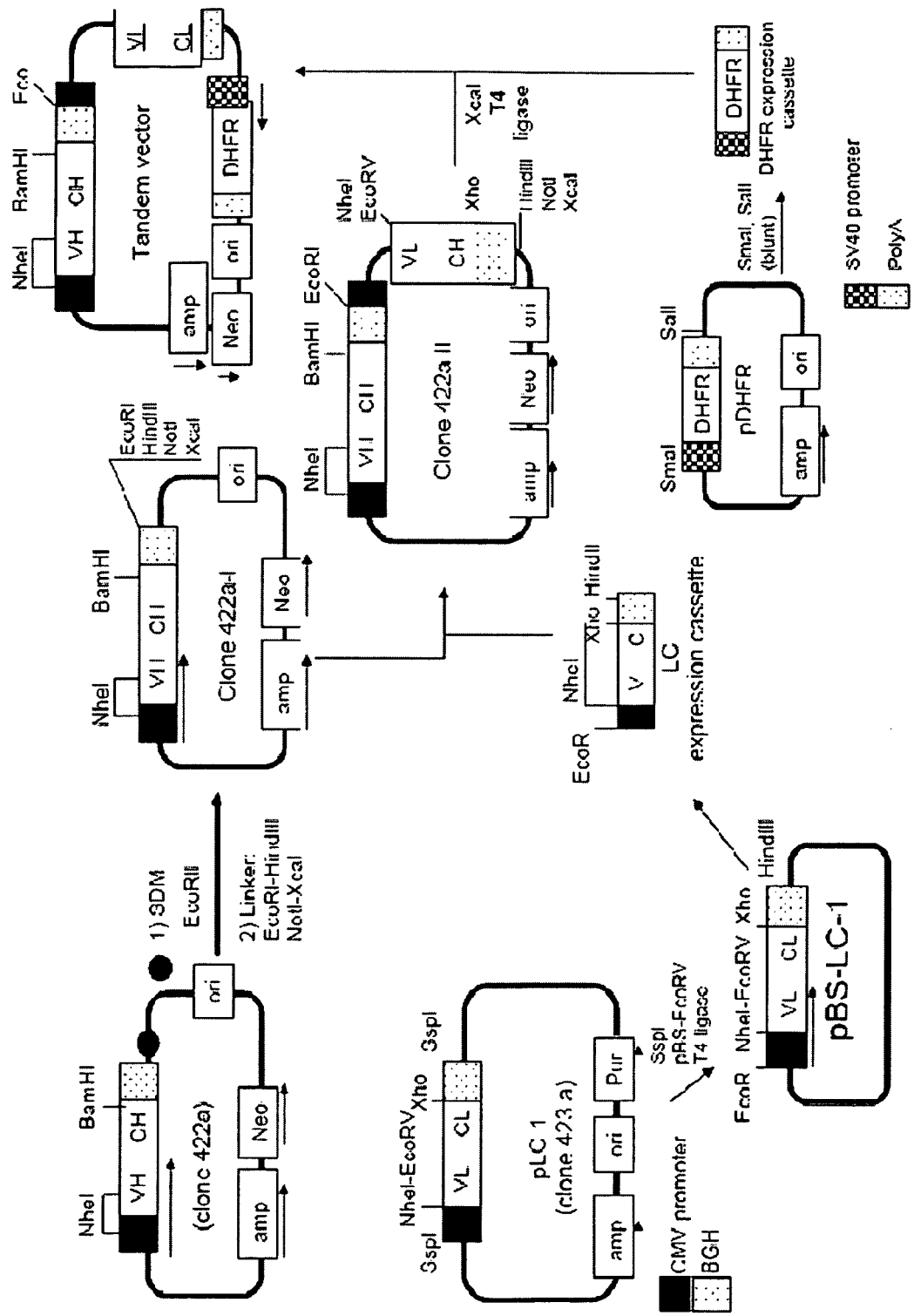
FIG. 12. Diagram showing the construction of a tandem vector encoding the HC and LC genes of the fusion protein. The TV was engineered from the cDNA expression vectors, clones 422a and 423a, for the HC and LC, respectively, as well as from a bacterial expression plasmid encoding the expression cassette for mouse DHFR.

Clones 422a and 423a were the precursors to the fusion protein tandem vector, as outlined in FIG. 12. In 2 steps, clone 422a was subjected to SDM to introduce an EcoRI site at the 3'-end of the fusion protein HC expression cassette; the sequences of the forward and reverse SDM primers are given in Table 4.

TABLE 4

Nucleotide sequences of ODNs used for engineering of TV-12

1) EcoRI-SDM FWD ODN (SEQ ID NO. 17)
AAAAGGCCAGGAACCGAATTCAGATCTCGTTGCTGGCGTTTT

2) EcoRI-SDM REV ODN (SEQ ID NO. 18)
AAAACGCCAGCAACGAGATCTGAATTCGGTTCCTGGCCTTTT

3) EcoRI linker FWD (SEQ ID NO. 19)
ATCGAATTCAAGCTTGCGGCCGCGTATACAGATCTATC

4) EcoRI linker REV (SEQ ID NO. 20)
GATAGATCTGTATACGCGGCCGCAAGCTTGAATTCGAT

EcoRI site in EcoRI-SDM ODN is underlined.
The EcoRI linker introduces EcoRI-HindIII-NotI-XcaI RE sites.

In step 2, the mutated clone 422a was digested with EcoRI, blunt-ended, and religated with the EcoRI-HindIII-NotI-XcaI linker to produce clone 422a-I (FIG. 12). The sequence of the ODNs used to produce this EcoRI linker are given in Table 4. Clone 422a-I was digested with EcoRI and HindIII, and closed with T4 ligase in the presence of the fusion protein LC expression cassette to produce clone 422a-II (FIG. 12). The fusion protein LC expression cassette was generated by digestion of clone pBS-LC-1 with EcoRI and HindIII. Clone pBS-LC-1 was produced from EcoRV-digested pBS (Bluescript), T4 ligase, and the fusion protein LC expression cassette produced by digestion of clone 423a with SspI (FIG. 12).

In parallel, a mouse DHFR expression cassette, containing the SV40 promoter and the hepatitis C virus polyA region, was produced from the pFR400 plasmid (designated pDHFR) by digestion of the plasmid with SmaI and SalI (FIG. 12). The final fusion protein tandem vector was produced by subcloning the DHFR expression cassette into XcaI digested clone 422a-II followed by closure with T4 ligase (FIG. 12). The fusion protein tandem vector was analyzed by restriction endonuclease, and the 11 kb plasmid was linearized by PvuI (lane 1, FIG. 3G). The 1.8 kb fusion protein LC and 1.5 kb DHFR expression cassettes, and the 8 kb vector backbone including the fusion protein HC expression cassette were released by digestion with EcoRI and HindIII (lane 2, FIG. 3G). The tandem vector was subjected to DNA sequencing in both directions, and the nucleotide sequence, and the deduced amino acid sequence of the fusion protein HC, the fusion protein LC, and the DHFR genes are shown in FIGS. 14, 15, and 16, respectively. The calculated MW of the fusion protein HC and LC are 62,220 and 25,760 Da, respectively, not accounting for any carbohydrate content of the fusion protein HC.

Example 2

Figure 17:
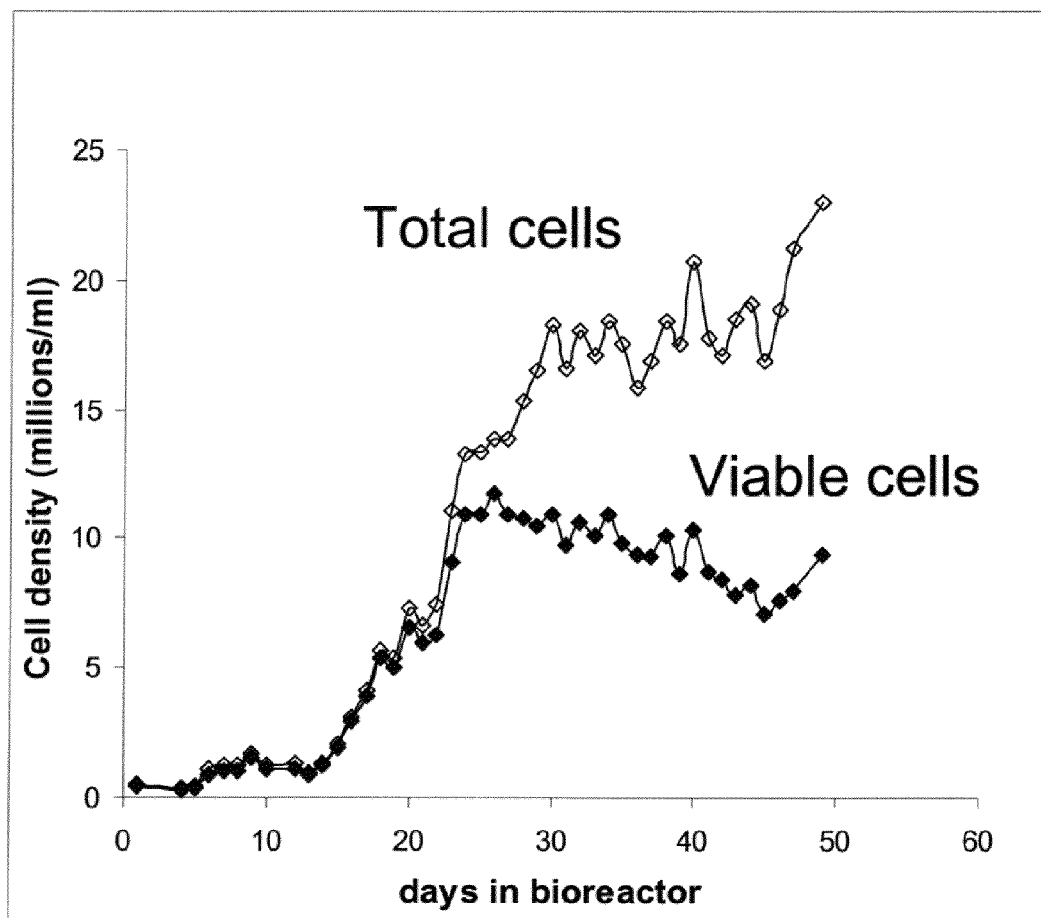
FIG. 17. Viable and total cell density of CHO cells in bioreactor maintained continuously for 50 days; the CHO cells had been stably transfected with the tandem vector encoding the fusion protein.
Figure 19:
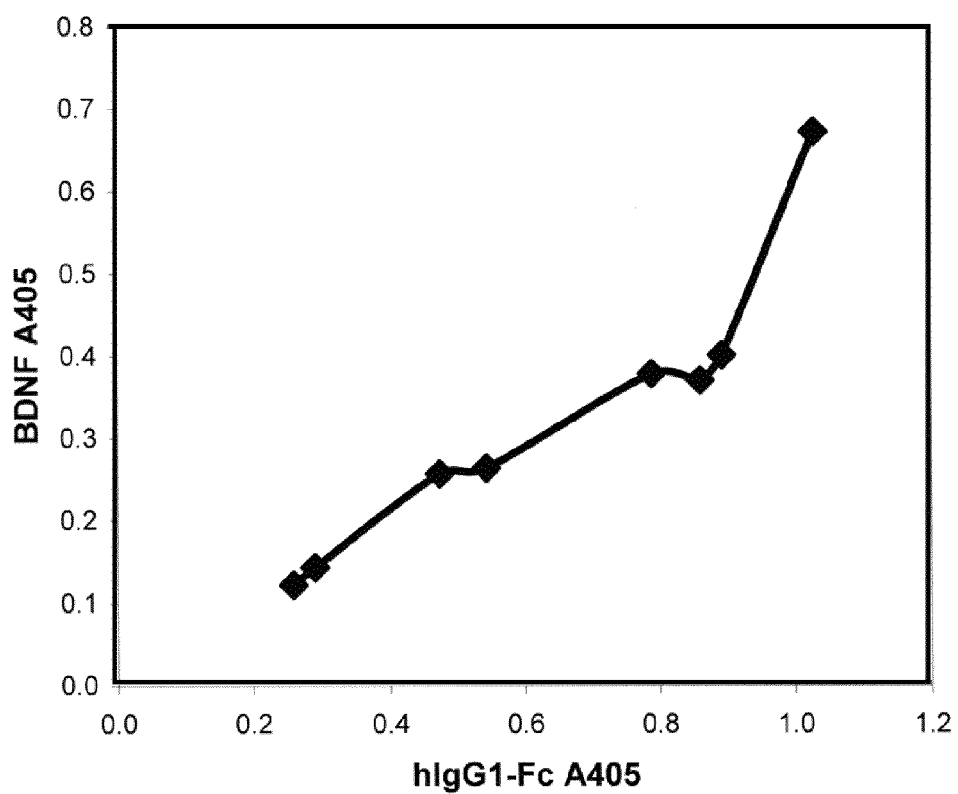
FIG. 19. Correlation of 2 different 'sandwich' immunoassays, where the secondary antibody is either directed against the Fc region of human IgG1 (x-axis) or against human BDNF (y-axis). The primary antibody in either assay is directed against the human kappa light chain. The measured level of fusion protein in CHO cell conditioned medium is the same whether the anti-Fc or the anti-BDNF antibody is used.

Electroporation of CHO Cells with Fusion Protein Tandem Vector and Cultivation in a Bioreactor The fusion protein tandem vector (FIG. 12) was linearized with PvuI and electroporated into CHO-K1 cells followed by selection with G418 (375 ug/ml) for 3 weeks. Positive clones were detected in 96 well plates with a human IgG ELISA that uses 2 primary antibodies to both the human IgG1 HC and the human kappa LC. Cell lines of high copy number of the transgene were selected by graded increases in MTX to 600 nM. The MTX-selected cell line was grown in T175 flasks and then transferred to a 20 L bioreactor with a 10 L volume of CHO cell serum free medium (SFM). As shown in FIG. 17, the CHO cells were maintained at high density in excess of 10 million viable cells/mL for nearly 50 days in perfusion mode in the bioreactor. The secretion by these cells of the fusion protein was detected by ELISA using antibodies to either human IgG or to human BDNF. As shown in FIG. 18, the fusion protein is a 1:1 fusion of the vBDNF to the carboxyl terminus of the HIRMAb heavy chain, which results in formation of the fusion protein heavy chain. This heavy chain complexes with the light chain, as shown in FIG. 18. Therefore, the fusion protein should react equally well to 3 antibodies directed against: (i) the human IgG1 HC, (ii) the human kappa LC; or (iii) human BDNF. As shown in FIG. 19, there is a direct correlation in measurement of the fusion protein in the CHO cell medium depending on whether anti-human IgG or anti-human BDNF antibodies are used in the ELISA. These ELISA results were confirmed with immunocytochemistry (ICC), which showed the CHO cells transfected with TV-120 were immunoreactive with antibodies to either human IgG or to human BDNF, and that the BDNF immune signal was eliminated by absorption of the anti-BDNF antibody with recombinant BDNF.

Example 3

Purification and Characterization of Bioreactor Produced Fusion Protein

Figure 20:
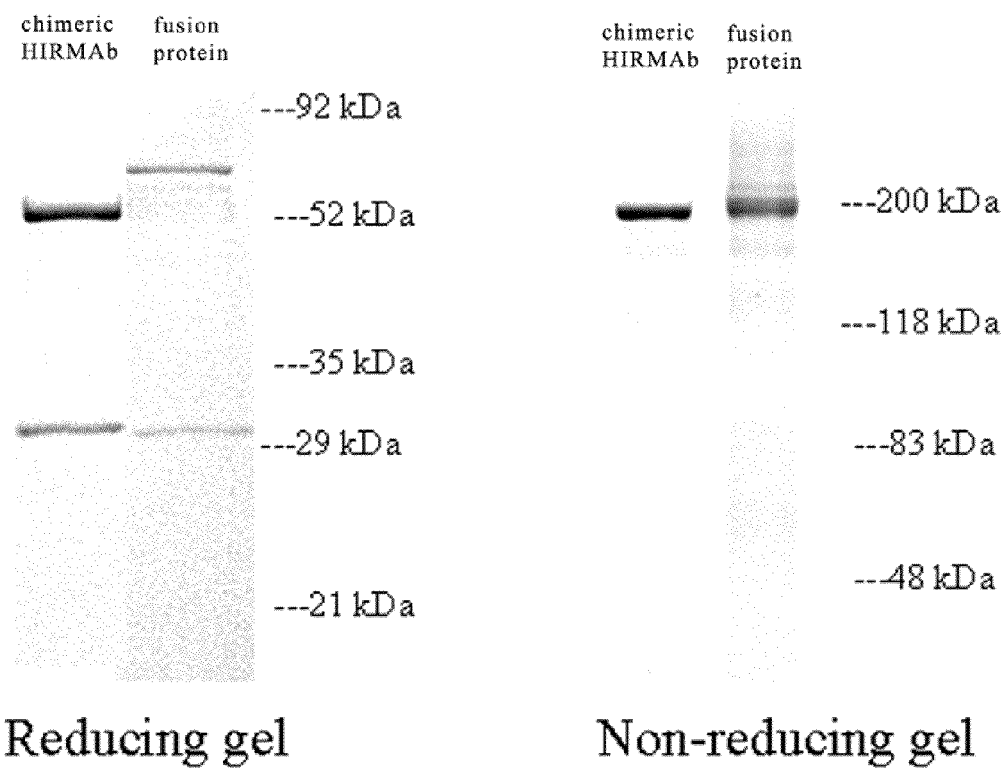
FIG. 20. Reducing (left) and non-reducing (right) sodium dodecyl sulfate polyacrylamide gel electrophoresis (SDS-PAGE) of chimeric HIRMAb and fusion protein. Under reducing conditions, the size of the light chain, 30 kDa, is identical for chimeric HIRMAb and the fusion protein; the size of the heavy chain of fusion protein is about 15 kDa larger than the chimeric HIRMAb heavy chain, owing to the presence of the BDNF. Under non-reducing conditions, the chimeric HIRMAb and the fusion protein migrate as single hetero-tetrameric species with molecular weights of 180 and 200 kDa, respectively.
Figure 21:
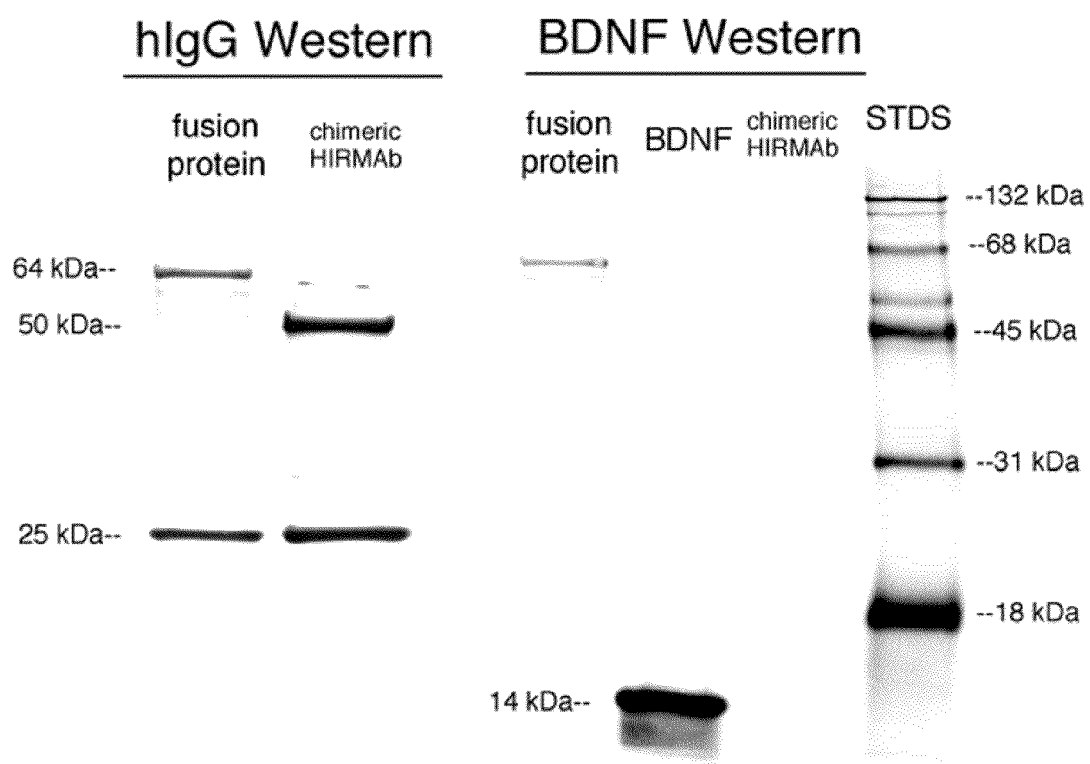
FIG. 21. (Left panel) Western blot with anti-human IgG primary antibody. The size of the heavy chain of the fusion protein and the chimeric HIRMAb is 64 kDa and 50 kDa, respectively, and the size of the light chain for either the fusion protein or the chimeric HIRMAb is 25 kDa. (Right panel) Western blot with anti-human BDNF antibody, which reacts with either fusion protein or BDNF, but not with chimeric HIRMAb. MW standards (STDS) are shown on the right side.
Figure 22:
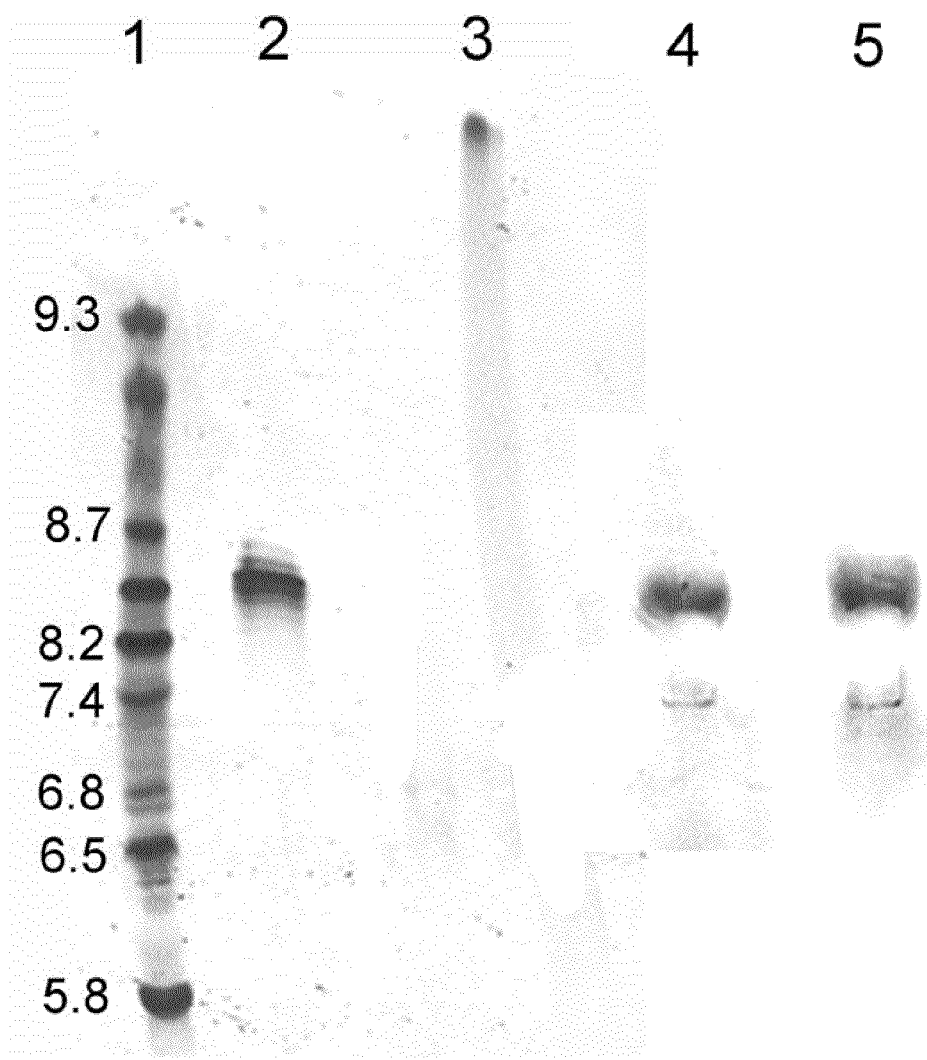
FIG. 22. Isoelectric focusing (IEF) of isoelectric point (pI) standards (lane 1), chimeric HIRMAb (lanes 2 and 4), BDNF (lane 3), and fusion protein (lane 5). Whereas BDNF is highly cationic with a pI>10, the pI of the fusion protein approximates the pI of the chimeric HIRMAb, which is about 8.5, and close to the theoretical pI of the fusion protein.

The conditioned medium obtained from the bioreactor under perfusion mode was passed through a 1 μm filter, and the medium collected in a 200 L Bioprocess container under sterile conditions, which were maintained at 4° C. in a glass door refrigerator contiguous with the bioreactor. Then, 200 L batches of conditioned medium were passed through 1 μm and 0.4 μm pre-filters for the removal of cell debris. The medium was then concentrated with tangential flow filtration (TFF). The TFF system was a Pellicon 2 model from Millipore and was comprised of five 0.5 m² filtration cassettes with a 30 kDa molecular weight cutoff and a total surface area of 2.5 m². A transmembrane gradient of 15 PSI was produced, which results in a reduction in volume of the 200 L to 2 L within 2 hours. The concentrated medium was passed through an 0.22μ filter prior to elution through 100 mL Prosep A (Millipore) recombinant protein A affinity column. Following application of the sample, the column was washed with buffer A (0.025 M NaCl, 0.025 M Tris, pH=7.4, 3 mM EDTA). The elution of CHO cell host protein (CHOP) was monitored at A280 with a Shimadzu detector. The fusion protein was eluted with 0.1 M citric acid (pH=3) in tubes containing Tris base to cause immediate neutralization to pH 7. The neutralized acid eluate pool was diluted with double distilled water until the conductivity was <7 mS, and the material was applied to a 50 mL Sepharose SP cation exchange column (Amersham) that has been equilibrated with a 0.02 M Tris, pH=7.5. Following washing in the Tris buffer, the residual CHOP was separated from the fusion protein with a linear NaCl gradient from 0 to 1 M NaCl. The fusion protein peak was pooled and buffer exchanged and concentrated with a Millipore diafiltration unit with a 30 kDa molecular weight cutoff. The final concentrated antibody solution was sterile filtered (0.22 μm) and stored at 4° C. The fusion protein was purified to homogeneity on sodium dodecyl sulfate polyacrylamide gel electrophoresis (SDS-PAGE), as demonstrated in FIG. 20. The size of the fusion protein heavy chain was 68 kDa as compared to the size of the HIRMAb heavy chain, which was 54 kDa. The difference between the size of the fusion protein and HIRMAb heavy chains reflects the added vBDNF monomer (14 kDa) fused to each heavy chain of the fusion protein. The fusion protein reacts with both anti-human IgG antibodies and anti-human BDNF antibodies on Western blotting with the expected molecular weight size of the immunoreactive bands (FIG. 21). Isoelectric focusing (IEF) shows the isoelectric point (pI) of recombinant BDNF was highly cationic with a pI>10 (FIG. 22). The observed pI of the fusion protein was 8.5, and approximates the pI of the HIRMAb (FIG. 22). The observed pI of the fusion protein, 8.5, was consistent with the calculated pI, which is 9.04 and 5.27 for the fusion protein HC and LC, respectively (http://scansite.mit.edu/).

Example 4

Figure 23:
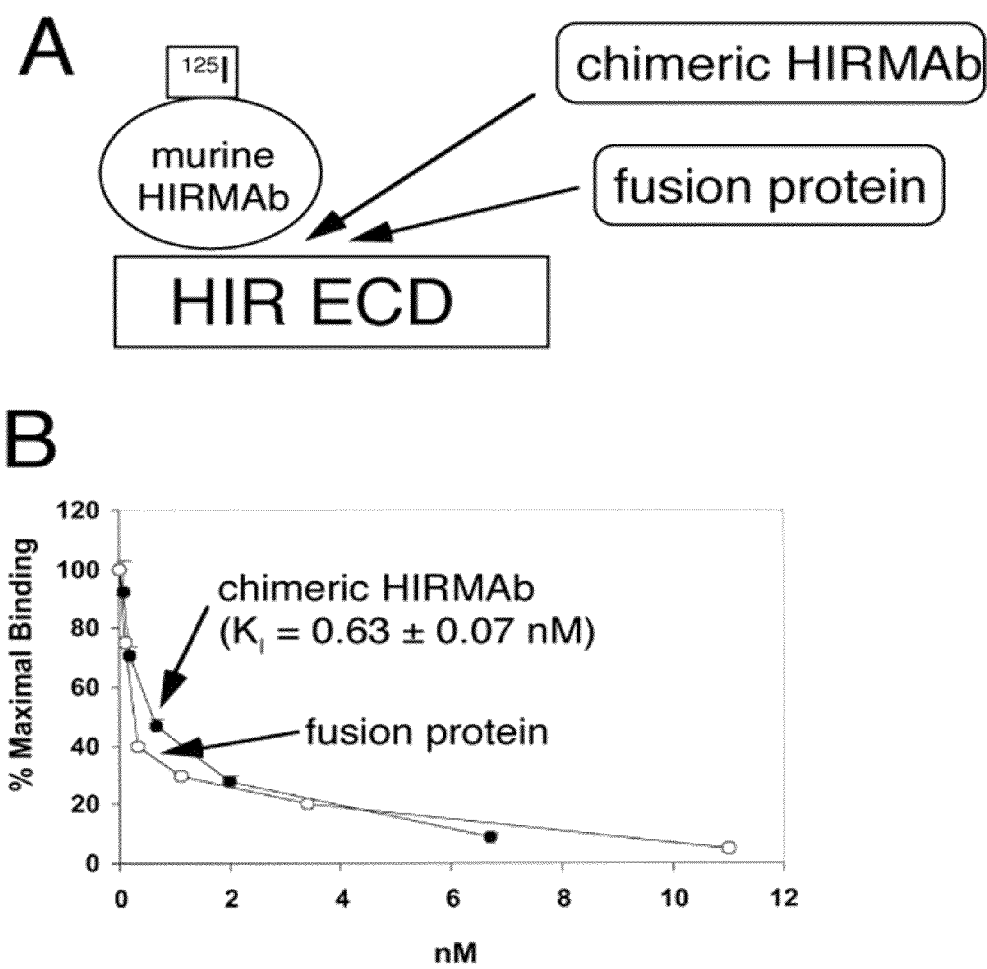
FIG. 23. (A) Outline for human insulin receptor (HIR) competitive ligand binding assay (CLBA). The HIR extracellular domain (ECD) is bound by the [$^{125}$I]-labeled murine HIRMAb, and this binding is competitively displaced by either the chimeric HIRMAb or the fusion protein, as shown in Panel B. (B) Displacement of binding of [$^{125}$I]-labeled murine HIRMAb to the HIR ECD by either chimeric HIRMAb or fusion protein. The affinity of the chimeric HIRMAb to the HIR ECD is high, and the affinity of the fusion protein for the HIR ECD is not significantly different from that of the chimeric HIRMAb. These results show that the fusion of the vBDNF to the carboxyl terminus of the chimeric HIRMAb heavy chain does not impair binding of the fusion protein to the HIR.

The Fusion Protein is Bi-Functional and Binds with High Affinity to Both the Human Insulin Receptor and to the Human trkB Receptor The affinity of the fusion protein for the HIR extracellular domain (ECD) was determined with a competitive ligand binding assay (CLBA) using the lectin affinity purified HIR ECD. CHO cells transfected with the HIR ECD were grown in serum free media (SFM), and the HIR ECD was purified with a wheat germ agglutinin affinity column. The HIR ECD was plated on Nunc-Maxisorb 96 well dishes and the binding of the murine HIRMAb to the HIR ECD was detected by radioactivity measurements following addition of [$^{125}$I] murine HIRMAb as the ligand in the binding assay (FIG. 23A). The binding of the [$^{125}$I] murine HIRMAb to the HIR ECD was displaced by the addition of unlabeled fusion protein or HIRMAb as demonstrated in FIG. 23B. The CLBA shows comparable binding of the HIRMAb or the fusion protein. A Scatchard analysis using a high affinity and low affinity binding site model and nonlinear regression analysis was performed to determine the affinity constant of the fusion protein binding to the HIR. Both the fusion protein and the HIRMAb bind equally well to the HIR with a high affinity binding constant, Ki=0.63±0.07 nM (FIG. 23B).

The TrkB CLBA was designed for measurement of the affinity of the fusion protein for recombinant human TrkB ECD. The design of a TrkB CLBA was made difficult by the cationic nature of BDNF, which causes a high degree of nonspecific binding in the assay and this reduces the sensitivity of the assay. The nonspecific binding of BDNF could be eliminated by conjugation of 2000 Da polyethyleneglycol (PEG) to the protein. A bifunctional PEG molecule, biotin-PEG$^{2000}$-hydrazide (Hz), was commercially obtained, and conjugated to BDNF to produce BDNF-PEG$^{2000}$-biotin, as outlined in FIG. 24A; this molecule was used as the "tracer" in the CLBA. The TrkB ECD was absorbed to ELISA plates and binding of BDNF-PEG$^{2000}$-biotin to the TrkB was detected calorimetrically with avidin and biotin peroxidase (FIG. 24A). Prior studies showed the ELISA signal (A490) was directly proportional to the amount of TrkB added to the well. In addition, the assay had a very low blank and the A490 was <0.04 when no TrkB is plated. The binding of the BDNF-PEG$^{2000}$-biotin to the TrkB was competitively displaced by the recombinant BDNF (FIG. 24B) or the fusion protein (FIG. 24C). The Scatchard analysis of the binding data using nonlinear regression analysis allowed for the computation of the Ki of binding of either BDNF or fusion protein to TrkB, as shown in FIGS. 24B and 24C, respectively. The affinity of the fusion protein for TrkB was not statistically different from the affinity of the recombinant BDNF (FIG. 19 B,C). The nonspecific binding (NSB) of the assay was comparable for either BDNF or the fusion protein. The NSB likely represents nonlinear cooperative binding of the neurotrophin to the TrkB extracellular domain. The TrkB CLBA results shown in FIG. 24 indicate the affinity of fusion protein for the TrkB receptor was not changed following fusion of the vBDNF to the carboxyl terminus of the HIRMAb heavy chain.

Neurotrophins such as BDNF require an obligatory formation of a homo-dimeric structure to be biologically active, and to bind with high affinity to the cognate receptor, e.g. TrkB. A naturally occurring homo-dimeric structure between two BDNF molecules was formed when the neurotrophin was fused to a carboxyl terminus of the CH3 region of an IgG molecule, as illustrated in FIG. 18. The surprising observation of the maintenance of the high affinity binding of BDNF for TrkB (FIG. 24), despite fusion to the HIRMAb heavy chain (FIG. 18), is consistent with the fact that BDNF normally binds to TrkB as a dimer.

Example 5

Figure 25:
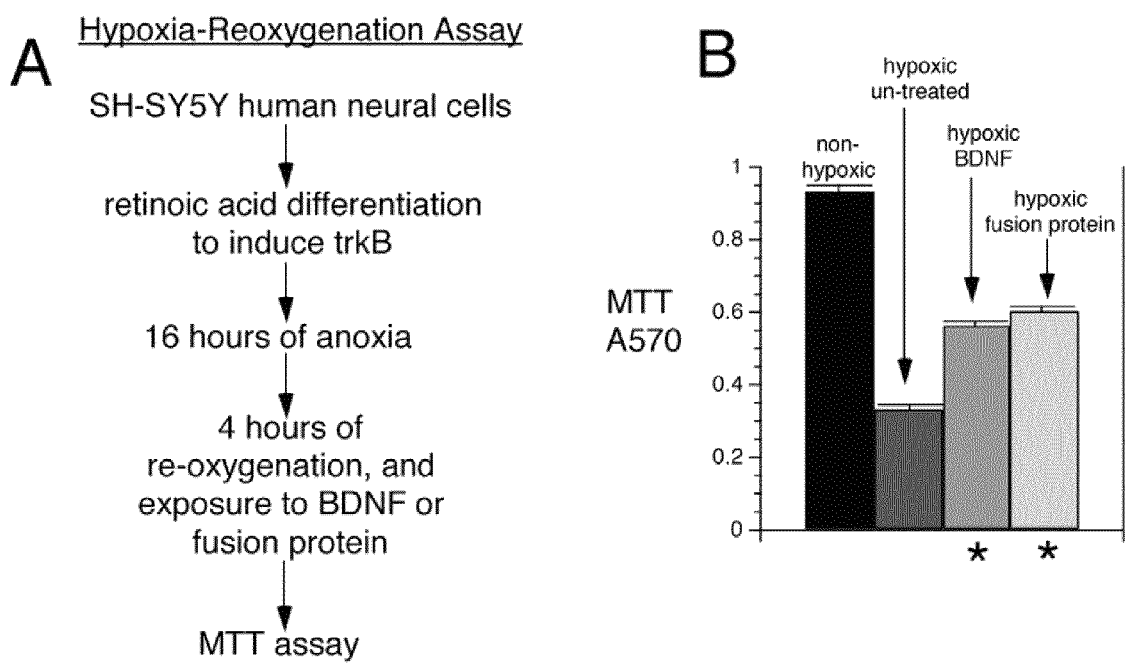
FIG. 25. (A) Design of hypoxia-reoxygenation neuroprotection assay in human neural SH-SY5Y cells. Exposure of the cells to retinoic acid for 7 days causes an up-regulation in the gene expression of trkB, the BDNF receptor. (B) Neuroprotection assay based on the measurement of mitochondrial respiration with 3-(4,5-Dimethylthiazol-2-yl)-2,5-diphenyl-2H-tetrazolium bromide (MTT). The maximal neuroprotection is established with 4 nM BDNF, and 4 nM fusion protein yields a comparable level of neuroprotection in human neural cells. The MTT level does not return to that of non-hypoxic cells, because only about 50% of the cells induce trkB in response to retinoic acid.

Human Neural Cells Subjected to Hypoxia are Neuroprotected by the Fusion Protein with Equal Activity as Recombinant BDNF Human SH-SY5Y neural cells were exposed to 10 uM retinoic acid for 7 days, which induces gene expression of trkB, the BDNF receptor. The cells were then exposed to 16 hours of oxygen deprivation in a sealed chamber, with oxygen sensor. Excitotoxic neural damage was then induced by 4 hours of re-oxygenation (FIG. 25A). During this 4 hour re-oxygenation period, the cells were exposed to either no treatment or equi-molar concentrations of human recombinant BDNF or fusion protein. As shown in FIG. 25B, the fusion protein was equipotent with native human BDNF with respect to inducing neuroprotection in human neural cells exposed to excitoxic ischemia-re-oxygenation.

Example 6

Figure 26:
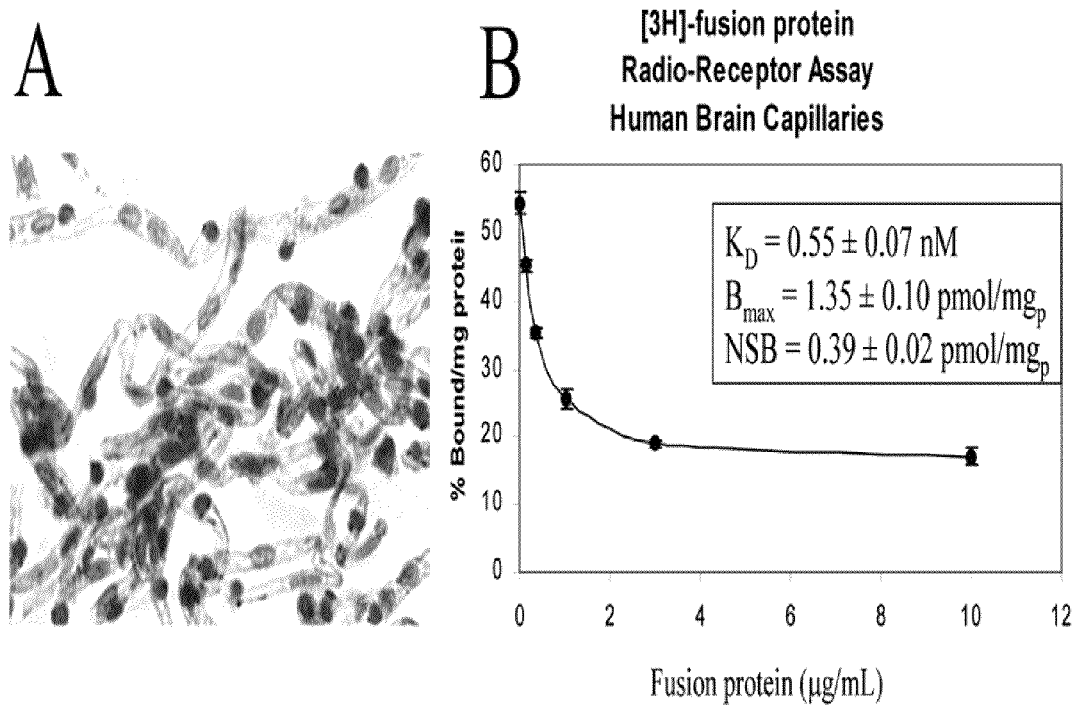
FIG. 26. (A) Light micrograph of capillaries isolated from human brain, used as an in vitro model system of the human BBB. (B) Radio-receptor assay of binding of [$^3$H]-fusion protein to the HIR on the human BBB; the binding is self-inhibited by unlabeled fusion protein. Fitting the saturation data to a Scatchard plot with a non-linear regression analysis yields the binding parameters: $K_D$=0.55±0.07 nM, $B_{max}$=1.35±0.10 pmol/mg$_p$.

High Affinity Binding of Fusion Protein to Human Blood-Brain Barrier Insulin Receptor in Isolated Human Brain Capillaries Isolated human brain capillaries are used as an in vitro model system of the human BBB (FIG. 26A). The fusion protein was radiolabeled with 3H—N-succinimidyl propionate, and added to the human brain capillaries to establish a radio-receptor assay (RRA) of fusion protein binding to the HIR of the human BBB. [$^3$H]-fusion protein is specifically bound to the BBB, as the binding is self-inhibited by unlabeled fusion protein (FIG. 26B). The fusion protein is bound by the insulin receptor of the human BBB, because the murine HIRMAb (mHIRMAb) also inhibits binding of [$^3$H]-fusion protein to the human BBB. The binding data in FIG. 26B were fit to a Scatchard plot with a non-linear regression analysis to produce the binding constants: $K_D$=0.55±0.07 nM, $B_{max}$=1.35±0.10 pmol/mg$_p$, and NSB=0.39±0.02 pmol/mg$_p$, where $K_D$ is the dissociation constant, $B_{max}$ is the maximal binding, and NSB is the non-saturable binding. The KD is <1 nM, which indicate the fusion protein binds the HIR on the human BBB with very high affinity.

Example 7

Pharmacokinetics and Brain Uptake of Fusion Protein by the Adult Rhesus Monkey

The fusion protein was tritiated with [$^3$H]-N-succinimidyl propionate to a specific activity of 2.0 µCi/µg. A 5 year old female Rhesus monkey, weighing 5.2 kg, was administered by a single intravenous injection a dose of 746 µCi (373 µg), and serum was collected at multiple time points over a 180 min period. The serum glucose of the anesthetized, overnight-fasted primate was constant throughout the 180 min study period, and averaged 72±2 mg %, which indicates that the administration of the HIRMAb based fusion protein caused no interference of the endogenous insulin receptor, and had no effect on glycemia control.

The serum removed from the anesthetized Rhesus monkey was analyzed for total radioactivity (FIG. 27A), and radioactivity that was precipitable by trichloroacetic acid (TCA) (FIG. 27B). At 180 minutes after drug injection, the animal was euthanized, and brain radioactivity was analyzed with the capillary depletion method (FIG. 27C), similar to prior work on the brain uptake of [$^{125}$I]-labeled murine HIRMAb in the Rhesus monkey. Based on the specific activity of the [$^3$H]-fusion protein, the brain radioactivity was converted to ng per gram (g) brain, as shown in FIG. 27D, and this level was compared to the reported endogenous concentration of BDNF in the adult primate brain.

The plasma pharmacokinetics analysis (FIG. 27A) shows that the fusion protein of the genetically engineered HIRMAb and the BDNF is removed from blood at the same rate as the original murine HIRMAb. This is an important finding, because it shows that the fusion of BDNF, a highly cationic protein, to the HIRMAb does not accelerate the blood clearance of the HIRMAb. Prior work shows that the attachment of the cationic BDNF to a monoclonal antibody greatly accelerates the blood clearance of the antibody, owing to the cationic nature of the BDNF, which greatly enhances hepatic uptake. The work in FIG. 27A shows that when the cationic BDNF was re-engineered as an IgG fusion protein, the plasma pharmacokinetics was dominated by the IgG moiety, and that the blood level of the BDNF remains high for a prolonged period.

The data in FIG. 27B show that when BDNF was re-formulated as an IgG fusion protein, the metabolic stability of the neurotrophin in blood was greatly enhanced, as compared to the native BDNF. Owing to its cationic nature, the native BDNF was rapidly removed from blood, and was rapidly degraded into TCA-soluble radioactive metabolites (FIG. 27B). However, the TCA-insoluble form of the labeled fusion protein remains high during the 3 hours after an intravenous injection in the primate (FIG. 27B). The data in FIGS. 27A,B show the advantages of re-engineering a neurotrophin pharmaceutical as a fusion protein. The native neurotrophin was rapidly removed from blood and was rapidly degraded. However, the plasma pharmacokinetics profile, and metabolic stability profile, of the neurotrophin resemble those of an IgG molecule, when the IgG-neurotrophin fusion protein was produced.

Native BDNF is not transported across the BBB. Similarly, a [$^3$H]-mouse IgG2a isotype control antibody was not transported across the BBB in the adult Rhesus monkey, as the brain volume of distribution ($V_D$) of the IgG at 180 minutes after an intravenous injection was equal to the plasma volume, 18 µL/g (FIG. 27C, open bars). Conversely, the brain $V_D$ of the [$^3$H]-fusion protein exceeds 140 µl/g brain (FIG. 27C, closed bars). Capillary depletion analysis separates the brain vasculature from the post-vascular supernatant, and allows detection of the transport of a drug through the BBB and into brain, as opposed to simple sequestration of the drug by the brain vasculature. The brain $V_D$ of the post-vascular supernatant of the [$^3$H]-fusion protein was equal to the $V_D$ of the brain homogenate (FIG. 27C), which indicates the fusion protein was transported through the BBB and into brain parenchyma.

The brain $V_D$ of the fusion protein was converted into ng fusion protein per gram brain, based on the specific activity of the [$^3$H]-fusion protein, and this allowed for calculation of the total mass of fusion protein in the brain, 24±1 ng/g, as shown in FIG. 27D. This value is >10-fold higher than the endogenous brain concentration of BDNF in the adult primate (45). Therefore, the administration of a dose of 373 µg to a 5.2 kg Rhesus monkey, which is equal to a normalized dose of 72 µg/kg of fusion protein, results in a marked increase in the brain concentration of BDNF. Such an increase in brain BDNF, following intravenous administration, is not possible with native BDNF, because the native BDNF does not cross the BBB. However, when BDNF is re-engineered in the form of the fusion protein, then pharmacologically active levels of the neurotrophin in brain are achieved (FIG. 27D).

The data shows that: (1) the plasma mean residence time (MRT) of the fusion protein, 312 minutes, was 100-fold greater than the MRT for native BDNF, which was 3.0 minutes, and (2) the systemic clearance of the fusion protein, 0.94 mL/min/kg, was 39-fold slower than the systemic clearance of the BDNF, which was 37 mL/min/kg. In other words, the average blood level of the recombinant protein was up to 100-fold greater when the recombinant protein was re-formulated as an IgG fusion protein. Thus, fusion of the BDNF to the molecular Trojan horse had 2 benefits: (1) the molecular Trojan horse carried the BDNF across the blood-brain barrier (BBB), whereas the BDNF alone cannot cross the BBB, and (2) the molecular Trojan horse prevented the rapid loss from blood of the neurotrophin; BDNF by itself lasts only about 3 minutes in the blood. Both of these properties serve to enhance the pharmacological effect of the BDNF in brain following administration into the blood stream. See, e.g., Table 5.

TABLE 5

Pharmacokinetic parameters for [$^3$H]-fusion protein and [$^3$H]-BDNF

| Parameter | [$^3$H]-fusion protein | [$^3$H]-BDNF |
|---|---|---|
| $A_1$ (% ID/ml) | 0.147 ± 0.020 | 5.28 ± 0.60 |
| $A_2$ (% ID/ml) | 0.061 ± 0.005 | 2.26 ± 0.32 |
| $k_1$ (min$^{-1}$) | 0.195 ± 0.050 | 1.75 ± 0.26 |
| $k_2$ (hr$^{-1}$) | 0.186 ± 0.042 | 15.6 ± 0.6 |
| $t_{1/2}^1$ (min) | 3.5 ± 0.9 | 0.42 ± 0.07 |
| $t_{1/2}^2$ (hr) | 3.7 ± 0.9 | 0.045 ± 0.001 |
| $CL_{SS}$ (ml/min/kg) | 0.94 ± 0.16 | 37.0 ± 2.5 |
| MRT (min) | 312 ± 78 | 3.0 ± 0.3 |

$A_1$, $A_2$, $k_1$ and $k_2$ are the intercepts and slopes of the bi-exponential function describing the decay in plasma concentration with time. The parameters for the fusion protein were determined for the Rhesus monkey, and the parameters for BDNF were determined in the adult rat. All data are normalized for differences in body weight.
$t_{1/2}^1$ and $t_{1/2}^2$ are computed from $k_1$ and $k_2$, respectively, and are the half-times of the decay curves for each exponent.
$CL_{SS}$ and MRT are the steady state clearance and mean residence time, respectively, and are computed from $A_1$, $A_2$, $k_1$, and $k_2$ using standard pharmacokinetic formulations.

Example 8

Neuroprotection in Regional Brain Ischemia by Conjugates of BDNF and a BBB Molecular Trojan Horse Numerous attempts have been made to develop neuroprotective agents for the treatment of acute stroke. There have been no successes to date because the neuroprotective drugs are either too toxic, in the case of certain small molecules, or ineffective, because the drug does not cross the BBB. BDNF is neuroprotective when injected directly in the brain in parallel with experimental stroke in rodents and regional brain ischemia. The BDNF must be injected across the skull bone into the brain, because this large molecule drug does not cross the BBB. Since the BBB is intact in the early hours after regional brain ischemia, and since BDNF does not cross the BBB, then there is no neuroprotective effect in the ischemic brain following the intravenous administration of BDNF alone. To deliver BDNF across the BBB, the neurotrophin was attached to a mouse MAb to the rat transferrin receptor (TfR). This peptidomimetic MAb carries BDNF across the BBB, and the combined BDNF-MAb conjugate is highly neuroprotective following delayed intravenous administration in experimental stroke, because the BDNF is able to cross the BBB and enter the brain from blood. Once inside the brain, and behind the BBB, the BDNF activates its cognate receptor, trkB, which then induces neuroprotection in ischemic neurons, and stops the apoptotic death cycle. The neuroprotective effect of the BDNF-MAb conjugate demonstrates a dose response effect, a time response effect, and is long-lasting, as the neuroprotection at 7 days is identical to the neuroprotection at 1 day after a single intravenous administration of the BDNF-MAb conjugate. See, e.g., Zhang and Pardridge (2001) Brain Res. 889:49-56, and Zhang and Pardridge (2001) Stroke 32:1378-1374, which are incorporated by reference herein in their entirety. The fusion protein would also be neuroprotective in human stroke, since the BDNF is fused to an MAb to the HIR, which rapidly binds to both the human BBB in vitro, and is rapidly transported across the primate BBB in vivo.

Example 9

Neuroprotection in Global Brain Ischemia of Conjugates of BDNF and a BBB Molecular Trojan Horse The direct injection of BDNF into the brain is also neuroprotective in transient forebrain ischemia (TFI), such as might occur after a cardiac arrest. However, intravenous BDNF is not neuroprotective in TFI, because the BDNF does not cross the BBB, and because the BBB is intact in the early hours after TFI, when neuroprotection is still possible. Conversely, intravenous BDNF was neuroprotective in TFI if the BDNF was attached to a mouse MAb against the rat transferrin receptor (TfR), which acts as a molecular Trojan horse to ferry the BDNF across the BBB and into brain. Adult rats were subjected to TFI, which resulted in a flat-line electroencephalogram (EEG) for approximately a 10-minute period. The animals were resuscitated and then administered 1 of 4 different therapeutics intravenously: (a) buffer, (b) unconjugated BDNF, (c) the receptor specific MAb without the BDNF attached, and (d) the BDNF-MAb conjugate. In the case of the animals treated with saline, unconjugated BDNF, or MAb alone, there was no neuroprotection of pyramidal neurons in the CA1 sector of hippocampus. However, in the case of the BDNF-MAb conjugate, there is complete normalization of CA1 pyramidal neuron density following delayed intravenous administration. See, e.g., Wu and Pardridge (199), PNAS (USA) 96:254-259, which is incorporated by reference herein in its entirety. This shows that BDNF is strongly neuroprotective in global brain ischemia following delayed intravenous administration, providing the BDNF is attached to a BBB molecular Trojan horse. The recombinant fusion protein of BDNF and a receptor specific MAb could be given following cardiac arrest to prevent permanent brain damage.

Example 10

BDNF is Neuroprotective in Brain and Spinal Cord Injury if the Neurotrophin can Access Brain Cells BDNF is neuroprotective in brain injury, providing the neurotrophin is injected directly through the skull bone, because BDNF does not cross the BBB. BDNF is also neuroprotective in brain subjected to excitotoxic injury by neurotoxins, and is neuroprotective in brain infected with the human immune deficiency virus (HIV)-1. BDNF is also neuroprotective in acute spinal cord injury; however, the BDNF must be administered by direct infusion into the spinal canal, because the BDNF does not cross the blood-spinal cord barrier, which is the same as the BBB in the forebrain. In all these cases, the intravenous administration of BDNF would not be neuroprotective, because the BDNF does not cross the BBB, and the BBB is intact in brain injury in the early hours after the injury, when neuroprotection is still possible. Conversely, the BDNF fusion protein would be neuroprotective in these conditions following intravenous administration, because the BDNF is fused to the BBB molecular Trojan horse, and is able to penetrate the brain and spinal cord from the blood following peripheral administration.

Example 11

BDNF is Neuroprotective in Chronic Neurodegenerative Conditions of Brain if the Neurotrophin can Access Brain Cells Neurotrophins, such as BDNF can be developed as drugs for peripheral routes of administration, providing the neurotrophin is enabled to cross the BBB. Fusion of BDNF to the chimeric HIRMAb offers a new approach to the non-invasive delivery of BDNF to the brain in humans for the chronic treatment of neurodegenerative disease, including prion diseases, Alzheimer's disease (AD), Parkinson's disease (PD), Huntington's disease (HD), ALS, transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration, and brain aging.

Example 12

BDNF as a Therapeutic in Retinal Degeneration and Blindness

The retina, like the brain, is protected from the blood by the blood-retinal barrier (BRB). The insulin receptor is expressed on both the BBB and the BRB, and the HIRMAb has been shown to deliver therapeutics to the retina via RMT across the BRB (Zhang et al, (2003) Mol. Ther. 7: 11-18). BDNF is neuroprotective in retinal degeneration, but it was necessary to inject the neurotrophin directly into the eyeball, because BDNF does not cross the BRB. The fusion protein could be used to treat retinal degeneration and blindness with a route of administration no more invasive than an intravenous or subcutaneous injection, because the HIRMAb would deliver the BDNF across the BRB, so that the neurotrophin would be exposed to retinal neural cells from the blood compartment.

Example 13

BDNF as a Therapeutic for Depression

A subset of patients with depression may have a brain deficiency of BDNF, and the correlation of single nucleotide polymorphisms (SNPs) with affective disorders has been reported. The direct injection of BDNF into the brain has durable anti-depressant effects in rodent model. The BDNF must be injected directly into the brain, because the neurotrophin does not cross the BBB. The chronic administration of the fusion protein would provide a means for elevating the brain levels of BDNF, and may be therapeutic in those patients with depression and a reduced production of brain BDNF.

Example 14

Method of Manufacturing IgG Fusion Proteins

The transfection of a eukaryotic cell line with immunoglobulin G (IgG) genes generally involves the co-transfection of the cell line with separate plasmids encoding the heavy chain (HC) and the light chain (LC) comprising the IgG. In the case of a IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The preferred approach to manufacturing the fusion protein is the production of a cell line that is transfected with a single plasmid DNA that contains all the required genes on a single strand of DNA, including the HC-fusion protein gene, the LC gene, the selection gene, e.g. neo, and the amplification gene, e.g. the dihydrofolate reductase gene. As shown in the diagram of the fusion protein tandem vector in FIG. 12, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

Example 15

Construction and Use of GDNF-Immunoglobulin Fusion Proteins

Glial-derived neurotrophic factor (GDNF) is a potent neuroprotective neurotrophin (Lin et al, *Science* 260:1130-1132 (1993)). GDNF could be developed as a neuroprotective drug for acute conditions, such as acute ischemic stroke, or chronic conditions, such as Parkinson's disease, or motor neuron disease, or post-stroke neural repair (Lapchak et al, *Neuroscience* 78:61-72 (1997); Kitagawa et al, *Stroke* 29:1417-1422 (1998); Bohn, *Exp. Neurol.* 190:263-275 (2004); Kobayashi, et al. *Stroke* 37:2361-2367 (2006)). However, GDNF, like other large molecule drugs, does not cross the blood-brain barrier (BBB) (Kastin et al, *Neurosci Lett.* 340:239-241 (2003)). Owing to the BBB problem, prior human clinical trials with recombinant GDNF delivered the protein to brain via invasive trans-cranial routes, such as intra-cerebroventricular injection (Lang et al, *Ann Neurol.* 59:459-466 (2006)) or convention enhanced diffusion (Patel et al, *Ann. Neurol.* 57:298-302 (2005)). However, both approaches were limited by poor GDNF penetration into the brain, as well as adverse events related to the invasive drug delivery system.

Large molecule drugs, such as GDNF, could be delivered to brain non-invasively, via the trans-vascular route across the BBB with the use of molecular Trojan horse technology (Pardridge, *Pharm. Res.* 27:1733-1744 (2007)). A BBB molecular Trojan horse is an endogenous peptide, or receptor-specific peptidomimetic monoclonal antibody (MAb) that undergoes receptor-mediated transport across the BBB via endogenous peptide receptors, such as the transferrin receptor or the insulin receptor. Prior work has developed genetically engineered chimeric or humanized MAb's to the human insulin receptor (HIR), as molecular Trojan horses for the human brain (Boado et al, *Biotechnol. Bioeng.* 96:381-391 (2007)). The non-transportable protein therapeutic is fused to the heavy chain (HC) of the HIRMAb. It is essential that the genetically engineered fusion protein retain bi-functionality, and both bind with high affinity to the HIR, to cause BBB transport, and bind to the cognate receptor on brain cells, to induce the desired pharmacologic effect, once the fusion protein penetrates the brain.

Figure 28:
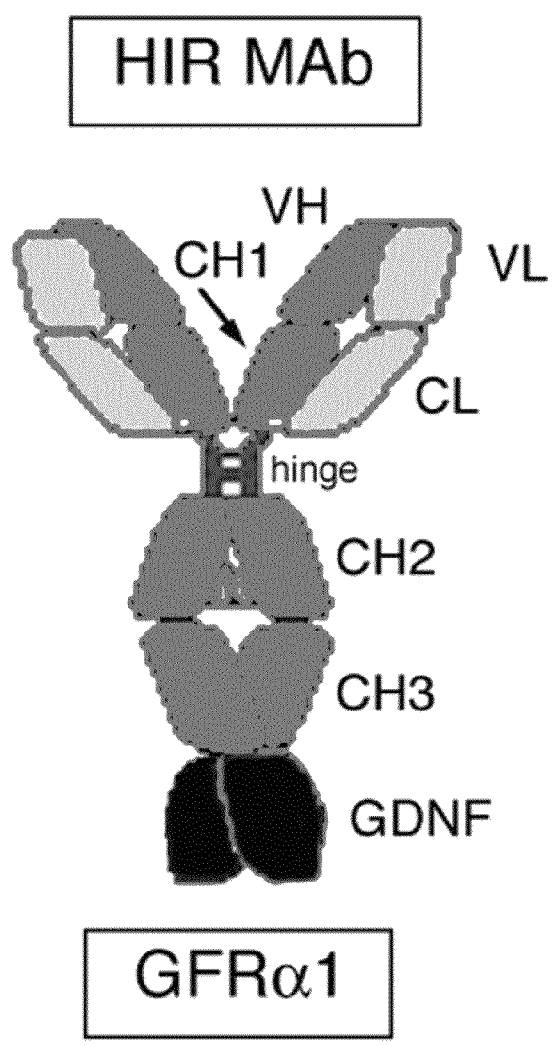
FIG. 28. Schematic illustration of the protein formed by fusion of the amino terminus of the mature GDNF to the carboxyl terminus of the CH3 region of the heavy chain of the chimeric HIRMAb. The fusion protein is a bi-functional molecule: the fusion protein binds the HIR, at the BBB, to mediate transport into the brain, and binds the GFRα1, to mediate GDNF biologic effects in brain behind the BBB.

The present studies described the genetic engineering of a fusion protein of the chimeric HIRMAb and human GDNF. The amino terminus of mature human GDNF is fused to the carboxyl terminus of the HC of the HIRMAb (FIG. 28). Following expression in COS cells, the bi-functionality of the HIRMAb-GDNF fusion protein is evaluated with receptor binding assays for both the HIR and the human GDNF receptor (GFR)-α1. The GDNF biologic activity of the fusion protein is also evaluated with bio-assays using 2 human neural cell lines, the SH-SY5Y line, and the SK-N-MC line. Finally, the in vivo neuroprotective effects of the HIRMAb-GDNF fusion protein is demonstrated in rat brain using the middle cerebral artery occlusion model (MCAO) of acute ischemic stroke.

Materials and Methods

Cloning of GDNF cDNA

The human prepro GDNF cDNA (GenBank P39905) corresponding to amino acids Met−−1-Ile211 was cloned by the polymerase chain reaction (PCR) using the oligodeoxynucleotides (ODNs) described in Table 6 and cDNA derived from reverse transcription of polyA+ RNA isolated from human U87 glial cells. DNA sequence analysis was performed and the nucleic acid and amino acid sequences of the cloned human prepro GDNF are given in SEQ ID NOs:43 and 44, respectively.

TABLE 6

Oligodeoxynucleotide Drimers used in the RT-PCR cloning of human GDNF and in the engineering of the HIRMAb-GDNF expression vector Human prepro GDNF FWD:
phosphate-ATGAAGTTATGGGATGTCGTGGCTG (SEQ ID NO: 40)

Human prepro GDNF REV:
phosphate-TCAGATACATCCACACCTTTTAGCG (SEQ ID NO: 41)

Mature human GDNF FWD:
phosphate-CATCACCAGATAAACAAATGGCAGTG (SEQ ID NO: 42)

The GDNF cDNA was cloned by PCR using 25 ng polyA+ RNA-derived cDNA, 0.2 µM forward and reverse ODN primers (Table 6), 0.2 mM deoxynucleosidetriphosphates, and 2.5 U PfuUltra DNA polymerase (Stratagene, San Diego, Calif.) in a 50 µl Pfu buffer (Stratagene). The amplification was performed in a Mastercycler temperature cycler (Eppendorf, Hamburg, Germany) with an initial denaturing step of 95° C. for 2 min followed by 30 cycles of denaturing at 95° C. for 30 sec, annealing at 55° C. for 30 sec and amplification at 72° C. for 1 min; followed by a final incubation at 72° C. for 10 min. PCR products were resolved in 0.8% agarose gel electrophoresis, and the expected major single band of ~0.6 kb corresponding to the human GDNF cDNA was produced (FIG. 29A). The human prepro GDNF cDNA was subcloned into the pcDNA3.1 eukaryotic expression plasmid, and was designated pCD-GDNF. The engineering of this plasmid was validated by DNA sequencing, and by expression of immunoreactive GDNF in COS cells transfected with pCD-GDNF.

Engineering of HIRMAb-GDNF Expression Vector

For the engineering of the pHIRMAb-GDNF heavy chain (HC) expression plasmid, the mature human GDNF cDNA (SEQ ID NO:51) corresponding to amino acids Ser 78-Ile211 (SEQ ID NO:52) of full length human GDNF was cloned by PCR using the pCD-GDNF as template.

(SEQ ID NO: 51)
TCACCAGATAAACAAATGGCAGTGCTTCCTAGAAGAGAGCGGAATCGGCA

GGCTGCAGCTGCCAACCCAGAGAATTCCAGAGGAAAAGGTCGGAGAGGCC

AGAGGGGCAAAAACCGGGGTTGTGTCTTAACTGCAATACATTTAAATGTC

ACTGACTTGGGTCTGGGCTATGAAACCAAGGAGGAACTGATTTTTAGGTA

CTGCAGCGGCTCTTGCGATGCAGCTGAGACAACGTACGACAAAATATTGA

AAAACTTATCCAGAAATAGAAGGCTGGTGAGTGACAAAGTAGGGCAGGCA

TGTTGCAGACCCATCGCCTTTGATGATGACCTGTCGTTTTTAGATGATAA

CCTGGTTTACCATATTCTAAGAAAGCATTCCGCTAAAAGGTGTGGATGTA

TCTGA (SEQ ID NO: 52)
SPDKQMAVLPRRERNRQAAAANPENSRGKGRRGQRGKNRGCVLTAIHLNV

TDLGLGYETKEELIFRYCSGSCDAAETTYDKILKNLSRNRRLVSDKVGQA

CCRPIAFDDDLSFLDDNLVYHILRKHSAKRCGCI

The PCR cloning reaction was performed as described above. The ODNs used for PCR are 5'-phosphorylated for direct insertion into the HpaI site of the pHIRMAb-HC expression plasmid (FIG. 29B). The pHIRMAb-HC plasmid encodes the HC of the chimeric HIRMAb, and dual transfection of COS cells with this plasmid and a light chain (LC) expression plasmid, pHIRMAb-LC, allows for transient expression of either the chimeric HIRMAb, or a fusion protein, in COS cells. The mature human GDNF forward (FWD) PCR primer (Table 6) introduces "CA" nucleotides to maintain the open reading frame and to introduce a Ser-Ser linker between the carboxyl terminus of the CH3 region of the HIRMAb HC and the amino terminus of the GDNF. The fusion of the GDNF monomer to the carboxyl terminus of each HC is depicted in FIG. 28. This design sterically restricts the GDNF to a dimeric configuration, which replicates the native dimeric conformation of GDNF that binds to the GFRα1 (Xu et al, 1998; Eketjall et al, 1999). The GDNF reverse (REV) PCR primer introduces a stop codon, "TGA," immediately after the terminal isoleucine of the mature GDNF protein, and it is identical to the human prepro GDNF REV ODN primer (Table 6) used in the cloning of the human prepro GDNF cDNA. The engineered pHIRMAb-GDNF expression vector was validated by DNA sequencing. The nucleic acid and amino acid sequences for fusion heavy chain (SEQ ID NOs 45 and 46) are as follow:

(SEQ ID NO: 45)
ATGGACTGGACCTGGAGGGTGTTCTGCCTGCTTGCAGTGGCCCCCGGAGC

CCACAGCCAGGTTCAGCTGCAGCAGTCTGGACCTGAGCTGGTGAAGCCTG

GGGCTTTAGTGAAGATATCCTGCAAGGCTTCTGGTTACACCTTCACAAAC

TACGATATACACTGGGTGAAGCAGAGGCCTGGACAGGGACTTGAGTGGAT

TGGATGGATTTATCCTGGAGATGGTAGTACTAAGTACAATGAGAAATTCA

AGGGCAAGGCCACACTGACTGCAGAGAAATCCTCCAGCACAGCCTACATG

CACCTCAGCAGCCTGACTTCTGAGAAATCTGCAGTCTATTTCTGTGCAAG

AGAGTGGGCTTACTGGGGCCAAGGGACTCTGGTCACTGTCTCTGCAGCTA

GCACCAAGGGCCCATCGGTCTTCCCCCTGGCACCCTCCTCCAAGAGCACC

TCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGT

GAATCACAAGCCCAGCAACACCAAGGTGGACAAGAAAGTTGAGCCCAAAT

CTTGTGACAAAACTCACACATGCCCACCGTGCCCAGCACCTGAACTCCTG

GGGGGACCGTCAGTCTTCCTCTTCCCCCCAAAACCCAAGGACACCCTCAT

GATCTCCCGGACCCCTGAGGTCACATGCGTGGTGGTGGACGTGAGCCACG

AAGACCCTGAGGTCAAGTTCAACTGGTACGTGGACGGCGTGGAGGTGCAT

AATGCCAAGACAAAGCCGCGGGAGGAGCAGTACAACAGCACGTACCGTGT

-continued

```
GGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACC

ATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGG

TCAAAGGCTTCTATCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAAGCTCACCGTGGACAAGAGCAGGTGGCAGC

AGGGGAACGTCTTCTCATGCTCCGTGATGCATGAGGCTCTGCACAACCAC

TACACGCAGAAGAGCCTCTCCCTGTCTCCGGGTAAAAGTTCATCACCAGA

TAAACAAATGGCAGTGCTTCCTAGAAGAGAGCGGAATCGGCAGGCTGCAG

CTGCCAACCCAGAGAATTCCAGAGGAAAAGGTCGGAGAGGCCAGAGGGGC

AAAAACCGGGGTTGTGTCTTAACTGCAATACATTTAAATGTCACTGACTT

GGGTCTGGGCTATGAAACCAAGGAGGAACTGATTTTTAGGTACTGCAGCG

GCTCTTGCGATGCAGCTGAGACAACGTACGACAAAATATTGAAAAACTTA

TCCAGAAATAGAAGGCTGGTGAGTGACAAAGTAGGGCAGGCATGTTGCAG

ACCCATCGCCTTTGATGATGACCTGTCGTTTTTAGATGATAACCTGGTTT

ACCATATTCTAAGAAAGCATTCCGCTAAAAGGTGTGGATGTATCTGA
```

(SEQ ID NO: 46)

```
MDWTWRVFCLLAVAPGAHSQVQLQQSGPELVKPGALVKISCKASGYTFTN

YDIHWVKQRPGQGLEWIGWIYPGDGSTKYNEKFKGKATLTADKSSSTAYM

HLSSLTSEKSAVYFCAREWAYWGQGTLVTVSAASTKGPSVFPLAPSSKST

SGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNH

YTQKSLSLSPGKSSSPDKQMAVLPRRERNRQAAAANPENSRGKGRRGQRG

KNRGCVLTAIHLNVTDLGLGYETKEELIFRYCSGSCDAAETTYDKILKNL

SRNRRLVSDKVGQACCRPIAFDDDLSFLDDNLVYHILRKHSAKRCGCI.
Also shown in FIG. 36.
```

The HIRMAb HC and LC cDNA expression cassettes are driven by the cytomegalovirus (CMV) promoter and contain the bovine growth hormone (BGH) polyadenylation (pA) sequence (FIG. 29B). The engineering of the universal pHIRMAb-HC vector was performed by insertion of a single HpaI site at the end of the HIRMAb HC CH3 open reading frame (orf) by site directed mutagenesis (SDM).

Transient Expression of HIRMAb-GDNF Fusion Protein in COS Cells

COS cells were dual transfected with pHIRMAb-LC and pHIRMAb-HC-GDNF using Lipofectamine 2000, with a ratio of 1:2.5, ug DNA:uL Lipofectamine. Following transfection, the cells were cultured in serum-free VP-SFM (Invitrogen, Carlsbad, Calif.). The conditioned serum free medium was collected at 3 and 7 days. The fusion protein was purified by protein A affinity chromatography.

Human IgG and GDNF ELISAs

Human IgG ELISA was performed in Immulon 2 high binding plates (Dynex Tech., Chantilly, Va.) with COS cell conditioned medium. A goat anti-human IgG primary antibody (Zymed-Invitrogen, Carlsbad, Calif.) was plated in 0.1 M $NaHCO_3$ (100 µl, 2 µg/ml) and incubated for overnight at 4 C. Plates were washed 0.01 M $Na_2HPO4$/0.15 M NaCl/pH=7.4/0.05% Tween-20 (PBST), and blocked with 1% gelatin in PBST for 30 min at 22° C. Plates were incubated with 100 µL/well of either human IgG1 standard or the fusion protein for 60 minutes at room temperature (RT). After washing with PBST, a goat anti-human kappa LC antibody conjugated to alkaline phosphatase (Sigma Chemical Co., St. Louis, Mo.) was plated for 60 min at 37° C. Color development was performed with p-nitrophenyl phosphate (Sigma) at pH=10.4 in the dark. The reaction was stopped with NaOH, and absorbance at 405 nm was measured in a BioRad ELISA plate reader. Human GDNF immunoreactivity in COS cell conditioned medium was measured with the double antibody sandwich GDNF Emax Immunoassay System kit from Promega (Madison, Wis.).

SDS-PAGE and Western Blotting

The homogeneity of protein A purified fusion protein produced by COS cells was evaluated with a reducing 12% sodium dodecyl sulfate polyacrylamide gel electrophoresis (SDS-PAGE), followed by Coomasie Blue staining. For Western blotting, immunoreactivity was tested with a primary rabbit antibody to human GDNF (Santa Cruz Biotechnology, Santa Cruz, Calif.) or a primary goat antiserum against human IgG heavy and light chains (Vector Labs, Burlingame, Calif.).

HIR Receptor Assay

The affinity of the fusion protein for the HIR extracellular domain (ECD) was determined with an ELISA using the lectin affinity purified HIR ECD. CHO cells transfected with the HIR ECD were grown in serum free media (SFM), and the HIR ECD was purified with a wheat germ agglutinin affinity column. The HIR ECD (0.2 µg/well) was plated on Immulon 2 high binding 96-well plates, and the binding of the chimeric HIRMAb, the HIRMAb-GDNF fusion protein, or human IgG1 to the HIR ECD was detected with a biotinylated goat anti-human IgG (H+L) antibody (0.3 µg/well), and the ABC Elite detection system (Vector Labs). The concentration that caused 50% binding to the HIR ECD, the ED50, was determined by non-linear regression analysis using the WinNonlin software.

GFRα1 Receptor Assay

Binding of recombinant GDNF (Peproαtech, Rocky Hill, N.J.), the chimeric HIRMAb, or the HIRMAb-GDNF fusion protein to the ECD of recombinant human GFRα1 was measured with an ELISA. A mouse anti-human (MAH) IgG (Zymed-Invitrogen) was plated in 96-well plates overnight at 2 µg/well. Following aspiration, washing, and blocking with 1% bovine serum albumin (BSA), the Fc fusion of the human GFRα1 ECD (R&D Systems, Minneapolis, Minn.) was plated at 0.4 µg/well. Following an incubation at room temperature (RT) for 60 min, the wells were washed with PBST, and the GDNF, antibody, or fusion protein was plated for 2 hours at RT. Following washing in PBST, a goat anti-GDNF antibody (R&D Systems) was plated at 0.4 ug/well for 30 min at RT. Following washing in PBST, a conjugate of alkaline phosphatase (AP) and a rabbit anti-goat (RAG) IgG(H+L) (Vector Labs) was plated and detection at 405 nm was performed with an ELISA plate reader after color development with para-nitrophenylphosphate (Sigma Chemical Co.).

SK-N-MC Bio-Assay

Human neural SK-N-MC cells were dual transfected with the c-ret kinase and a luciferase reporter plasmid under the influence of the 5'-flanking sequence (FS) of the rat tyrosine hydroxylase (TH) gene. The cells were grown in collagen coated 24-well dishes to 70% confluency in Dulbecco's modified Eagle medium (DMEM) with 10% fetal bovine serum (FBS) and 400 µg/mL G418. To begin the assay, the medium was aspirated, and 400 µL/well of fresh DMEM/10% FBS was added along with either recombinant GDNF or fusion protein. After a 24 hour incubation at 37° C., the wells were aspirated, and the cells extracted with 200 µL/well of Luciferase Reporter Lysis buffer (Promega, Madison, Wis.). Following centrifugation, luciferase enzyme activity was measured in the lysate with a luminometer, and luciferase enzyme activity, reported as picogram (pg) of luciferase, was normalized per mg sample protein using the bicinchoninic acid (BCA) protein assay (Pierce Chemical Co., Rockford, Ill.).

SH-SY5Y Bio-Assay

Human neural SH-SY5Y cells were plated in 96 well plates in DMEM/Ham F12 (1:1) in 10% FBS and grown until the cells reached 70% confluency. The medium was supplemented with 10 µM retinoic acid to induce differentiation of the cells over a 10 day period. After cell differentiation, the medium was changed, and supplemented with either GDNF or HIRMAb-GDNF fusion protein at zero time, and cell proliferation was measured over the 5 days with the CellTiter 96® AQueous Non-Radioactive Cell Proliferation Assay (Promega), which uses the tetrazolium compound, (3-(4,5-dimethylthiazol-2-yl)-5-(3-carboxymethoxyphenyl)-2-(4-sulfophenyl)-2H-tetrazolium, inner salt; MTS), and the electron coupling reagent, phenazine methosulfate (PMS). Absorbance at 490 nm is a measure of formazan production, which is proportional to the number of viable cells.

Middle Cerebral Artery Occlusion Model

The permanent middle cerebral artery occlusion (MCAO) model was performed as described previously in adult Sprague-Dawley rats (Zhang and Pardridge, *Brain Res.* 889:49-56 (2001)). The right middle cerebral artery of the anesthetized rat was occluded by insertion of an intra-luminal 4-0 nylon suture; the suture was coated in 0.1% poly-L-lysine and dried at 60° C. for 1 hour. Within 15 minutes of the occlusion, the rat was treated with an intra-cerebral injection of either HIRMAb-GDNF fusion protein (130 µg in 10 mL) or an equal volume of saline. Since the fusion protein is 17% GDNF, the dose of fusion protein is equivalent to a dose of GDNF of 22 µg, which is a dose that causes pharmacological effects in the brain (Sullivan et al, 1998). The drug was injected into the brain under stereotaxic guidance with the following coordinates: 0.2 mm posterior to bregma, 4.0 mm lateral to the midline, and 5.0 mm deep from the dural surface. The arterial nylon suture was left in place for permanent occlusion of the middle cerebral artery. A total of 20 rats were used for the study; 9 rats (5 treated with saline and 4 treated with HIRMAb-GDNF) expired prematurely and were excluded from the study. The rats were allowed to recover, and were euthanized 24 hours later, and coronal sections of brain were prepared with a rat brain matrix (ASI Instruments, Warren, Mich.), followed by staining with 2% 2,3,5-triphenyltetrazolium chloride (TTC), as described previously (Zhang and Pardridge, *Brain Res.* 889:49-56 (2001)). TTC stains healthy brain red, and infarcted brain is colorless. The stained brain sections were scanned on a UMAX PowerLook II flatbed scanner, and the area of the hemispheric infarct volumes was determined with the NIH Image software. The volume of the infarct was computed from the area of the infarcted zone and length (2 mm) of the coronal slices of brain hemisphere (Zhang and Pardridge, *Brain Res.* 889:49-56 (2001)). The scanned color image was converted to an inverted grayscale image in Photoshop, so that infarcted brain appears black and healthy brain appears white.

The neurologic deficit was determined 24 hours after the occlusion, as described previously (Zhang and Pardridge, *Stroke* 32:1378-1384 (2001)), and scored as follows: 0, no deficit; 1, failure to extend contralateral forepaw fully; 2, decreased grip of contralateral forelimb while tail is pulled; 3, spontaneous circling to left; 4, walks only when stimulated with decreased level of consciousness.

Results

DNA sequencing of the expression cassette of the pCD-GDNF encompassed 1,752 nucleotides (nt), including a 715 nt CMV promoter, a 636 nt prepro GDNF open reading frame, and a 401 nt BGH sequence, which predicted a 211 amino acid human preproGDNF protein, including a 19 amino acid signal peptide with 100% identity with the known sequence for human GDNF (P39905). Transfection of COS cells with pCD-GDNF resulted in high levels of immunoreactive GDNF the medium at 3 and 7 days following transfection.

The cDNA corresponding to the 134 amino acid mature GDNF was amplified by PCR using the ODNs in Table 6 and the pCD-GDNF as template, and this cDNA was subcloned into the HpaI site of the pHIRMAb-HC plasmid, as outlined in FIG. 29B. DNA sequencing of the expression cassette of the pHIRMAb-GDNF plasmid encompassed 2,890 nt, including a 714 nt CMV promoter, a 9 nt full Kozak site (GCCGCCACC), a 1,797 nt HIRMAb HC-GDNF fusion protein open reading frame, and a 370 nt BGH sequence. The plasmid encoded for a 598 amino acid protein, comprised of a 19 amino acid IgG signal peptide, the 443 amino acid HIRMAb HC, a 2 amino acid linker (Ser-Ser), and the 134 amino acid human GDNF minus the signal peptide or propeptide. The predicted molecular weight of the heavy chain fusion protein, minus glycosylation, is 63,860 Da, with a predicted isoelectric point (pI) of 9.03.

Dual transfection of COS cells with the pHIRMAb-GDNF and the pHIRMAb-LC resulted in medium human IgG levels of 2.0 µg/mL, as determined with a human Fc specific ELISA. The level of immunoreactive GDNF in the medium was measured with a GDNF-specific ELISA. The data from both the human IgG and human GDNF ELISAs are given in Table 7, and the medium levels are expressed as nM concentrations to allow for comparison of the 2 assays.

TABLE 7

HIRMAb-GDNF fusion protein concentrations in the medium of transfected COS cells following transfection with pHIRMAb-LC and pHIRMAb-GDNF

| Target of primary antibody | 3 day concentration (nM) | 7 day concentration (nM) |
| --- | --- | --- |
| Anti-human IgG Fc | 3.1 ± 0.2 | 11.3 ± 1.4 |
| Anti-human GDNF | 2.0 ± 0.5 | 12.6 ± 3.1 |

Mean ± SE (n = 3 dishes per point). The medium immunoreactive human IgG or GDNF was <0.1 nM in dishes treated with Lipofectamine 2000 alone.

As shown in Table 7, the concentration of the HIRMAb-GDNF fusion protein the medium was the same irrespective of whether the human IgG or GDNF ELISA is used.

Figure 30:
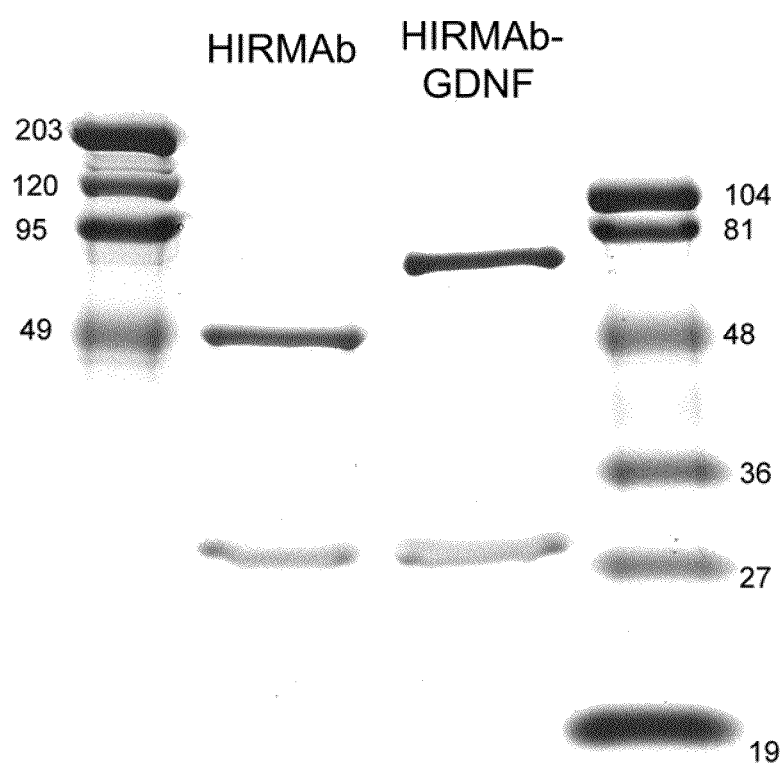
FIG. 30. Reducing SDS-PAGE and Coomasie blue staining of protein A affinity purified, COS-cell chimeric HIRMAb and the HIRMAb-GDNF fusion protein. Both are purified to homogeneity and are comprised of a heavy chain and a light chain. The molecular weight (MW) of the heavy chain (HC) of the HIRMAb-GDNF fusion protein is about 15 kDa larger than the MW of the HC of the chimeric HIRMAb, owing to fusion of the 15 kDa GDNF.
Figure 31:
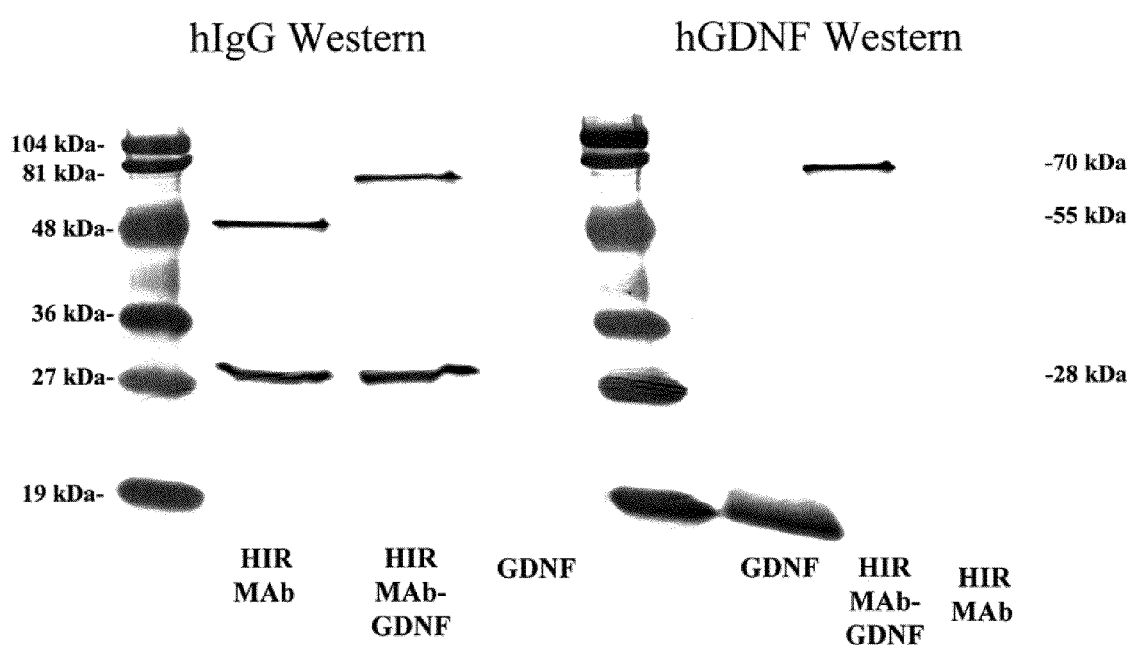
FIG. 31. Western blot with either anti-human (h) IgG primary antibody (left) or an anti-human GDNF primary antiserum (right). The immunoreactivity of the COS cell derived HIRMAb-GDNF fusion protein is compared to the chimeric HIRMAb and to recombinant GDNF. Both the HIRMAb-GDNF fusion protein and the HIRMAb have identical light chains on the anti-hIgG Western. The HIRMAb-GDNF fusion heavy chain reacts with both the anti-hIgG and the anti-human GDNF antibody, whereas the HIRMAb heavy chain only reacts with the anti-hIgG antibody. The size of the HIRMAb-GDNF fusion heavy chain, 70 kDa, is about 15 kDa larger than the size of the heavy chain of the HIRMAb, owing to the fusion of the 15 kDa GDNF to the 55 kDa HIRMAb heavy chain.

The HIRMAb-GDNF fusion protein was purified by protein A affinity chromatography. Following SDS-PAGE and Coomasie blue staining, the size of the light chain (LC) was the same for both the HIRMAb and the HIRMAb-GDNF fusion protein (FIG. 30). The size of the heavy chain (HC) of the fusion protein was about 15 kDa larger than the HC of the HIRMAb (FIG. 30). On Western blotting, the LC of either the HIRMAb or the HIRMAb-GDNF fusion protein reacted equally on the Western with a primary antibody directed against the human IgG (H+L), as shown in FIG. 31. The size of the HC of the fusion protein was about 15 kDa larger than the size of the HC of the HIRMAb on both Western blots using either the anti-human IgG primary antibody (FIG. 31) or the anti-human GDNF primary antibody (FIG. 31). The anti-GDNF primary antibody reacts with the HC of the fusion protein, and with recombinant GDNF, but does not react with the HIRMAb (FIG. 31).

Figure 32:
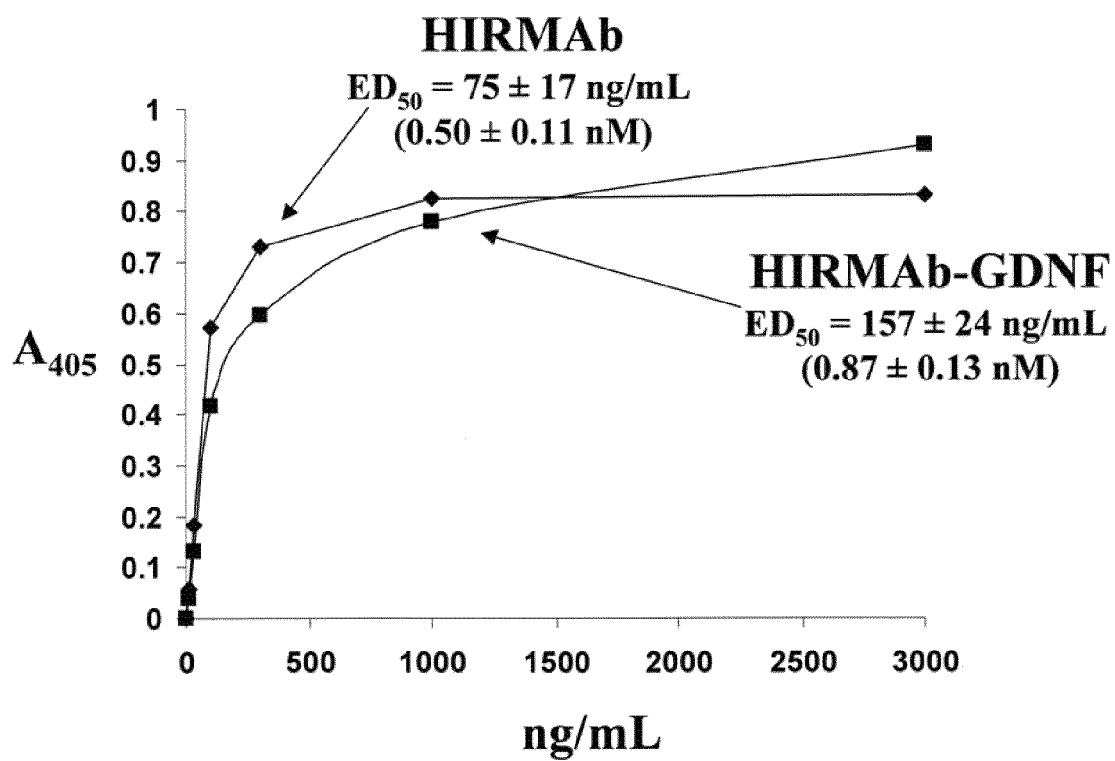
FIG. 32. Binding of either the COS cell-derived chimeric HIRMAb or the HIRMAb-GDNF fusion protein to the HIR extracellular domain (ECD) is saturable. The ED50 of HIRMAb-GDNF binding to the HIR ECD is comparable to the ED50 of the binding of the chimeric HIRMAb.

The affinity of the fusion protein for the HIR extracellular domain (ECD) was determined with a ligand binding assay using lectin affinity purified HIR ECD (Methods). There is comparable binding of either the chimeric HIRMAb or the HIRMAb-GDNF fusion protein for the HIR ECD with ED50 of $0.50\pm0.11$ nM and $0.87\pm0.14$ nM, respectively (FIG. 32).

The affinity of either GDNF or the HIRMAb-GDNF fusion protein for the ECD of the human GFR$\alpha$1 was measured with an ELISA, which is outlined in FIG. 33A. Human GDNF bound to the GFR$\alpha$1 with an ED50 of $1.03\pm0.18$ nM (FIG. 33B, top panel). The affinity of the HIRMAb-GDNF fusion protein for the GFR$\alpha$1 was also high, with an ED50 of $1.68\pm0.17$ nM (FIG. 33B, bottom panel). The biologic activity of GDNF or the HIRMAb-GDNF fusion protein was also evaluated with bio-assays in human neural cell lines. The human neural SK-N-MC cell line was dual transfected with the c-ret kinase, and with a luciferase expression plasmid under the influence of the 5'-flanking sequence (FS) of the rat TH promoter. Addition of GDNF to the medium activates the TH promoter via activation of the GFR$\alpha$1/c-ret kinase system, and this leads to increased luciferase expression (FIG. 34A). GDNF increased luciferase expression with an ED50 of $1.03\pm0.31$ nM, and the HIRMAb-GDNF fusion protein also increased luciferase expression with an ED50 of $1.68\pm0.45$ nM (FIG. 34B). Both GDNF and the HIRMAb-GDNF fusion protein activated cell division of human neural SH-SY5Y cells following retinoic acid differentiation, and both proteins increased cell division about 50% over a 5 day incubation period (Table 8).

TABLE 8

Enhanced proliferation of retinoic acid differentiated human neural SH-SY5Y cells by human GDNF or HIRMAb-GDNF

| Treatment | A490 |
|---|---|
| GDNF (3 nM) | $0.43 \pm 0.02$ [a] |
| HIRMAb-GNDF (5 nM) | $0.42 \pm 0.03$ [a] |
| control | $0.29 \pm 0.01$ |

Mean ± SE (n = 6);
[a] $p < 0.005$. Cell proliferation measured with the MTS assay as described herein.

The intra-cerebral injection of the HIRMAb-GDNF fusion protein caused a 77% reduction in hemispheric stroke volume, from $331\pm33$ mm3 to $77\pm22$ mm3 (mean±SE, n=5-6 rats per group), which was significant at the $p<0.001$ level (Student's t-test), as shown in FIG. 35A. Similarly, the cortical stroke volume was reduced 86% from $241\pm26$ mm3 to $34\pm9$ mm3 ($p<0.001$), and the sub-cortical stroke volume was reduced 52% from $90\pm10$ mm3 to $43\pm16$ mm3 ($p<0.025$), as shown in FIG. 35A. A representative TTC stain of the brain 24 hours after permanent MCAO and intra-cerebral injection of either saline or the HIRMAb-GDNF fusion protein is shown in FIGS. 35B and 35C, respectively. The neurologic deficit score was $3.0\pm0.7$ and $1.3\pm0.6$ (mean±SE, n=5-6 rats per group) in the saline treated and HIRMAb-GDNF treated rats, respectively, and this improvement in neurologic deficit was significant at the $p<0.05$ level (Student's t-test).

Discussion

Figure 33:
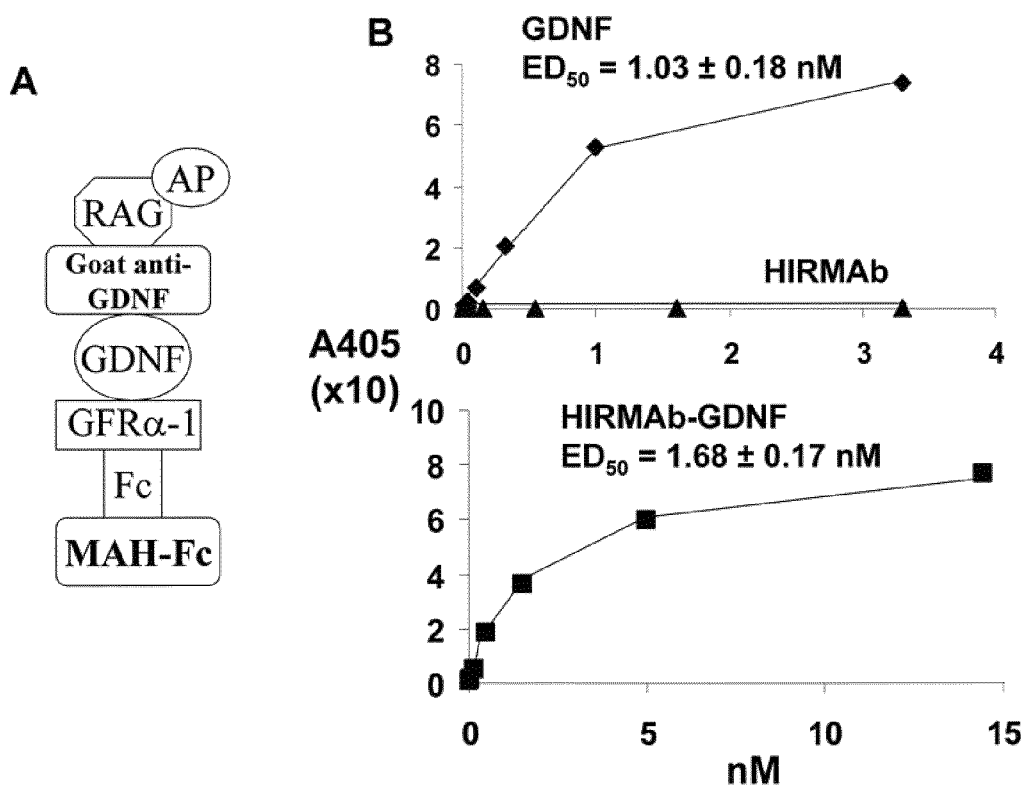
FIG. 33. (A) Outline of GFRα1 receptor binding assay. The GFRα1:Fc fusion protein is captured by a mouse anti-human (MAH) Fc antibody. The GDNF, or HIRMAb-GDNF fusion protein, binds to the GFRα1, and this binding is detected with a goat anti-GDNF antibody and a rabbit anti-goat (RAG) antibody conjugated to alkaline phosphatase (AP). (B) Binding of either the COS cell derived chimeric HIRMAb or the HIRMAb-GDNF fusion protein to the GFRα1 extracellular domain (ECD) is saturable. The ED50 of HIRMAb-GDNF binding to the GFRα1 ECD is comparable to the ED50 of the binding of recombinant GDNF. There is no binding to the GFRα1 by the chimeric HIRMAb.

The results of this study were consistent with the following conclusions. First, a bi-functional IgG-GDNF fusion protein was genetically engineered, wherein mature human GDNF was fused to the carboxyl terminus of the heavy chain (HC) of a chimeric HIRMAb (FIG. 28), and expressed and secreted in COS cells (Table 8, FIGS. 30 and 31). Second, the HIRMAb-GDNF fusion protein was bi-functional and bound the HIR and human GFR$\alpha$1 with high affinity (FIGS. 32 and 33). Third, the HIRMAb-GDNF fusion protein had activity in bio-assays of human neural cells comparable to recombinant human GDNF (FIG. 34, Table 8). Fourth, the HIRMAb-GDNF was neuroprotective in rat brain in vivo in the permanent MCAO stroke model, and caused a marked reduction in stroke volume (FIG. 35).

GDNF is a member of the transforming growth factor (TGF)-$\alpha$ gene family, along with other neurotrophins, such as neuturin, persephin, or artemin. GDNF reacts with its cognate receptor, GFR$\alpha$1, as a homo-dimer (Eketjall et al, 1999). Therefore, the GDNF fusion construct described in this work (FIG. 28) places GDNF in a dimeric configuration that mimicked the conformation of the neurotrophin at the receptor. The prepro GDNF could be fused to the amino terminus of the HIRMAb HC. However, this would interfere with HIRMAb binding to the HIR, which would impair transport of the fusion protein across the BBB via the insulin receptor. Moreover, the mature GDNF protein folded into a biologically active conformation, despite the absence of the prepro GDNF peptide in the fusion protein described in this work. The goal of fusion protein engineering was to retain the bi-functional characteristics of the fusion construct, and this was accomplished in the case of the HIRMAb-GDNF fusion protein.

The fusion protein was secreted in high amounts to the medium by COS cells co-transfected with the HC expression plasmid, pHIRMAb-GDNF (FIG. 29B), and the LC expression plasmid, pHIRMAb-LC (Table 7). The HC of the fusion protein is about 15 kDa larger than the HC of the chimeric HIRMAb, based on either SDS-PAGE gels with Coomassie blue staining (FIG. 30), or on Western blot analysis using primary antibodies to either human IgG or human GDNF (FIG. 31). The anti-human IgG antibody reacts equally with the LC of the fusion protein or the chimeric HIRMAb, since both proteins use the same LC. Both the HIRMAb-GDNF fusion protein and the HIRMAb bind with high affinity to the HIR, and with comparable affinity (FIG. 32).

The HIRMAb-GDNF fusion protein retains high affinity binding to the human GFR$\alpha$1 receptor, and the affinity constant of binding is comparable to that of recombinant GDNF (FIG. 33B). The high affinity binding of the HIRMAb-GDNF fusion protein to the GFR$\alpha$1 was translated into biological activity in two different human neural cell lines. The SH-SH5Y cell line expresses the GFR$\alpha$1, but does not express the c-ret kinase in the undifferentiated state (Xiao et al, *J. Neurochem.* 82:701-808 (2002)). Both the GFR$\alpha$1 and the c-ret kinase must be expressed to enable GDNF activation of a neural cell (Cik et al, 2000). However, differentiation of SH-SH5Y cells by retinoic acid causes an induction of the expression of the c-ret kinase (Xiao et al, *J. Neurochem.* 82:701-808 (2002)). Following differentiation by retinoic acid, the SH-SY5Y cells demonstrate enhanced proliferation in response to either recombinant human GDNF or the HIRMAb-GDNF fusion protein (Table 8). The SK-N-MC human neural cell line also expresses the GFR$\alpha$1 receptor, but not the c-ret kinase (Hirata and Kiuchi, *Brain Res.* 983:1-12 (2003)). However, following co-transfection of these neural cells with a c-ret kinase cDNA and a plasmid encoding luciferase under the influence of 2 kb of the 5'-FS of the rat TH promoter, these cells respond to GDNF (Tanaka et al, *Brain res. Brain Res. Protoc.* 11:119-122 (2003)). As outlined in FIG. 34A, the extracellular GDNF binds the GFRα1, which activates the c-ret kinase, which induces a signal transduction cascade leading to activation of the TH promoter. Accordingly, both recombinant GDNF and the HIRMAb-GDNF fusion protein caused an approximate 500% increase in cellular luciferase enzyme activity. The GDNF ED50 in the luciferase assay is 1.0±0.1 nM, and the HIRMAb-GDNF ED50 in this assay is 1.7±0.5 nM (FIG. 34B). These ED50 values are identical to the ED50 of saturable binding of either GDNF or the HIRMAb-GDNF fusion protein in the GFRα1 binding assay (FIG. 33B). This correlation indicates that the rate-limiting step in activation of neural pathways by GDNF is binding to the cell membrane GFRα1 receptor.

The intra-cerebral injection of the HIRMAb-GDNF fusion protein in rat brain following permanent middle cerebral artery occlusion (MCAO) resulted in a 77% reduction in hemispheric stroke volume from 331±33 mm$^3$ to 77±22 mm3 ($p<0.001$), as shown in FIG. 35A. The neuroprotection was both cortical and sub-cortical, as the cortical stroke volume was reduced 86% from 241±26 mm$^3$ to 34±9 mm3 ($p<0.001$), and the sub-cortical stroke volume is reduced 52% from 90±10 mm3 to 43±16 mm3 ($p<0.025$) (FIG. 35A). A representative TTC stain of the rat brain at 24 hours after the permanent MCAO is shown in FIG. 35B, for the saline treated rat, and in FIG. 35C for the HIRMAb-GDNF fusion protein treated rat. The reduction in stroke volume was correlated with a functional improvement as the neurologic deficit was reduced from 3.0±0.3 to 1.3±0.6 ($p<0.05$) in the rats treated with the HIRMAb-GDNF fusion protein as compared to the saline treated rats. These findings of in vivo neuroprotection of the HIRMAb-GDNF fusion protein correlated with the tissue culture bio-assays (Table 8, FIG. 34B), and confirmed the neuroprotective effects of the HIRMAb-GDNF fusion protein on neural cells in brain. The MCAO findings confirmed prior work showing the beneficial effects of intra-cerebral GDNF in acute stroke (Kitagawa et al, 1998). Recent work showed that chronic treatment of the brain with intra-cerebral GDNF may promote striatal neurogenesis following stroke (Kobayashi et al, *Stroke* 37:2361-2367 (2007)). Irrespective of whether the brain is treated acutely or chronically with GDNF, the neurotrophin had to be re-engineered to cross the BBB before clinical trials in human stroke can be initiated.

The HIRMAb-GDNF fusion protein could not be delivered to rat brain in the MCAO model following intravenous administration, because the HIRMAb part of the fusion protein is not reactive with the rodent insulin receptor. However, the HIRMAb is active in Old World primates, such as the Rhesus monkey (Pardridge et al, *Pharm. Res.* 12:807-816 (1995)). Recent work has shown that fusion proteins of the HIRMAb and brain-derived neurotrophic factor (Boado et al, *Biotechnol Bioeng.* 97:1376-1386 (2007)), a single chain Fv antibody (Boado et al, *Bioconjug Chem.* 18:447-455 (2007)), or iduronidase, a lysosomal enzyme (Boado et al, *Biotechnol Bioeng.* 99: 475-484 (2008)), all are rapidly transported across the Rhesus monkey BBB in vivo. In the primate brain, the uptake of the fusion protein is approximately 1% of the injected dose (ID) (Boado et al, *Biotechnol Bioeng.* 99: 474-484 (2008)). Since the weight of the human brain is about 10-fold greater than the weight of the Rhesus monkey brain, it is expected that the brain uptake of the HIRMAb-GDNF fusion protein by the human brain will be about 0.1% of the ID. Given an injection dose of 25 mg, the expected brain concentration of the fusion protein is about 25 ng/gram human brain, which is equivalent to 5 ng/gram of GDNF, since the fusion protein is about 20% GDNF and 80% HIRMAb. The concentration of GDNF in the human brain is 0.2-1 ng/gram (Wiesenhofer et al, *Acta Neuropathol. (Berl)* 99:131-137 (2000)). Therefore, the dosing of 25 mg of the HIRMAb-GDNF fusion protein to a 60 kg human could result in pharmacologically significant increase in GDNF in the brain. In experimental Parkinson's disease, pharmacological effects are achieved with just a 3-fold increase in brain GDNF concentration (Eslamboli et al, *J. Neurosci.* 25:769-777 (2005)). Aberrant neuronal sprouting is induced when the brain GDNF concentration is increased >100-fold (Eslamboli et al, *J. Neurosci.* 25:769-777 (2005))). However, such large increases in brain GDNF will not be produced by therapeutic dosing of the HIRMAb-GDNF fusion protein in humans.

In conclusion, these studies described the genetic engineering, transient expression in COS cells, and validation of a HIRMAb-GDNF fusion protein, which represents a re-engineering of this neurotrophin to enable transport across the human BBB in vivo. The fusion protein can be administered by systemic injection to humans for treatment of multiple neurologic disorders, including stroke, neural repair, Parkinson's disease, or motor neuron disease.

Example 16

Figure 37:
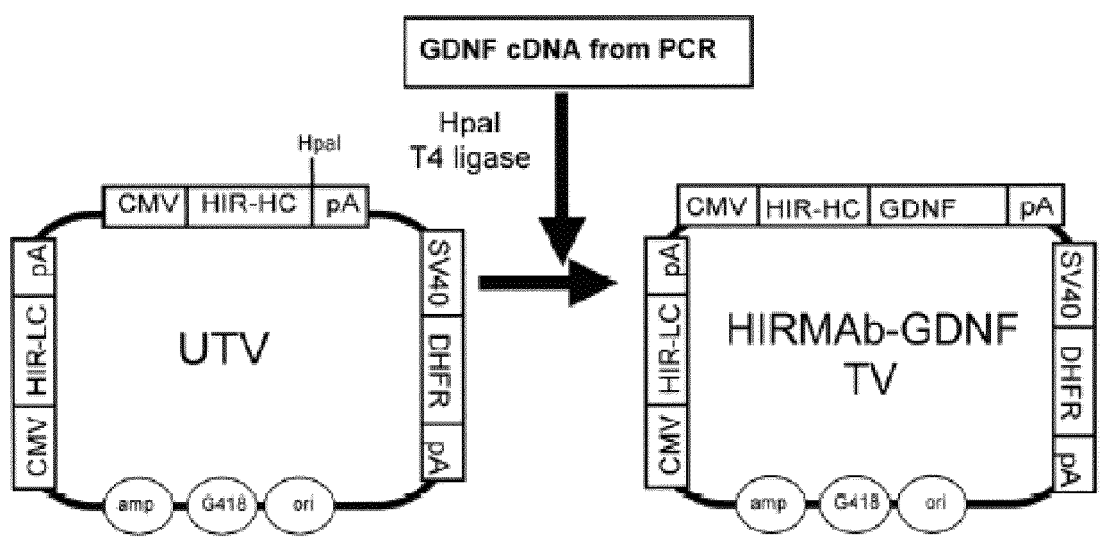
FIG. 37. Tandem vector (TV) encoding multiple genes on a single piece of DNA. The GDNF cDNA, produced by PCR, is subcloned into the HpaI site of the universal tandem vector (UTV) to generate the HIRMAb-GDNF TV, which allows for expression in CHO cells of the fusion heavy chain (HC) gene, the light chain (LC) gene, and the dihydrofolate reductase (DHFR) gene.

Expression of HIRMAb-GDNF Fusion Protein Following Stable Transfection of CHO Cells A tandem vector (TV) encoding the HIRMAb-GDNF fusion protein was engineered as shown in FIG. 37, and is designated HIRMAb-GDNF TV. The TV contains on a single piece of DNA the fusion heavy chain (HC), the light chain (LC), and the gene for DHFR. DNA sequencing of the entire 6,300+ nucleotides (nt) of the HIRMAb-GDNF TV using custom oligodeoxynucleotides (ODNs) showed the sequence was comprised of 6,342 nt (SEQ ID NO. 47), which included the following domains:

731 nt cytomegalovirus (CMV) promoter
9 nt Kozak sequence (GCCGCCACC)
705 nt open reading frame (orf) encoding the HIRMAb LC
291 nt bovine growth hormone (BGH) polyA (pA) sequence
23 nt linker
714 nt CMV promoter
9 nt Kozak sequence
1,797 ORF encoding the fusion gene of the HIRMAb HC and GDNF
296 nt BGH pA
254 SV40 promoter
9 nt Kozak sequence
564 murine DHFR orf
940 hepatitis B virus (HBV) pA The HIRMAb-GDNF TV also included the expression cassette encoding neo, the neomycin resistance gene, to enable selection with G418 (FIG. 37). It was necessary to include the HC fusion gene, the LC gene, and the DHFR gene on a single piece of DNA, or tandem vector (FIG. 37) to allow for equally high expression of all 3 genes in the transfected CHO cell.

Figure 36:
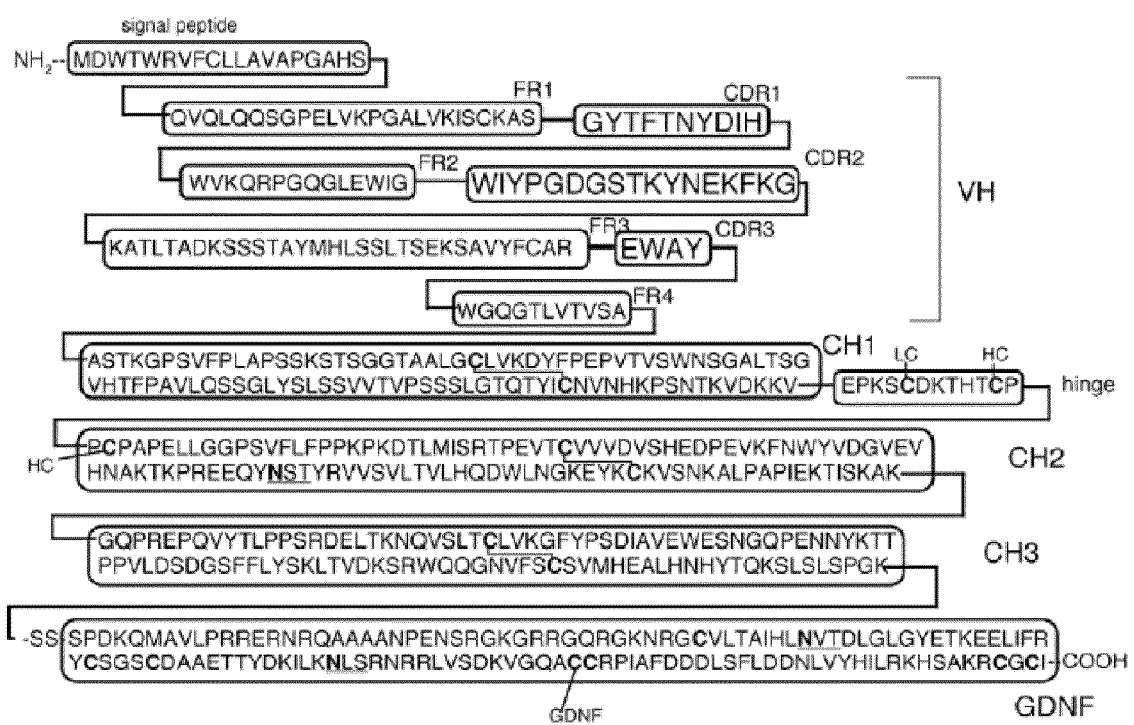
FIG. 36. Domain structure and amino acid sequence of the heavy chain (HC) of the HIRMAb-GDNF fusion protein. The polypeptide is comprised of a signal peptide, followed by the variable region of the heavy chain (VH) of the chimeric HIRMAb. The 3 CDRs and 4 FRs are shown. The VH region is followed by the human IgG1 constant region, which is comprised of the CH1, hinge, CH2, and CH3 domains, followed by a 2-amino acid (Ser-Ser) linker, followed by the mature human GDNF. The single N-linked glycosylation site within the CH2 region, and the 2 N-linked glycosylation sites within the GDNF are underlined with the asparagine (N) residues in bold font. Cysteine (C) residues, which form inter-chain disulfide bonds are shown, and include a linkage between the HC hinge region and the light chain (LC), the HC hinge region and the paired HC, the HC CH2 region and the paired HC, and the GDNF-GDNF linkage.
Figure 38:
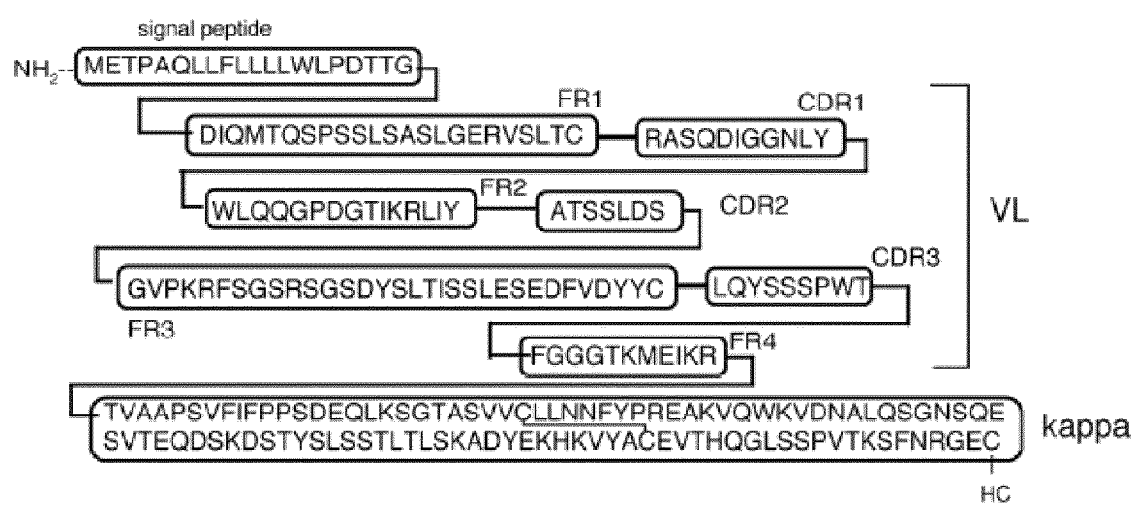
FIG. 38. Domain structure of the light chain of the HIRMAb.

The HIRMAb-GDNF TV sequence encoded for a 579 amino acid (AA) HC fusion protein (SEQ ID NO 48), which was comprised of a 19 AA IgG signal peptide, the 443 AA HIRMAb HC, a 2 AA linker, and the 134 AA human GDNF. The predicted molecular weight (MW) of the non-glycosylated HC was 63,860 Daltons (Da) and the predicted isoelectric point (pI) of the fusion HC protein was 9.03. The HIRMAb-GDNF TV sequence encoded for a 234 AA LC protein (SEQ ID NO 49), which was comprised of a 20 AA IgG signal peptide, and the 214 AA HIRMAb LC. The predicted MW of the LC was 23,398 Da and the predicted pI of the LC protein was 5.45. The HIRMAb-GDNF TV sequence encoded for a DHFR protein (SEQ ID NO 50), that had an AA sequence 100% identical with the known AA sequence of murine DHFR. The domain structure of the HC is shown in FIG. 36 and the domain structure of the LC is shown in FIG. 38.

Electroporation of CHO Cells.

DG44 CHO cells were grown in serum-free medium (SFM), containing 1×HT supplement (hypoxanthine and thymidine). DG44 CHO cells ($5 \times 10^6$ viable cells) were electroporated with 5 µg PvuI-linearized TV plasmid DNA. The cell-DNA suspension is then incubated for 10 min on ice. Cells are electroporated with pre-set protocol for CHO cells, i.e., square wave with pulse of 15 msec and 160 volts. After electroporation, cells are incubated for 10 min on ice. The cell suspension is transferred to 50 ml culture medium and plated at 125 µl per well in 40×96-well plates (10,000 cells per well), and 4,000 wells per study.

Selection and Amplification with Methotrexate and Screening IgG ELISA.

Following electroporation (EP), the CHO cells were placed in the incubator at 37° C. and 8% $CO_2$. Owing to the presence of the neo gen in the TV, transfected cell lines are initially selected with G418. The TV also contains the gene for DHFR, so the transfected cells were also selected with 20 nM methotrexate (MTX) and HT-deficient medium. Once visible colonies are detected at about 21 days after EP, the conditioned medium was sampled for human IgG by ELISA. Plates were removed from the incubator and transferred to the sterile hood where 100 µL samples were taken from each well using a Precision Pipettor system and transferred into a sterile 96-well tissue culture plate, which was then used for the human IgG ELISA. The media taken from the EP plates for the ELISA was replaced with 100 µL of SFM and cells were returned to the incubator at 37° C. and 8% $CO_2$. Wells with high human IgG signals in the ELISA were transferred from the 96-well plate to a 24-well plate with 1 mL of SFM. The 24-well plates were returned to the incubator at 37° C. and 8% $CO_2$. The following week IgG ELISA was performed on the clones in the 24-well plates. This was repeated through the 6-well plates to T75 flasks and finally to 60 mL and 125 mL square plastic bottles on an orbital shaker. After the cells adapted to the 60 mL bottle on the orbital shaker at 120 RPM they were transferred into a 125 mL plastic square bottle with 12 mL of SFM. At this stage, the final MTX concentration was 80 nM, and the medium IgG concentration, which is a measure of HIRMAb-GDNF fusion protein in the medium was >10 mg/L at a cell density of $10^6$/mL.

Dilutional Cloning of CHO Cells.

Clones selected for dilutional cloning (DC) were removed from the orbital shaker in the incubator and transferred to the sterile hood. The cells were diluted to 500 mL in F-12K medium with 5% dialyzed fetal bovine serum (d-FBS) and penicillin/streptomycin, and the final dilution was 8 cells per mL, so that 4,000 wells in 40×96-well plates were plated at a cell density of 1 cell per well (CPW). After the cell suspension was prepared, within the sterile hood, a 125 µL aliquot was dispensed into each well of a 96-well plate using an 8-channel pipettor or a Precision Pipettor system. The plates were then returned to the incubator at 37° C. and 8% $CO_2$. The cells diluted to 1 cell/well cannot survive without serum. On day 6 or 7, DC plates were removed from the incubator and transferred to the sterile hood where 125 µL of F-12K medium with 5% dialyzed fetal bovine serum (d-FBS) was added to each well. After this step, the selection media contained 5% d-FBS, 30 nM MTX and 0.25 mg/mL Geneticin. On day 21 after the initial 1 CPW plating, aliquots from each of the 4,000 wells were removed for human IgG ELISA, using robotics equipment. DC plates were removed from the incubator and transferred to the sterile hood, where 100 µL of media was removed per well of the 96-well plate and transferred into a new, sterile sample 96-well plate using an 8-channel pipettor or a Precision Pipettor system.

ELISA Screening of 4,000 Wells.

On day 20 after the initial 1 CPW plating, 44 96-well Immunoassay plates were plated with 100 µL of 1 µg/mL solution of Primary antibody, a mouse anti-human IgG in 0.1M $NaHCO_3$. Plates were incubated overnight in the 4° C. Revco refrigerator. The following day, the plates were washed with 1×TBST 5 times, and 100 µL of 1 µg/mL solution of secondary antibody and blocking buffer were added. Immulon plates were washed with 1×TBST 5 times. 100 µL of 1 mg/mL of 4-nitrophenyl phosphate di(2-amino-2-ethyl-1,3-propanediol) salt in 01M glycine buffer were added to the Immulon 96-well Immunoassay plates using the BioTek uFill. Plates were read on a microplate reader. The assay produced IgG output data for 4,000 wells/experiment. The highest producing 24-48 wells were selected for further propagation.

Adaptation of Cloned Cells to Serum-Free Medium (SFM).

The highest producing 24-well plates from the 1 CPW DC transferred to the sterile hood were gradually subcloned through 6-well dishes, T75 flasks, and 125 mL square plastic bottles on an orbital shaker. During this process the serum was reduced to zero, at the final stage of centrifugation of the cells and resuspension in SFM.

Second Round Dilutional Cloning.

The above procedures were repeated with a second round of dilutional cloning, again at 0.5 cells/well (CPW). At this stage, approximately 40% of the wells showed any cell growth, and all wells showing growth also secreted human IgG. These results confirmed that on average only 1 cell is plated per well with these procedures, and that the CHO cell line originated from a single cell.

Downstream Processing and 3-Column Purification of the HIRMAb-GDNF Fusion Protein.

Following the second round of dilutional cloning, the highest producing cell line secreting the HIRMAb-GDNF fusion protein was propagated in serum-free medium to a total volume of 2,000 mL in several 1 L square plastic bottles on an orbital shaker. The HIRMAb-GDNF fusion protein was purified from the CHO cell conditioned medium using the following down-stream processing:

Depth filtration with a 0.2 $m^2$ 0.65 um GF filter in series with an 0.05 $m^2$ 0.2 µm ultrafilter Volume reduction to 400 mL using a Pellicon-2 tangential flow filtration (TFF) system Ultra-filtration with a 0.2 mm ultra-filter and application to a 7 mL column of protein A. Following application to the column, the column was eluted with 1 M NaCl, which lutes DNA non-specifically absorbed to the column, and the product is eluted as a single peak with 0.1 M sodium acetate/pH=3.7. The acid eluate was neutralized with 1 M Tris base and concentrated to 5 mL.

Cation exchange (CATEX) chromatography in bind-elute mode was performed with a 5 mL column of SP Sepharose FF equilibrated with 0.02 M MES and 0.05 M NaCl. The conductivity of the sample was reduced to <5 mS/cm prior to application to the column. The column was successively eluted with step gradients of 0.02 M MES/pH=5.5 containing 0.25 M NaCl, 0.35 M NaCl, 0.5 M NaCl, and 1M NaCl. The HIRMAb-GDNF fusion protein eluted in 0.5 M NaCl.

Anion exchange (ANEX) chromatography in flow-through mode was performed with a 5 mL column of Q Sepharose FF equilibrated with 0.025 M MES/pH=5.5 and 0.05 M NaCl. The conductivity of the sample was reduced to <7 mS/cm. The HIRMAb-GDNF fusion protein eluted in the flow-through.

Biochemical Characterization of 3-Column Purified CHO Cell Derived HIRMAb-GDNF Fusion Protein.

The purity and potency of the CHO derived HIRMAb-GDNF fusion protein was assessed with the following procedures:

(a) SDS-PAGE.

The HIRMAb-GDNF fusion protein was purified to homogeneity based on reducing and non-reducing sodium dodecyl sulfate polyacrylamide gel electrophoresis (SDS-PAGE). A characteristic "fingerprint" of the HIRMAb-GDNF fusion protein is the detection of 3 heavy chain glycoforms, which arise from differential glycosylation of the GDNF part of the fusion protein. This pattern is reproducible from run to run.

(b) GDNF and Human IgG Western Blot.

Figure 39:
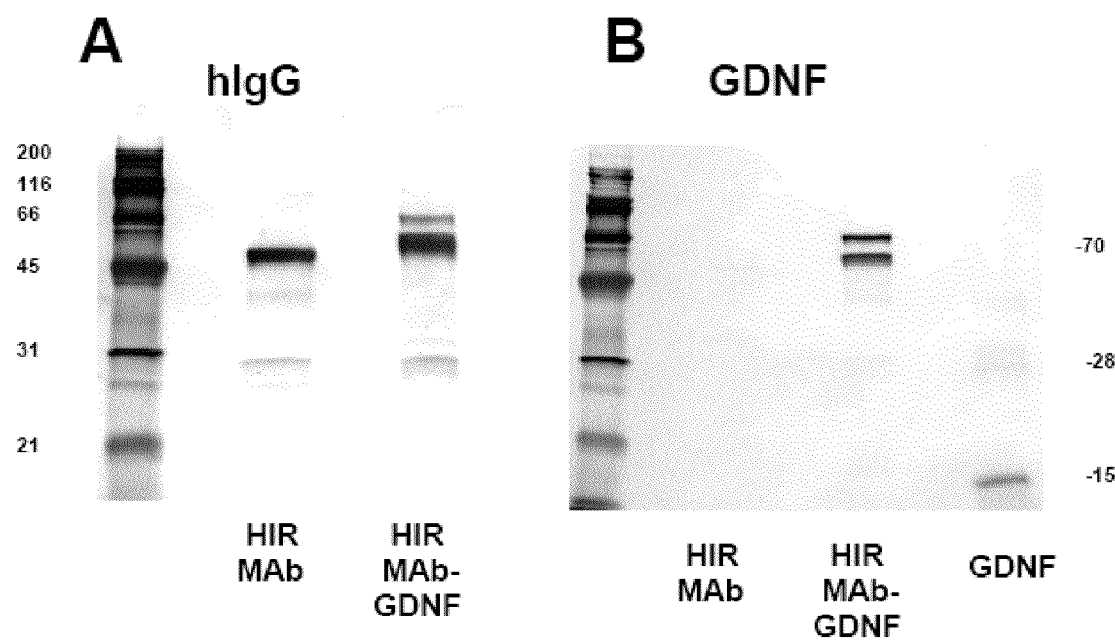
FIG. 39. Western blot with a primary antibody against either human IgG (A) or human GDNF (B). The CHO-derived chimeric HIRMAb and the CHO-derived HIRMAb-GDNF fusion protein are applied in panel A, and the HIRMAb, the HIRMAb-GDNF fusion protein, and GDNF are applied in panel B. The migration of molecular weight standards is shown in lane 1 of panel A.

The CHO derived HIRMAb-GDNF fusion protein was electrophoresed on a 12% SDS-PAGE gel and blotted to nitrocellulose for Western blotting with primary antibodies to either human IgG (left panel, FIG. 39), or to human GDNF (right panel, FIG. 39). Both the anti-human IgG antibody and the anti-human GDNF antibody reacted specifically with the heavy chain of the HIRMAb-GDNF fusion protein.

(c) Human Insulin Receptor (HIR) Binding of AGT-190.

Figure 40:
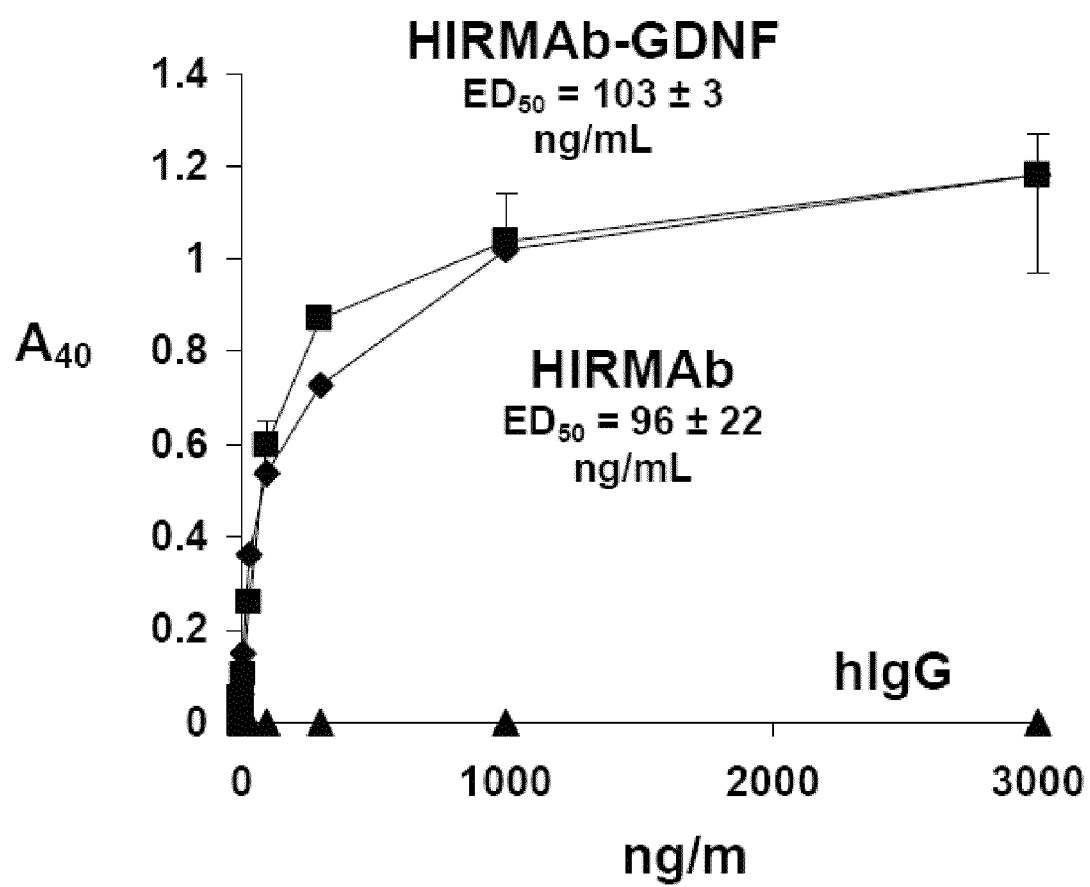
FIG. 40. The affinity of the CHO-derived HIRMAb and the CHO-derived HIRMAb-GDNF fusion protein for binding to the extracellular domain of the human insulin receptor (HIR) is measured in this ELISA format. The concentration of antibody that causes 50% saturation of binding, the ED50, was determined by non-linear regression analysis. The 2 proteins have the same affinity for the HIR, indicating fusion of GDNF to the C-terminus of the heavy chain of the HIRMAb does not affect binding to the HIR.

The extracellular domain (ECD) of the HIR was purified by lectin affinity chromatography from serum free medium conditioned by CHO cells that were permanently transfected with the HIR ECD. The HIR ECD was plated in ELISA wells to bind the chimeric HIRMAb without GDNF fused and the HIRMAb-GDNF fusion protein. As shown in FIG. 40, the affinity of the CHO-derived HIRMAb-GDNF fusion protein binding to the HIR is high, and not significantly different from the binding of the chimeric HIRMAb. These data indicate the affinity of the HIRMAb for the HIR is not affected by the fusion of GDNF to the carboxyl terminus of the IgG. The binding constant (ED50) shown in FIG. 40 was determined by non-linear regression analysis of the binding isotherm.

(d) GFRa1 Binding of the HIRMAb-GDNF Fusion Protein.

The affinity of either GDNF or the HIRMAb-GDNF fusion protein for the GDNF receptor, GFRa1, was determined with a specific ELISA format, which is outlined in FIG. 33. In this assay, GDNF binds with high affinity for the GFRa1 extracellular domain (ECD), and the affinity of the CHO-derived HIRMAb-GDNF fusion protein for the GFRa1 (ED50=1.44±0.07 nM) was comparable to GDNF (ED50=1.00±0.09 nM).

(e) GDNF Bio-Assay in Rat Brain In Vivo.

The intra-cerebral injection of GDNF in experimental stroke results in neuroprotection, as reflected in a reduced stroke volume. Therefore, the permanent middle cerebral artery occlusion (MCAO) model was used as a rapid in vivo bio-assay of CHO-derived HIRMAb-GDNF fusion protein neuroprotective properties in vivo, similar to that shown for the COS derived fusion protein (FIG. 35). The intra-cerebral injection of the HIRMAb-GDNF fusion protein caused a 74% reduction in hemispheric stroke volume, from 338±33 mm$^3$ to 87±27 mm$^3$ (mean±SE, n=5-6 rats per group), which was significant at the p<0.001 level (Student's t-test). Similarly, the cortical stroke volume was reduced 80% from 238±25 mm$^3$ to 48±18 mm$^3$ (p<0.001), and the sub-cortical stroke volume was reduced 39% from 101±10 mm$^3$ to 39±11 mm$^3$ (p<0.025). The neurologic deficit score was 3.6±0.2 and 1.4±0.7 (mean±SE, n=5-6 rats per group) in the saline treated and CHO-derived HIRMAb-GDNF fusion protein treated rats, respectively, and this improvement in neurologic deficit was significant at the p<0.05 level.

(f) Size Exclusion High Performance Liquid Chromatography.

Figure 41:
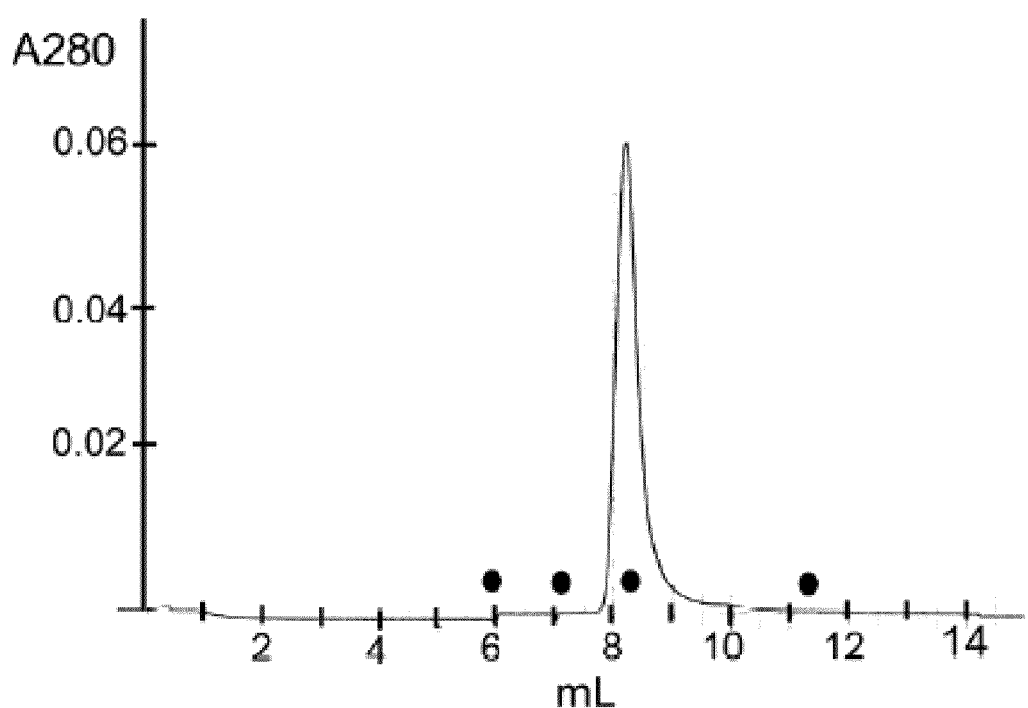
FIG. 41. Size exclusion high performance liquid chromatography of the HIRMAb-GDNF fusion protein shows the absence of aggregates in the CHO-derived protein.
Figure 42:
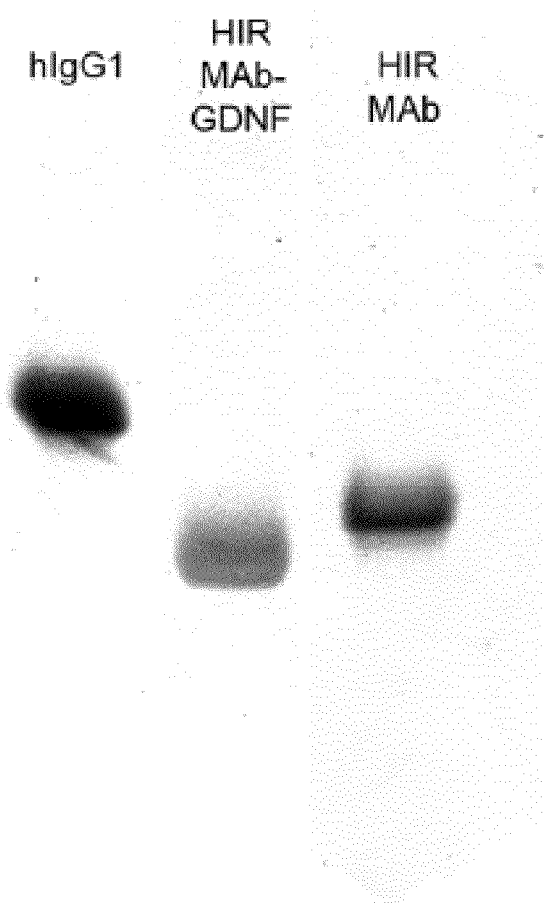
FIG. 42. Native polyacrylamide gel electrophoresis of the HIRMAb, control human IgG1, or the HIRMAb-GDNF fusion protein shows the absence of aggregates in the CHO-derived fusion protein.

The absence of aggregates in the purified HIRMAb-GDNF fusion protein was demonstrated with size exclusion chromatography (SEC) high performance liquid chromatography (HPLC) using a G3000 SWXL column, 0.78×30 cm and an HPLC pump at 0.5 mL/min with detection at 280 nm. As shown in FIG. 41, the CHO-derived HIRMAb-GDNF fusion protein elutes as a single peak, removed from the void volume, with no detectable aggregates. The absence of aggregates is also demonstrated by the native polyacrylamide gel electrophoresis (FIG. 42).

(g) Carbohydrate Analysis.

The CHO-derived HIRMAb-GDNF fusion protein was analyzed for neutral monosaccharide content and for the N-terminal oligopeptide fingerprint. The fusion protein is glycosylated at 3 different N-linked asparagine sites, including 1 site within the CH2 region and 2 sites within the GDNF region of the fusion protein heavy chain. The neutral monosaccharide content (moles monosaccharide/mole fusion protein) was 7.7 for N-acetyl glucosamine, 5.3 for mannose, 2.3 for galactose, 1.6 for fucose, and 0.19 for N-acetyl galactosamine. These 4 sugars are organized as 1 of 4 different terminal structures, designated G0, G1(1,6), G1(1, 3), or G2, depending on whether there is 0, 1, or 2 terminal galactose moieties, respectively. The profile for AGT-190 is G0>G1>G2, which is typical of CHO-derived recombinant proteins, and indicative of relative reduced terminal galactosylation. The glycosylation of HIRMAb-GDNF fusion protein on at least 3 different asparagine residues explains the heterogeneity of the heavy chain on Western blotting (FIG. 39).

(h) Binding to Human Blood-Brain Barrier.

Figure 43:
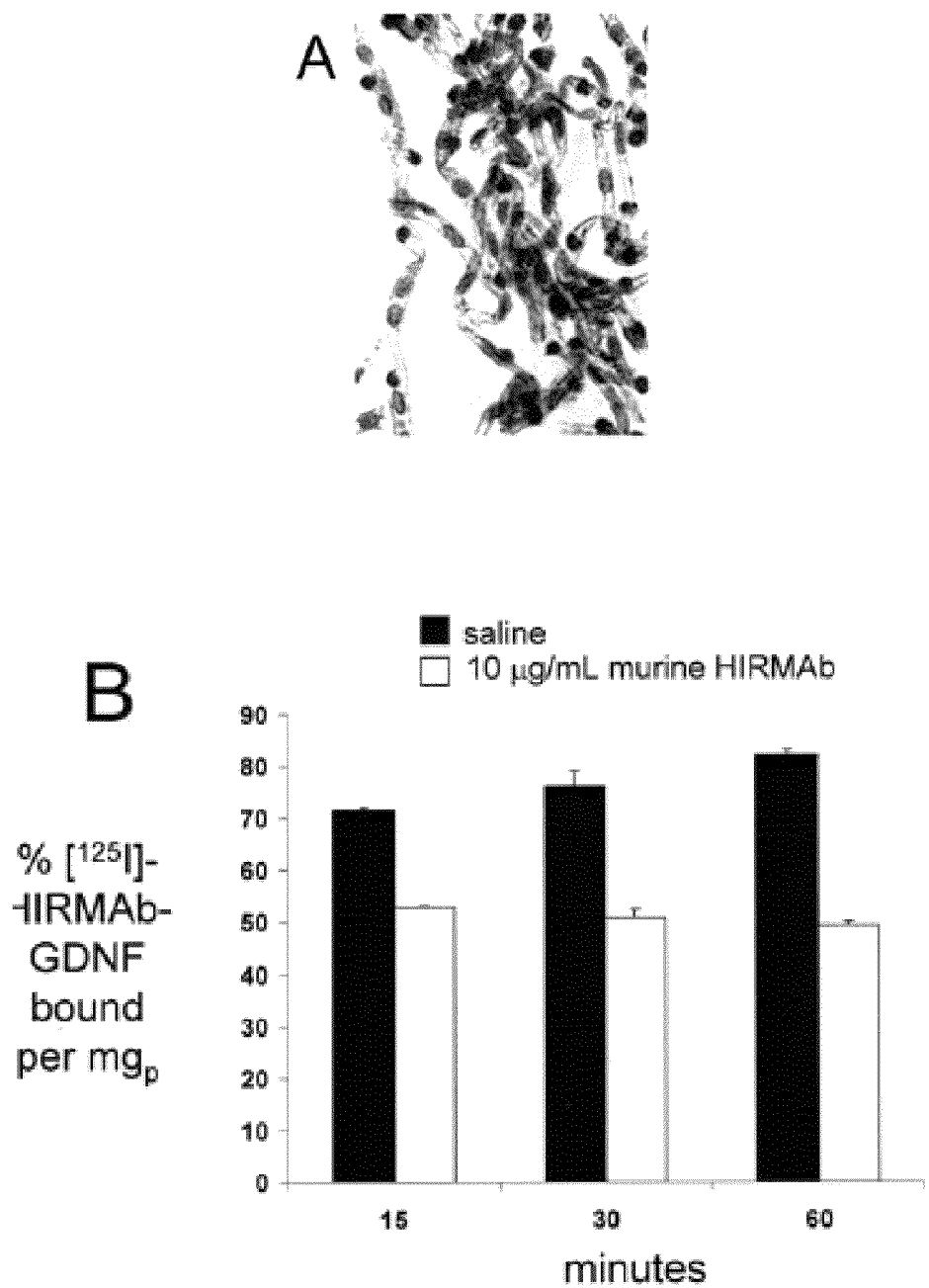
FIG. 43. (A) Light micrograph of isolated human brain capillaries, used as an in vitro model system of the human BBB. (B) Binding of the $^3$H-HIRMAb-GDNF fusion protein to the isolated brain capillaries is inhibited by the murine HIRMAb. The component of HIRMAb-GDNF uptake by the capillaries that is resistant to HIRMAb inhibition represents endocytosed fusion protein.

Capillaries, which form the BBB in vivo, were isolated from human autopsy brain in a purified preparation as shown by light microscopy (FIG. 43). The HIRMAb-GDNF fusion protein was radio-labeled by tritiation, and a radio-receptor assay was performed to demonstrate binding of the labeled HIRMAb-GDNF fusion protein to the HIR at the human BBB, using the isolated human brain capillaries. There was a high level of binding of the HIRMAb-GDNF fusion protein to the human brain capillary and the binding was displaced by unlabeled murine HIRMAb (FIG. 43B).

Example 17

Treatment of Parkinson's Disease with the HIRMAb-GDNF Fusion Protein

Parkinson's disease (PD) is a neurodegenerative condition that affects the dopaminergic neurons of the nigral-striatal tract. GDNF is a potent trophic factor for these dopaminergic neurons. The intra-cerebral injection of the GDNF protein into the brain of rats with experimental PD can protect these neurons, and blocks further axotomy of the fibers projecting from the substantia nigra to the striatum. Accordingly, recombinant human GDNF has been developed as a new therapeutic for PD. However, GDNF does not cross the BBB. Therefore, GDNF was administered via a trans-cranial route using intracerebroventricular (ICV) injection. However, GDNF delivered by ICV injection was found to not penetrate into the brain parenchyma and was ineffective in patients with PD, and this delivery approach was abandoned. Subsequently, GDNF has been administered by convection enhanced diffusion (CED). In this approach, a reservoir holding the GDNF is implanted in the abdomen, and a catheter is run through the skin from the reservoir to the brain via a trans-cranial passage. The reservoir has a pump that continuously pumps the GDNF fluid into the brain. However, this highly invasive procedure was found to lead to toxic effects in the brain, was not effective owing to lack of penetration of the GDNF to the nigra-striatal tract, and was abandoned. These failed trans-cranial approaches to the treatment of PD with GDNF highlighted the importance of re-engineering this neurotrophin so that the molecule can cross the BBB. The trans-BBB delivery route has two unique advantages. First, the GDNF can be given by a non-invasive systemic injection, such as an intravenous, subcutaneous, or intra-muscular injection, and no neurosurgical procedure is required. Second, the GDNF enters the brain via the trans-vascular route. Since every neuron in the brain is perfused by its own blood vessel, the GDNF is delivered to every cell comprising the nigra-striatal tract of brain. The GDNF could be given on a weekly or bi-weekly basis to patients with PD at doses ranging from 1, 3, 10, 30, or 100 mg. The considerations in Example 7 suggest that 25-30 mg may be a preferred dose.

Example 18

Acute and Chronic Treatment of Stroke with the HIRMAb-GDNF Fusion Protein

GDNF is highly neuroprotective in experimental stroke (Kitagawa et al, Stroke 29:1417-1422 (1998)). Activation of the GDNF receptor, GFRα1, inhibits apoptosis in the neuron that is induced by an ischemic event. The demonstration of GDNF's neuroprotective effects in experimental stroke have uniformly involved intra-cerebral injection of the neurotrophin, because the GDNF does not cross the BBB, and because the BBB is intact in the first 5 hours after stroke, when the rescue of dying neurons is still possible. The HIRMAb-GDNF is a re-engineered form of GDNF that is both equipotent with GDNF as a neuroprotective agent, and is able to cross the human BBB following systemic administration. Thus, the patient suffering from an acute stroke could be rapidly treated with intravenous HIRMAb-GDNF in the emergency room. The HIRMAb-GDNF fusion protein will rapidly enter the brain and activate GFRα1 receptors on neurons to inhibit the apoptosis cycle induced by the stroke. In addition, chronic treatment with systemic HIRMAb-GDNF fusion protein could be therapeutic in the rehabilitation phase of stroke, since the intra-cerebral infusion of GDNF into the post-stroke brain induces neurogenesis, and neural repair in the post-stroke period (Kobayashi et al, 2006).

Example 19

Treatment of Motor Neuron Disease with the HIRMAb-GDNF Fusion Protein

Motor neuron diseases such as amyotrophic lateral sclerosis (ALS) and spinal muscular atrophy (SMA) cause progressive paralysis leading to premature death. GDNF is highly neuroprotective of spinal cord motor neurons (Bohn supra). However, it is unlikely that GDNF will be developed as a drug for ALS or SMA, given the failed clinical trials of other neurotrophic factors for these conditions. Both BDNF and ciliary neurotrophic factor (CNTF) were administered to ALS patients in the 1990s by subcutaneous administration. The subcutaneous administration phase III clinical trials failed, because BDNF and CNTF, like GDNF, do not cross the BBB. However, with the re-engineering of GDNF as the HIRMAb-GDNF fusion protein demonstrated herein, conditions such as ALS or SMA could now be amenable to treatment by systemic administration. The HIRMAb fusion proteins cross the blood-spinal cord barrier, which as been demonstrated by brain scanning of adult Rhesus monkeys following intravenous administration of the HIRMAb fusion protein (Boado et al, *Biotechnol. Bioeng,* 97(6):1376-1386 (2007); Boado et al, *Bioconjug. Chem.* 18:447-455 (2007)).

Example 20

Treatment of Brain or Spinal Cord Injury with the HIRMAb-GDNF Fusion Protein

GDNF promotes neural repair in the period following acute experimental brain injury, such as with a lateral fluid percussion injury (Bakshi et al, *Eur. J. Neurosci.* 23:2119-2134 (2006)). GDNF does not cross the BBB, and the BBB is intact in the days/weeks after head injury, when the brain attempts to heal from the acute insult. Therefore, the beneficial effects of GDNF on acute head injury could only be demonstrated by the intra-cerebral injection of genetically modified stem cells that secrete GDNF. Although the trans-cranial injection approach may be feasible in the rat brain, the human brain is 1000-fold larger than a rat brain. Diffusion of the GDNF from the depot injection site becomes limiting, and the GDNF cannot penetrate to the wound area, beyond the local injection site. Alternatively, if the GDNF is delivered to brain via the trans-vascular route, then every injured neuron in the brain is exposed to the GDNF. The latter is feasible with the weekly, bi-weekly, or daily systemic administration of the HIRMAb-GDNF fusion protein during the post-injury repair and rehabilitation period.

Similarly, motor neurons of the spinal cord are responsive to GDNF, and GDNF can promote neural repair following experimental spinal cord injury (Lu et al, *J. Neurotrauma* 19:1081-1090 (2002)). However, because the opening of the BBB following spinal cord injury is only transient, it is not possible to treat spinal cord injury with systemic GDNF administration. Instead, the GDNF expressing plasmid DNA was injected directly into the rat spinal cord following the acute spinal cord injury. However, the size of the spinal cord in humans is 1000-fold larger than that of the rat. Therefore, it is not possible to distribute GDNF to the entire lesioned area following direct spinal injection of the GDNF therapeutic in humans. Alternatively, GDNF is delivered to all injured neurons in the spinal cord following a trans-vascular delivery, and this is possible with the systemic administration of the HIRMAb-GDNF fusion protein.

Example 21

Treatment of Drug and Alcohol Addiction with the HIRMAb-GDNF Fusion Protein

The intra-cerebral injection of GDNF results in treatment of animals addicted to either opioid, or non-opioid drugs. With respect to non-opioid drugs, the intra-cerebral injection of GDNF decreases cocaine self-administration in rats (Green-Sadan et al, Eur. J. Neurosci., 18: 2093-2098, 2003). Similarly, the intra-cerebral injection of GDNF decreases ethanol self-administration (He et al, J. Neurosci., 25: 619-628, 2005). The GDNF has to be administered via a transcranial route, because GDNF does not cross the BBB. The drug, ibogaine, decreases withdrawal symptoms to chronic opioid drugs, cocaine, or alcohol, and works by increasing GDNF in regions of the brain such as the ventral tegmental area (VTA) (He and Ron, FASEB J, 20: E1820-D1827, 2006). Although ibogaine is a small molecule that crosses the BBB, its application in the treatment of addiction is limited by severe side effects. GDNF is implicated in another study related to cocaine addiction. Cocaine increases tyrosine hydroxylase in the VTA, and this effect of cocaine is blocked by the intra-cerebral injection of GDNF (Messer et al, Neuron, 26: 247-257, 2000). With respect to methamphetamine addiction, a decrease in brain concentration of GDNF, such as occurs in GDNF knock-out heterozygote mice, results in increased methamphetamine self-administration (Yan et al, FASEB J, 21: 1994-2004, 2007). These forms of addiction could be treated by systemic administration of GDNF if this neurotrophin was re-formulated to cross the BBB, which is the case for the HIRMAb-GDNF fusion protein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a neurotherapeutic peptide comprising an amino acid sequence which is at least 80% identical to the amino acid sequence of mature human GDNF (SEQ ID NO:52), wherein the neurotherapeutic peptide is covalently linked at its amino terminus to the carboxy terminus of the heavy chain or light chain of an antibody that is capable of crossing the blood brain barrier (BBB) by binding on an endogenous BBB receptor.

2. The composition of claim 1 wherein the endogenous BBB receptor is selected from the group consisting of the insulin receptor, transferrin receptor, leptin receptor, lipoprotein receptor, and the IGF receptor.

3. The composition of claim 2 wherein the endogenous BBB receptor mediated transport system is the insulin BBB receptor mediated transport system.

4. The composition of claim 1, wherein the antibody is a monoclonal antibody (MAb).

5. The composition of claim 4 wherein the MAb is a chimeric MAb.

6. The composition of claim 5, wherein the chimeric antibody contains at least 80% human sequence.

7. The composition of claim 1, wherein the neurotherapeutic peptide comprises an amino acid sequence that is at least 95% identical to the amino acid sequence of mature human GDNF (SEQ ID NO:52).

8. The composition of claim 7, wherein the neurotherapeutic peptide comprises the amino acid sequence of mature human GDNF (SEQ ID NO:52).

9. The composition of claim 4, wherein the neurotherapeutic peptide is covalently linked at its amino terminus to the carboxy terminus of the heavy chain of the MAb.

10. A composition for treating a neurological disorder comprising a neurotherapeutic peptide comprising an amino acid sequence which is at least 80% identical to the amino acid sequence of mature human GDNF (SEQ ID NO:52) covalently linked at its amino terminus to the carboxy terminus of the light chain or heavy chain of an immunoglobulin that is capable of crossing the blood brain barrier, wherein the composition is capable of crossing the BBB in an amount that is effective in treating the neurological disorder.

11. A recombinant mammalian cell comprising the composition of claim 10.

12. A method for treating Parkinson's disease, a motor neuron disease, spinal cord injury, brain injury, focal brain ischemia, or global brain ischemia in an individual comprising peripherally administering to the individual an effective amount of a composition comprising a neurotherapeutic peptide comprising an amino acid sequence which is at least 80% identical to the amino acid sequence of mature human GDNF (SEQ ID NO:52), wherein the neurotherapeutic peptide is covalently linked at its amino terminus to the carboxy terminus of the heavy chain or light chain of an antibody that is capable of crossing the blood brain barrier (BBB) by binding an endogenous BBB receptor.

13. The method of claim 12, wherein the neurotherapeutic peptide comprises an amino acid sequence at least 95% identical to the amino acid sequence of mature human GDNF (SEQ ID NO:52).

14. The method of claim 12, wherein the neurotherapeutic peptide comprises the amino acid sequence of mature human GDNF (SEQ ID NO:52).

15. The method of claim 12 wherein the administering is selected from the group consisting of oral, intravenous, intramuscular, subcutaneous, intraperitoneal, rectal, transbuccal, intranasal, transdermal, and inhalation administration.

16. The method of claim 12, wherein the administering is intravenous, intramuscular, or subcutaneous.

17. The method of claim 12, wherein the individual is administered a dose of the composition that is about 1 to about 100 mg.

18. A method for treating drug addiction or alcohol addiction in an individual, comprising administering to the individual an effective amount of a composition comprising a neurotherapeutic peptide comprising an amino acid sequence which is at least 80% identical to the amino acid sequence of mature human GDNF (SEQ ID NO:52), wherein the neurotherapeutic peptide is covalently linked at its amino terminus to the carboxy terminus of the heavy chain or light chain of an antibody that is capable of crossing the blood brain barrier (BBB) by binding an endogenous BBB receptor.

19. The method of claim 18, wherein the neurotherapeutic peptide comprises an amino acid sequence at least 95% identical to the amino acid sequence of mature human GDNF (SEQ ID NO:52).

20. The method of claim 18, wherein the neurotherapeutic peptide comprises the amino acid sequence of mature human GDNF (SEQ ID NO:52).

21. The method of claim 18, wherein the administering is selected from the group consisting of oral, intravenous, intramuscular, subcutaneous, intraperitoneal, rectal, transbuccal, intranasal, transdermal, and inhalation administration.

22. The method of claim 18, wherein the administering is intravenous, intramuscular, or subcutaneous.

23. The method of claim 18, wherein the individual is administered a dose of the composition that is about 1 to about 100 mg.

* * * * *